United States Patent
Chen et al.

(10) Patent No.: US 10,583,201 B2
(45) Date of Patent: *Mar. 10, 2020

(54) EFFICIENT DELIVERY OF THERAPEUTIC MOLECULES IN VITRO AND IN VIVO

(71) Applicant: Massachusetts Eye and Ear Infirmary, Boston, MA (US)

(72) Inventors: Zheng-Yi Chen, Somerville, MA (US); David Liu, Cambridge, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/518,183

(22) PCT Filed: Oct. 9, 2015

(86) PCT No.: PCT/US2015/000109
§ 371 (c)(1),
(2) Date: Apr. 10, 2017

(87) PCT Pub. No.: WO2016/057061
PCT Pub. Date: Apr. 14, 2016

(65) Prior Publication Data
US 2017/0326254 A1 Nov. 16, 2017

Related U.S. Application Data

(60) Provisional application No. 62/062,628, filed on Oct. 10, 2014.

(51) Int. Cl.
| | |
|---|---|
| C12Q 1/10 | (2006.01) |
| A61K 49/22 | (2006.01) |
| A61K 48/00 | (2006.01) |
| A61K 9/127 | (2006.01) |
| A61K 9/00 | (2006.01) |
| C12N 15/10 | (2006.01) |
| C12N 15/11 | (2006.01) |
| A61P 27/16 | (2006.01) |
| A61K 38/45 | (2006.01) |
| A61K 38/46 | (2006.01) |
| C12N 9/12 | (2006.01) |
| C12N 9/22 | (2006.01) |
| A61K 38/00 | (2006.01) |

(52) U.S. Cl.
CPC ........ *A61K 48/0033* (2013.01); *A61K 9/0046* (2013.01); *A61K 9/127* (2013.01); *A61K 38/45* (2013.01); *A61K 38/465* (2013.01); *A61K 48/0075* (2013.01); *A61P 27/16* (2018.01); *C12N 9/1241* (2013.01); *C12N 9/22* (2013.01); *C12N 15/102* (2013.01); *C12N 15/11* (2013.01); *C12N 15/111* (2013.01); *C12Y 207/07* (2013.01); *C12Y 301/00* (2013.01); *A61K 38/00* (2013.01); *C07K 2319/00* (2013.01); *C12N 2310/14* (2013.01); *C12N 2310/20* (2017.05); *C12N 2320/32* (2013.01)

(58) Field of Classification Search
None
See application file for complete search history.

(56) References Cited

U.S. PATENT DOCUMENTS 7,526,784 B2 * 4/2009 Jarman ................ G11B 27/105
725/28

OTHER PUBLICATIONS

Kohrman, et al. (2013) "Gene Therapy for Deafness", Gene Therapy, 20: 1119-23. (Year: 2013).*
Jocelyn Kaiser (May 3, 2016) "The gene editor CRISPR won't fully fix sick people any time soon. Here's why", Biology Technology, CRISPR, DOI: 10.1126/science.aaf5689, 12 pages long as printed) (found at https://www.sciencemag.org/news/2016/05/gene-editor-crispr-won-t-fully-fix-sick-people-anytime-soon-here-s-why).*
Rip, et al. (2014) "Glutathione PEGylated liposomes: pharmacokinetics and delivery of cargo across the blood-brain barrier in rats", Journal of Drug Targeting, 22(5): 460-67.*

* cited by examiner

*Primary Examiner* — Robert M Kelly
(74) *Attorney, Agent, or Firm* — Mintz Levin Cohn Ferris Glovsky and Popeo, P.C.; Nicholas A. Zachariades; Ingrid A. Beattie

(57) ABSTRACT

A chimeric molecule of one or more proteins or peptides fused, complexed or linked to one or more anionic molecules. Efficient in vitro and in vivo delivery is attained by encapsulating these molecules in cationic lipids or cationic liposomes. Methods of treatment include the intracellular delivery of these molecules to a specific therapeutic target.

10 Claims, 16 Drawing Sheets

Specification includes a Sequence Listing.

a b

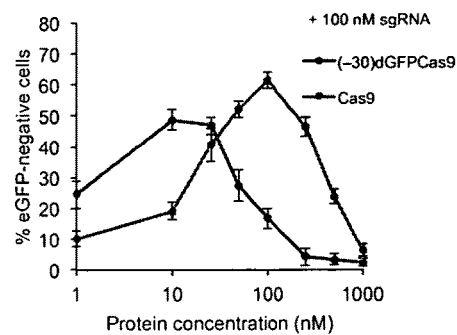
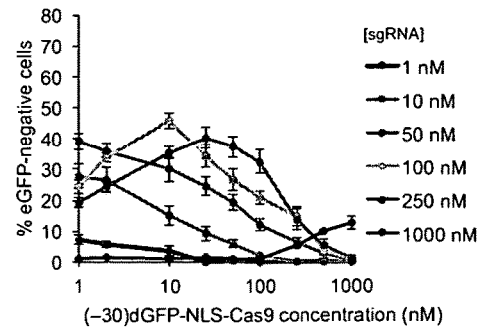
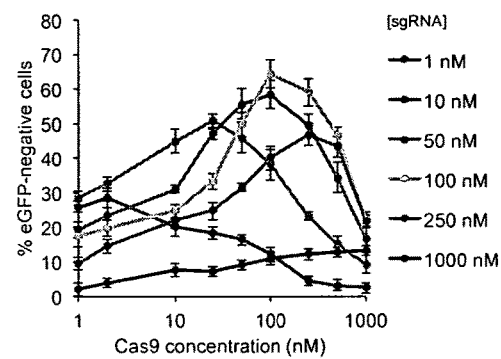
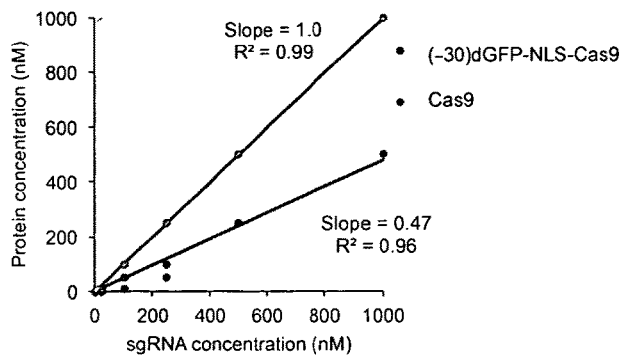
FIGURES 12A-12D
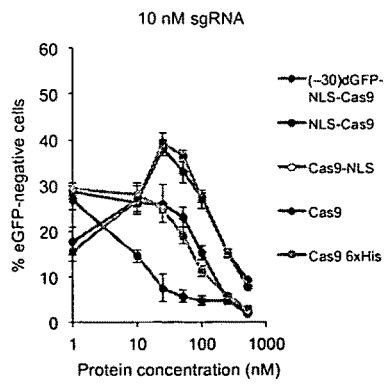
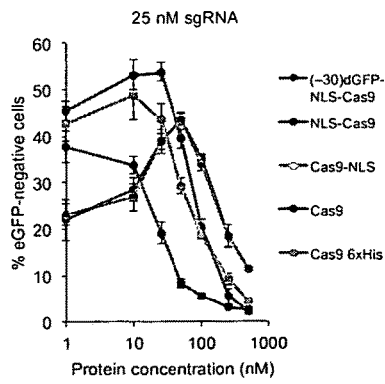
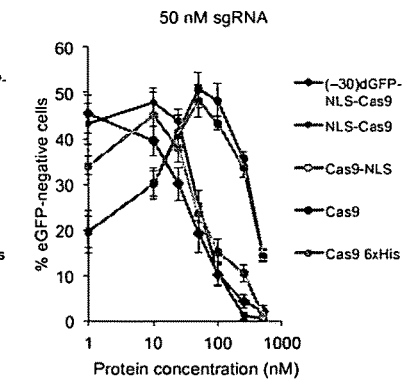
FIGURES 13A-13C

SEQUENCE LISTING

```
<160> NUMBER OF SEQ ID NOS: 168

<210> SEQ ID NO 1
<211> LENGTH: 620
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Gly Ala Ser Lys Gly Glu Arg Leu Phe Arg Gly Lys Val Pro Ile
1               5                   10                  15

Leu Val Glu Leu Lys Gly Asp Val Asn Gly His Lys Phe Ser Val Arg
            20                  25                  30

Gly Lys Gly Lys Gly Asp Ala Thr Arg Gly Lys Leu Thr Leu Lys Phe
        35                  40                  45
```

-continued

```
Ile Cys Thr Thr Gly Lys Leu Pro Val Pro Trp Pro Thr Leu Val Thr
 50                  55                  60
Thr Leu Thr Tyr Gly Val Gln Cys Phe Ser Arg Tyr Pro Lys His Met
 65                  70                  75                  80
Lys Arg His Asp Phe Phe Lys Ser Ala Met Pro Lys Gly Tyr Val Gln
                     85                  90                  95
Glu Arg Thr Ile Ser Phe Lys Lys Asp Gly Lys Tyr Lys Thr Arg Ala
                100                 105                 110
Glu Val Lys Phe Glu Gly Arg Thr Leu Val Asn Arg Ile Lys Leu Lys
            115                 120                 125
Gly Arg Asp Phe Lys Glu Lys Gly Asn Ile Leu Gly His Lys Leu Arg
130                 135                 140
Tyr Asn Phe Asn Ser His Lys Val Tyr Ile Thr Ala Asp Lys Arg Lys
145                 150                 155                 160
Asn Gly Ile Lys Ala Lys Phe Lys Ile Arg His Asn Val Lys Asp Gly
                165                 170                 175
Ser Val Gln Leu Ala Asp His Tyr Gln Gln Asn Thr Pro Ile Gly Arg
                180                 185                 190
Gly Pro Val Leu Leu Pro Arg Asn His Tyr Leu Ser Thr Arg Ser Lys
            195                 200                 205
Leu Ser Lys Asp Pro Lys Glu Lys Arg Asp His Met Val Leu Leu Glu
210                 215                 220
Phe Val Thr Ala Ala Gly Ile Lys His Gly Arg Asp Glu Arg Tyr Lys
225                 230                 235                 240
Thr Gly Gly Ser Gly Gly Ser Gly Gly Ser Gly Gly Ser Gly Gly Ser
                245                 250                 255
Gly Gly Ser Gly Gly Ser Gly Gly Ser Gly Gly Thr Ala Ser Asn Leu
            260                 265                 270
Leu Thr Val His Gln Asn Leu Pro Ala Leu Pro Val Asp Ala Thr Ser
            275                 280                 285
Asp Glu Val Arg Lys Asn Leu Met Asp Met Phe Arg Asp Arg Gln Ala
290                 295                 300
Phe Ser Glu His Thr Trp Lys Met Leu Leu Ser Val Cys Arg Ser Trp
305                 310                 315                 320
Ala Ala Trp Cys Lys Leu Asn Asn Arg Lys Trp Phe Pro Ala Glu Pro
                325                 330                 335
Glu Asp Val Arg Asp Tyr Leu Leu Tyr Leu Gln Ala Arg Gly Leu Ala
                340                 345                 350
Val Lys Thr Ile Gln Gln His Leu Gly Gln Leu Asn Met Leu His Arg
            355                 360                 365
Arg Ser Gly Leu Pro Arg Pro Ser Asp Ser Asn Ala Val Ser Leu Val
370                 375                 380
Met Arg Arg Ile Arg Lys Glu Asn Val Asp Ala Gly Glu Arg Ala Lys
385                 390                 395                 400
Gln Ala Leu Ala Phe Glu Arg Thr Asp Phe Asp Gln Val Arg Ser Leu
                405                 410                 415
Met Glu Asn Ser Asp Arg Cys Gln Asp Ile Arg Asn Leu Ala Phe Leu
                420                 425                 430
Gly Ile Ala Tyr Asn Thr Leu Leu Arg Ile Ala Glu Ile Ala Arg Ile
            435                 440                 445
Arg Val Lys Asp Ile Ser Arg Thr Asp Gly Gly Arg Met Leu Ile His
450                 455                 460
```

```
Ile Gly Arg Thr Lys Thr Leu Val Ser Thr Ala Gly Val Glu Lys Ala
465                 470                 475                 480

Leu Ser Leu Gly Val Thr Lys Leu Val Glu Arg Trp Ile Ser Val Ser
            485                 490                 495

Gly Val Ala Asp Asp Pro Asn Asn Tyr Leu Phe Cys Arg Val Arg Lys
            500                 505                 510

Asn Gly Val Ala Ala Pro Ser Ala Thr Ser Gln Leu Ser Thr Arg Ala
            515                 520                 525

Leu Glu Gly Ile Phe Glu Ala Thr His Arg Leu Ile Tyr Gly Ala Lys
        530                 535                 540

Asp Asp Ser Gly Gln Arg Tyr Leu Ala Trp Ser Gly His Ser Ala Arg
545                 550                 555                 560

Val Gly Ala Ala Arg Asp Met Ala Arg Ala Gly Val Ser Ile Pro Glu
                565                 570                 575

Ile Met Gln Ala Gly Gly Trp Thr Asn Val Asn Ile Val Met Asn Tyr
            580                 585                 590

Ile Arg Asn Leu Asp Ser Glu Thr Gly Ala Met Val Arg Leu Leu Glu
        595                 600                 605

Asp Gly Asp Gly Gly Ser His His His His His His
    610                 615                 620
```

<210> SEQ ID NO 2
<211> LENGTH: 620
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

```
Met Gly Ala Ser Lys Gly Glu Glu Leu Phe Thr Gly Val Val Pro Ile
1               5                   10                  15

Leu Val Glu Leu Asp Gly Asp Val Asn Gly His Lys Phe Ser Val Arg
            20                  25                  30

Gly Glu Gly Glu Gly Asp Ala Thr Asn Gly Lys Leu Thr Leu Lys Phe
        35                  40                  45

Ile Cys Thr Thr Gly Lys Leu Pro Val Pro Trp Pro Thr Leu Val Thr
50                  55                  60

Thr Leu Thr Tyr Gly Val Gln Cys Phe Ser Arg Tyr Pro Asp His Met
65                  70                  75                  80

Lys Gln His Asp Phe Phe Lys Ser Ala Met Pro Glu Gly Tyr Val Gln
            85                  90                  95

Glu Arg Thr Ile Ser Phe Lys Asp Asp Gly Thr Tyr Lys Thr Arg Ala
            100                 105                 110

Glu Val Lys Phe Glu Gly Asp Thr Leu Val Asn Arg Ile Glu Leu Lys
        115                 120                 125

Gly Ile Asp Phe Lys Glu Asp Gly Asn Ile Leu Gly His Lys Leu Glu
    130                 135                 140

Tyr Asn Phe Asn Ser His Asn Val Tyr Ile Thr Ala Asp Lys Gln Lys
145                 150                 155                 160

Asn Gly Ile Lys Ala Asn Phe Lys Ile Arg His Asn Val Glu Asp Gly
            165                 170                 175

Ser Val Gln Leu Ala Asp His Tyr Gln Gln Asn Thr Pro Ile Gly Asp
            180                 185                 190

Gly Pro Val Leu Leu Pro Asp Asn His Tyr Leu Ser Thr Gln Ser Ala
        195                 200                 205
```

```
Leu Ser Lys Asp Pro Asn Glu Lys Arg Asp His Met Val Leu Leu Glu
        210                 215                 220
Phe Val Thr Ala Ala Gly Ile Thr His Gly Met Asp Glu Leu Tyr Lys
225                 230                 235                 240
Thr Gly Gly Ser Gly Gly Ser Gly Gly Ser Gly Gly Ser Gly Gly Ser
                245                 250                 255
Gly Gly Ser Gly Gly Ser Gly Gly Ser Gly Gly Thr Ala Ser Asn Leu
                260                 265                 270
Leu Thr Val His Gln Asn Leu Pro Ala Leu Pro Val Asp Ala Thr Ser
        275                 280                 285
Asp Glu Val Arg Lys Asn Leu Met Asp Met Phe Arg Asp Arg Gln Ala
        290                 295                 300
Phe Ser Glu His Thr Trp Lys Met Leu Leu Ser Val Cys Arg Ser Trp
305                 310                 315                 320
Ala Ala Trp Cys Lys Leu Asn Asn Arg Lys Trp Phe Pro Ala Glu Pro
                325                 330                 335
Glu Asp Val Arg Asp Tyr Leu Leu Tyr Leu Gln Ala Arg Gly Leu Ala
                340                 345                 350
Val Lys Thr Ile Gln Gln His Leu Gly Gln Leu Asn Met Leu His Arg
        355                 360                 365
Arg Ser Gly Leu Pro Arg Pro Ser Asp Ser Asn Ala Val Ser Leu Val
        370                 375                 380
Met Arg Arg Ile Arg Lys Glu Asn Val Asp Ala Gly Glu Arg Ala Lys
385                 390                 395                 400
Gln Ala Leu Ala Phe Glu Arg Thr Asp Phe Asp Gln Val Arg Ser Leu
                405                 410                 415
Met Glu Asn Ser Asp Arg Cys Gln Asp Ile Arg Asn Leu Ala Phe Leu
                420                 425                 430
Gly Ile Ala Tyr Asn Thr Leu Leu Arg Ile Ala Glu Ile Ala Arg Ile
        435                 440                 445
Arg Val Lys Asp Ile Ser Arg Thr Asp Gly Gly Arg Met Leu Ile His
        450                 455                 460
Ile Gly Arg Thr Lys Thr Leu Val Ser Thr Ala Gly Val Glu Lys Ala
465                 470                 475                 480
Leu Ser Leu Gly Val Thr Lys Leu Val Glu Arg Trp Ile Ser Val Ser
                485                 490                 495
Gly Val Ala Asp Asp Pro Asn Asn Tyr Leu Phe Cys Arg Val Arg Lys
                500                 505                 510
Asn Gly Val Ala Ala Pro Ser Ala Thr Ser Gln Leu Ser Thr Arg Ala
        515                 520                 525
Leu Glu Gly Ile Phe Glu Ala Thr His Arg Leu Ile Tyr Gly Ala Lys
        530                 535                 540
Asp Asp Ser Gly Gln Arg Tyr Leu Ala Trp Ser Gly His Ser Ala Arg
545                 550                 555                 560
Val Gly Ala Ala Arg Asp Met Ala Arg Ala Gly Val Ser Ile Pro Glu
                565                 570                 575
Ile Met Gln Ala Gly Gly Trp Thr Asn Val Asn Ile Val Met Asn Tyr
                580                 585                 590
Ile Arg Asn Leu Asp Ser Glu Thr Gly Ala Met Val Arg Leu Leu Glu
        595                 600                 605
Asp Gly Asp Gly Gly Ser His His His His His
        610                 615                 620
```

-continued

<210> SEQ ID NO 3
<211> LENGTH: 620
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Met Gly Ala Ser Lys Gly Glu Glu Leu Phe Thr Gly Val Val Pro Ile
1               5                   10                  15

Leu Val Glu Leu Asp Gly Asp Val Asn Gly His Lys Phe Ser Val Arg
            20                  25                  30

Gly Glu Gly Glu Gly Asp Ala Thr Asn Gly Lys Leu Thr Leu Lys Phe
        35                  40                  45

Ile Cys Thr Thr Gly Lys Leu Pro Val Pro Trp Pro Thr Leu Val Thr
50                  55                  60

Thr Leu Thr Tyr Gly Val Gln Cys Phe Ser Arg Tyr Pro Asp His Met
65                  70                  75                  80

Asp Gln His Asp Phe Phe Lys Ser Ala Met Pro Glu Gly Tyr Val Gln
                85                  90                  95

Glu Arg Thr Ile Ser Phe Lys Asp Asp Gly Thr Tyr Lys Thr Arg Ala
            100                 105                 110

Glu Val Lys Phe Glu Gly Asp Thr Leu Val Asn Arg Ile Glu Leu Lys
        115                 120                 125

Gly Ile Asp Phe Lys Glu Asp Gly Asn Ile Leu Gly His Lys Leu Glu
    130                 135                 140

Tyr Asn Phe Asn Ser His Asp Val Tyr Ile Thr Ala Asp Lys Gln Glu
145                 150                 155                 160

Asn Gly Ile Lys Ala Glu Phe Glu Ile Arg His Asn Val Glu Asp Gly
                165                 170                 175

Ser Val Gln Leu Ala Asp His Tyr Gln Gln Asn Thr Pro Ile Gly Asp
            180                 185                 190

Gly Pro Val Leu Leu Pro Asp Asp His Tyr Leu Ser Thr Glu Ser Ala
        195                 200                 205

Leu Ser Lys Asp Pro Asn Glu Asp Arg Asp His Met Val Leu Leu Glu
    210                 215                 220

Phe Val Thr Ala Ala Gly Ile Asp His Gly Met Asp Glu Leu Tyr Lys
225                 230                 235                 240

Thr Gly Gly Ser Gly Gly Ser Gly Gly Ser Gly Gly Ser Gly Gly Ser
                245                 250                 255

Gly Gly Ser Gly Gly Ser Gly Gly Ser Gly Gly Thr Ala Ser Asn Leu
            260                 265                 270

Leu Thr Val His Gln Asn Leu Pro Ala Leu Pro Val Asp Ala Thr Ser
        275                 280                 285

Asp Glu Val Arg Lys Asn Leu Met Asp Met Phe Arg Asp Arg Gln Ala
    290                 295                 300

Phe Ser Glu His Thr Trp Lys Met Leu Leu Ser Val Cys Arg Ser Trp
305                 310                 315                 320

Ala Ala Trp Cys Lys Leu Asn Asn Arg Lys Trp Phe Pro Ala Glu Pro
                325                 330                 335

Glu Asp Val Arg Asp Tyr Leu Leu Tyr Leu Gln Ala Arg Gly Leu Ala
            340                 345                 350

Val Lys Thr Ile Gln Gln His Leu Gly Gln Leu Asn Met Leu His Arg
        355                 360                 365
```

Arg Ser Gly Leu Pro Arg Pro Ser Asp Ser Asn Ala Val Ser Leu Val
    370                 375                 380

Met Arg Arg Ile Arg Lys Glu Asn Val Asp Ala Gly Glu Arg Ala Lys
385                 390                 395                 400

Gln Ala Leu Ala Phe Glu Arg Thr Asp Phe Asp Gln Val Arg Ser Leu
                405                 410                 415

Met Glu Asn Ser Asp Arg Cys Gln Asp Ile Arg Asn Leu Ala Phe Leu
            420                 425                 430

Gly Ile Ala Tyr Asn Thr Leu Leu Arg Ile Ala Glu Ile Ala Arg Ile
            435                 440                 445

Arg Val Lys Asp Ile Ser Arg Thr Asp Gly Gly Arg Met Leu Ile His
    450                 455                 460

Ile Gly Arg Thr Lys Thr Leu Val Ser Thr Ala Gly Val Glu Lys Ala
465                 470                 475                 480

Leu Ser Leu Gly Val Thr Lys Leu Val Glu Arg Trp Ile Ser Val Ser
                485                 490                 495

Gly Val Ala Asp Asp Pro Asn Asn Tyr Leu Phe Cys Arg Val Arg Lys
            500                 505                 510

Asn Gly Val Ala Ala Pro Ser Ala Thr Ser Gln Leu Ser Thr Arg Ala
            515                 520                 525

Leu Glu Gly Ile Phe Glu Ala Thr His Arg Leu Ile Tyr Gly Ala Lys
    530                 535                 540

Asp Asp Ser Gly Gln Arg Tyr Leu Ala Trp Ser Gly His Ser Ala Arg
545                 550                 555                 560

Val Gly Ala Ala Arg Asp Met Ala Arg Ala Gly Val Ser Ile Pro Glu
                565                 570                 575

Ile Met Gln Ala Gly Gly Trp Thr Asn Val Asn Ile Val Met Asn Tyr
            580                 585                 590

Ile Arg Asn Leu Asp Ser Glu Thr Gly Ala Met Val Arg Leu Leu Glu
    595                 600                 605

Asp Gly Asp Gly Gly Ser His His His His His
610                 615                 620

<210> SEQ ID NO 4
<211> LENGTH: 620
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Gly Ala Ser Lys Gly Glu Glu Leu Phe Asp Gly Val Val Pro Ile
1               5                   10                  15

Leu Val Glu Leu Asp Gly Asp Val Asn Gly His Glu Phe Ser Val Arg
            20                  25                  30

Gly Glu Gly Glu Gly Asp Ala Thr Glu Gly Glu Leu Thr Leu Lys Phe
        35                  40                  45

Ile Cys Thr Thr Gly Glu Leu Pro Val Pro Trp Pro Thr Leu Val Thr
    50                  55                  60

Thr Leu Thr Tyr Gly Val Gln Cys Phe Ser Asp Tyr Pro Asp His Met
65                  70                  75                  80

Asp Gln His Asp Phe Phe Lys Ser Ala Met Pro Glu Gly Tyr Val Gln
                85                  90                  95

Glu Arg Thr Ile Ser Phe Lys Asp Asp Gly Thr Tyr Lys Thr Arg Ala

```
                100             105             110
    Glu Val Lys Phe Glu Gly Asp Thr Leu Val Asn Arg Ile Glu Leu Lys
                115             120             125
    Gly Ile Asp Phe Lys Glu Asp Gly Asn Ile Leu Gly His Lys Leu Glu
                130             135             140
    Tyr Asn Phe Asn Ser His Asp Val Tyr Ile Thr Ala Asp Lys Gln Glu
    145             150             155             160
    Asn Gly Ile Lys Ala Glu Phe Glu Ile Arg His Asn Val Glu Asp Gly
                165             170             175
    Ser Val Gln Leu Ala Asp His Tyr Gln Gln Asn Thr Pro Ile Gly Asp
                180             185             190
    Gly Pro Val Leu Leu Pro Asp His Tyr Leu Ser Thr Glu Ser Ala
                195             200             205
    Leu Ser Lys Asp Pro Asn Glu Asp Arg Asp His Met Val Leu Leu Glu
                210             215             220
    Phe Val Thr Ala Ala Gly Ile Asp His Gly Met Asp Glu Leu Tyr Lys
    225             230             235             240
    Thr Gly Gly Ser Gly Gly Ser Gly Gly Ser Gly Gly Ser Gly Gly Ser
                245             250             255
    Gly Gly Ser Gly Gly Ser Gly Gly Ser Gly Gly Thr Ala Ser Asn Leu
                260             265             270
    Leu Thr Val His Gln Asn Leu Pro Ala Leu Pro Val Asp Ala Thr Ser
                275             280             285
    Asp Glu Val Arg Lys Asn Leu Met Asp Met Phe Arg Asp Arg Gln Ala
                290             295             300
    Phe Ser Glu His Thr Trp Lys Met Leu Leu Ser Val Cys Arg Ser Trp
    305             310             315             320
    Ala Ala Trp Cys Lys Leu Asn Asn Arg Lys Trp Phe Pro Ala Glu Pro
                325             330             335
    Glu Asp Val Arg Asp Tyr Leu Leu Tyr Leu Gln Ala Arg Gly Leu Ala
                340             345             350
    Val Lys Thr Ile Gln Gln His Leu Gly Gln Leu Asn Met Leu His Arg
                355             360             365
    Arg Ser Gly Leu Pro Arg Pro Ser Asp Ser Asn Ala Val Ser Leu Val
                370             375             380
    Met Arg Arg Ile Arg Lys Glu Asn Val Asp Ala Gly Glu Arg Ala Lys
    385             390             395             400
    Gln Ala Leu Ala Phe Glu Arg Thr Asp Phe Asp Gln Val Arg Ser Leu
                405             410             415
    Met Glu Asn Ser Asp Arg Cys Gln Asp Ile Arg Asn Leu Ala Phe Leu
                420             425             430
    Gly Ile Ala Tyr Asn Thr Leu Leu Arg Ile Ala Glu Ile Ala Arg Ile
                435             440             445
    Arg Val Lys Asp Ile Ser Arg Thr Asp Gly Gly Arg Met Leu Ile His
                450             455             460
    Ile Gly Arg Thr Lys Thr Leu Val Ser Thr Ala Gly Val Glu Lys Ala
    465             470             475             480
    Leu Ser Leu Gly Val Thr Lys Leu Val Glu Arg Trp Ile Ser Val Ser
                485             490             495
    Gly Val Ala Asp Asp Pro Asn Asn Tyr Leu Phe Cys Arg Val Arg Lys
                500             505             510
    Asn Gly Val Ala Ala Pro Ser Ala Thr Ser Gln Leu Ser Thr Arg Ala
                515             520             525
```

```
Leu Glu Gly Ile Phe Glu Ala Thr His Arg Leu Ile Tyr Gly Ala Lys
        530                 535                 540

Asp Asp Ser Gly Gln Arg Tyr Leu Ala Trp Ser Gly His Ser Ala Arg
545                 550                 555                 560

Val Gly Ala Ala Arg Asp Met Ala Arg Ala Gly Val Ser Ile Pro Glu
                565                 570                 575

Ile Met Gln Ala Gly Gly Trp Thr Asn Val Asn Ile Val Met Asn Tyr
                580                 585                 590

Ile Arg Asn Leu Asp Ser Glu Thr Gly Ala Met Val Arg Leu Leu Glu
                595                 600                 605

Asp Gly Asp Gly Gly Ser His His His His His His
        610                 615                 620

<210> SEQ ID NO 5
<211> LENGTH: 353
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Ala Ser Asn Leu Leu Thr Val His Gln Asn Leu Pro Ala Leu Pro
1               5                   10                  15

Val Asp Ala Thr Ser Asp Glu Val Arg Lys Asn Leu Met Asp Met Phe
                20                  25                  30

Arg Asp Arg Gln Ala Phe Ser Glu His Thr Trp Lys Met Leu Leu Ser
            35                  40                  45

Val Cys Arg Ser Trp Ala Ala Trp Cys Lys Leu Asn Asn Arg Lys Trp
        50                  55                  60

Phe Pro Ala Glu Pro Glu Asp Val Arg Asp Tyr Leu Leu Tyr Leu Gln
65                  70                  75                  80

Ala Arg Gly Leu Ala Val Lys Thr Ile Gln Gln His Leu Gly Gln Leu
                85                  90                  95

Asn Met Leu His Arg Arg Ser Gly Leu Pro Arg Pro Ser Asp Ser Asn
            100                 105                 110

Ala Val Ser Leu Val Met Arg Arg Ile Arg Lys Glu Asn Val Asp Ala
        115                 120                 125

Gly Glu Arg Ala Lys Gln Ala Leu Ala Phe Glu Arg Thr Asp Phe Asp
130                 135                 140

Gln Val Arg Ser Leu Met Glu Asn Ser Asp Arg Cys Gln Asp Ile Arg
145                 150                 155                 160

Asn Leu Ala Phe Leu Gly Ile Ala Tyr Asn Thr Leu Leu Arg Ile Ala
                165                 170                 175

Glu Ile Ala Arg Ile Arg Val Lys Asp Ile Ser Arg Thr Asp Gly Gly
            180                 185                 190

Arg Met Leu Ile His Ile Gly Arg Thr Lys Thr Leu Val Ser Thr Ala
        195                 200                 205

Gly Val Glu Lys Ala Leu Ser Leu Gly Val Thr Lys Leu Val Glu Arg
210                 215                 220

Trp Ile Ser Val Ser Gly Val Ala Asp Asp Pro Asn Asn Tyr Leu Phe
225                 230                 235                 240

Cys Arg Val Arg Lys Asn Gly Val Ala Ala Pro Ser Ala Thr Ser Gln
                245                 250                 255

Leu Ser Thr Arg Ala Leu Glu Gly Ile Phe Glu Ala Thr His Arg Leu
```

|     |     |     |     |     | 260 |     |     |     | 265 |     |     |     |     | 270 |     |
| --- | --- | --- | --- | --- | --- | --- | --- | --- | --- | --- | --- | --- | --- | --- | --- |
| Ile | Tyr | Gly | Ala | Lys | Asp | Asp | Ser | Gly | Gln | Arg | Tyr | Leu | Ala | Trp | Ser |
|     |     |     | 275 |     |     |     |     | 280 |     |     |     |     | 285 |     |     |

Gly His Ser Ala Arg Val Gly Ala Ala Arg Asp Met Ala Arg Ala Gly
            290                 295                 300

Val Ser Ile Pro Glu Ile Met Gln Ala Gly Gly Trp Thr Asn Val Asn
305                 310                 315                 320

Ile Val Met Asn Tyr Ile Arg Asn Leu Asp Ser Glu Thr Gly Ala Met
                325                 330                 335

Val Arg Leu Leu Glu Asp Gly Asp Gly Gly Ser His His His His His
            340                 345                 350

His

<210> SEQ ID NO 6
<211> LENGTH: 1368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp

```
            260                 265                 270
Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
            290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
                370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
                450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
                530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
                610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685
```

-continued

Ala Asn Arg Asn Phe Met Gln Leu Ile His Asp Asp Ser Leu Thr Phe
690             695                 700

Lys Glu Asp Ile Gln Lys Ala Gln Val Ser Gly Gln Gly Asp Ser Leu
705             710              715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
                740              745                 750

Arg His Lys Pro Glu Asn Ile Val Ile Glu Met Ala Arg Glu Asn Gln
            755                 760              765

Thr Thr Gln Lys Gly Gln Lys Asn Ser Arg Glu Arg Met Lys Arg Ile
770             775                 780

Glu Glu Gly Ile Lys Glu Leu Gly Ser Gln Ile Leu Lys Glu His Pro
785             790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840              845

Asp Asp Ser Ile Asp Asn Lys Val Leu Thr Arg Ser Asp Lys Asn Arg
850             855                 860

Gly Lys Ser Asp Asn Val Pro Ser Glu Glu Val Val Lys Lys Met Lys
865             870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905              910

Lys Ala Gly Phe Ile Lys Arg Gln Leu Val Glu Thr Arg Gln Ile Thr
            915                 920              925

Lys His Val Ala Gln Ile Leu Asp Ser Arg Met Asn Thr Lys Tyr Asp
            930                 935              940

Glu Asn Asp Lys Leu Ile Arg Glu Val Lys Val Ile Thr Leu Lys Ser
945             950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
            1010                1015            1020

Lys Ser Glu Gln Glu Ile Gly Lys Ala Thr Ala Lys Tyr Phe Phe
            1025                1030            1035

Tyr Ser Asn Ile Met Asn Phe Phe Lys Thr Glu Ile Thr Leu Ala
            1040                1045            1050

Asn Gly Glu Ile Arg Lys Arg Pro Leu Ile Glu Thr Asn Gly Glu
            1055                1060            1065

Thr Gly Glu Ile Val Trp Asp Lys Gly Arg Asp Phe Ala Thr Val
            1070                1075            1080

Arg Lys Val Leu Ser Met Pro Gln Val Asn Ile Val Lys Lys Thr
            1085                1090            1095

```
Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 7
<211> LENGTH: 1374
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
                20                  25                  30

Lys Val Leu Gly Asn Thr Asp Arg His Ser Ile Lys Lys Asn Leu Ile
            35                  40                  45

Gly Ala Leu Leu Phe Asp Ser Gly Glu Thr Ala Glu Ala Thr Arg Leu
        50                  55                  60

Lys Arg Thr Ala Arg Arg Arg Tyr Thr Arg Arg Lys Asn Arg Ile Cys
65                  70                  75                  80
```

```
Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495
```

```
Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
```

-continued

```
            915                 920                 925
Lys His Val Ala Gln Ile Leu Asp Ser Arg Met Asn Thr Lys Tyr Asp
    930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
                995                 1000                1005
Val Tyr Gly Asp Tyr Lys Val Tyr Asp Val Arg Lys Met Ile Ala
    1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Asp Ser Pro Thr Val Ala Tyr Ser Val
    1130                1135                1140
Leu Val Val Ala Lys Val Glu Lys Gly Lys Ser Lys Lys Leu Lys
    1145                1150                1155
Ser Val Lys Glu Leu Leu Gly Ile Thr Ile Met Glu Arg Ser Ser
    1160                1165                1170
Phe Glu Lys Asn Pro Ile Asp Phe Leu Glu Ala Lys Gly Tyr Lys
    1175                1180                1185
Glu Val Lys Lys Asp Leu Ile Ile Lys Leu Pro Lys Tyr Ser Leu
    1190                1195                1200
Phe Glu Leu Glu Asn Gly Arg Lys Arg Met Leu Ala Ser Ala Gly
    1205                1210                1215
Glu Leu Gln Lys Gly Asn Glu Leu Ala Leu Pro Ser Lys Tyr Val
    1220                1225                1230
Asn Phe Leu Tyr Leu Ala Ser His Tyr Glu Lys Leu Lys Gly Ser
    1235                1240                1245
Pro Glu Asp Asn Glu Gln Lys Gln Leu Phe Val Glu Gln His Lys
    1250                1255                1260
His Tyr Leu Asp Glu Ile Ile Glu Gln Ile Ser Glu Phe Ser Lys
    1265                1270                1275
Arg Val Ile Leu Ala Asp Ala Asn Leu Asp Lys Val Leu Ser Ala
    1280                1285                1290
Tyr Asn Lys His Arg Asp Lys Pro Ile Arg Glu Gln Ala Glu Asn
    1295                1300                1305
Ile Ile His Leu Phe Thr Leu Thr Asn Leu Gly Ala Pro Ala Ala
    1310                1315                1320
```

```
Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

His His His His His His
    1370

<210> SEQ ID NO 8
<211> LENGTH: 1382
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Pro Lys Lys Lys Arg Lys Val Met Asp Lys Lys Tyr Ser Ile Gly
1               5                   10                  15

Leu Ala Ile Gly Thr Asn Ser Val Gly Trp Ala Val Ile Thr Asp Glu
            20                  25                  30

Tyr Lys Val Pro Ser Lys Lys Phe Lys Val Leu Gly Asn Thr Asp Arg
        35                  40                  45

His Ser Ile Lys Lys Asn Leu Ile Gly Ala Leu Leu Phe Asp Ser Gly
    50                  55                  60

Glu Thr Ala Glu Ala Thr Arg Leu Lys Arg Thr Ala Arg Arg Arg Tyr
65                  70                  75                  80

Thr Arg Arg Lys Asn Arg Ile Cys Tyr Leu Gln Glu Ile Phe Ser Asn
                85                  90                  95

Glu Met Ala Lys Val Asp Asp Ser Phe Phe His Arg Leu Glu Glu Ser
            100                 105                 110

Phe Leu Val Glu Glu Asp Lys Lys His Glu Arg His Pro Ile Phe Gly
        115                 120                 125

Asn Ile Val Asp Glu Val Ala Tyr His Glu Lys Tyr Pro Thr Ile Tyr
    130                 135                 140

His Leu Arg Lys Lys Leu Val Asp Ser Thr Asp Lys Ala Asp Leu Arg
145                 150                 155                 160

Leu Ile Tyr Leu Ala Leu Ala His Met Ile Lys Phe Arg Gly His Phe
                165                 170                 175

Leu Ile Glu Gly Asp Leu Asn Pro Asp Asn Ser Asp Val Asp Lys Leu
            180                 185                 190

Phe Ile Gln Leu Val Gln Thr Tyr Asn Gln Leu Phe Glu Glu Asn Pro
        195                 200                 205

Ile Asn Ala Ser Gly Val Asp Ala Lys Ala Ile Leu Ser Ala Arg Leu
    210                 215                 220

Ser Lys Ser Arg Arg Leu Glu Asn Leu Ile Ala Gln Leu Pro Gly Glu
225                 230                 235                 240

Lys Lys Asn Gly Leu Phe Gly Asn Leu Ile Ala Leu Ser Leu Gly Leu
                245                 250                 255

Thr Pro Asn Phe Lys Ser Asn Phe Asp Leu Ala Glu Asp Ala Lys Leu
            260                 265                 270

Gln Leu Ser Lys Asp Thr Tyr Asp Asp Asp Leu Asp Asn Leu Leu Ala
        275                 280                 285

Gln Ile Gly Asp Gln Tyr Ala Asp Leu Phe Leu Ala Ala Lys Asn Leu
```

-continued

```
                290                 295                 300
Ser Asp Ala Ile Leu Leu Ser Asp Ile Leu Arg Val Asn Thr Glu Ile
305                 310                 315                 320

Thr Lys Ala Pro Leu Ser Ala Ser Met Ile Lys Arg Tyr Asp Glu His
                325                 330                 335

His Gln Asp Leu Thr Leu Leu Lys Ala Leu Val Arg Gln Gln Leu Pro
                340                 345                 350

Glu Lys Tyr Lys Glu Ile Phe Phe Asp Gln Ser Lys Asn Gly Tyr Ala
                355                 360                 365

Gly Tyr Ile Asp Gly Gly Ala Ser Gln Glu Glu Phe Tyr Lys Phe Ile
                370                 375                 380

Lys Pro Ile Leu Glu Lys Met Asp Gly Thr Glu Glu Leu Leu Val Lys
385                 390                 395                 400

Leu Asn Arg Glu Asp Leu Leu Arg Lys Gln Arg Thr Phe Asp Asn Gly
                405                 410                 415

Ser Ile Pro His Gln Ile His Leu Gly Glu Leu His Ala Ile Leu Arg
                420                 425                 430

Arg Gln Glu Asp Phe Tyr Pro Phe Leu Lys Asp Asn Arg Glu Lys Ile
                435                 440                 445

Glu Lys Ile Leu Thr Phe Arg Ile Pro Tyr Tyr Val Gly Pro Leu Ala
                450                 455                 460

Arg Gly Asn Ser Arg Phe Ala Trp Met Thr Arg Lys Ser Glu Glu Thr
465                 470                 475                 480

Ile Thr Pro Trp Asn Phe Glu Glu Val Val Asp Lys Gly Ala Ser Ala
                485                 490                 495

Gln Ser Phe Ile Glu Arg Met Thr Asn Phe Asp Lys Asn Leu Pro Asn
                500                 505                 510

Glu Lys Val Leu Pro Lys His Ser Leu Leu Tyr Glu Tyr Phe Thr Val
                515                 520                 525

Tyr Asn Glu Leu Thr Lys Val Lys Tyr Val Thr Glu Gly Met Arg Lys
                530                 535                 540

Pro Ala Phe Leu Ser Gly Glu Gln Lys Lys Ala Ile Val Asp Leu Leu
545                 550                 555                 560

Phe Lys Thr Asn Arg Lys Val Thr Val Lys Gln Leu Lys Glu Asp Tyr
                565                 570                 575

Phe Lys Lys Ile Glu Cys Phe Asp Ser Val Glu Ile Ser Gly Val Glu
                580                 585                 590

Asp Arg Phe Asn Ala Ser Leu Gly Thr Tyr His Asp Leu Leu Lys Ile
                595                 600                 605

Ile Lys Asp Lys Asp Phe Leu Asp Asn Glu Glu Asn Glu Asp Ile Leu
610                 615                 620

Glu Asp Ile Val Leu Thr Leu Thr Leu Phe Glu Asp Arg Glu Met Ile
625                 630                 635                 640

Glu Glu Arg Leu Lys Thr Tyr Ala His Leu Phe Asp Asp Lys Val Met
                645                 650                 655

Lys Gln Leu Lys Arg Arg Arg Tyr Thr Gly Trp Gly Arg Leu Ser Arg
                660                 665                 670

Lys Leu Ile Asn Gly Ile Arg Asp Lys Gln Ser Gly Lys Thr Ile Leu
                675                 680                 685

Asp Phe Leu Lys Ser Asp Gly Phe Ala Asn Arg Asn Phe Met Gln Leu
                690                 695                 700

Ile His Asp Asp Ser Leu Thr Phe Lys Glu Asp Ile Gln Lys Ala Gln
705                 710                 715                 720
```

-continued

```
Val Ser Gly Gln Gly Asp Ser Leu His Glu His Ile Ala Asn Leu Ala
            725                 730                 735

Gly Ser Pro Ala Ile Lys Lys Gly Ile Leu Gln Thr Val Lys Val Val
            740                 745                 750

Asp Glu Leu Val Lys Val Met Gly Arg His Lys Pro Glu Asn Ile Val
            755                 760                 765

Ile Glu Met Ala Arg Glu Asn Gln Thr Thr Gln Lys Gly Gln Lys Asn
770                 775                 780

Ser Arg Glu Arg Met Lys Arg Ile Glu Glu Gly Ile Lys Glu Leu Gly
785                 790                 795                 800

Ser Gln Ile Leu Lys Glu His Pro Val Glu Asn Thr Gln Leu Gln Asn
            805                 810                 815

Glu Lys Leu Tyr Leu Tyr Tyr Leu Gln Asn Gly Arg Asp Met Tyr Val
            820                 825                 830

Asp Gln Glu Leu Asp Ile Asn Arg Leu Ser Asp Tyr Asp Val Asp His
            835                 840                 845

Ile Val Pro Gln Ser Phe Leu Lys Asp Asp Ser Ile Asp Asn Lys Val
            850                 855                 860

Leu Thr Arg Ser Asp Lys Asn Arg Gly Lys Ser Asp Asn Val Pro Ser
865                 870                 875                 880

Glu Glu Val Val Lys Lys Met Lys Asn Tyr Trp Arg Gln Leu Leu Asn
            885                 890                 895

Ala Lys Leu Ile Thr Gln Arg Lys Phe Asp Asn Leu Thr Lys Ala Glu
            900                 905                 910

Arg Gly Gly Leu Ser Glu Leu Asp Lys Ala Gly Phe Ile Lys Arg Gln
            915                 920                 925

Leu Val Glu Thr Arg Gln Ile Thr Lys His Val Ala Gln Ile Leu Asp
            930                 935                 940

Ser Arg Met Asn Thr Lys Tyr Asp Glu Asn Asp Lys Leu Ile Arg Glu
945                 950                 955                 960

Val Lys Val Ile Thr Leu Lys Ser Lys Leu Val Ser Asp Phe Arg Lys
            965                 970                 975

Asp Phe Gln Phe Tyr Lys Val Arg Glu Ile Asn Asn Tyr His His Ala
            980                 985                 990

His Asp Ala Tyr Leu Asn Ala Val Val Gly Thr Ala Leu Ile Lys Lys
            995                 1000                1005

Tyr Pro Lys Leu Glu Ser Glu Phe Val Tyr Gly Asp Tyr Lys Val
        1010                1015                1020

Tyr Asp Val Arg Lys Met Ile Ala Lys Ser Glu Gln Glu Ile Gly
        1025                1030                1035

Lys Ala Thr Ala Lys Tyr Phe Phe Tyr Ser Asn Ile Met Asn Phe
        1040                1045                1050

Phe Lys Thr Glu Ile Thr Leu Ala Asn Gly Glu Ile Arg Lys Arg
        1055                1060                1065

Pro Leu Ile Glu Thr Asn Gly Glu Thr Gly Glu Ile Val Trp Asp
        1070                1075                1080

Lys Gly Arg Asp Phe Ala Thr Val Arg Lys Val Leu Ser Met Pro
        1085                1090                1095

Gln Val Asn Ile Val Lys Lys Thr Glu Val Gln Thr Gly Gly Phe
        1100                1105                1110

Ser Lys Glu Ser Ile Leu Pro Lys Arg Asn Ser Asp Lys Leu Ile
        1115                1120                1125
```

-continued

```
Ala Arg Lys Lys Asp Trp Asp Pro Lys Lys Tyr Gly Gly Phe Asp
1130                1135                1140

Ser Pro Thr Val Ala Tyr Ser Val Leu Val Val Ala Lys Val Glu
    1145                1150                1155

Lys Gly Lys Ser Lys Lys Leu Lys Ser Val Lys Glu Leu Leu Gly
    1160                1165                1170

Ile Thr Ile Met Glu Arg Ser Ser Phe Glu Lys Asn Pro Ile Asp
    1175                1180                1185

Phe Leu Glu Ala Lys Gly Tyr Lys Glu Val Lys Lys Asp Leu Ile
    1190                1195                1200

Ile Lys Leu Pro Lys Tyr Ser Leu Phe Glu Leu Glu Asn Gly Arg
    1205                1210                1215

Lys Arg Met Leu Ala Ser Ala Gly Glu Leu Gln Lys Gly Asn Glu
    1220                1225                1230

Leu Ala Leu Pro Ser Lys Tyr Val Asn Phe Leu Tyr Leu Ala Ser
    1235                1240                1245

His Tyr Glu Lys Leu Lys Gly Ser Pro Glu Asp Asn Glu Gln Lys
    1250                1255                1260

Gln Leu Phe Val Glu Gln His Lys His Tyr Leu Asp Glu Ile Ile
    1265                1270                1275

Glu Gln Ile Ser Glu Phe Ser Lys Arg Val Ile Leu Ala Asp Ala
    1280                1285                1290

Asn Leu Asp Lys Val Leu Ser Ala Tyr Asn Lys His Arg Asp Lys
    1295                1300                1305

Pro Ile Arg Glu Gln Ala Glu Asn Ile Ile His Leu Phe Thr Leu
    1310                1315                1320

Thr Asn Leu Gly Ala Pro Ala Ala Phe Lys Tyr Phe Asp Thr Thr
    1325                1330                1335

Ile Asp Arg Lys Arg Tyr Thr Ser Thr Lys Glu Val Leu Asp Ala
    1340                1345                1350

Thr Leu Ile His Gln Ser Ile Thr Gly Leu Tyr Glu Thr Arg Ile
    1355                1360                1365

Asp Leu Ser Gln Leu Gly Gly Asp His His His His His His
    1370                1375                1380
```

<210> SEQ ID NO 9
<211> LENGTH: 1384
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95
```

```
Phe Phe His Arg Leu Glu Glu Ser Phe Leu Val Glu Asp Lys Lys
                100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510
```

```
Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
```

-continued

```
            930             935             940
Glu Asn Asp Lys Leu Ile Arg Glu Val Lys Val Ile Thr Leu Lys Ser
945             950             955             960

Lys Leu Val Ser Asp Phe Arg Lys Asp Phe Gln Phe Tyr Lys Val Arg
            965             970             975

Glu Ile Asn Asn Tyr His His Ala His Asp Ala Tyr Leu Asn Ala Val
            980             985             990

Val Gly Thr Ala Leu Ile Lys Lys Tyr Pro Lys Leu Glu Ser Glu Phe
            995             1000            1005

Val Tyr Gly Asp Tyr Lys Val Tyr Asp Val Arg Lys Met Ile Ala
    1010            1015            1020

Lys Ser Glu Gln Glu Ile Gly Lys Ala Thr Ala Lys Tyr Phe Phe
    1025            1030            1035

Tyr Ser Asn Ile Met Asn Phe Phe Lys Thr Glu Ile Thr Leu Ala
    1040            1045            1050

Asn Gly Glu Ile Arg Lys Arg Pro Leu Ile Glu Thr Asn Gly Glu
    1055            1060            1065

Thr Gly Glu Ile Val Trp Asp Lys Gly Arg Asp Phe Ala Thr Val
    1070            1075            1080

Arg Lys Val Leu Ser Met Pro Gln Val Asn Ile Val Lys Lys Thr
    1085            1090            1095

Glu Val Gln Thr Gly Gly Phe Ser Lys Glu Ser Ile Leu Pro Lys
    1100            1105            1110

Arg Asn Ser Asp Lys Leu Ile Ala Arg Lys Lys Asp Trp Asp Pro
    1115            1120            1125

Lys Lys Tyr Gly Gly Phe Asp Ser Pro Thr Val Ala Tyr Ser Val
    1130            1135            1140

Leu Val Val Ala Lys Val Glu Lys Gly Lys Ser Lys Lys Leu Lys
    1145            1150            1155

Ser Val Lys Glu Leu Leu Gly Ile Thr Ile Met Glu Arg Ser Ser
    1160            1165            1170

Phe Glu Lys Asn Pro Ile Asp Phe Leu Glu Ala Lys Gly Tyr Lys
    1175            1180            1185

Glu Val Lys Lys Asp Leu Ile Ile Lys Leu Pro Lys Tyr Ser Leu
    1190            1195            1200

Phe Glu Leu Glu Asn Gly Arg Lys Arg Met Leu Ala Ser Ala Gly
    1205            1210            1215

Glu Leu Gln Lys Gly Asn Glu Leu Ala Leu Pro Ser Lys Tyr Val
    1220            1225            1230

Asn Phe Leu Tyr Leu Ala Ser His Tyr Glu Lys Leu Lys Gly Ser
    1235            1240            1245

Pro Glu Asp Asn Glu Gln Lys Gln Leu Phe Val Glu Gln His Lys
    1250            1255            1260

His Tyr Leu Asp Glu Ile Ile Glu Gln Ile Ser Glu Phe Ser Lys
    1265            1270            1275

Arg Val Ile Leu Ala Asp Ala Asn Leu Asp Lys Val Leu Ser Ala
    1280            1285            1290

Tyr Asn Lys His Arg Asp Lys Pro Ile Arg Glu Gln Ala Glu Asn
    1295            1300            1305

Ile Ile His Leu Phe Thr Leu Thr Asn Leu Gly Ala Pro Ala Ala
    1310            1315            1320

Phe Lys Tyr Phe Asp Thr Thr Ile Asp Arg Lys Arg Tyr Thr Ser
    1325            1330            1335
```

```
Thr Lys Glu Val Leu Asp Ala Thr Leu Ile His Gln Ser Ile Thr
    1340            1345                1350
Gly Leu Tyr Glu Thr Arg Ile Asp Leu Ser Gln Leu Gly Gly Asp
    1355            1360                1365
Pro Lys Lys Lys Arg Lys Val Met Asp Lys His His His His His
    1370            1375                1380
His
```

```
<210> SEQ ID NO 10
<211> LENGTH: 1653
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Gly Ala Ser Lys Gly Glu Arg Leu Phe Arg Gly Lys Val Pro Ile
1               5                   10                  15
Leu Val Glu Leu Lys Gly Asp Val Asn Gly His Lys Phe Ser Val Arg
                20                  25                  30
Gly Lys Gly Lys Gly Asp Ala Thr Arg Gly Lys Leu Thr Leu Lys Phe
            35                  40                  45
Ile Cys Thr Thr Gly Lys Leu Pro Val Pro Trp Pro Thr Leu Val Thr
50                  55                  60
Thr Leu Thr Ser Gly Val Gln Cys Phe Ser Arg Tyr Pro Lys His Met
65                  70                  75                  80
Lys Arg His Asp Phe Phe Lys Ser Ala Met Pro Lys Gly Tyr Val Gln
                85                  90                  95
Glu Arg Thr Ile Ser Phe Lys Lys Asp Gly Lys Tyr Lys Thr Arg Ala
            100                 105                 110
Glu Val Lys Phe Glu Gly Arg Thr Leu Val Asn Arg Ile Lys Leu Lys
        115                 120                 125
Gly Arg Asp Phe Lys Glu Lys Gly Asn Ile Leu Gly His Lys Leu Arg
130                 135                 140
Tyr Asn Phe Asn Ser His Lys Val Tyr Ile Thr Ala Asp Lys Arg Lys
145                 150                 155                 160
Asn Gly Ile Lys Ala Lys Phe Lys Ile Arg His Asn Val Lys Asp Gly
                165                 170                 175
Ser Val Gln Leu Ala Asp His Tyr Gln Gln Asn Thr Pro Ile Gly Arg
            180                 185                 190
Gly Pro Val Leu Leu Pro Arg Asn His Tyr Leu Ser Thr Arg Ser Lys
        195                 200                 205
Leu Ser Lys Asp Pro Lys Glu Lys Arg Asp His Met Val Leu Leu Glu
    210                 215                 220
Phe Val Thr Ala Ala Gly Ile Lys His Gly Arg Asp Glu Arg Tyr Lys
225                 230                 235                 240
Thr Gly Gly Ser Gly Gly Ser Gly Gly Ser Gly Gly Ser Gly Gly Ser
                245                 250                 255
Gly Gly Ser Gly Gly Ser Gly Gly Thr Ala Leu Ala Leu
            260                 265                 270
Pro Lys Lys Lys Arg Lys Val Met Asp Lys Lys Tyr Ser Ile Gly Leu
        275                 280                 285
Asp Ile Gly Thr Asn Ser Val Gly Trp Ala Val Ile Thr Asp Glu Tyr
    290                 295                 300
```

```
Lys Val Pro Ser Lys Lys Phe Lys Val Leu Gly Asn Thr Asp Arg His
305                 310                 315                 320

Ser Ile Lys Lys Asn Leu Ile Gly Ala Leu Leu Phe Asp Ser Gly Glu
                325                 330                 335

Thr Ala Glu Ala Thr Arg Leu Lys Arg Thr Ala Arg Arg Arg Tyr Thr
            340                 345                 350

Arg Arg Lys Asn Arg Ile Cys Tyr Leu Gln Glu Ile Phe Ser Asn Glu
        355                 360                 365

Met Ala Lys Val Asp Asp Ser Phe Phe His Arg Leu Glu Glu Ser Phe
370                 375                 380

Leu Val Glu Glu Asp Lys Lys His Glu Arg His Pro Ile Phe Gly Asn
385                 390                 395                 400

Ile Val Asp Glu Val Ala Tyr His Glu Lys Tyr Pro Thr Ile Tyr His
                405                 410                 415

Leu Arg Lys Lys Leu Val Asp Ser Thr Asp Lys Ala Asp Leu Arg Leu
            420                 425                 430

Ile Tyr Leu Ala Leu Ala His Met Ile Lys Phe Arg Gly His Phe Leu
        435                 440                 445

Ile Glu Gly Asp Leu Asn Pro Asp Asn Ser Asp Val Asp Lys Leu Phe
450                 455                 460

Ile Gln Leu Val Gln Thr Tyr Asn Gln Leu Phe Glu Glu Asn Pro Ile
465                 470                 475                 480

Asn Ala Ser Gly Val Asp Ala Lys Ala Ile Leu Ser Ala Arg Leu Ser
                485                 490                 495

Lys Ser Arg Arg Leu Glu Asn Leu Ile Ala Gln Leu Pro Gly Glu Lys
            500                 505                 510

Lys Asn Gly Leu Phe Gly Asn Leu Ile Ala Leu Ser Leu Gly Leu Thr
        515                 520                 525

Pro Asn Phe Lys Ser Asn Phe Asp Leu Ala Glu Asp Ala Lys Leu Gln
530                 535                 540

Leu Ser Lys Asp Thr Tyr Asp Asp Asp Leu Asp Asn Leu Leu Ala Gln
545                 550                 555                 560

Ile Gly Asp Gln Tyr Ala Asp Leu Phe Leu Ala Ala Lys Asn Leu Ser
                565                 570                 575

Asp Ala Ile Leu Leu Ser Asp Ile Leu Arg Val Asn Thr Glu Ile Thr
            580                 585                 590

Lys Ala Pro Leu Ser Ala Ser Met Ile Lys Arg Tyr Asp Glu His His
        595                 600                 605

Gln Asp Leu Thr Leu Leu Lys Ala Leu Val Arg Gln Gln Leu Pro Glu
610                 615                 620

Lys Tyr Lys Glu Ile Phe Phe Asp Gln Ser Lys Asn Gly Tyr Ala Gly
625                 630                 635                 640

Tyr Ile Asp Gly Gly Ala Ser Gln Glu Glu Phe Tyr Lys Phe Ile Lys
                645                 650                 655

Pro Ile Leu Glu Lys Met Asp Gly Thr Glu Glu Leu Leu Val Lys Leu
            660                 665                 670

Asn Arg Glu Asp Leu Leu Arg Lys Gln Arg Thr Phe Asp Asn Gly Ser
        675                 680                 685

Ile Pro His Gln Ile His Leu Gly Glu Leu His Ala Ile Leu Arg Arg
690                 695                 700

Gln Glu Asp Phe Tyr Pro Phe Leu Lys Asp Asn Arg Glu Lys Ile Glu
705                 710                 715                 720
```

```
Lys Ile Leu Thr Phe Arg Ile Pro Tyr Tyr Val Gly Pro Leu Ala Arg
            725                 730                 735

Gly Asn Ser Arg Phe Ala Trp Met Thr Arg Lys Ser Glu Glu Thr Ile
        740                 745                 750

Thr Pro Trp Asn Phe Glu Glu Val Val Asp Lys Gly Ala Ser Ala Gln
    755                 760                 765

Ser Phe Ile Glu Arg Met Thr Asn Phe Asp Lys Asn Leu Pro Asn Glu
770                 775                 780

Lys Val Leu Pro Lys His Ser Leu Leu Tyr Glu Tyr Phe Thr Val Tyr
785                 790                 795                 800

Asn Glu Leu Thr Lys Val Lys Tyr Val Thr Glu Gly Met Arg Lys Pro
                805                 810                 815

Ala Phe Leu Ser Gly Glu Gln Lys Lys Ala Ile Val Asp Leu Leu Phe
            820                 825                 830

Lys Thr Asn Arg Lys Val Thr Val Lys Gln Leu Lys Glu Asp Tyr Phe
        835                 840                 845

Lys Lys Ile Glu Cys Phe Asp Ser Val Glu Ile Ser Gly Val Glu Asp
    850                 855                 860

Arg Phe Asn Ala Ser Leu Gly Thr Tyr His Asp Leu Leu Lys Ile Ile
865                 870                 875                 880

Lys Asp Lys Asp Phe Leu Asp Asn Glu Glu Asn Glu Asp Ile Leu Glu
                885                 890                 895

Asp Ile Val Leu Thr Leu Thr Leu Phe Glu Asp Arg Glu Met Ile Glu
            900                 905                 910

Glu Arg Leu Lys Thr Tyr Ala His Leu Phe Asp Asp Lys Val Met Lys
        915                 920                 925

Gln Leu Lys Arg Arg Arg Tyr Thr Gly Trp Gly Arg Leu Ser Arg Lys
    930                 935                 940

Leu Ile Asn Gly Ile Arg Asp Lys Gln Ser Gly Lys Thr Ile Leu Asp
945                 950                 955                 960

Phe Leu Lys Ser Asp Gly Phe Ala Asn Arg Asn Phe Met Gln Leu Ile
                965                 970                 975

His Asp Asp Ser Leu Thr Phe Lys Glu Asp Ile Gln Lys Ala Gln Val
            980                 985                 990

Ser Gly Gln Gly Asp Ser Leu His Glu His Ile Ala Asn Leu Ala Gly
        995                 1000                1005

Ser Pro Ala Ile Lys Lys Gly Ile Leu Gln Thr Val Lys Val Val
    1010                1015                1020

Asp Glu Leu Val Lys Val Met Gly Arg His Lys Pro Glu Asn Ile
    1025                1030                1035

Val Ile Glu Met Ala Arg Glu Asn Gln Thr Thr Gln Lys Gly Gln
    1040                1045                1050

Lys Asn Ser Arg Glu Arg Met Lys Arg Ile Glu Glu Gly Ile Lys
    1055                1060                1065

Glu Leu Gly Ser Gln Ile Leu Lys Glu His Pro Val Glu Asn Thr
    1070                1075                1080

Gln Leu Gln Asn Glu Lys Leu Tyr Leu Tyr Tyr Leu Gln Asn Gly
    1085                1090                1095

Arg Asp Met Tyr Val Asp Gln Glu Leu Asp Ile Asn Arg Leu Ser
    1100                1105                1110

Asp Tyr Asp Val Asp His Ile Val Pro Gln Ser Phe Leu Lys Asp
    1115                1120                1125

Asp Ser Ile Asp Asn Lys Val Leu Thr Arg Ser Asp Lys Asn Arg
```

-continued

```
            1130                1135                1140

Gly Lys Ser Asp Asn Val Pro Ser Glu Val Val Lys Lys Met
        1145                1150                1155

Lys Asn Tyr Trp Arg Gln Leu Leu Asn Ala Lys Leu Ile Thr Gln
        1160                1165                1170

Arg Lys Phe Asp Asn Leu Thr Lys Ala Glu Arg Gly Gly Leu Ser
        1175                1180                1185

Glu Leu Asp Lys Ala Gly Phe Ile Lys Arg Gln Leu Val Glu Thr
        1190                1195                1200

Arg Gln Ile Thr Lys His Val Ala Gln Ile Leu Asp Ser Arg Met
        1205                1210                1215

Asn Thr Lys Tyr Asp Glu Asn Asp Lys Leu Ile Arg Glu Val Lys
        1220                1225                1230

Val Ile Thr Leu Lys Ser Lys Leu Val Ser Asp Phe Arg Lys Asp
        1235                1240                1245

Phe Gln Phe Tyr Lys Val Arg Glu Ile Asn Asn Tyr His His Ala
        1250                1255                1260

His Asp Ala Tyr Leu Asn Ala Val Val Gly Thr Ala Leu Ile Lys
        1265                1270                1275

Lys Tyr Pro Lys Leu Glu Ser Glu Phe Val Tyr Gly Asp Tyr Lys
        1280                1285                1290

Val Tyr Asp Val Arg Lys Met Ile Ala Lys Ser Glu Gln Glu Ile
        1295                1300                1305

Gly Lys Ala Thr Ala Lys Tyr Phe Phe Tyr Ser Asn Ile Met Asn
        1310                1315                1320

Phe Phe Lys Thr Glu Ile Thr Leu Ala Asn Gly Glu Ile Arg Lys
        1325                1330                1335

Arg Pro Leu Ile Glu Thr Asn Gly Glu Thr Gly Glu Ile Val Trp
        1340                1345                1350

Asp Lys Gly Arg Asp Phe Ala Thr Val Arg Lys Val Leu Ser Met
        1355                1360                1365

Pro Gln Val Asn Ile Val Lys Lys Thr Glu Val Gln Thr Gly Gly
        1370                1375                1380

Phe Ser Lys Glu Ser Ile Leu Pro Lys Arg Asn Ser Asp Lys Leu
        1385                1390                1395

Ile Ala Arg Lys Lys Asp Trp Asp Pro Lys Lys Tyr Gly Gly Phe
        1400                1405                1410

Asp Ser Pro Thr Val Ala Tyr Ser Val Leu Val Val Ala Lys Val
        1415                1420                1425

Glu Lys Gly Lys Ser Lys Lys Leu Lys Ser Val Lys Glu Leu Leu
        1430                1435                1440

Gly Ile Thr Ile Met Glu Arg Ser Ser Phe Glu Lys Asn Pro Ile
        1445                1450                1455

Asp Phe Leu Glu Ala Lys Gly Tyr Lys Glu Val Lys Lys Asp Leu
        1460                1465                1470

Ile Ile Lys Leu Pro Lys Tyr Ser Leu Phe Glu Leu Glu Asn Gly
        1475                1480                1485

Arg Lys Arg Met Leu Ala Ser Ala Gly Glu Leu Gln Lys Gly Asn
        1490                1495                1500

Glu Leu Ala Leu Pro Ser Lys Tyr Val Asn Phe Leu Tyr Leu Ala
        1505                1510                1515

Ser His Tyr Glu Lys Leu Lys Gly Ser Pro Glu Asp Asn Glu Gln
        1520                1525                1530
```

```
Lys Gln Leu Phe Val Glu Gln His Lys His Tyr Leu Asp Glu Ile
        1535                1540                1545

Ile Glu Gln Ile Ser Glu Phe Ser Lys Arg Val Ile Leu Ala Asp
    1550                1555                1560

Ala Asn Leu Asp Lys Val Leu Ser Ala Tyr Asn Lys His Arg Asp
    1565                1570                1575

Lys Pro Ile Arg Glu Gln Ala Glu Asn Ile Ile His Leu Phe Thr
    1580                1585                1590

Leu Thr Asn Leu Gly Ala Pro Ala Ala Phe Lys Tyr Phe Asp Thr
    1595                1600                1605

Thr Ile Asp Arg Lys Arg Tyr Thr Ser Thr Lys Glu Val Leu Asp
    1610                1615                1620

Ala Thr Leu Ile His Gln Ser Ile Thr Gly Leu Tyr Glu Thr Arg
    1625                1630                1635

Ile Asp Leu Ser Gln Leu Gly Gly Asp His His His His His His
    1640                1645                1650

<210> SEQ ID NO 11
<211> LENGTH: 1653
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Gly Ala Ser Lys Gly Glu Glu Leu Phe Asp Gly Val Val Pro Ile
1               5                   10                  15

Leu Val Glu Leu Asp Gly Asp Val Asn Gly His Glu Phe Ser Val Arg
                20                  25                  30

Gly Glu Gly Glu Gly Asp Ala Thr Glu Gly Glu Leu Thr Leu Lys Phe
            35                  40                  45

Ile Cys Thr Thr Gly Glu Leu Pro Val Pro Trp Pro Thr Leu Val Thr
    50                  55                  60

Thr Leu Thr Ser Gly Val Gln Cys Phe Ser Asp Tyr Pro Asp His Met
65              70                  75                  80

Asp Gln His Asp Phe Phe Lys Ser Ala Met Pro Glu Gly Tyr Val Gln
                85                  90                  95

Glu Arg Thr Ile Ser Phe Lys Asp Asp Gly Thr Tyr Lys Thr Arg Ala
            100                 105                 110

Glu Val Lys Phe Glu Gly Asp Thr Leu Val Asn Arg Ile Glu Leu Lys
        115                 120                 125

Gly Ile Asp Phe Lys Glu Asp Gly Asn Ile Leu Gly His Lys Leu Glu
    130                 135                 140

Tyr Asn Phe Asn Ser His Asp Val Tyr Ile Thr Ala Asp Lys Gln Glu
145                 150                 155                 160

Asn Gly Ile Lys Ala Glu Phe Glu Ile Arg His Asn Val Glu Asp Gly
                165                 170                 175

Ser Val Gln Leu Ala Asp His Tyr Gln Gln Asn Thr Pro Ile Gly Asp
            180                 185                 190

Gly Pro Val Leu Leu Pro Asp Asp His Tyr Leu Ser Thr Glu Ser Ala
        195                 200                 205

Leu Ser Lys Asp Pro Asn Glu Asp Arg Asp His Met Val Leu Leu Glu
    210                 215                 220

Phe Val Thr Ala Ala Gly Ile Asp His Gly Met Asp Glu Leu Tyr Lys
```

-continued

```
            225                 230                 235                 240
        Thr Gly Gly Ser Gly Gly Ser Gly Gly Ser Gly Gly Ser
                        245                 250                 255
        Gly Gly Ser Gly Gly Ser Gly Gly Thr Ala Leu Ala Leu
                    260                 265                 270
        Pro Lys Lys Arg Lys Val Met Asp Lys Lys Tyr Ser Ile Gly Leu
                275                 280                 285
        Asp Ile Gly Thr Asn Ser Val Gly Trp Ala Val Ile Thr Asp Glu Tyr
        290                 295                 300
        Lys Val Pro Ser Lys Lys Phe Lys Val Leu Gly Asn Thr Asp Arg His
        305                 310                 315                 320
        Ser Ile Lys Lys Asn Leu Ile Gly Ala Leu Leu Phe Asp Ser Gly Glu
                        325                 330                 335
        Thr Ala Glu Ala Thr Arg Leu Lys Arg Thr Ala Arg Arg Arg Tyr Thr
                        340                 345                 350
        Arg Arg Lys Asn Arg Ile Cys Tyr Leu Gln Glu Ile Phe Ser Asn Glu
                        355                 360                 365
        Met Ala Lys Val Asp Asp Ser Phe Phe His Arg Leu Glu Glu Ser Phe
                370                 375                 380
        Leu Val Glu Glu Asp Lys Lys His Glu Arg His Pro Ile Phe Gly Asn
        385                 390                 395                 400
        Ile Val Asp Glu Val Ala Tyr His Glu Lys Tyr Pro Thr Ile Tyr His
                        405                 410                 415
        Leu Arg Lys Lys Leu Val Asp Ser Thr Asp Lys Ala Asp Leu Arg Leu
                        420                 425                 430
        Ile Tyr Leu Ala Leu Ala His Met Ile Lys Phe Arg Gly His Phe Leu
                        435                 440                 445
        Ile Glu Gly Asp Leu Asn Pro Asp Asn Ser Asp Val Asp Lys Leu Phe
                450                 455                 460
        Ile Gln Leu Val Gln Thr Tyr Asn Gln Leu Phe Glu Glu Asn Pro Ile
        465                 470                 475                 480
        Asn Ala Ser Gly Val Asp Ala Lys Ala Ile Leu Ser Ala Arg Leu Ser
                        485                 490                 495
        Lys Ser Arg Arg Leu Glu Asn Leu Ile Ala Gln Leu Pro Gly Glu Lys
                        500                 505                 510
        Lys Asn Gly Leu Phe Gly Asn Leu Ile Ala Leu Ser Leu Gly Leu Thr
                        515                 520                 525
        Pro Asn Phe Lys Ser Asn Phe Asp Leu Ala Glu Asp Ala Lys Leu Gln
                530                 535                 540
        Leu Ser Lys Asp Thr Tyr Asp Asp Asp Leu Asp Asn Leu Leu Ala Gln
        545                 550                 555                 560
        Ile Gly Asp Gln Tyr Ala Asp Leu Phe Leu Ala Ala Lys Asn Leu Ser
                        565                 570                 575
        Asp Ala Ile Leu Leu Ser Asp Ile Leu Arg Val Asn Thr Glu Ile Thr
                        580                 585                 590
        Lys Ala Pro Leu Ser Ala Ser Met Ile Lys Arg Tyr Asp Glu His His
                        595                 600                 605
        Gln Asp Leu Thr Leu Leu Lys Ala Leu Val Arg Gln Gln Leu Pro Glu
                        610                 615                 620
        Lys Tyr Lys Glu Ile Phe Phe Asp Gln Ser Lys Asn Gly Tyr Ala Gly
        625                 630                 635                 640
        Tyr Ile Asp Gly Gly Ala Ser Gln Glu Glu Phe Tyr Lys Phe Ile Lys
                        645                 650                 655
```

Pro Ile Leu Glu Lys Met Asp Gly Thr Glu Leu Leu Val Lys Leu
      660                 665                 670

Asn Arg Glu Asp Leu Leu Arg Lys Gln Arg Thr Phe Asp Asn Gly Ser
        675                 680                 685

Ile Pro His Gln Ile His Leu Gly Glu Leu His Ala Ile Leu Arg Arg
    690                 695                 700

Gln Glu Asp Phe Tyr Pro Phe Leu Lys Asp Asn Arg Glu Lys Ile Glu
705                 710                 715                 720

Lys Ile Leu Thr Phe Arg Ile Pro Tyr Tyr Val Gly Pro Leu Ala Arg
                725                 730                 735

Gly Asn Ser Arg Phe Ala Trp Met Thr Arg Lys Ser Glu Glu Thr Ile
        740                 745                 750

Thr Pro Trp Asn Phe Glu Glu Val Val Asp Lys Gly Ala Ser Ala Gln
        755                 760                 765

Ser Phe Ile Glu Arg Met Thr Asn Phe Asp Lys Asn Leu Pro Asn Glu
    770                 775                 780

Lys Val Leu Pro Lys His Ser Leu Leu Tyr Glu Tyr Phe Thr Val Tyr
785                 790                 795                 800

Asn Glu Leu Thr Lys Val Lys Tyr Val Thr Glu Gly Met Arg Lys Pro
                805                 810                 815

Ala Phe Leu Ser Gly Glu Gln Lys Lys Ala Ile Val Asp Leu Leu Phe
        820                 825                 830

Lys Thr Asn Arg Lys Val Thr Val Lys Gln Leu Lys Glu Asp Tyr Phe
        835                 840                 845

Lys Lys Ile Glu Cys Phe Asp Ser Val Glu Ile Ser Gly Val Glu Asp
    850                 855                 860

Arg Phe Asn Ala Ser Leu Gly Thr Tyr His Asp Leu Leu Lys Ile Ile
865                 870                 875                 880

Lys Asp Lys Asp Phe Leu Asp Asn Glu Glu Asn Glu Asp Ile Leu Glu
                885                 890                 895

Asp Ile Val Leu Thr Leu Thr Leu Phe Glu Asp Arg Glu Met Ile Glu
        900                 905                 910

Glu Arg Leu Lys Thr Tyr Ala His Leu Phe Asp Asp Lys Val Met Lys
        915                 920                 925

Gln Leu Lys Arg Arg Arg Tyr Thr Gly Trp Gly Arg Leu Ser Arg Lys
    930                 935                 940

Leu Ile Asn Gly Ile Arg Asp Lys Gln Ser Gly Lys Thr Ile Leu Asp
945                 950                 955                 960

Phe Leu Lys Ser Asp Gly Phe Ala Asn Arg Asn Phe Met Gln Leu Ile
                965                 970                 975

His Asp Asp Ser Leu Thr Phe Lys Glu Asp Ile Gln Lys Ala Gln Val
        980                 985                 990

Ser Gly Gln Gly Asp Ser Leu His Glu His Ile Ala Asn Leu Ala Gly
    995                 1000                1005

Ser Pro Ala Ile Lys Lys Gly Ile Leu Gln Thr Val Lys Val Val
    1010                1015                1020

Asp Glu Leu Val Lys Val Met Gly Arg His Lys Pro Glu Asn Ile
    1025                1030                1035

Val Ile Glu Met Ala Arg Glu Asn Gln Thr Thr Gln Lys Gly Gln
    1040                1045                1050

Lys Asn Ser Arg Glu Arg Met Lys Arg Ile Glu Glu Gly Ile Lys
    1055                1060                1065

```
Glu Leu Gly Ser Gln Ile Leu Lys Glu His Pro Val Glu Asn Thr
1070                1075                1080

Gln Leu Gln Asn Glu Lys Leu Tyr Leu Tyr Tyr Leu Gln Asn Gly
1085                1090                1095

Arg Asp Met Tyr Val Asp Gln Glu Leu Asp Ile Asn Arg Leu Ser
1100                1105                1110

Asp Tyr Asp Val Asp His Ile Val Pro Gln Ser Phe Leu Lys Asp
1115                1120                1125

Asp Ser Ile Asp Asn Lys Val Leu Thr Arg Ser Asp Lys Asn Arg
1130                1135                1140

Gly Lys Ser Asp Asn Val Pro Ser Glu Glu Val Lys Lys Met
1145                1150                1155

Lys Asn Tyr Trp Arg Gln Leu Leu Asn Ala Lys Leu Ile Thr Gln
1160                1165                1170

Arg Lys Phe Asp Asn Leu Thr Lys Ala Glu Arg Gly Gly Leu Ser
1175                1180                1185

Glu Leu Asp Lys Ala Gly Phe Ile Lys Arg Gln Leu Val Glu Thr
1190                1195                1200

Arg Gln Ile Thr Lys His Val Ala Gln Ile Leu Asp Ser Arg Met
1205                1210                1215

Asn Thr Lys Tyr Asp Glu Asn Asp Lys Leu Ile Arg Glu Val Lys
1220                1225                1230

Val Ile Thr Leu Lys Ser Lys Leu Val Ser Asp Phe Arg Lys Asp
1235                1240                1245

Phe Gln Phe Tyr Lys Val Arg Glu Ile Asn Asn Tyr His His Ala
1250                1255                1260

His Asp Ala Tyr Leu Asn Ala Val Val Gly Thr Ala Leu Ile Lys
1265                1270                1275

Lys Tyr Pro Lys Leu Glu Ser Glu Phe Val Tyr Gly Asp Tyr Lys
1280                1285                1290

Val Tyr Asp Val Arg Lys Met Ile Ala Lys Ser Glu Gln Glu Ile
1295                1300                1305

Gly Lys Ala Thr Ala Lys Tyr Phe Phe Tyr Ser Asn Ile Met Asn
1310                1315                1320

Phe Phe Lys Thr Glu Ile Thr Leu Ala Asn Gly Glu Ile Arg Lys
1325                1330                1335

Arg Pro Leu Ile Glu Thr Asn Gly Glu Thr Gly Glu Ile Val Trp
1340                1345                1350

Asp Lys Gly Arg Asp Phe Ala Thr Val Arg Lys Val Leu Ser Met
1355                1360                1365

Pro Gln Val Asn Ile Val Lys Lys Thr Glu Val Gln Thr Gly Gly
1370                1375                1380

Phe Ser Lys Glu Ser Ile Leu Pro Lys Arg Asn Ser Asp Lys Leu
1385                1390                1395

Ile Ala Arg Lys Lys Asp Trp Asp Pro Lys Tyr Gly Gly Phe
1400                1405                1410

Asp Ser Pro Thr Val Ala Tyr Ser Val Leu Val Val Ala Lys Val
1415                1420                1425

Glu Lys Gly Lys Ser Lys Lys Leu Lys Ser Val Lys Glu Leu Leu
1430                1435                1440

Gly Ile Thr Ile Met Glu Arg Ser Ser Phe Glu Lys Asn Pro Ile
1445                1450                1455

Asp Phe Leu Glu Ala Lys Gly Tyr Lys Glu Val Lys Lys Asp Leu
```

-continued

```
                    1460                1465                1470

Ile Ile Lys Leu Pro Lys Tyr Ser Leu Phe Glu Leu Glu Asn Gly
    1475                1480                1485

Arg Lys Arg Met Leu Ala Ser Ala Gly Glu Leu Gln Lys Gly Asn
    1490                1495                1500

Glu Leu Ala Leu Pro Ser Lys Tyr Val Asn Phe Leu Tyr Leu Ala
    1505                1510                1515

Ser His Tyr Glu Lys Leu Lys Gly Ser Pro Glu Asp Asn Glu Gln
    1520                1525                1530

Lys Gln Leu Phe Val Glu Gln His Lys His Tyr Leu Asp Glu Ile
    1535                1540                1545

Ile Glu Gln Ile Ser Glu Phe Ser Lys Arg Val Ile Leu Ala Asp
    1550                1555                1560

Ala Asn Leu Asp Lys Val Leu Ser Ala Tyr Asn Lys His Arg Asp
    1565                1570                1575

Lys Pro Ile Arg Glu Gln Ala Glu Asn Ile Ile His Leu Phe Thr
    1580                1585                1590

Leu Thr Asn Leu Gly Ala Pro Ala Ala Phe Lys Tyr Phe Asp Thr
    1595                1600                1605

Thr Ile Asp Arg Lys Arg Tyr Thr Ser Thr Lys Glu Val Leu Asp
    1610                1615                1620

Ala Thr Leu Ile His Gln Ser Ile Thr Gly Leu Tyr Glu Thr Arg
    1625                1630                1635

Ile Asp Leu Ser Gln Leu Gly Gly Asp His His His His His His
    1640                1645                1650

<210> SEQ ID NO 12
<211> LENGTH: 1467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160
```

-continued

```
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
            180                 185                 190
Asn Gln Leu Phe Glu Glu Asn Pro Ile Asn Ala Ser Gly Val Asp Ala
        195                 200                 205
Lys Ala Ile Leu Ser Ala Arg Leu Ser Lys Ser Arg Arg Leu Glu Asn
    210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
            260                 265                 270
Asp Asp Leu Asp Asn Leu Leu Ala Gln Ile Gly Asp Gln Tyr Ala Asp
        275                 280                 285
Leu Phe Leu Ala Ala Lys Asn Leu Ser Asp Ala Ile Leu Leu Ser Asp
    290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
        355                 360                 365
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
Pro Tyr Tyr Val Gly Pro Leu Ala Arg Gly Asn Ser Arg Phe Ala Trp
    450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
        515                 520                 525
Tyr Val Thr Glu Gly Met Arg Lys Pro Ala Phe Leu Ser Gly Glu Gln
    530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
```

-continued

```
                580             585             590
Thr Tyr His Asp Leu Leu Lys Ile Ile Lys Asp Lys Asp Phe Leu Asp
            595             600             605

Asn Glu Glu Asn Glu Asp Ile Leu Glu Asp Ile Val Leu Thr Leu Thr
        610             615             620

Leu Phe Glu Asp Arg Glu Met Ile Glu Glu Arg Leu Lys Thr Tyr Ala
625             630             635             640

His Leu Phe Asp Asp Lys Val Met Lys Gln Leu Lys Arg Arg Arg Tyr
            645             650             655

Thr Gly Trp Gly Arg Leu Ser Arg Lys Leu Ile Asn Gly Ile Arg Asp
            660             665             670

Lys Gln Ser Gly Lys Thr Ile Leu Asp Phe Leu Lys Ser Asp Gly Phe
        675             680             685

Ala Asn Arg Asn Phe Met Gln Leu Ile His Asp Asp Ser Leu Thr Phe
        690             695             700

Lys Glu Asp Ile Gln Lys Ala Gln Val Ser Gly Gln Gly Asp Ser Leu
705             710             715             720

His Glu His Ile Ala Asn Leu Ala Gly Ser Pro Ala Ile Lys Lys Gly
            725             730             735

Ile Leu Gln Thr Val Lys Val Val Asp Glu Leu Val Lys Val Met Gly
            740             745             750

Arg His Lys Pro Glu Asn Ile Val Ile Glu Met Ala Arg Glu Asn Gln
            755             760             765

Thr Thr Gln Lys Gly Gln Lys Asn Ser Arg Glu Arg Met Lys Arg Ile
        770             775             780

Glu Glu Gly Ile Lys Glu Leu Gly Ser Gln Ile Leu Lys Glu His Pro
785             790             795             800

Val Glu Asn Thr Gln Leu Gln Asn Glu Lys Leu Tyr Leu Tyr Tyr Leu
            805             810             815

Gln Asn Gly Arg Asp Met Tyr Val Asp Gln Glu Leu Asp Ile Asn Arg
            820             825             830

Leu Ser Asp Tyr Asp Val Asp Ala Ile Val Pro Gln Ser Phe Leu Lys
        835             840             845

Asp Asp Ser Ile Asp Asn Lys Val Leu Thr Arg Ser Asp Lys Asn Arg
        850             855             860

Gly Lys Ser Asp Asn Val Pro Ser Glu Glu Val Val Lys Lys Met Lys
865             870             875             880

Asn Tyr Trp Arg Gln Leu Leu Asn Ala Lys Leu Ile Thr Gln Arg Lys
            885             890             895

Phe Asp Asn Leu Thr Lys Ala Glu Arg Gly Gly Leu Ser Glu Leu Asp
            900             905             910

Lys Ala Gly Phe Ile Lys Arg Gln Leu Val Glu Thr Arg Gln Ile Thr
        915             920             925

Lys His Val Ala Gln Ile Leu Asp Ser Arg Met Asn Thr Lys Tyr Asp
        930             935             940

Glu Asn Asp Lys Leu Ile Arg Glu Val Lys Val Ile Thr Leu Lys Ser
945             950             955             960

Lys Leu Val Ser Asp Phe Arg Lys Asp Phe Gln Phe Tyr Lys Val Arg
            965             970             975

Glu Ile Asn Asn Tyr His His Ala His Asp Ala Tyr Leu Asn Ala Val
            980             985             990

Val Gly Thr Ala Leu Ile Lys Lys  Tyr Pro Lys Leu Glu  Ser Glu Phe
        995              1000              1005
```

-continued

Val Tyr Gly Asp Tyr Lys Val Tyr Asp Val Arg Lys Met Ile Ala
1010                1015                1020

Lys Ser Glu Gln Glu Ile Gly Lys Ala Thr Ala Lys Tyr Phe Phe
1025                1030                1035

Tyr Ser Asn Ile Met Asn Phe Phe Lys Thr Glu Ile Thr Leu Ala
1040                1045                1050

Asn Gly Glu Ile Arg Lys Arg Pro Leu Ile Glu Thr Asn Gly Glu
1055                1060                1065

Thr Gly Glu Ile Val Trp Asp Lys Gly Arg Asp Phe Ala Thr Val
1070                1075                1080

Arg Lys Val Leu Ser Met Pro Gln Val Asn Ile Val Lys Lys Thr
1085                1090                1095

Glu Val Gln Thr Gly Gly Phe Ser Lys Glu Ser Ile Leu Pro Lys
1100                1105                1110

Arg Asn Ser Asp Lys Leu Ile Ala Arg Lys Lys Asp Trp Asp Pro
1115                1120                1125

Lys Lys Tyr Gly Gly Phe Asp Ser Pro Thr Val Ala Tyr Ser Val
1130                1135                1140

Leu Val Val Ala Lys Val Glu Lys Gly Lys Ser Lys Lys Leu Lys
1145                1150                1155

Ser Val Lys Glu Leu Leu Gly Ile Thr Ile Met Glu Arg Ser Ser
1160                1165                1170

Phe Glu Lys Asn Pro Ile Asp Phe Leu Glu Ala Lys Gly Tyr Lys
1175                1180                1185

Glu Val Lys Lys Asp Leu Ile Ile Lys Leu Pro Lys Tyr Ser Leu
1190                1195                1200

Phe Glu Leu Glu Asn Gly Arg Lys Arg Met Leu Ala Ser Ala Gly
1205                1210                1215

Glu Leu Gln Lys Gly Asn Glu Leu Ala Leu Pro Ser Lys Tyr Val
1220                1225                1230

Asn Phe Leu Tyr Leu Ala Ser His Tyr Glu Lys Leu Lys Gly Ser
1235                1240                1245

Pro Glu Asp Asn Glu Gln Lys Gln Leu Phe Val Glu Gln His Lys
1250                1255                1260

His Tyr Leu Asp Glu Ile Ile Glu Gln Ile Ser Glu Phe Ser Lys
1265                1270                1275

Arg Val Ile Leu Ala Asp Ala Asn Leu Asp Lys Val Leu Ser Ala
1280                1285                1290

Tyr Asn Lys His Arg Asp Lys Pro Ile Arg Glu Gln Ala Glu Asn
1295                1300                1305

Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
1325                1330                1335

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
1355                1360                1365

Gly Ser Pro Lys Lys Lys Arg Lys Val Ser Ser Asp Tyr Lys Asp
1370                1375                1380

His Asp Gly Asp Tyr Lys Asp His Asp Ile Asp Tyr Lys Asp Asp
1385                1390                1395

```
Asp Asp Lys Ala Ala Gly Gly Gly Ser Gly Arg Ala Asp Ala
    1400            1405            1410

Leu Asp Asp Phe Asp Leu Asp Met Leu Gly Ser Asp Ala Leu Asp
    1415            1420            1425

Asp Phe Asp Leu Asp Met Leu Gly Ser Asp Ala Leu Asp Asp Phe
    1430            1435            1440

Asp Leu Asp Met Leu Gly Ser Asp Ala Leu Asp Phe Asp Leu
    1445            1450            1455

Asp Met Leu His His His His His His
    1460            1465

<210> SEQ ID NO 13
<211> LENGTH: 1374
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285
```

-continued

```
Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700
```

```
Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
```

```
                    1115                1120                1125
Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

His His His His His
    1370

<210> SEQ ID NO 14
<211> LENGTH: 1860
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
atgggtgcta gcaaaggtga agagctgttt gacggtgtag taccgatctt agtggaatta      60
gacggcgacg tgaacggtca cgaatttagc gtgcgcggcg agggcgaagg tgacgctacc     120
gagggtgaat tgaccctgaa gtttatttgc acaacaggcg aattaccgt tccgtggccc      180 accttagtga ccaccctgac ctatggcgtt cagtgcttca gtgattaccc agatcatatg     240
gatcaacacg atttttcaa tcagccatg cctgaaggat atgttcaaga gcgtacaatc      300
agcttcaagg acgatggcac ctataaaacg cgtgcggaag tgaaatttga aggcgacaca     360 ttagtaaaacc gtatcgaact gaaaggtatc gacttcaaag aagacggcaa cattttaggc     420
cataagctgg aatataactt taattctcat gacgtgtata ttacggccga taaacaggaa     480
```

```
aacggtatca aggcagaatt tgaaattcgc cataacgtgg aggacggcag cgttcaatta    540
gcggatcatt atcaacaaaa cacgccgatt ggtgatgggc ctgtactgtt acctgacgat    600
cactacctga gcacggagtc agccctgagc aaagatccga acgaagaccg cgatcacatg    660
gttctgttag aattcgtgac cgctgcaggc attgatcatg gaatggacga gctgtacaag    720
accggtggta gcggtggttc tggtggttct ggtggtagcg gcggtagcgg tggtagcggt    780
ggtagcggtg gcagcggcgg taccgcgagc aatttactga ccgtacacca aaatttgcct    840
gcattgccgg tcgatgcaac gagtgatgag gttcgcaaga acctgatgga catgttcagg    900
gatcgccagg cgttttctga gcatacctgg aaaatgcttc tgtccgtttg ccggtcgtgg    960
gcggcatggt gcaagttgaa taaccggaaa tggtttcccg cagaacctga gatgttcgc    1020 gattatcttc tatatcttca ggcgcgcggt ctggcagtaa aaactatcca gcaacatttg   1080
ggccagctaa acatgcttca tcgtcggtcc gggctgccac gaccaagtga cagcaatgct   1140
gtttcactgg ttatgcggcg tatccgaaaa gaaaacgttg atgccggtga acgtgcaaaa   1200
caggctctag cgttcgaacg cactgatttc gaccaggttc gttcactcat ggaaaatagc   1260
gatcgctgcc aggatatacg taatctggca tttctgggga ttgcttataa caccctgtta   1320
cgtatagccg aaattgccag gatcagggtt aaagatatct cacgtactga cggtgggaga   1380
atgttaatcc atattggcag aacgaaaacg ctggttagca ccgcaggtgt agagaaggca   1440
cttagcctgg gggtaactaa actggtcgag cgatggattt ccgtctctgg tgtagctgat   1500
gatccgaata actacctgtt ttgccgggtc agaaaaaatg gtgttgccgc gccatctgcc   1560
accagccagc tatcaactcg cgccctggaa gggattttg aagcaactca tcgattgatt    1620
tacggcgcta aggatgactc tggtcagaga tacctggcct ggtctggaca cagtgccgt    1680 gtcggagccg cgcgagatat ggcccgcgct ggagtttcaa taccggagat catgcaagct   1740
ggtggctgga ccaatgtaaa tattgtcatg aactatatcc gtaacctgga tagtgaaaca   1800
ggggcaatgg tgcgcctgct ggaagatggc gacggcggat cccatcacca ccaccatcac   1860
```

<210> SEQ ID NO 15
<211> LENGTH: 1059
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 15

```
atggcgagca atttactgac cgtacaccaa aatttgcctg cattgccggt cgatgcaacg     60
agtgatgagg ttcgcaagaa cctgatggac atgttcaggg atcgccaggc gttttctgag    120
catacctgga aaatgcttct gtccgtttgc cggtcgtggg cggcatggtg caagttgaat    180
aaccggaaat ggtttcccgc agaacctgaa gatgttcgcg attatcttct atatcttcag    240
gcgcgcggtc tggcagtaaa aactatccag caacatttgg gccagctaaa catgcttcat    300
cgtcggtccg ggctgccacg accaagtgac agcaatgctg tttcactggt tatgcggcgt    360
atccgaaaag aaaacgttga tgccggtgaa cgtgcaaaac aggctctagc gttcgaacgc    420
actgatttcg accaggttcg ttcactcatg gaaaatagcg atcgctgcca ggatatacgt    480
aatctggcat ttctggggat tgcttataac accctgttac gtatagccga aattgccagg    540
atcagggtta aagatatctc acgtactgac ggtgggagaa tgttaatcca tattggcaga    600
acgaaaacgc tggttagcac cgcaggtgta gagaaggcac ttagcctggg ggtaactaaa    660
```

```
ctggtcgagc gatggatttc cgtctctggt gtagctgatg atccgaataa ctacctgttt      720
tgccgggtca gaaaaaatgg tgttgccgcg ccatctgcca ccagccagct atcaactcgc      780
gccctggaag ggatttttga agcaactcat cgattgattt acggcgctaa ggatgactct      840
ggtcagagat acctggcctg gtctggacac agtgcccgtg tcggagccgc gcagatatg       900
gcccgcgctg gagtttcaat accggagatc atgcaagctg gtggctggac caatgtaaat      960
attgtcatga actatatccg taacctggat agtgaaacag gggcaatggt gcgcctgctg     1020
gaagatggcg acggcggatc ccatcaccac caccatcac                            1059
```

<210> SEQ ID NO 16
<211> LENGTH: 4959
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
atgggtgcta gcaaaggtga agagctgttt gacggtgtag taccgatctt agtggaatta       60
gacggcgacg tgaacggtca cgaatttagc gtgcgcggcg agggcgaagg tgacgctacc      120
gagggtgaat tgaccctgaa gtttatttgc acaacaggcg aattaccccgt tccgtggccc      180
accttagtga ccaccctgac ctatggcgtt cagtgcttca gtgattaccc agatcatatg      240
gatcaacacg attttttcaa atcagccatg cctgaaggat atgttcaaga gcgtacaatc      300
agcttcaagg acgatggcac ctataaaacg cgtgcgaagt gaaatttga aggcgacaca      360
ttagtaaacc gtatcgaact gaaaggtatc gacttcaaag aagacggcaa catttttaggc      420
cataagctgg aatataactt taattctcat gacgtgtata ttacggccga taaacaggaa      480
aacggtatca aggcagaatt tgaaattcgc cataacgtgg aggacggcag cgttcaatta      540
gcggatcatt atcaacaaaa cacgccgatt ggtgatgggc ctgtactgtt acctgacgat      600
cactacctga gcacggagtc agccctgagc aaagatccga acgaagaccg cgatcacatg      660
gttctgttag aattcgtgac cgctgcaggc attgatcatg gaatgggacga gctgtacaag      720
accggtggta gcggtggttc tggtggttct ggtggtagcg gcggtagcgg tggtagcggt      780
ggtagcggtg gcagcggcgg taccgcgctc gcgctgccca agaagaagag gaaggtgatg      840
gataagaaat actcaatagg cttagatatc ggcacaaata gcgtcggatg gcggtgatc       900
actgatgaat ataaggttcc gtctaaaaag ttcaaggttc tgggaaatac agaccgccac      960
agtatcaaaa aaaatcttat aggggctctt ttatttgaca gtggagagac agcggaagcg     1020
actcgtctca acggacagc tcgtagaagg tatacacgtc ggaagaatcg tatttgttat     1080
ctacaggaga ttttttcaaa tgagatggcg aaagtagatg atagtttctt tcatcgactt     1140
gaagagtctt ttttggtgga agaagacaag aagcatgaac gtcatcctat ttttggaaat     1200
atagtagatg aagttgctta tcatgagaaa tatccaacta tctatcatct gcgaaaaaaa     1260
ttggtagatt ctactgataa agcggatttg cgcttaatct atttggcctt agcgcatatg     1320
attaagtttc gtggtcattt tttgattgag ggagattaa atcctgataa tagtgatgtg     1380
gacaaactat ttatccagtt ggtacaaacc tacaatcaat tatttgaaga aaaccctatt     1440
aacgcaagtg gagtagatgc taaagcgatt ctttctgcac gattgagtaa atcaagacga     1500
ttagaaaaat tcattgctca gctccccggt gagaagaaaa atggcttatt tgggaatctc     1560
attgctttgt cattgggttt gacccctaat tttaaatcaa attttgattt ggcagaagat     1620
```

```
gctaaattac agctttcaaa agatacttac gatgatgatt tagataattt attggcgcaa    1680
attggagatc aatatgctga tttgttttg gcagctaaga atttatcaga tgctattta      1740 ctttcagata tcctaagagt aaatactgaa ataactaagg ctcccctatc agcttcaatg    1800
attaaacgct acgatgaaca tcatcaagac ttgactcttt taaaagcttt agttcgacaa    1860
caacttccag aaaagtataa agaaatcttt tttgatcaat caaaaaacgg atatgcaggt    1920
tatattgatg ggggagctag ccaagaagaa ttttataaat ttatcaaacc aattttagaa    1980
aaaatggatg gtactgagga attattggtg aaactaaatc gtgaagattt gctgcgcaag    2040
caacggacct tgacaacgg ctctattccc catcaaattc acttgggtga gctgcatgct     2100
attttgagaa gacaagaaga cttttatcca tttttaaaag acaatcgtga aagattgaa     2160 aaaatcttga cttttcgaat tccttattat gttggtccat ggcgcgtgg caatagtcgt     2220 tttgcatgga tgactcggaa gtctgaagaa acaattaccc catggaattt tgaagaagtt    2280
gtcgataaag gtgcttcagc tcaatcattt attgaacgca tgacaaactt tgataaaaat    2340
cttccaaatg aaaagtact accaaaacat agtttgcttt atgagtattt tacggtttat     2400
aacgaattga caaggtcaa atatgttact gaaggaatgc gaaaaccagc atttcttca      2460 ggtgaacaga agaaagccat tgttgattta ctcttcaaaa caaatcgaaa agtaaccgtt    2520
aagcaattaa agaagatta tttcaaaaaa atagaatgtt ttgatagtgt tgaaatttca    2580
ggagttgaag atagatttaa tgcttcatta ggtacctacc atgatttgct aaaaattatt    2640
aaagataaag atttttgga taatgaagaa aatgaagata tcttagagga tattgtttta   2700
acattgacct tatttgaaga tagggagatg attgaggaaa gacttaaaac atatgctcac    2760
ctctttgatg ataaggtgat gaaacagctt aaacgtcgcc gttatactgg ttggggacgt    2820
ttgtctcgaa aattgattaa tggtattagg gataagcaat ctggcaaaac aatattagat    2880
tttttgaaat cagatggttt tgccaatcgc aattttatgc agctgatcca tgatgatagt    2940
ttgacattta aagaagacat tcaaaaagca caagtgtctg gacaaggcga tagtttacat    3000
gaacatattg caaatttagc tggtagccct gctattaaaa aaggtatttt acagactgta    3060
aaagttgttg atgaattggt caaagtaatg gggcggcata agccagaaaa tatcgttatt    3120
gaaatggcac gtgaaaatca gacaactcaa aagggccaga aaaattcgcg agagcgtatg    3180
aaacgaatcg aagaaggtat caagaatta ggaagtcaga ttcttaaaga gcatcctgtt    3240
gaaaatactc aattgcaaaa tgaaaagctc tatctctatt atctccaaaa tggaagagac    3300
atgtatgtgg accaagaatt agatattaat cgtttaagtg attatgatgt cgatcacatt    3360
gttccacaaa gtttccttaa agacgattca atagacaata aggtcttaac gcgttctgat    3420
aaaaatcgtg gtaaatcgga taacgttcca agtgaagaag tagtcaaaaa gatgaaaaac    3480
tattggagac aacttctaaa cgccaagtta atcactcaac gtaagtttga aatttaacg    3540 aaagctgaac gtggaggttt gagtgaactt gataaagctg gttttatcaa acgccaattg    3600
gttgaaactc gccaaatcac taagcatgtg gcacaaattt tggatagtcg catgaatact    3660
aaatacgatg aaaatgataa acttattcga gaggttaaag tgattacctt aaaatctaaa    3720
ttagtttctg acttccgaaa agatttccaa ttctataaag tacgtgagat taacaattac    3780
catcatgccc atgatgcgta tctaaatgcc gtcgttggaa ctgctttgat taagaaatat    3840
ccaaaacttg aatcggagtt tgtctatggt gattataaag tttatgatgt tcgtaaaatg    3900
attgctaagt ctgagcaaga aataggcaaa gcaaccgcaa atatttctt ttactctaat    3960
```

```
atcatgaact tcttcaaaac agaaattaca cttgcaaatg gagagattcg caaacgccct    4020
ctaatcgaaa ctaatgggga aactggagaa attgtctggg ataaagggcg agattttgcc    4080
acagtgcgca aagtattgtc catgccccaa gtcaatattg tcaagaaaac agaagtacag    4140
acaggcggat tctccaagga gtcaattta ccaaaaagaa attcggacaa gcttattgct    4200
cgtaaaaaag actgggatcc aaaaaaatat ggtggttttg atagtccaac ggtagcttat    4260
tcagtcctag tggttgctaa ggtggaaaaa gggaaatcga agaagttaaa atccgttaaa    4320
gagttactag ggatcacaat tatggaaaga agttcctttg aaaaaaatcc gattgacttt    4380
ttagaagcta aaggatataa ggaagttaaa aaagacttaa tcattaaact acctaaatat    4440 agtcttttg agttagaaaa cggtcgtaaa cggatgctgg ctagtgccgg agaattacaa    4500
aaaggaaatg agctggctct gccaagcaaa tatgtgaatt ttttatattt agctagtcat    4560
tatgaaaagt tgaagggtag tccagaagat aacgaacaaa acaattgtt tgtggagcag    4620 cataagcatt atttagatga gattattgag caaatcagtg aattttctaa gcgtgttatt    4680
ttagcagatg ccaatttaga taaagttctt agtgcatata acaaacatag agacaaacca    4740
atacgtgaac aagcagaaaa tattattcat ttatttacgt tgacgaatct tggagctccc    4800
gctgctttta aatattttga tacaacaatt gatcgtaaac gatatacgtc tacaaaagaa    4860
gttttagatg ccactcttat ccatcaatcc atcactggtc tttatgaaac acgcattgat    4920
ttgagtcagc taggaggtga ccatcaccac caccatcac                           4959
```

<210> SEQ ID NO 17
<211> LENGTH: 4959
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
atgggtgcta gcaaaggtga acgtctgttt cgtggtaaag taccgatctt agtggaatta      60
aagggcgacg tgaacggtca taaatttagc gtgcgcggca aaggcaaagg tgacgctacc     120
cgtggtaaat tgaccctgaa gtttatttgc acaacaggga aattacccgt tccgtggccc     180
accttagtga ccaccctgac ctatggcgtt cagtgcttca gtcgttaccc taaacatatg     240
aaacgtcacg attttttcaa atcagccatg cctaaaggat atgttcaaga gcgtacaatc     300
agcttcaaga aggatggcaa atataaaacg cgtgcggaag tgaaatttga aggccgcaca     360
ttagtaaatc gtatcaaact gaaggtcgt gacttcaaag aaaaaggcaa catttaggc      420 cataaactgc gttataactt taattctcat aaggtgtata ttacggccga taaacgcaag    480
aatggtatca aggcaaaatt caaaattcgc cataacgtga agacggcag cgttcaatta    540 gcggatcatt atccaacaaaa cacgccgatt ggtcgcgggc ctgtactgtt acctcgcaac    600
cactacctga gcacccgttc taaactgagc aaagatccga agaaaaaacg cgatcacatg    660
gttctgttag aattcgtgac cgctgcaggc attaagcacg gacgcgacga acgctacaag    720
accggtggta gcggtggttc tggtggttct ggtggtagcg gcggtagcgg tggtagcggt    780
ggtagcggtg gcagcggcgg taccgcgctc gcgctgccca gaagaagag gaaggtgatg    840 gataagaaat actcaatagg cttagatatc ggcacaaata gcgtcggatg ggcggtgatc    900
actgatgaat ataaggttcc gtctaaaaag ttcaaggttc tgggaaatac agaccgccac    960
agtatcaaaa aaatcttat aggggctctt ttatttgaca gtggagagac agcggaagcg   1020
```

```
actcgtctca aacggacagc tcgtagaagg tatacacgtc ggaagaatcg tatttgttat    1080
ctacaggaga ttttttcaaa tgagatggcg aaagtagatg atagtttctt tcatcgactt    1140
gaagagtctt ttttggtgga agaagacaag aagcatgaac gtcatcctat ttttggaaat    1200
atagtagatg aagttgctta tcatgagaaa tatccaacta tctatcatct gcgaaaaaaa    1260
ttggtagatt ctactgataa agcggatttg cgcttaatct atttggcctt agcgcatatg    1320
attaagtttc gtggtcattt tttgattgag ggagatttaa atcctgataa tagtgatgtg    1380
gacaaactat ttatccagtt ggtacaaacc tacaatcaat tatttgaaga aaaccctatt    1440
aacgcaagtg gagtagatgc taaagcgatt ctttctgcac gattgagtaa atcaagacga    1500
ttagaaaatc tcattgctca gctccccggt gagaagaaaa atggcttatt tgggaatctc    1560
attgctttgt cattgggttt gacccctaat tttaaatcaa attttgattt ggcagaagat    1620
gctaaattac agctttcaaa agatacttac gatgatgatt tagataattt attggcgcaa    1680
attggagatc aatatgctga tttgttttg gcagctaaga atttatcaga tgctatttta    1740
cttcagata tcctaagagt aaatactgaa ataactaagg ctccctatc agcttcaatg    1800
attaaacgct acgatgaaca tcatcaagac ttgactcttt taaaagcttt agttcgacaa    1860
caacttccag aaaagtataa agaaatcttt tttgatcaat caaaaaacgg atatgcaggt    1920
tatattgatg ggggagctag ccaagaagaa ttttataaat ttatcaaacc aattttagaa    1980
aaaatggatg gtactgagga attattggtg aaactaaatc gtgaagattt gctgcgcaag    2040
caacggacct ttgacaacgg ctctattccc catcaaattc acttgggtga gctgcatgct    2100
attttgagaa gacaagaaga cttttatcca tttttaaaag acaatcgtga gaagattgaa    2160
aaaatcttga cttttcgaat tccttattat gttggtccat ggcgcgtgg caatagtcgt    2220
tttgcatgga tgactcggaa gtctgaagaa acaattaccc catggaattt tgaagaagtt    2280
gtcgataaag gtgcttcagc tcaatcattt attgaacgca tgacaaactt tgataaaaat    2340
cttccaaatg aaaagtact accaaaacat agtttgcttt atgagtattt tacgttttat    2400
aacgaattga caaaggtcaa atatgttact gaaggaatgc gaaaaccagc atttctttca    2460
ggtgaacaga agaaagccat tgttgattta ctcttcaaaa caaatcgaaa agtaaccgtt    2520
aagcaattaa aagaagatta tttcaaaaaa atagaatgtt ttgatagtgt tgaaatttca    2580
ggagttgaag atagatttaa tgcttcatta ggtacctacc atgatttgct aaaaattatt    2640
aaagataaag attttttgga taatgaagaa aatgaagata tcttagagga tattgtttta    2700
acattgacct tatttgaaga tagggagatg attgaggaaa gacttaaaac atatgctcac    2760
ctctttgatg ataaggtgat gaaacagctt aaacgtcgcc gttatactgg ttggggacgt    2820
ttgtctcgaa aattgattaa tggtattagg gataagcaat ctggcaaaac aatattagat    2880
ttttgaaat cagatggttt tgccaatcgc aattttatgc agctgatcca tgatgatagt    2940
ttgacattta aagaagacat tcaaaaagca caagtgtctg acaaggcga tagtttacat    3000
gaacatattg caaatttagc tggtagccct gctattaaaa aaggtatttt acagactgta    3060
aaagttgttg atgaattggt caaagtaatg gggcggcata agccagaaaa tatcgttatt    3120
gaaatggcac gtgaaaatca gacaactcaa aagggccaga aaattcgcg agagcgtatg    3180
aaacgaatcg aagaaggtat caagaattaa ggaagtcaga ttcttaaaga gcatcctgtt    3240
gaaaatactc aattgcaaaa tgaaaagctc tatctctatt atctccaaaa tggaagagac    3300
atgtatgtgg accaagaatt agatattaat cgtttaagtg attatgatgt cgatcacatt    3360
gttccacaaa gtttccttaa agacgattca atagacaata aggtcttaac gcgttctgat    3420
```

```
aaaaatcgtg gtaaatcgga taacgttcca agtgaagaag tagtcaaaaa gatgaaaaac   3480
tattggagac aacttctaaa cgccaagtta atcactcaac gtaagtttga taatttaacg   3540
aaagctgaac gtggaggttt gagtgaactt gataaagctg gttttatcaa acgccaattg   3600
gttgaaactc gccaaatcac taagcatgtg gcacaaattt tggatagtcg catgaatact   3660
aaatacgatg aaaatgataa acttattcga gaggttaaag tgattacctt aaaatctaaa   3720
ttagtttctg acttccgaaa agatttccaa ttctataaag tacgtgagat taacaattac   3780
catcatgccc atgatgcgta tctaaatgcc gtcgttggaa ctgctttgat taagaaatat   3840
ccaaaacttg aatcggagtt tgtctatggt gattataaag tttatgatgt tcgtaaaatg   3900
attgctaagt ctgagcaaga aataggcaaa gcaaccgcaa atatttctt ttactctaat    3960
atcatgaact tcttcaaaac agaaattaca cttgcaaatg gagagattcg caaacgccct   4020
ctaatcgaaa ctaatgggga aactggagaa attgtctggg ataaagggcg agattttgcc   4080
acagtgcgca aagtattgtc catgccccaa gtcaatattg tcaagaaaac agaagtacag   4140
acaggcggat tctccaagga gtcaattta ccaaaaagaa attcggacaa gcttattgct    4200
cgtaaaaaag actgggatcc aaaaaaatat ggtggttttg atagtccaac ggtagcttat   4260
tcagtcctag tggttgctaa ggtggaaaaa gggaaatcga agaagttaaa atccgttaaa   4320
gagttactag ggatcacaat tatggaaaga agttcctttg aaaaaaatcc gattgacttt   4380
ttagaagcta aaggatataa ggaagttaaa aaagacttaa tcattaaact acctaaatat   4440
agtcttttg agttagaaaa cggtcgtaaa cggatgctgg ctagtgccgg agaattacaa    4500
aaaggaaatg agctggctct gccaagcaaa tatgtgaatt ttttatattt agctagtcat   4560
tatgaaaagt tgaagggtag tccagaagat aacgaacaaa aacaattgtt tgtggagcag   4620
cataagcatt atttagatga gattattgag caaatcagtg aattttctaa gcgtgttatt   4680
ttagcagatg ccaatttaga taaagttctt agtgcatata caaacatag agacaaacca    4740
atacgtgaac aagcagaaaa tattattcat ttatttacgt tgacgaatct ggagctccc    4800
gctgctttta aatattttga tacaacaatt gatcgtaaac gatatacgtc tacaaaagaa   4860
gttttagatg ccactcttat ccatcaatcc atcactggtc tttatgaaac acgcattgat   4920
ttgagtcagc taggaggtga ccatcaccac caccatcac                          4959
```

<210> SEQ ID NO 18
<211> LENGTH: 4152
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18

```
atggataaga aatactcaat aggcttagat atcggcacaa atagcgtcgg atgggcggtg    60
atcactgatg aatataaggt tccgtctaaa aagttcaagg ttctgggaaa tacagaccgc   120
cacagtatca aaaaaaatct tatagggct cttttatttg acagtggaga gacagcggaa    180
gcgactcgtc tcaaacggac agctcgtaga aggtatacac gtcggaagaa tcgtatttgt   240
tatctacagg agatttttc aaatgagatg gcgaaagtag atgatagttt ctttcatcga   300
cttgaagagt cttttttggt ggaagaagac aagaagcatg aacgtcatcc tatttttgga   360
aatatagtag atgaagttgc ttatcatgag aaatatccaa ctatctatca tctgcgaaaa   420
aaattggtag attctactga taaagcggat ttgcgcttaa tctatttggc cttagcgcat   480
```

```
atgattaagt tcgtggtca ttttttgatt gagggagatt taaatcctga taatagtgat    540
gtggacaaac tatttatcca gttggtacaa acctacaatc aattatttga agaaaaccct    600
attaacgcaa gtggagtaga tgctaaagcg attctttctg cacgattgag taaatcaaga    660
cgattagaaa atctcattgc tcagctcccc ggtgagaaga aaaatggctt atttgggaat    720
ctcattgctt tgtcattggg tttgacccct aattttaaat caaattttga tttggcagaa    780
gatgctaaat tacagctttc aaaagatact tacgatgatg atttagataa tttattggcg    840
caaattggag atcaatatgc tgatttgttt ttggcagcta agaatttatc agatgctatt    900
ttactttcag atatcctaag agtaaatact gaaataacta aggctcccct atcagcttca    960
atgattaaac gctacgatga acatcatcaa gacttgactc ttttaaaagc tttagttcga   1020
caacaacttc cagaaaagta taagaaatc ttttttgatc aatcaaaaaa cggatatgca    1080
ggttatattg atggggagc tagccaagaa gaattttata aatttatcaa accaatttta    1140
gaaaaaatgg atggtactga ggaattattg gtgaaactaa atcgtgaaga tttgctgcgc    1200
aagcaacgga cctttgacaa cggctctatt ccccatcaaa ttcacttggg tgagctgcat    1260
gctattttga aagacaaga agactttat ccattttaa aagacaatcg tgagaagatt     1320
gaaaaaatct tgacttttcg aattccttat tatgttggtc cattggcgcg tggcaatagt    1380
cgttttgcat ggatgactcg gaagtctgaa gaaacaatta ccccatggaa ttttgaagaa    1440
gttgtcgata aggtgcttc agctcaatca tttattgaac gcatgacaaa ctttgataaa    1500
aatcttccaa atgaaaaagt actaccaaaa catagtttgc tttatgagta ttttacggtt    1560
tataacgaat tgacaaaggt caaatatgtt actgaaggaa tgcgaaaacc agcatttctt    1620
tcaggtgaac agaagaaagc cattgttgat ttactcttca aaacaaatcg aaaagtaacc    1680
gttaagcaat taaagaaga ttatttcaaa aaaatagaat gttttgatag tgttgaaatt    1740
tcaggagttg aagatagatt taatgcttca ttaggtacct accatgattt gctaaaaatt    1800
attaaagata aagatttttt ggataatgaa gaaaatgaag atatcttaga ggatattgtt    1860
ttaacattga ccttatttga agataggag atgattgagg aaagacttaa acatatgct    1920 caccctcttg atgataaggt gatgaaacag cttaaacgtc gccgttatac tggttgggga    1980
cgtttgtctc gaaaattgat taatggtatt agggataagc aatctggcaa acaatatta    2040 gattttttga aatcagatgg ttttgccaat cgcaattta tgcagctgat ccatgatgat    2100
agtttgacat ttaagaaga cattcaaaaa gcacaagtgt ctggacaagg cgatagttta    2160
catgaacata ttgcaaattt agctggtagc cctgctatta aaaaaggtat tttacagact    2220
gtaaaagttg ttgatgaatt ggtcaaagta atgggcggc ataagccaga aaatatcgtt     2280
attgaaatgg cacgtgaaaa tcagacaact caaaagggcc agaaaattc gcgagagcgt    2340 atgaaacgaa tcgaagaagg tatcaaagaa ttaggaagtc agattcttaa agagcatcct    2400
gttgaaaata ctcaattgca aaatgaaaag ctctatctct attatctcca aaatggaaga    2460
gacatgtatg tggaccaaga attagatatt aatcgtttaa gtgattatga tgtcgatcac    2520
attgttccac aaagtttcct taagacgat tcaatagaca ataaggtctt aacgcgttct    2580
gataaaaatc gtggtaaatc ggataacgtt ccaagtgaag aagtagtcaa aaagatgaaa    2640
aactattgga gacaacttct aaacgccaag ttaatcactc aacgtaagtt tgataattta    2700
acgaaagctg aacgtggagg tttgagtgaa cttgataaag ctggttttat caaacgccaa    2760
ttggttgaaa ctcgccaaat cactaagcat gtggcacaaa ttttggatag tcgcatgaat    2820
```

-continued

```
actaaatacg atgaaaatga taaacttatt cgagaggtta aagtgattac cttaaaatct    2880
aaattagttt ctgacttccg aaaagatttc caattctata aagtacgtga gattaacaat    2940
taccatcatg cccatgatgc gtatctaaat gccgtcgttg gaactgcttt gattaagaaa    3000
tatccaaaac ttgaatcgga gtttgtctat ggtgattata aagtttatga tgttcgtaaa    3060
atgattgcta agtctgagca agaaataggc aaagcaaccg caaaatattt cttttactct    3120
aatatcatga acttcttcaa aacagaaatt acacttgcaa atggagagat cgcaaacgc     3180 cctctaatcg aaactaatgg ggaaactgga gaaattgtct gggataaagg gcgagatttt    3240
gccacagtgc gcaaagtatt gtccatgccc caagtcaata ttgtcaagaa aacagaagta    3300
cagacaggcg gattctccaa ggagtcaatt ttaccaaaaa gaaattcgga caagcttatt    3360
gctcgtaaaa aagactggga tccaaaaaaa tatggtggtt ttgatagtcc aacggtagct    3420
tattcagtcc tagtggttgc taaggtggaa aagggaaat cgaagaagtt aaaatccgtt    3480
aaagagttac tagggatcac aattatggaa agaagttcct ttgaaaaaaa tccgattgac    3540
tttttagaag ctaaaggata taggaagtt aaaaagact taatcattaa actacctaaa     3600
tatagtcttt ttgagttaga aaacggtcgt aaacggatgc tggctagtgc cggagaatta    3660
caaaaaggaa atgagctggc tctgccaagc aaatatgtga atttttta tttagctagt      3720 cattatgaaa agttgaaggg tagtccagaa gataacgaac aaaaacaatt gtttgtggag    3780
cagcataagc attatttaga tgagattatt gagcaaatca gtgaattttc taagcgtgtt    3840 atttagcag atgccaattt agataaagtt cttagtgcat ataacaaaca tagagacaaa    3900
ccaatacgtg aacaagcaga aaatattatt catttattta cgttgacgaa tcttggagct    3960
cccgctgctt ttaaatattt tgatacaaca attgatcgta aacgatatac gtctacaaaa    4020
gaagttttag atgccactct tatccatcaa tccatcactg gtctttatga aacacgcatt    4080
gatttgagtc agctaggagg tgaccccaag aagaagagga aggtgatgga taagcatcac    4140
caccaccatc ac                                                        4152
```

<210> SEQ ID NO 19
<211> LENGTH: 4401
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 19

```
atggataaga aatactcaat aggcttagct atcggcacaa atagcgtcgg atgggcggtg     60
atcactgatg aatataaggt tccgtctaaa aagttcaagg ttctgggaaa tacagaccgc    120
cacagtatca aaaaaaatct tatagggct cttttatttg acagtggaga gacagcggaa     180
gcgactcgtc tcaaacggac agctcgtaga aggtatacac gtcggaagaa tcgtatttgt    240
tatctacagg agatttttc aaatgagatg gcgaaagtag atgatagttt ctttcatcga    300
cttgaagagt cttttttggt ggaagaagac aagaagcatg aacgtcatcc tatttttgga    360
aatatagtag atgaagttgc ttatcatgag aaatatccaa ctatctatca tctgcgaaaa    420
aaattggtag attctactga taaagcggat ttgcgcttaa tctatttggc cttagcgcat    480
atgattaagt ttcgtggtca ttttttgatt gagggagatt taaatcctga taatagtgat    540
gtggacaaac tatttatcca gttggtacaa acctacaatc aattatttga agaaaaccct    600
attaacgcaa gtggagtaga tgctaaagcg attctttctg cacgattgag taaatcaaga    660
```

```
cgattagaaa atctcattgc tcagctcccc ggtgagaaga aaaatggctt atttgggaat    720
ctcattgctt tgtcattggg tttgacccct aattttaaat caaattttga tttggcagaa    780
gatgctaaat tacagctttc aaaagatact tacgatgatg atttagataa tttattggcg    840
caaattggag atcaatatgc tgatttgttt ttggcagcta agaatttatc agatgctatt    900
ttactttcag atatcctaag agtaaatact gaaataacta aggctcccct atcagcttca    960
atgattaaac gctacgatga acatcatcaa gacttgactc ttttaaaagc tttagttcga   1020
caacaacttc cagaaaagta taagaaatc tttttttgatc aatcaaaaaa cggatatgca   1080
ggttatattg atgggggagc tagccaagaa gaatttttata aatttatcaa accaattta   1140 gaaaaaatgg atggtactga ggaattattg gtgaaactaa atcgtgaaga tttgctgcgc   1200
aagcaacgga cctttgacaa cggctctatt ccccatcaaa ttcactttggg tgagctgcat   1260 gctattttga gaagacaaga agactttttat ccattttttaa aagacaatcg tgagaagatt   1320
gaaaaaatct tgactttttcg aattccttat tatgttggtc cattggcgcg tggcaatagt   1380
cgttttgcat ggatgactcg gaagtctgaa gaaacaatta ccccatggaa ttttgaagaa   1440
gttgtcgata aggtgcttc agctcaatca tttattgaac gcatgacaaa ctttgataaa   1500
aatcttccaa atgaaaaagt actaccaaaa catagtttgc tttatgagta ttttacggtt   1560
tataacgaat tgacaaaggt caaatatgtt actgaaggaa tgcgaaaacc agcatttctt   1620
tcaggtgaac agaagaaagc cattgttgat ttactcttca aaacaaatcg aaaagtaacc   1680
gttaagcaat taaaagaaga ttatttcaaa aaaatagaat gttttgatag tgttgaaatt   1740
tcaggagttg aagatagatt taatgcttca ttaggtacct accatgattt gctaaaaatt   1800
attaaagata aagatttttt ggataatgaa gaaatgaag atatcttaga ggatattgtt   1860
ttaacattga ccttatttga agatagggag atgattgagg aaagacttaa aacatatgct   1920
cacctctttg atgataaggt gatgaaacag cttaaacgtc gccgttatac tggttgggga   1980
cgtttgtctc gaaaattgat taatggtatt agggataagc aatctggcaa aacaatatta   2040 gatttttttga aatcagatgg ttttgccaat cgcaatttta tgcagctgat ccatgatgat   2100
agtttgacat ttaagaaga cattcaaaaa gcacaagtgt ctggacaagg cgatagttta   2160
catgaacata ttgcaaattt agctggtagc cctgctatta aaaaaggtat tttacagact   2220
gtaaaagttg ttgatgaatt ggtcaaagta atggggcggc ataagccaga aaatatcgtt   2280
attgaaatgg cacgtgaaaa tcagacaact caaaagggcc agaaaaattc gcgagagcgt   2340
atgaaacgaa tcgaagaagg tatcaaagaa ttaggaagtc agattcttaa agagcatcct   2400
gttgaaaata ctcaattgca aaatgaaaag ctctatctct attatctcca aaatggaaga   2460
gacatgtatg tggaccaaga attagatatt aatcgtttaa gtgattatga tgtcgatgcc   2520
attgttccac aaagtttcct taaagacgat tcaatagaca ataaggtctt aacgcgttct   2580
gataaaaatc gtggtaaatc ggataacgtt ccaagtgaag aagtagtcaa aaagatgaaa   2640
aactattgga gacaacttct aaacgccaag ttaatcactc aacgtaagtt tgataattta   2700
acgaaagctg aacgtggagg tttgagtgaa cttgataaag ctggttttat caaacgccaa   2760
ttggttgaaa ctcgccaaat cactaagcat gtggcacaaa ttttggatag tcgcatgaat   2820
actaaatacg atgaaaatga taaacttatt cgagaggtta agtgattac cttaaaatct   2880 aaattagttt ctgacttccg aaaagatttc caattctata agtacgtgga gattaacaat   2940
taccatcatg cccatgatgc gtatctaaat gccgtcgttg aactgctttt gattaagaaa   3000 tatccaaaaac ttgaatcgga gtttgtctat ggtgattata agtttatga tgttcgtaaa   3060
```

```
atgattgcta agtctgagca agaaataggc aaagcaaccg caaaatattt cttttactct    3120
aatatcatga acttcttcaa aacagaaatt acacttgcaa atggagagat tcgcaaacgc    3180
cctctaatcg aaactaatgg ggaaactgga gaaattgtct gggataaagg gcgagatttt    3240
gccacagtgc gcaaagtatt gtccatgccc caagtcaata ttgtcaagaa aacagaagta    3300
cagacaggcg gattctccaa ggagtcaatt ttaccaaaaa gaaattcgga caagcttatt    3360
gctcgtaaaa aagactggga tccaaaaaaa tatggtggtt ttgatagtcc aacggtagct    3420
tattcagtcc tagtggttgc taaggtggaa aaagggaaat cgaagaagtt aaaatccgtt    3480
aaagagttac tagggatcac aattatggaa agaagttcct ttgaaaaaaa tccgattgac    3540
tttttagaag ctaaaggata taaggaagtt aaaaaagact aatcattaa actacctaaa     3600 tatagtctttt tgagttaga aaacggtcgt aacggatgc tggctagtgc cggagaatta    3660
caaaaaggaa atgagctggc tctgccaagc aaatatgtga attttttata tttagctagt    3720
cattatgaaa agttgaaggg tagtccagaa gataacgaac aaaaacaatt gtttgtggag    3780
cagcataagc attatttaga tgagattatt gagcaaatca gtgaattttc taagcgtgtt    3840
attttagcag atgccaattt agataaagtt cttagtgcat ataacaaaca tagagacaaa    3900
ccaatacgtg aacaagcaga aaatattatt catttattta cgttgacgaa tcttggagct    3960
cccgctgctt ttaaatattt tgatacaaca attgatcgta aacgatatac gtctacaaaa    4020
gaagttttag atgccactct tatccatcaa tccatcactg gtctttatga aacacgcatt    4080
gatttgagtc agctaggagg tgacggttct cccaagaaga agaggaaagt ctcgagcgac    4140
tacaaagacc atgacggtga ttataaagat catgacatcg attacaagga tgacgatgac    4200
aaggctgcag gaggcggtgg aagcgggcgc gccgacgcgc tggacgattt cgatctcgac    4260
atgctgggtt ctgatgccct cgatgacttt gacctggata tgttgggaag cgacgcattg    4320
gatgactttg atctggacat gctcggctcc gatgctctgg acgatttcga tctcgatatg    4380
ttacatcacc accaccatca c                                              4401
```

<210> SEQ ID NO 20
<211> LENGTH: 37
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 20
taatacgact cactataggg cacgggcagc ttgccgg                           37

<210> SEQ ID NO 21
<211> LENGTH: 55
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 21
taatacgact cactataggc ctcgaacttc acctcggcgg aaaggacgaa acacc       55

<210> SEQ ID NO 22
<211> LENGTH: 54
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 22
taatacgact cactataggc tgaagggcat cgacttcaga aaggacgaaa cacc          54

<210> SEQ ID NO 23
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
taatacgact cactataggc agctcgatgc ggttcaccag aaaggacgaa acacc         55

<210> SEQ ID NO 24
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
taatacgact cactataggc aaggaggacg gcaacatccg aaaggacgaa acacc         55

<210> SEQ ID NO 25
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
taatacgact cactatagga gtccgagcag aagaagaaga aaggacgaaa cacc          54

<210> SEQ ID NO 26
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
taatacgact cactataggg gtgggggag tttgctccga aaggacgaaa cacc           54

<210> SEQ ID NO 27
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
taatacgact cactataggc agatgtagtg tttccacaga aaggacgaaa cacc          54

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 28
aaaaaaagca ccgactcggt g                                           21

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ctgtacaaaa aagcaggctt ta                                          22

<210> SEQ ID NO 30
<211> LENGTH: 83
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aaaaaaagca ccgactcggt gccactttt caagttgata acggactagc cttattttaa     60
cttgctattt ctagctctaa aac                                         83

<210> SEQ ID NO 31
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gaaaggacga aacaccggcc tcgaacttca cctcggcggt tttagagcta gaaatagcaa    60

<210> SEQ ID NO 32
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gaaaggacga aacaccggca gctcgatgcg gttcaccagt tttagagcta gaaatagcaa    60

<210> SEQ ID NO 33
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gaaaggacga aacaccggct gaagggcatc gacttcagtt ttagagctag aaatagcaa     59

<210> SEQ ID NO 34
<211> LENGTH: 60
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 34
gaaaggacga aacaccggca aggaggacgg caacatccgt tttagagcta gaaatagcaa    60

<210> SEQ ID NO 35
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gaaaggacga aacaccggca gatgtagtgt ttccacagtt ttagagctag aaatagcaa     59

<210> SEQ ID NO 36
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gaaaggacga aacaccggag tccgagcaga agaagaagtt ttagagctag aaatagcaa     59

<210> SEQ ID NO 37
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gaaaggacga aacaccgggg tgggggagt ttgctccgtt ttagagctag aaatagcaa      59

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tacggcaagc tgaccctgaa                                                20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gtccatgccg agagtgatcc                                                20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
gccaggggct gttatcttgg                                               20

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
atgcacagaa gcacaggttg a                                             21

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ctgtgtcctc ttcctgccct                                               20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ctctccgagg agaaggccaa                                               20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ccacacagct tcccgttctc                                               20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gagagccgtt ccctctttgc                                               20

<210> SEQ ID NO 46
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cactctttcc ctacacgacg ctcttccgat ctcctcccca ttggcctgct tc    52

<210> SEQ ID NO 47
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cactctttcc ctacacgacg ctcttccgat cttcgtcctg ctctcactta gac    53

<210> SEQ ID NO 48
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cactctttcc ctacacgacg ctcttccgat cttttgtgg cttggcccca gt    52

<210> SEQ ID NO 49
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cactctttcc ctacacgacg ctcttccgat cttgcagtct catgacttgg cct    53

<210> SEQ ID NO 50
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cactctttcc ctacacgacg ctcttccgat cttttctgagg gctgctacct gt    52

<210> SEQ ID NO 51
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cactctttcc ctacacgacg ctcttccgat ctacatgaag caactccagt ccca    54

<210> SEQ ID NO 52
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 52
cactctttcc ctacacgacg ctcttccgat ctagcagacc cactgagtca actg        54

<210> SEQ ID NO 53
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
cactctttcc ctacacgacg ctcttccgat ctcccgccac agtcgtgtca t            51

<210> SEQ ID NO 54
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
cactctttcc ctacacgacg ctcttccgat ctcgccccgg tacaaggtga              50

<210> SEQ ID NO 55
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cactctttcc ctacacgacg ctcttccgat ctgtaccgta cattgtagga tgttt        55

<210> SEQ ID NO 56
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
cactctttcc ctacacgacg ctcttccgat ctcctcatct ccctcaagca ggc          53

<210> SEQ ID NO 57
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cactctttcc ctacacgacg ctcttccgat ctattctgct cttgaggtta tttgt        55

<210> SEQ ID NO 58
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
```
cactctttcc ctacacgacg ctcttccgat ctcacctctg cctcaagagc agaaaa    56

<210> SEQ ID NO 59
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cactctttcc ctacacgacg ctcttccgat cttgtgtgtg tgtgtgtgta ggact    55

<210> SEQ ID NO 60
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ggagttcaga cgtgtgctct tccgatcttc atctgtgccc ctccctcc    48

<210> SEQ ID NO 61
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ggagttcaga cgtgtgctct tccgatctcg agaaggaggt gcaggag    47

<210> SEQ ID NO 62
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ggagttcaga cgtgtgctct tccgatctcg ggagctgttc agaggctg    48

<210> SEQ ID NO 63
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ggagttcaga cgtgtgctct tccgatctct cacctgggcg agaaaggt    48

<210> SEQ ID NO 64
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ggagttcaga cgtgtgctct tccgatctaa aactcaaaga aatgcccaat ca        52

<210> SEQ ID NO 65
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ggagttcaga cgtgtgctct tccgatctag acgctgctcg ctccattc              48

<210> SEQ ID NO 66
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ggagttcaga cgtgtgctct tccgatctac aggcatgaat cactgcacct            50

<210> SEQ ID NO 67
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ggagttcaga cgtgtgctct tccgatctgc ggcaacttca gacaaccga             49

<210> SEQ ID NO 68
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ggagttcaga cgtgtgctct tccgatctga cccagggca ccagtt                 46

<210> SEQ ID NO 69
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ggagttcaga cgtgtgctct tccgatctct gccttcattg cttaaaagtg gat        53

<210> SEQ ID NO 70
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ggagttcaga cgtgtgctct tccgatctac agttgaagga aggaaacatg c          51

<210> SEQ ID NO 71
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ggagttcaga cgtgtgctct tccgatctgc tgcatttgcc catttcca                48

<210> SEQ ID NO 72
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ggagttcaga cgtgtgctct tccgatctgt tggggagga ggagcttat                49

<210> SEQ ID NO 73
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ggagttcaga cgtgtgctct tccgatctct aagagctata agggcaaatg act          53

<210> SEQ ID NO 74
<211> LENGTH: 56
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (33)..(36)
<223> OTHER INFORMATION: a, c, t, g, unknown or other

<400> SEQUENCE: 74
cactctttcc ctacacgacg ctcttccgat ctnnnnacgt aaacggccac aagttc       56

<210> SEQ ID NO 75
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ggagttcaga cgtgtgctct tccgatctgt cgtccttgaa gaagatggtg              50

<210> SEQ ID NO 76
<211> LENGTH: 54
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 76
cactctttcc ctacacgacg ctcttccgat ctccaggtga aggtgtggtt ccag      54

<210> SEQ ID NO 77
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ggagttcaga cgtgtgctct tccgatctcc cctagtcatt ggaggtgac           49

<210> SEQ ID NO 78
<211> LENGTH: 23
<212> TYPE: DNA
<213> ORGANISM: Mus sp.

<400> SEQUENCE: 78
gagtccgagc agaagaagaa ggg                                       23

<210> SEQ ID NO 79
<211> LENGTH: 23
<212> TYPE: DNA
<213> ORGANISM: Mus sp.

<400> SEQUENCE: 79
gaggccgagc agaagaaaga cgg                                       23

<210> SEQ ID NO 80
<211> LENGTH: 23
<212> TYPE: DNA
<213> ORGANISM: Mus sp.

<400> SEQUENCE: 80
gagtcctagc aggagaagaa gag                                       23

<210> SEQ ID NO 81
<211> LENGTH: 23
<212> TYPE: DNA
<213> ORGANISM: Mus sp.

<400> SEQUENCE: 81
gagtctaagc agaagaagaa gag                                       23

<210> SEQ ID NO 82
<211> LENGTH: 23
<212> TYPE: DNA
<213> ORGANISM: Mus sp.

<400> SEQUENCE: 82
gagttagagc agaagaagaa agg                                       23

<210> SEQ ID NO 83
<211> LENGTH: 23
<212> TYPE: DNA
<213> ORGANISM: Mus sp.

<400> SEQUENCE: 83
gggtgggggg agtttgctcc tgg                                       23

<210> SEQ ID NO 84
```

```
<211> LENGTH: 23
<212> TYPE: DNA
<213> ORGANISM: Mus sp.

<400> SEQUENCE: 84
ggatggaggg agtttgctcc tgg                                              23

<210> SEQ ID NO 85
<211> LENGTH: 23
<212> TYPE: DNA
<213> ORGANISM: Mus sp.

<400> SEQUENCE: 85
gggagggtgg agtttgctcc tgg                                              23

<210> SEQ ID NO 86
<211> LENGTH: 23
<212> TYPE: DNA
<213> ORGANISM: Mus sp.

<400> SEQUENCE: 86
cgggggaggg agtttgctcc tgg                                              23

<210> SEQ ID NO 87
<211> LENGTH: 23
<212> TYPE: DNA
<213> ORGANISM: Mus sp.

<400> SEQUENCE: 87 ggggaggga agtttgctcc tgg                                               23

<210> SEQ ID NO 88
<211> LENGTH: 23
<212> TYPE: DNA
<213> ORGANISM: Mus sp.

<400> SEQUENCE: 88
gcagatgtag tgtttccaca ggg                                              23

<210> SEQ ID NO 89
<211> LENGTH: 23
<212> TYPE: DNA
<213> ORGANISM: Mus sp.

<400> SEQUENCE: 89
acatatgtag tatttccaca ggg                                              23

<210> SEQ ID NO 90
<211> LENGTH: 23
<212> TYPE: DNA
<213> ORGANISM: Mus sp.

<400> SEQUENCE: 90
ccagatgtag tattcccaca ggg                                              23

<210> SEQ ID NO 91
<211> LENGTH: 23
<212> TYPE: DNA
<213> ORGANISM: Mus sp.

<400> SEQUENCE: 91
ctagatgaag tgcttccaca tgg                                              23
```

```
<210> SEQ ID NO 92
<211> LENGTH: 20
<212> TYPE: DNA
<213> ORGANISM: Mus sp.

<400> SEQUENCE: 92
ggcctgcttc gtggcaatgc                                               20

<210> SEQ ID NO 93
<211> LENGTH: 20
<212> TYPE: DNA
<213> ORGANISM: Mus sp.

<400> SEQUENCE: 93
acctgggcca gggagggagg                                               20

<210> SEQ ID NO 94
<211> LENGTH: 20
<212> TYPE: DNA
<213> ORGANISM: Mus sp.

<400> SEQUENCE: 94
ctcacttaga ctttctctcc                                               20

<210> SEQ ID NO 95
<211> LENGTH: 20
<212> TYPE: DNA
<213> ORGANISM: Mus sp.

<400> SEQUENCE: 95
ctcggagtct agctcctgca                                               20

<210> SEQ ID NO 96
<211> LENGTH: 20
<212> TYPE: DNA
<213> ORGANISM: Mus sp.

<400> SEQUENCE: 96
tggccccagt ctctcttcta                                               20

<210> SEQ ID NO 97
<211> LENGTH: 20
<212> TYPE: DNA
<213> ORGANISM: Mus sp.

<400> SEQUENCE: 97
cagcctctga acagctcccg                                               20

<210> SEQ ID NO 98
<211> LENGTH: 20
<212> TYPE: DNA
<213> ORGANISM: Mus sp.

<400> SEQUENCE: 98
tgacttggcc tttgtaggaa                                               20

<210> SEQ ID NO 99
<211> LENGTH: 20
<212> TYPE: DNA
<213> ORGANISM: Mus sp.

<400> SEQUENCE: 99
gaggctactg aaacataagt                                               20
```

```
<210> SEQ ID NO 100
<211> LENGTH: 20
<212> TYPE: DNA
<213> ORGANISM: Mus sp.

<400> SEQUENCE: 100
tgctacctgt acatctgcac                                       20

<210> SEQ ID NO 101
<211> LENGTH: 20
<212> TYPE: DNA
<213> ORGANISM: Mus sp.

<400> SEQUENCE: 101
catcaatgat tgggcatttc                                       20

<210> SEQ ID NO 102
<211> LENGTH: 20
<212> TYPE: DNA
<213> ORGANISM: Mus sp.

<400> SEQUENCE: 102
actccagtcc caaatatgta                                       20

<210> SEQ ID NO 103
<211> LENGTH: 20
<212> TYPE: DNA
<213> ORGANISM: Mus sp.

<400> SEQUENCE: 103
actagggggc gctcggccac                                       20

<210> SEQ ID NO 104
<211> LENGTH: 20
<212> TYPE: DNA
<213> ORGANISM: Mus sp.

<400> SEQUENCE: 104
ctgagtcaac tgtaagcatt                                       20

<210> SEQ ID NO 105
<211> LENGTH: 20
<212> TYPE: DNA
<213> ORGANISM: Mus sp.

<400> SEQUENCE: 105
ggccaggtgc agtgattcat                                       20

<210> SEQ ID NO 106
<211> LENGTH: 20
<212> TYPE: DNA
<213> ORGANISM: Mus sp.

<400> SEQUENCE: 106
tcgtgtcatc ttgtttgtgc                                       20

<210> SEQ ID NO 107
<211> LENGTH: 20
<212> TYPE: DNA
<213> ORGANISM: Mus sp.

<400> SEQUENCE: 107
ggcagagccc agcggacact                                       20
```

<210> SEQ ID NO 108
<211> LENGTH: 20
<212> TYPE: DNA
<213> ORGANISM: Mus sp.

<400> SEQUENCE: 108
caaggtgagc ctgggtctgt                                              20

<210> SEQ ID NO 109
<211> LENGTH: 20
<212> TYPE: DNA
<213> ORGANISM: Mus sp.

<400> SEQUENCE: 109
atcactgccc aagaagtgca                                              20

<210> SEQ ID NO 110
<211> LENGTH: 20
<212> TYPE: DNA
<213> ORGANISM: Mus sp.

<400> SEQUENCE: 110
ttgtaggatg tttagcagca                                              20

<210> SEQ ID NO 111
<211> LENGTH: 20
<212> TYPE: DNA
<213> ORGANISM: Mus sp.

<400> SEQUENCE: 111
acttgctctc tttagagaac                                              20

<210> SEQ ID NO 112
<211> LENGTH: 20
<212> TYPE: DNA
<213> ORGANISM: Mus sp.

<400> SEQUENCE: 112
ctcaagcagg ccccgctggt                                              20

<210> SEQ ID NO 113
<211> LENGTH: 20
<212> TYPE: DNA
<213> ORGANISM: Mus sp.

<400> SEQUENCE: 113
ttttggacca aaccttttg                                               20

<210> SEQ ID NO 114
<211> LENGTH: 20
<212> TYPE: DNA
<213> ORGANISM: Mus sp.

<400> SEQUENCE: 114
tgaggttatt tgtccattgt                                              20

<210> SEQ ID NO 115
<211> LENGTH: 20
<212> TYPE: DNA
<213> ORGANISM: Mus sp.

<400> SEQUENCE: 115

-continued

| | |
|---|---|
| taaggggagt atttacacca | 20 |

<210> SEQ ID NO 116
<211> LENGTH: 20
<212> TYPE: DNA
<213> ORGANISM: Mus sp.

<400> SEQUENCE: 116

| | |
|---|---|
| tcaagagcag aaaatgtgac | 20 |

<210> SEQ ID NO 117
<211> LENGTH: 20
<212> TYPE: DNA
<213> ORGANISM: Mus sp.

<400> SEQUENCE: 117

| | |
|---|---|
| cttgcaggga ccttctgatt | 20 |

<210> SEQ ID NO 118
<211> LENGTH: 20
<212> TYPE: DNA
<213> ORGANISM: Mus sp.

<400> SEQUENCE: 118

| | |
|---|---|
| tgtgtgtagg actaaactct | 20 |

<210> SEQ ID NO 119
<211> LENGTH: 20
<212> TYPE: DNA
<213> ORGANISM: Mus sp.

<400> SEQUENCE: 119

| | |
|---|---|
| gatagcagta tgaccttggg | 20 |

<210> SEQ ID NO 120
<211> LENGTH: 20
<212> TYPE: DNA
<213> ORGANISM: Mus sp.

<400> SEQUENCE: 120

| | |
|---|---|
| agcgtgtccg gcgagggcga | 20 |

<210> SEQ ID NO 121
<211> LENGTH: 20
<212> TYPE: DNA
<213> ORGANISM: Mus sp.

<400> SEQUENCE: 121

| | |
|---|---|
| agcgtgtccg gcgagggcga | 20 |

<210> SEQ ID NO 122
<211> LENGTH: 25
<212> TYPE: DNA
<213> ORGANISM: Mus sp.

<400> SEQUENCE: 122

| | |
|---|---|
| cagaatcgga ggacaaaata caaac | 25 |

<210> SEQ ID NO 123
<211> LENGTH: 25
<212> TYPE: DNA
<213> ORGANISM: Mus sp.

<400> SEQUENCE: 123
acgaagcagg ccaacgggga ggaca                                              25

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 124

His His His His His His His His His His
1               5                   10

<210> SEQ ID NO 125
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 125

His His His His His His
1               5

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Arg Arg Arg Arg Arg Arg Arg Arg Arg
1               5

<210> SEQ ID NO 127
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser
            20                  25

<210> SEQ ID NO 128
<211> LENGTH: 133
<212> TYPE: DNA
<213> ORGANISM: Mus sp.

<400> SEQUENCE: 128
gggcgatgcc acctacggca agctgaccct gaagttcatc tgcaccaccg gcaagctgcc     60
cgtgccctgg cccacccctcg tgaccaccct gacctacggc gtgcagtgct tcagccgcta    120
ccccgaccac atg                                                       133

<210> SEQ ID NO 129
<211> LENGTH: 44

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
gggcgatcgg cgtgcagtgc ttcagccgct accccgacca catg            44

<210> SEQ ID NO 130
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
gggcgatgcc acctacggca agctgaccct gaagttcatc tgcaccaccg cgaccacatg    60

<210> SEQ ID NO 131
<211> LENGTH: 131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131
gggcgatgcc acctacggca agctgaccct gaagttcatc tgcacccggc aagctgcccg    60
tgccctggcc cacccctgtg accaccctga cctacggcgt gcagtgcttc agccgctacc   120
ccgaccacat g                                                         131

<210> SEQ ID NO 132
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132
gggcgatgcc acctacggca agctgcccgt gccctggccc accctcgtga ccaccctgac    60
ctacggcgtg cagtgcttca gccgctaccc cgaccacatg                         100

<210> SEQ ID NO 133
<211> LENGTH: 131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 133
gggcgatgcc acctacggca agctgaccct gaagttcatc tgcaccacgc aagctgcccg    60
tgccctggcc cacccctgtg accaccctga cctacggcgt gcagtgcttc agccgctacc   120
ccgaccacat g                                                         131

<210> SEQ ID NO 134
<211> LENGTH: 131
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 134
gggcgatgcc acctacggca agctgaccct gaagttcatc tgcaccaccg gcaagctgcg    60
tgccctggcc caccctcgtg accaccctga cctacggcgt gcagtgcttc agccgctacc   120
ccgaccacat g                                                       131

<210> SEQ ID NO 135
<211> LENGTH: 131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 135
gggcgatgcc acctacggca agctgaccct gaagttcatc tgcaccaccg gcaagctgcc    60
cgccctggcc caccctcgtg accaccctga cctacggcgt gcagtgcttc agccgctacc   120
ccgaccacat g                                                       131

<210> SEQ ID NO 136
<211> LENGTH: 125
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136
gggcgatgcc acctacggca agctgaccct gaagttcatc tggcaagctg cccgtgccct    60
ggcccaccct cgtgaccacc ctgacctacg gcgtgcagtg cttcagccgc taccccgacc   120
acatg                                                              125

<210> SEQ ID NO 137
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
gggcgatgcc acctacggca agctgaccct gaagttcatc tgcaccaccg cgcagtgctt    60
cagccgctac cccgaccaca tg                                            82

<210> SEQ ID NO 138
<211> LENGTH: 131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138
gggcgatgcc acctacggca agctgaccct gaagttcatc tgcaccaccc aagctgcccg    60
tgccctggcc caccctcgtg accaccctga cctacggcgt gcagtgcttc agccgctacc   120
ccgaccacat g                                                       131

<210> SEQ ID NO 139
<211> LENGTH: 135

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 139
gggcgatgcc acctacggca agctgaccct gaagttcatc tgcaccaccg atgcaagctg    60
cccgtgccct ggcccaccct cgtgaccacc ctgacctacg gcgtgcagtg cttcagccgc   120
taccccgacc acatg                                                    135

<210> SEQ ID NO 140
<211> LENGTH: 166
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 140
gggcgatgcc acctacggca agctgaccct gaagttcatc tgcaccaccg gcaagctgac    60
cctgaagttc atctgcacca ccggcaagct gcccgtgccc tggcccaccc tcgtgaccac   120
cctgacctac ggcgtgcagt gcttcagccg ctaccccgac cacatg                  166

<210> SEQ ID NO 141
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 141
gggcgatgcc acctacggca agctgaccct gaagaaatga agaaatgaag aaatgcccgt    60
gccctggccc accctcgtga ccaccctgac ctacggcgtg cagtgcttca gccgctaccc   120
cgaccacatg                                                          130

<210> SEQ ID NO 142
<211> LENGTH: 80
<212> TYPE: DNA
<213> ORGANISM: Mus sp.

<400> SEQUENCE: 142
ggcagaagct ggaagaggaa gggccggagt ctgagcagaa gaagaagggt tcccaccata    60
tcaaccggtg gcgcatcgcc                                               80

<210> SEQ ID NO 143
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
ggcagaagct ggaagaggaa gggccggagt ctgagcagaa gaagggttcc caccatatca    60
accggtggcg catcgcc                                                  77

<210> SEQ ID NO 144
<211> LENGTH: 78
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 144
ggcagaagct ggaagaggaa gggccggagt ctgagcagaa agaagggttc ccaccatatc    60
aaccggtggc gcatcgcc                                                  78

<210> SEQ ID NO 145
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
ggcagaagct ggaagaggaa gggccggagt ctgagagaag ggttcccacc atatcaaccg    60
gtggcgcatc gcc                                                       73

<210> SEQ ID NO 146
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
ggcagaagct ggaagaggaa gggccggagt ctgagcagag aagggttccc accatatcaa    60
ccggtggcgc atcgcc                                                    76

<210> SEQ ID NO 147
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
ggcagaagct ggaagaggaa gggccggagt ctgagaaggg ttcccaccat atcaaccggt    60
ggcgcatcgc c                                                         71

<210> SEQ ID NO 148
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
ggcagaagct ggaagaggaa gggccggagt ctgagcagaa gaaccaccat atcaaccggt    60
ggcgcatcgc c                                                         71

<210> SEQ ID NO 149
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 149
ggcagaagct ggaagaggaa gggccggagt ctagaagggt tcccaccata tcaaccggtg    60
gcgcatcgcc                                                          70

<210> SEQ ID NO 150
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
ggcagaagct ggaagaggaa gggccggagt ctgagcagaa gaagaagggt tcaccatatc    60
aaccggtggc gcatcgcc                                                 78

<210> SEQ ID NO 151
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
ggcagaagct ggaagaggaa gggccggagt ctgagcagaa gggttcccac catatcaacc    60
ggtggcgcat cgcc                                                     74

<210> SEQ ID NO 152
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
ggcagaagct ggaagaggaa gggccggagt ctgagcaggg ttcccaccat atcaaccggt    60
ggcgcatcgc c                                                        71

<210> SEQ ID NO 153
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
ggcagaagct ggaagaggaa gggccggagt ctgagcagaa gaccatatcc caccatatca    60
accggtggcg catcgcc                                                  77

<210> SEQ ID NO 154
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
ggcagaagct ggaagaggaa gggccggagt ctgagcagaa gaccatatcc aaccatatca    60

```
accggtggcg catcgcc                                                   77

<210> SEQ ID NO 155
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
ggcagaagct ggaagaggaa gggccggagt ctgagcagaa gaagaagaag ggttcccacc    60
atatcaaccg gtggcgcatc gcc                                            83

<210> SEQ ID NO 156
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
tcaaggctgt gcagatgctc tgggtgaacc tcatcatgga cacgtttgcc tccctggccc    60
tggccacaga gccacctacg gagactctgc ttctga                              96

<210> SEQ ID NO 157
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
taatacgact cactataggg caaggctgtg cagatgctct gttttagagc tagaaatagc    60

<210> SEQ ID NO 158
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
taatacgact cactataggg ctctgggtga acctcatcag ttttagagct agaaatagca    60

<210> SEQ ID NO 159
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
taatacgact cactataggg aggcaaacgt gtccatgatg gttttagagc tagaaatagc    60

<210> SEQ ID NO 160
<211> LENGTH: 60
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 160
taatacgact cactataggg catggacacg tttgcctccc gttttagagc tagaaatagc    60

<210> SEQ ID NO 161
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
taatacgact cactataggg catggacacg tttgccttcc gttttagagc tagaaatagc    60

<210> SEQ ID NO 162
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
taatacgact cactataggg cacgtttgcc tccctggccc gttttagagc tagaaatagc    60

<210> SEQ ID NO 163
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
taatacgact cactataggg cacgtttgcc ttcctggccc gttttagagc tagaaatagc    60

<210> SEQ ID NO 164
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
taatacgact cactataggg ctctgtggcc agggccaggg gttttagagc tagaaatagc    60

<210> SEQ ID NO 165
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
taatacgact cactataggg ctctgtggcc agggccagga gttttagagc tagaaatagc    60

<210> SEQ ID NO 166
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 166
taatacgact cactataggg tggctctgtg gccagggcca gttttagagc tagaaatagc    60

<210> SEQ ID NO 167
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
taatacgact cactataggg cctggccaca gagccaccta gttttagagc tagaaatagc    60

<210> SEQ ID NO 168
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
taatacgact cactataggg ctacggagac tctgcttctg gttttagagc tagaaatagc    60
```

EFFICIENT DELIVERY OF THERAPEUTIC MOLECULES IN VITRO AND IN VIVO

CROSS REFERENCE TO RELATED APPLICATIONS

This is a national stage filing in accordance with 35 U.S.C. § 371 of PCT/US2015/000109, filed Oct. 9, 2015, which claims the benefit of the priority of U.S. Provisional Patent Application No. 62/062,628, filed Oct. 10, 2014, the contents of each are incorporated herein by reference.

SEQUENCE SUBMISSION

The present application is being filed along with a Sequence Listing in electronic format. The Sequence Listing is entitled "46265_506N01US_Seq_Listing_20JUL2017", was created on Jul. 20, 2017, and is 189,143 bytes in size. The information in the electronic format of the Sequence Listing is part of the present application and is incorporated herein by reference in its entirety.

FIELD OF THE INVENTION

The present invention relates to protein therapeutics including genome-editing. Embodiments are directed to cationic lipid reagents for delivery of proteins that are fused to an anionic molecule. These anionic molecules include, an oligonucleotide, a polynucleotide, negatively supercharged proteins, that contain natural anionic domains, or that natively bind to anionic nucleic acids.

BACKGROUND

Therapeutic proteins including peptide hormones, cytokines, and monoclonal antibodies have achieved widespread success as research tools and are among the fastest growing classes of drugs. Many powerful and potentially therapeutic proteins have been discovered or engineered over the past two decades, including enzymes capable of metabolic complementation (Hartung, S. D. et al. *Gene. Mol. Ther.* 9, 866-875 (2004)), neutralizing antibodies against intracellular targets (Wang, J. et al. *Nat. Biotechnol.* 26, 901-908 (2008)), engineered transcription factors (Urnov, F. D., et al. *Nat. Rev. Genet.* 11, 636-646 (2010)), and programmable genome-editing enzymes (Sander, J. D. & Joung, J. K. *Nat. Biotechnol.* 32, 347-355 (2014); Gaj, T., et al. *Trends Biotechnol.* 31, 397-405 (2013)). While protein biologics have proven effective for extracellular targets, their use to address intracellular targets is comparatively undeveloped due to the inability of most proteins to spontaneously enter mammalian cells. Enabling exogenous proteins to access intracellular targets is most commonly achieved by delivery of their encoding DNA sequences through chemical transfection (Midoux, P., et al. *Br. J. Pharmacol.* 157, 166-178 (2009)), electroporation (Bodles-Brakhop, A. M., et al. *Mol. Ther.* 17, 585-592 (2009)), or viral delivery (Kay, M. A., et al. *Nat. Med.* 7, 33-40 (2001)). The introduction of exogenous DNA into cells, however, raises the possibility of permanent recombination into the genome, potential disruption of endogenous genes, and long-term exposure to the encoded agent. For some research or therapeutic applications, including genome editing applications that seek to effect a one-time, permanent modification of genomic DNA, the The recent development of methods to deliver in vitro transcribed mRNAs or mRNA analogs has offered an alternative to DNA delivery without requiring nuclear transport of an encoding gene, and with greatly reduced potential for genomic insertion of the foreign nucleic acid. While promising, mRNA delivery continues to face challenges including immunogenicity and RNA stability. While chemical modifications and the inclusion of base analogs can mitigate some of these issues, the large-scale production of high-quality modified mRNAs remains a challenge (Zangi, L. et al. *Nat. Biotechnol.* 31, 898-907 (2013)). Moreover, proteins containing important natural or synthetic post-translational modifications may not be amenable to production by endogenous translation machinery. Therefore, while both DNA and mRNA delivery have become powerful research tools with therapeutic implications, the development of effective and general protein delivery methods remains an important challenge for the molecular life sciences.

Current or conventional protein delivery technologies are based on fusion or conjugation to cationic molecules that facilitate endocytosis, such as unstructured peptides (Wadia, J. S., et al. *Nat. Med.* 10, 310-315 (2004); Daniels, D. S. & Schepartz, A. *J. Am. Chem. Soc.* 129, 14578-14579 (2007)) or engineered superpositively charged proteins (Cronican, J. J. et al. *ACS Chem. Biol.* 5, 747-752 (2010); Thompson, D. B., et al. *Methods Enzymol.* 503, 293-319 (2012); Thompson, D. B., et al. *Chem. Biol.* 19, 831-843 (2012)). While such delivery can be effective in cell culture, and has even shown some success in vivo, cationic protein-based delivery methods have not seen widespread adoption. Unprotected proteins can be rapidly degraded by extracellular and endosomal proteases (Heitz, F., et al. *Br. J. Pharmacol.* 157, 195-206 (2009)), or neutralized by binding to serum proteins, blood cells, and the extracellular matrix (Caron, N. J. et al. *Mol. Ther. J. Am. Soc. Gene Ther.* 3, 310-318 (2001); Chesnoy, S. & Huang, L. *Annu. Rev. Biophys. Biomol. Struct.* 29, 27-47 (2000)). In addition, the low efficiency of endosomal escape and avoidance of lysosomal degradation are major challenges to all endocytic protein delivery strategies, as evidenced by ongoing interest in endosome altering (Thompson, D. B., et al. *Chem. Biol.* 19, 831-843 (2012); Al-Taei, S. et al. *Bioconjug. Chem.* 17, 90-100 (2006)) and destabilizing strategies (Shete, H. K., *J. Nanosci. Nanotechnol.* 14, 460-474 (2014)). These challenges have proven especially difficult in vivo (Aguilera, T. A., et al. *Integr. Biol. Quant. Biosci. Nano Macro* 1, 371-381 (2009)).

Nucleic acid delivery has benefited greatly from the development of liposomal reagents over the past two decades. Cationic lipid formulations have enabled DNA and RNA transfection to become a routine technique in basic research and have even been used in clinical trials (Coelho, T. et al. *N Engl. J. Med.* 369, 819-829 (2013)). The lipid bilayer of the vehicle protects encapsulated nucleic acids from degradation and can prevent neutralization by antibodies (Judge, A. D., et al. *Mol. Ther. J. Am. Soc. Gene Ther.* 13, 494-505 (2006)). Importantly, fusion of liposomes with the endosomal membrane during endosome maturation can enable the efficient endosomal escape of cationic lipid-delivered cargo (Basha, G. et al. *Mol. Ther. J. Am. Soc. Gene Ther.* 19, 2186-2200 (2011)). More advanced reversibly ionizable lipid nanoparticles enable efficient encapsulation and delivery of nucleic acids, while avoiding non-specific electrostatic interactions and sequestration (Semple, S. C. et al. *Nat. Biotechnol.* 28, 172-176 (2010)).

Because proteins, in contrast to nucleic acids, are chemically diverse with no dominant electrostatic property, no lipid formulation is likely to drive the efficient delivery of all proteins into mammalian cells. While proteins can be encapsulated non-specifically and delivered by rehydrated lipids in vitro (Boeckle, S., et al. *J. Control. Release Off. J.*

Control. Release Soc. 112, 240-248 (2006); Allen, T. M. & Cullis, P. R. Adv. Drug Deliv. Rev. 65, 36-48 (2013)), the efficacy of encapsulation is dependent on protein concentration, is generally inefficient (Zelphati, O. et al. *J. Biol. Chem.* 276, 35103-35110 (2001)), and has not seen widespread application. Specialty commercial reagents developed specifically for protein delivery (Adrian, J. E. et al. *J. Control. Release Off. J. Control. Release Soc.* 144, 341-349 (2010); Morris, M. C., et al. *Nat. Biotechnol.* 19, 1173-1176 (2001)) have also failed to garner popularity perhaps due to their low potency and unreliability with a variety protein cargoes (Colletier, J.-P., et al. *BMC Biotechnol.* 2, 9 (2002)).

SUMMARY

Embodiments of the invention are directed to compositions comprising therapeutically effective anionically charged molecules and compositions for their efficient and specific delivery in vitro and in vivo.

In some embodiments, a composition comprises a cationic lipid encapsulating one or more chimeric molecules comprising one or more proteins or peptides fused, complexed or linked to one or more anionic molecules. In some embodiments, a composition comprises a cationic lipid encapsulating one or more chimeric molecules comprising at least one protein, peptide, polynucleotide, oligonucleotide or combinations thereof, fused, complexed or linked to one or more anionic molecules. These one or more anionic molecules confer an overall net negative charge to the chimeric molecule and comprise one or more anionic domains or bind to an anionic nucleic acid domain. In some embodiments, the anionic molecules comprise: oligonucleotides, polynucleotides, proteins, peptides, peptide nucleic acids (PNA), synthetic molecules or combinations thereof. In some embodiments, the oligonucleotides or polynucleotides comprise: ribonucleic acids (RNA), deoxyribonucleic acids (DNA), synthetic RNA or DNA sequences, modified RNA or DNA sequences, complementary DNA (cDNA), short guide RNA (sgRNA), interference RNA, mRNA, nucleic acid sequences comprising one or more modified nucleobases or backbones, or combinations thereof.

In embodiments, the one or more proteins or peptides are cationic, anionic or are neutrally charged. In some embodiments, the proteins or peptides comprise: enzymes, hormones, chemotherapeutic agents, immunotherapeutic agents, gene editing agents, synthetic molecules or combinations thereof. In some embodiments, the gene editing agents comprise: transcriptional activators, transcriptional repressors, transcription factors, enhancer modulating molecules, recombinases, nucleases, nucleic acid binding-proteins, nucleic acid binding-polynucleotides or oligonucleotides, DNA-binding proteins or DNA-binding nucleic acids, or combinations thereof.

In other embodiments, methods of treatment comprises administering a therapeutically effective amount of a cationic lipid encapsulating one or more chimeric molecules comprising one or more proteins or peptides fused, complexed or linked to one or more anionic molecules.

Other aspects are described infra.

BRIEF DESCRIPTION OF THE DRAWINGS

(FIG. 1A) Recombinases, transcriptional-activator-like effector (TALE) proteins, and Cas9 endonucleases bind nucleic acids and are natively cationic (net theoretical charges are shown in black) and are not efficiently complexed with cationic lipids. These proteins can be rendered highly anionic, however, by fusion to either a supernegatively charged protein such as (−30)GFP, or by complexation with polyanionic nucleic acids. (FIG. 1B) It was envisioned that cationic lipids commonly used to transfect DNA and RNA would complex with the resulting highly anionic proteins or protein:nucleic acid complexes, mediating their delivery into mammalian cells.

FIG. 2A is a schematic representation showing the fusion of either highly cationic (+36)GFP or highly anionic (−30)GFP to Cre recombinase. A HeLa reporter cell line was used that expresses DsRed upon Cre-mediated recombination to evaluate Cre delivery efficiency. FIG. 2B is a scan of a photograph showing HeLa dsRed cells treated with 10 nM (−30)GFP-Cre and the cationic lipid RNAiMAX. Cells were visualized after incubation for 48 hours in media containing 10% fetal bovine serum (FBS). FIG. 2C is a graph showing delivery of (+36)GFP-Cre in 10% FBS media or in serum-free media, and (−30)GFP-Cre with or without the cationic lipid RNAiMAX (0.8 µL) in full-serum media. FIG. 2D is a graph showing the effect of cationic lipid dose on functional (−30)GFP-Cre delivery efficacy after 48 h. FIG. 2E is a graph showing the comparison of several commercially available cationic lipids and polymers for functional delivery efficacy of (−30)dGFP-Cre. FIG. 2F is a graph showing RNAiMAX-mediated delivery of multiple anionic peptide or protein sequences fused to Cre. The net theoretical charge of the VP64 activation domain and the 3×FLAG tag is −22 and −7, respectively. All experiments were performed in 48-well plate format using 275 µL DMEM with 10% FBS and no antibiotics. Error bars reflect s.d. from three biological replicates performed on different days.

FIG. 3A is a schematic representation showing the design of an 18.5-repeat TALE activator fused C-terminally to a VP64 activation domain and N-terminally to (−30)GFP and an NLS. The overall net theoretical charge of the fusion is −43. FIG. 3B is a graph showing the activation of NTF3 transcription by traditional transfection of plasmids encoding TALE-VP64 activators that target sites in the NTF3 gene, or by RNAiMAX cationic lipid-mediated delivery of the corresponding NTF3-targeting (−30)GFP-TALE-VP64 proteins. For protein delivery experiments, 25 nM VEGF TALE, 25 nM NTF3 TALE 1, or 25 nM NTF3 TALEs 1-5 (5 nM each) were delivered with 1.5 µL RNAiMAX in 275 µL DMEM-FBS without antibiotics for 4 hours before being harvested. For plasmid transfections, a total of 700 ng of one or all five NTF3 TALE expression plasmids (140 ng each) were transfected with 0.8 µL Lipofectamine 2000 and harvested 48 hours later. Gene expression levels of harvested cells were measured by qRT-PCR and are normalized to GAPDH expression levels. Incubation times for TALE activators by plasmid transfection and protein delivery were those found to give maximal increases in NTF3 mRNA levels. Error bars reflect s.d. from three biological replicates performed on different days.

FIG. 4A is a graph showing the cationic lipid-mediated delivery of Cas9 protein variants complexed with an EGFP-targeting sgRNA or a VEGF-targeting sgRNA to U2OS EGFP reporter cells, using 100 nM of either (−30)dGFP-Cas9 or regular Cas9 protein with 250 nM or 100 nM EGFP sgRNA, respectively, and 0.8 μL RNAiMAX. Results are compared to that of standard transfection of Cas9 and sgRNA expression plasmids, using 0.8 μL Lipofectamine 2000. FIG. 4B is a blot showing the results from the T7 endonuclease I (T7EI) assay to measure modification of EGFP from no treatment (lane 1), treatment with EGFP-targeting sgRNA alone (lane 2), Cas9 protein alone (lane 3), Cas9 protein+VEGF-targeting sgRNA+RNAiMAX (lane 4), transfection of plasmids expressing Cas9 and EGFP-targeting sgRNA (lane 5), or Cas9 protein+EGFP-targeting sgRNA+RNAiMAX (lane 6). FIG. 4C is a blot showing the results from a T7EI assay of genome modification at EGFP and three endogenous genes with a single delivery of Cas9 complexed with four sgRNAs and RNAiMAX was performed 48 hours after each treatment. Indel efficiencies calculated by densitometry are shown below the gel image. FIG. 4D is a graph showing the delivery of Cas9 D10A nickase and pairs of sgRNAs either by plasmid transfection or by RNAiMAX-mediated protein: sgRNA complex delivery under conditions described in FIG. 4A. EGFP-disrupting sgRNAs GFP g1+GFP g5, or GFP g3+GFP g7, are expected to result in gene disruption, while GFP g5+GFP g7 target the same strand and are therefore expected to be non-functional. FIG. 4E is a graph showing the delivery of catalytically dead (dCas9)-VP64 transcriptional activators that target NTF3 either by plasmid transfection or RNAiMAX-mediated protein delivery. Delivery of both VEGF g3 and VEGF g5 sgRNAs served as a negative control for NTF3 gene activation. All experiments were performed in 48-well format using 275 μL DMEM-FBS without antibiotics. Error bars reflect s.d. from six biological replicates performed on different days.

FIG. 5A is a blot from a T7EI assay which was performed for on-target modification of endogenous CLTA, EMX, and VEGF genes in HEK293T cells. FIGS. 5B, 5C and 5D are graphs showing the on-target:off-target DNA modification ratio resulting from Cas9:sgRNA for plasmid transfection or cationic lipid-mediated protein:sgRNA delivery. The conditions for each treatment were adjusted to result in ~10% on-target cleavage, enabling a comparison of DNA cleavage specificity between the two delivery methods under conditions in which on-target gene modification efficiencies are comparable. P values for a single biological replicate are listed in Table 2. Each on- and off-target sample was sequenced once with >10,000 sequences analyzed per on-target sample and an average of >111,000 sequences analyzed per off-target sample (Table 2). All protein:sgRNA deliveries and plasmid transfections were performed in 24-well format using 1.6 μL RNAiMAX in 550 μL DMEM-FBS without antibiotics. Error bars reflect s.d. from three biological replicates performed on different days.

FIG. 6A: The scala media (cochlear duct) of P0 floxP-tdTomato mice (n=4) were injected with 0.3 μL of 23 nM (−30)GFP-Cre in 50% RNAiMAX or with RNAiMAX alone (control). After 5 days, tdTomato expression indicative of Cre-mediated recombination was visualized using immunohistology. Red=tdTomato; green=Myo7a; white=Sox2; blue=DAPI. Yellow brackets indicate the outer hair cell (OHC) region. FIG. 6B: Ten days after (−30)GFP-Cre delivery, intact espin (Esp)-expressing stereocilia of tdTomato-positive outer hair cells were present (arrow), similar to stereocilia in control cochlea. Red=tdTomato; green=Esp; white=Sox2; blue=DAPI. FIG. 6C: Identical to FIG. 6A except using Lipofectamine 2000 instead of RNAiMAX. (n=4). The upper and lower panels are images of mice cochlea at low and high magnification, respectively, detailing the efficiency of delivery as well as the effect on cochlear architecture and hair cell loss. FIG. 6D: The scala media (cochlear duct) of P2 Atoh1-GFP mice (n=3) were injected with 0.3 μL of 33 μM Cas9, 33 μM EGFP sgRNA in 50% RNAiMAX or Lipofectamine 2000 undiluted commercial solution. Cas9-mediated gene disruption results in the loss of GFP expression when visualized 10 days later. The upper panels show GFP signal only, while lower panels include additional immunohistological markers. Yellow boxes in the lower panels highlight hair cells that have lost GFP expression. Comparing to FIG. 6C, no obvious OHC loss was observed in the Cas9+RNAiMax or Cas9+Lipofectamine 2000 delivery groups. Red=tdTomato; green=Myo7a; white/light blue=Sox2; blue=DAPI. All scale bars, shown in white, are 10 μm.

FIG. 7A is a graph showing the optimization of (−30)GFP-Cre delivery in BSR-TdTomato cells, a second reporter cell line used for measuring Cre recombination efficiency. FIG. 7B is a graph showing the optimization of Cre expression plasmid transfection in HeLa DsRed reporter cells by varying both plasmid dose and Lipofectamine 2000 dose and measuring the presence of DsRed fluorescent cells 48 hours after transfection by FACS. Based on these results, 500 ng of Cre expression plasmid was chosen for 48-well format experiments using 275 μL of DMEM-FBS without antibiotics. FIG. 7C is a graph showing the effect of RNAiMAX dosage on (−30)GFP-Cre recombination efficiency in HeLa dsRed reporter cells and corresponding toxicity as measured by FACS using the TO-PRO-3 live/dead stain (Life Technologies). FIG. 7D is a graph showing the effect of Lipofectamine 2000 dosage on transfected Cre plasmid DsRed recombination efficiency and corresponding toxicity as measured by FACS using the TO-PRO-3 live/dead stain. For FIGS. 7A-7D, error bars reflect s.d. from three biological replicates performed on different days.

FIG. 8A: Quantification of GFP fluorescence from cells treated with either (−30)GFP-Cre and RNAiMAX or (+36)GFP-Cre after washing cells with PBS+heparin (20 U/mL) to remove unbound protein. FIG. 8B: Functional Cre recombinase delivery efficiency of (−30)GFP-Cre+1.5 μL RNAiMAX relative to Cre recombinase delivery efficiency arising from fusion with (+36)GFP. FIG. 8C: Comparison of mCherry uptake by (−30)GFP-fusion+1.5 μM RNAiMAX treatment versus (+36)GFP fusion by measuring mean mCherry fluorescence of total cell population 48 h after treatment and washing cells with PBS+heparin. FIG. 8D: Total cellular GFP fluorescence of (−30)GFP-Cre or (+36)GFP-Cre in the presence or absence of RNAiMAX. Data shown reflects a single biological replicate.

FIG. 9A: HEK293T cells were treated with either NTF3 TALE plasmid by transfection of by liposomal delivery of NTF3 TALE proteins. Cells were harvested after empirically determined optimal incubation time for both treatments and analyzed by qRT-PCR for mRNA levels of NTF3. FIG. 9B: Time course of TALE activation for protein delivery and plasmid transfection by measuring NTF3 mRNA levels and then normalizing each method to the highest activation value achieved over any time point for that method. Optimal protein (25-50 nM) and lipid dosage (1.5 μL RNAiMAX) was chosen for comparison of two delivery techniques in FIG. 3B. All protein-delivery and transfection experiments were performed in a 48-well plate with 275 μL DMEM-FBS without antibiotics. Error bars reflect s.d. from six biological replicates performed on different days.

FIG. 10A is a schematic of EGFP disruption in U2OS cells by NHEJ induced by Cas9 double-stranded breaks. FIG. 10B: Delivery of EGFP-targeting sgRNA or an off-target sgRNA complexed with (−30)dGFP-Cas9 using RNAiMAX along with a plasmid transfection positive control (orange). FIG. 10C: Confirmation that disruption of EGFP fluorescence is not a result of cellular toxicity by treating samples with the TO-PRO-3 live/dead stain (Life Technologies, Carlsbad Calif.) and analyzing the resulting cells by flow cytometry. FIG. 10D: Testing the TO-PRO-3 stain by addition of a cell permeabilizing, but not completely membrane lysing, detergent (0.5% Tween).

FIG. 11A is a graph showing the optimization of transfection efficiency for Cas9 expression plasmid in U2OS EGFP reporter cell line was performed by varying both the amount of Cas9 plasmid and the dose of Lipofectamine 2000. Input sgRNA expression plasmid was held constant at 250 ng input DNA for all treatments. All treatments were performed in a 48-well plate with 275 μL DMEM-FBS without antibiotics. After 48 hours, cells were assayed for loss of eGFP by FACS. FIG. 11B is a graph measuring toxicity of various Cas9 plasmid/Lipofectamine 2000 transfection conditions after 48 hours using TO-PRO-3 live/dead stain and quantifying cellular toxicity by FACS. From FIGS. 11A and 11B a Cas9 plasmid dose of 750 ng and a Lipofectamine 2000 dose of 0.8 μL were chosen as plasmid transfection conditions that resulted in maximal gene disruption for the remaining studies in this work. For FIGS. 11A and 11B, error bars reflect s.d. from three biological replicates performed on different days.

FIGS. 12A-12D are graphs showing the optimization of Cas9:sgRNA functional delivery. FIG. 12A: Cationic lipid-mediated delivery efficiency of two tested constructs showing that the more anionic (−30)dGFP-NLS-Cas9 facilitates more efficient delivery at low protein and sgRNA concentrations compared with native Cas9. FIG. 12B: Delivery optimization of (−30)dGFP-NLS-Cas9 as a function of protein and sgRNA concentration. FIG. 12C: Delivery of Cas9 protein without any fusions or tags as a function of protein and sgRNA concentration. FIG. 12D: Optimal sgRNA to protein ratio for RNAiMAX-mediated delivery of (−30)dGFP-NLS-Cas9 and native Cas9. All experiments were performed in a 48-well plate using a volume of 275 μL DMEM-FBS without antibiotics and EGFP gene disruption was measured by FACS. For FIGS. 12A-12C, error bars reflect s.d. from three biological replicates performed on different days.

FIGS. 13A-13C are graphs showing the effect of the NLS and/or (−30)dGFP on functional Cas9 delivery as a function of both sgRNA and Cas9 concentration. EGFP gene disruption in U2OS EGFP reporter cell line was measured at three fixed sgRNA concentrations: FIG. 13A: 10 nM, FIG. 13B: 25 nM, and FIG. 13C: 50 nM, along with varying protein concentrations shown in the graphs. Delivery was performed using 0.8 μL RNAiMAX in 48-well format using 275 μL DMEM-FBS without antibiotics and assayed by FACS 48 hours later for loss of eGFP fluorescence signal. For FIGS. 13A-13C, error bars reflect s.d. from three biological replicates performed on different days.

FIG. 14A: EGFP gene disruption at different Cas9 protein concentrations and a constant dose of 100 nM EGFP sgRNA in U2OS EGFP reporter cells treated with either 0.8 μL of RNAiMAX or 0.8 μL Lipofectamine 2000. After 16 hours, media was removed and fresh media was added to cells until end point of assay 48 hours post protein delivery treatment. The live cell population was determined by FACS using TO-PRO-3 live/dead stain. FIG. 14B: Toxicity profile for Cas9:sgRNA delivery to U2OS cells as a function of Lipofectamine 2000 dose. FIG. 14C: Toxicity profile for U2OS cells as a function of RNAiMAX dose. FIG. 14D: Cellular toxicity for a broad range of Cas9:sgRNA treatments using 1:1 protein:sgRNA delivery conditions at optimal doses of RNAiMAX or Lipofectamine 2000 by TO-PRO-3 live/dead stain and FACS. Dose of RNAiMAX and Lipofectamine 2000 were both 0.8 μL in a volume of 275 μL in a 48-well plate format. For FIGS. 14A-14D, error bars reflect s.d. from three biological replicates performed on different days.

FIG. 15A: HEK293T cells were treated with dCas9-VP64 activator at varying protein concentrations and a mixture of all six NTF3-targeting sgRNAs for 12 hours using 0.8 μL RNAiMAX in 275 μL DMEM-FBS without antibiotics in a 48-well plate format. NTF3 mRNA levels were determined by qRT-PCR and normalized to those of GAPDH. Total sgRNA concentrations are listed (each sgRNA is present at one-sixth of the listed total concentration). FIG. 15B: Time course for NTF3 gene activation by protein:sgRNA delivery and plasmid transfection. NTF3 mRNA levels were measured at several time points using all six sgRNAs either from expression plasmids (in the case of the dCas9-VP64 activator plasmid transfection treatment), or as in vitro transcribed sgRNAs complexed with 100 nM dCas9-VP64 activator and cationic lipids (in the case of protein:sgRNA delivery). For FIGS. 15A and 15B, error bars reflect s.d. from six biological replicates performed on different days.

FIG. 16A: On-target and off-target indel frequencies for the CLTA gene. FIG. 16B: On-target and off-target indel frequencies for the EMX gene. FIG. 16C: On-target and off-target indel frequencies for the VEGF gene. Each on- and off-target sample was sequenced once with >10,000 sequences analyzed per on-target sample and an average of >111,000 sequences analyzed per off-target sample (Table 2). For FIGS. 16A-16C, error bars reflect s.d. from three biological replicates performed on different days.

FIG. 17A: Indel modification frequencies measured by high-throughput sequencing for VEGF on- and off-target sites at varying doses of Cas9:sgRNA. FIG. 17B: On-target:off-target specificity ratio at different Cas9:sgRNA concentrations. FIG. 17C: Comparison of on-target:off target specificity ratio for protein delivery and plasmid transfection at VEGF off-target site #1 as a function of on-target indel modification frequency at a range of modification frequencies for both treatments (~1% to ~40% indel modification frequency). FIGS. 17D, 17E, 17F: Same as FIG. 17C for VEGF off-target sites #2, #3, and #4. Each on- and off-target sample was sequenced once with >10,000 sequences analyzed per on-target sample and an average of >111,000 sequences analyzed per off-target sample. All data shown were from a single biological replicate.

FIG. 19A: FACS showing Alexa647 fluorescence of cells treated with 50 nM Alexa647-conjugated Cas9 and 100 nM EGFP sgRNA, or of untreated cells. FIG. 19B: U2OS EGFP reporter cells were treated with 50 nM Alexa647-conjugated Cas9 protein, 100 nM sgRNA EGFP1, and 0.8 µL of Lipofectamine 2000. After a 4-hour incubation at 37° C., cells were washed extensively with PBS containing 20 U/mL of heparin to remove electrostatically-bound cationic lipid complexes, and then trypsinized. In a plate reader (Tecan M1000 Pro) with fluorescence excitation at 650 nm and emission at 665 nm, wells each containing 10,000 Cas9-Alexa647-treated cells were measured for whole population fluorescence. Standard curves were established by measuring the fluorescence of known quantities of Cas9-Alexa647 in either DMEM containing 10% FBS, or in a suspension of trypsinized U2-OS cells at 10,000 cells per well, with protein either diluted directly, or pre-complexed with 0.8 µL Lipofectamine 2000 then diluted. A two-fold serial dilution starting from 50 pmol to 0.048 pmols was performed to generate the standard curve samples. Values for 0.048 pmol to 3.125 pmol are shown. The intersection of the dotted black lines shows the measured total Alexa647 fluorescence of 10,000 cells treated with 50 nM Alexa647-conjugated Cas9 and 100 nM EGFP sgRNA and washed as described above. 50 nM Cas9-Alexa647-treated cells showed a total cell-associated Alexa647-labeled protein signal of 0.5 pmol per well. This quantity represents 4% of the input protein in the Cas9-Alexa647:sgRNA treatment, and corresponds to $(6.02 \times 10^{23}) \cdot 5.0 \times 10^{-13}$ moles Cas9-Alexa647/10,000 cells per well=$3 \times 10^7$ molecules of Cas9-Alexa647 per cell. Assuming a total protein content per cell of roughly $7.9 \times 10^9$ molecules (estimate from *Molecular Cell Biology*, Section 1.2, $4^{th}$ edition), internalized Cas9-Alexa647 represented 0.4% of total cellular protein. All values shown are the average of three technical replicates.

FIG. 20A: Floating spheres treated with 100 nM Cas9 protein, and 0.8 µL Lipofectamine 2000 but no sgRNA (control) retained strong GFP fluorescence (right), while those treated with 100 nM Cas9:sgRNA and 0.8 µL Lipofectamine 2000 exhibited decreased GFP fluorescence under identical imaging conditions (left). Scale bars are 100 µm. FIG. 20B: After cell attachment, virtually all control progenitor cells were GFP positive (right panels). Cas9:sgRNA treatment led to significant reduction in GFP expression (left panels) and many progenitor cells showed complete GFP knockdown (arrows) after cell attachment. Scale bars are 20 µm. FIG. 20C: T7EI assay on stem cells harvested after imaging confirm cleavage of GFP reporter. Similar gene target modification efficiencies were observed from cationic lipid-mediated Cas9:sgRNA delivery (24%) and from co-transfection of Cas9 and EGFP sgRNA plasmids (20%).

FIG. 21A: Representative examples of genomic DNA sequences at the EGFP on-target locus that are modified following cationic lipid-mediated delivery of Cas9 and EGFP sgRNA in Atoh1-GFP mouse hair cells. For each example shown, the unmodified genomic site is the first sequence, followed by the most abundant eight sequences containing deletions and three sequences containing insertions. The numbers before each sequence indicate sequencing counts. The sgRNA target sites are bold and underlined in green. Insertions and deletions are shown in red. PAM site is shown in blue. FIG. 21B: Identical analysis as in FIG. 21A for EMX on-target site in Atoh1-GFP mouse hair cells. Indels shown here for both the EGFP and EMX genomic loci are from a single biological replicate chosen from a representative set of sequenced samples all showing similar indel profiles.

DETAILED DESCRIPTION

Figures 1A, 1B:
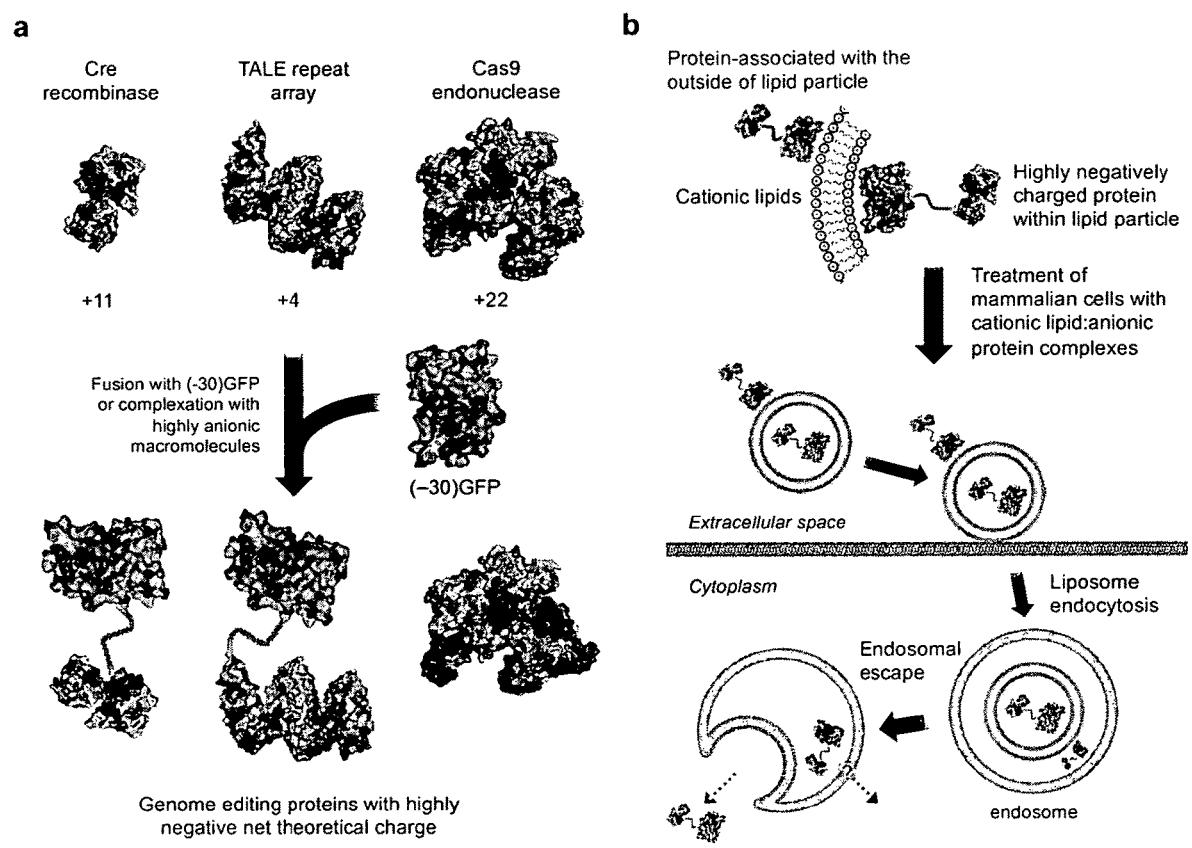
FIGS. 1A, 1B are a schematic representation of an embodiment of a strategy for delivering proteins into mammalian cells by fusion or non-covalent complexation with polyanionic macromolecules and complexation with cationic lipids.

Embodiments of the invention are directed to compositions for the efficient intracellular delivery of proteins to the nucleus or cytoplasm. Conventional methods of protein delivery typically rely on cationic peptides or proteins to facilitate endocytosis, but suffer from low tolerance for serum proteins, poor endosomal escape, and limited in vivo efficacy. Herein, it is reported that cationic lipid reagents can potently deliver proteins that are fused to polynucleotides, oligonucleotides, negatively supercharged proteins, that contain natural anionic domains, or that natively bind to anionic nucleic acids.

The following description of the preferred embodiments is merely exemplary in nature and is in no way intended to limit the invention, its application or uses. Embodiments of the invention may be practiced without the theoretical aspects presented. Moreover, the theoretical aspects are presented with the understanding that Applicants do not seek to be bound by the theory presented.

It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the terms "comprising," "comprise" or "comprised," and variations thereof, in reference to defined or described elements of an item, composition, apparatus, method, process, system, etc. are meant to be inclusive or open ended, permitting additional elements, thereby indicating that the defined or described item, composition, apparatus, method, process, system, etc. includes those specified elements—or, as appropriate, equivalents thereof—and that other elements can be included and still fall within the scope/definition of the defined item, composition, apparatus, method, process, system, etc.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value or range. Alternatively, particularly with respect to biological systems or processes, the term can mean within an order of magnitude within 5-fold, and also within 2-fold, of a value. Where particular values are described in the application and claims, unless otherwise stated the term "about" meaning within an acceptable error range for the particular value should be assumed.

"Optional" or "optionally" means that the subsequently described event or circumstance can or cannot occur, and that the description includes instances where the event or circumstance occurs and instances where it does not.

As used herein, a "chimeric" molecule is one which comprises one or more unrelated types of components or contain two or more chemically distinct regions which can be conjugated to each other, fused, linked, translated, attached via a linker, chemically synthesized, expressed from a nucleic acid sequence, etc. For example, a peptide and a nucleic acid sequence, a peptide and a detectable label, unrelated peptide sequences, and the like. The term "chimeric" molecule is an "anionic" molecule in that one or more "anionic" domains are present and confer an overall net anionic charge to the molecule. For example, the chimeric molecule may have one or more anionic domains, cationic domains, a neutral charge domain, but the charge of the entire molecule is anionic.

As used herein, unless otherwise indicated, the terms "peptide", "polypeptide" or "protein" are used interchangeably herein, and refer to a polymer of amino acids of varying sizes. These terms do not connote a specific length of a polymer of amino acids. Thus, for example, the terms oligopeptide, protein, and enzyme are included within the definition of polypeptide or peptide, whether produced using recombinant techniques, chemical or enzymatic synthesis, or be naturally occurring. This term also includes polypeptides that have been modified or derivatized, such as by glycosylation, acetylation, phosphorylation, and the like.

As used herein, a "nucleic acid" or "nucleic acid sequence" or "cDNA" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs, and refers to nucleic acid sequences in which one or more introns have been removed. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, for instance, DNA which is part of a hybrid gene encoding additional polypeptide sequences.

A "polynucleotide" means a single strand or parallel and anti-parallel strands of a nucleic acid. Thus, a polynucleotide may be either a single-stranded or a double-stranded nucleic acid.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

As used herein, the terms "nucleic acid sequence", "polynucleotide," and "gene" are used interchangeably throughout the specification and include complementary DNA (cDNA), linear or circular oligomers or polymers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like.

The nucleic acid sequences may be "chimeric," that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide. These sequences typically comprise at least one region wherein the sequence is modified in order to exhibit one or more desired properties.

The term "target nucleic acid" refers to a nucleic acid (often derived from a biological sample), to which the oligonucleotide is designed to specifically hybridize. It is either the presence or absence of the target nucleic acid that is to be detected, or the amount of the target nucleic acid that is to be quantified. The target nucleic acid has a sequence that is complementary to the nucleic acid sequence of the corresponding oligonucleotide directed to the target. The term target nucleic acid may refer to the specific subsequence of a larger nucleic acid to which the oligonucleotide is directed or to the overall sequence (e.g., gene or mRNA) whose expression level it is desired to detect. The difference in usage will be apparent from context.

In the present context, the terms "nucleobase" covers naturally occurring nucleobases as well as non-naturally occurring nucleobases. It should be clear to the person skilled in the art that various nucleobases which previously have been considered "non-naturally occurring" have subsequently been found in nature. Thus, "nucleobase" includes not only the known purine and pyrimidine heterocycles, but also heterocyclic analogues and tautomers thereof. Illustrative examples of nucleobases are adenine, guanine, thymine, cytosine, uracil, purine, xanthine, diaminopurine, 8-oxo-N6-methyladenine, 7-deazaxanthine, 7-deazaguanine, N4,N4-ethanocytosin, N6,N6-ethano-2,6-diaminopurine, 5-methylcytosine, 5-(C3-C6)-alkynylcytosine, 5-fluorouracil, 5-bromouracil, pseudoisocytosine, 2-hydroxy-5-methyl-4-triazolopyridin, isocytosine, isoguanin, inosine and the "non-naturally occurring" nucleobases described in Benner et al., U.S. Pat. No. 5,432,272. The term "nucleobase" is intended to cover every and all of these examples as well as analogues and tautomers thereof. Especially interesting nucleobases are adenine, guanine, thymine, cytosine, and uracil, which are considered as the naturally occurring nucleobases in relation to therapeutic and diagnostic application in humans.

As used herein, "nucleoside" includes the natural nucleosides, including 2'-deoxy and 2'-hydroxyl forms, e.g., as described in Kornberg and Baker, DNA Replication, 2nd Ed. (Freeman, San Francisco, 1992).

"Analogs" in reference to nucleosides includes synthetic nucleosides having modified base moieties and/or modified sugar moieties, e.g., described generally by Scheit, Nucleotide Analogs, John Wiley, New York, 1980; Freier & Altmann, Nucl. Acid. Res., 1997, 25(22), 4429-4443, Toulmé, J. J., Nature Biotechnology 19:17-18 (2001); Manoharan M., Biochemica et Biophysica Acta 1489:117-139(1999); Freier S. M., Nucleic Acid Research, 25:4429-4443 (1997), Uhlman, E., Drug Discovery & Development, 3: 203-213 (2000), Herdewin P., Antisense & Nucleic Acid Drug Dev., 10:297-310 (2000),); 2'-O, 3'-C-linked [3.2.0] bicycloarabinonucleosides (see e.g. N. K Christiensen., et al, J. Am. Chem. Soc., 120: 5458-5463 (1998). Such analogs include synthetic nucleosides designed to enhance binding properties, e.g., duplex or triplex stability, specificity, or the like.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type target gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs,) or single base mutations in which the polynucleotide sequence varies by one base. The presence of SNPs may be indicative of, for example, a certain population with a propensity for a disease state, that is susceptibility versus resistance.

As used herein, "variant" of polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan).

Analogous minor variations may also include amino acid deletions or insertions, or both. Guidance in determining which amino acid residues may be substituted, inserted, or deleted without abolishing biological activity may be found using computer programs well known in the art, for example, LASERGENE software (DNASTAR).

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. Accordingly, "treating" or "treatment" of a state, disorder or condition includes: (1) preventing or delaying the appearance of clinical symptoms of the state, disorder or condition developing in a human or other mammal that may be afflicted with or predisposed to the state, disorder or condition but does not yet experience or display clinical or subclinical symptoms of the state, disorder or condition; (2) inhibiting the state, disorder or condition, i.e., arresting, reducing or delaying the development of the disease or a relapse thereof (in case of maintenance treatment) or at least one clinical or subclinical symptom thereof; or (3) relieving the disease, i.e., causing regression of the state, disorder or condition or at least one of its clinical or subclinical symptoms. The benefit to an individual to be treated is either statistically significant or at least perceptible to the patient or to the physician.

The terms "patient" or "individual" or "subject" are used interchangeably herein, and refers to a mammalian subject to be treated, with human patients being preferred. In some cases, the methods of the invention find use in experimental animals, in veterinary application, and in the development of animal models for disease; including, but not limited to, rodents including mice, rats, and hamsters, and primates.

As defined herein, a "therapeutically effective" amount of a compound or agent (i.e., an effective dosage) means an amount sufficient to produce a therapeutically (e.g., clinically) desirable result. The compositions can be administered from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compounds of the invention can include a single treatment or a series of treatments.

As defined herein, an "effective" amount of a compound or agent (i.e., an effective dosage) means an amount sufficient to produce a (e.g., clinically) desirable result.

As used herein, a "pharmaceutically acceptable" component/carrier etc. is one that is suitable for use with humans and/or animals without undue adverse side effects (such as toxicity, irritation, and allergic response) commensurate with a reasonable benefit/risk ratio.

The terms "determining", "measuring", "evaluating", "detecting", "assessing" and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

As used herein, the term "agent" is meant to encompass any molecule, chemical entity, composition, drug, therapeutic agent, chemotherapeutic agent, or biological agent capable of preventing, ameliorating, or treating a disease or other medical condition. The term includes small molecule compounds, antisense reagents, siRNA reagents, antibodies, enzymes, peptides organic or inorganic molecules, natural or synthetic compounds and the like. An agent can be assayed in accordance with the methods of the invention at any stage during clinical trials, during pre-trial testing, or following FDA-approval.

By the term "modulate," it is meant that any of the mentioned activities, are, e.g., increased, enhanced, increased, agonized (acts as an agonist), promoted, decreased, reduced, suppressed blocked, or antagonized (acts as an agonist). Modulation can increase activity more than 1-fold, 2-fold, 3-fold, 5-fold, 10-fold, 100-fold, etc., over baseline values. Modulation can also decrease its activity below baseline values. Modulation can also normalize an activity to a baseline value.

As used herein, the term "kit" refers to any delivery system for delivering materials. Inclusive of the term "kits" are kits for both research and clinical applications. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contain a subportion of the total kit components. The containers may be delivered to the intended recipient together or separately. For example, a first container may contain an enzyme for use in an assay, while a second container contains oligonucleotides or liposomes. The term "fragmented kit" is intended to encompass kits containing Analyte specific reagents (ASR's) regulated under section 520 (e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

General Techniques

For further elaboration of general techniques useful in the practice of this invention, the practitioner can refer to standard textbooks and reviews in cell biology, tissue culture, embryology, and physiology.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

Compositions

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes or gene products disclosed herein, which in some embodiments relate to mammalian nucleic acid and amino acid sequences, are intended to encompass homologous and/or orthologous genes and gene products from other animals including, but not limited to other mammals, fish, amphibians, reptiles, and birds. In preferred embodiments, the genes, nucleic acid sequences, amino acid sequences, peptides, polypeptides and proteins are human.

In some embodiments, a composition comprises a cationic lipid encapsulating one or more chimeric molecules. These chimeric molecules comprise one or more proteins or peptides fused, complexed or linked to one or more anionic molecules. In other embodiments, a chimeric molecule comprises at least one protein, peptide, polynucleotide, oligonucleotide or combinations thereof, fused, complexed or linked to one or more anionic molecules. The anionic molecules can vary as long as they comprise one or more anionic domains or bind to an anionic nucleic acid domain. It is preferred that the anionic molecules confer an overall net negative charge to the chimeric molecule. Without wishing to be bound by theory, it was hypothesized that proteins that are engineered to be highly negatively charged or that are naturally highly anionic may be able to take advantage of the same electrostatics-driven complexation and encapsulation used by cationic liposomal reagents for nucleic acid delivery. While few proteins natively possess the density of negative charges found in the phosphate backbone of nucleic acids, it was speculated that translational fusion to, or non-covalent complexation with, a polyanionic molecule may render the resulting protein or protein complex sufficiently anionic to be efficiently complexed by common cationic lipid reagents. The results for the work, described in the Examples section which follows, showed that delivery efficiency depends on the net charge of the fusion protein, and natively anionic peptide tags such as 3×FLAG and VP64 can also enable lipid-mediated protein delivery.

Accordingly, in some embodiments, the anionic molecules comprise: oligonucleotides, polynucleotides, proteins, peptides, peptide nucleic acids (PNA), synthetic molecules or combinations thereof. In some embodiments, the oligonucleotides or polynucleotides comprise: ribonucleic acids (RNA), deoxyribonucleic acids (DNA), synthetic RNA or DNA sequences, modified RNA or DNA sequences, complementary DNA (cDNA), short guide RNA (sgRNA), a short interfering RNA (siRNA), a micro, interfering RNA (miRNA), a small, temporal RNA (stRNA), a short, hairpin RNA (shRNA), mRNA, nucleic acid sequences comprising one or more modified nucleobases or backbones, or combinations thereof.

The one or more proteins, peptides, polynucleotides, oligonucleotides or combinations thereof, fused, complexed or linked to one or more anionic molecules can possess any charge as long as the overall net charge of the chimeric molecule is anionic. Accordingly, in some embodiments, the proteins, peptides, polynucleotides, oligonucleotides or combinations thereof, are cationic, anionic or are neutrally charged. Examples of proteins or peptides of the chimeric molecule which can be complexed or linked to the polyanionic molecule or domain comprise: enzymes, hormones, chemotherapeutic agents, immunotherapeutic agents, gene editing agents, synthetic molecules or combinations thereof.

In some embodiments, the protein or peptide is a therapeutic agent for delivery to a specific target. The target can be any desired intracellular target. In some embodiments, the target is a nucleic acid sequence or gene. In embodiments where it is desired to manipulate, modulate or edit a gene, the protein or peptide is a gene or genome editing agent. In some embodiments, the gene editing agents comprise: transcriptional activators, transcriptional repressors, transcription factors, enhancer modulating molecules, recombinases, nucleases, nucleic acid binding-proteins, nucleic acid binding-polynucleotides or oligonucleotides, DNA-binding proteins or DNA-binding nucleic acids, or combinations thereof. In some embodiments, the target is a protein or peptide. Accordingly, in some embodiments, the chimeric or anionic molecule comprises one or more gene editing agents, transcriptional modulators, translational modulators, post-translational modulators, and/or modulators that regulate protein expression, function, activity or combinations thereof.

In one embodiment, the chimeric molecule comprises one or more detectable labels, anions, radiolabels, tags, targeting agents, negatively charged proteins or peptides, or combinations thereof. These molecules can be selected based on the user's desired goal, e.g. for diagnostic or research purposes, or to increase the anionic charge, targeting signals and the like. Accordingly, a liposomal formulation for complexing protein and nucleic acid (e.g. transcription factors with their target binding region as oligonucleotides) for inner ear cell types delivery in vivo, is used to treat deafness or associated disorders thereof as the chimeric molecule can be tailored for regeneration (e.g. hair cell and auditory neuron regeneration), repair (e.g. re-establishment of connections between hair cells and neurons for hearing recovery) and prevention (e.g. by protein function of isl1 that prevents hair cell death during aging and noise exposure, thus preserving hearing).

In other embodiments, a chimeric molecule comprises at least one proteins, peptides, polynucleotides, oligonucleotides or combinations thereof, fused, complexed or linked to one or more anionic molecules. Preferably, the one or more anionic molecules comprise one or more anionic domains or bind to an anionic nucleic acid domain. In embodiments, the chimeric molecule comprises an overall net negative charge. In some embodiments, the anionic molecules comprise: oligonucleotides, polynucleotides, proteins, peptides, peptide nucleic acids (PNA), synthetic molecules or combinations thereof. In some embodiments, the oligonucleotides or polynucleotides comprise: ribonucleic acids (RNA), deoxyribonucleic acids (DNA), synthetic RNA or DNA sequences, modified RNA or DNA sequences, complementary DNA (cDNA), short guide RNA (sgRNA), a short interfering RNA (siRNA), a micro, interfering RNA (miRNA), a small, temporal RNA (stRNA), a short, hairpin RNA (shRNA), mRNA, nucleic acid sequences comprising one or more modified nucleobases or backbones, or combinations thereof. The chimeric molecule also comprises one or more proteins or peptides which are cationic, anionic or are neutrally charged. Examples of proteins include without limitation: enzymes, hormones, chemotherapeutic agents, immunotherapeutic agents, genome or gene editing agents, synthetic molecules or combinations thereof. The gene or genome editing agents comprise: transcriptional activators, transcriptional repressors, recombinases, nucleases, DNA-binding proteins or nucleic acids, or combinations thereof. In other embodiments, the chimeric molecule optionally comprises one or more detectable labels, radiolabels, tags, anions, targeting agents or combinations thereof.

In other embodiments, a cationic liposome encapsulates an anionic molecule comprising a proteins, peptides, polynucleotides, oligonucleotides or combinations thereof, complexed, fused or linked to a negatively charged molecule. In some embodiments, the negatively charged molecule comprises oligonucleotides, polynucleotides, proteins, peptides, peptide nucleic acids (PNA), synthetic molecules or combinations thereof. In other embodiments, the polynucleotide or oligonucleotide is a guide RNA. In some embodiments, the protein or peptide is a negatively charged fluorescent protein. In yet other embodiments, the one or more proteins or peptides are cationic, anionic or are neutrally charged. In yet another embodiment, the negatively charged fluorescent protein is fused or linked to one or more proteins or peptides. In some embodiments, the protein or peptide comprises: enzymes, hormones, chemotherapeutic agents, immunotherapeutic agents, gene editing agents, synthetic molecules or combinations thereof. In some embodiments, the gene editing agents comprise: transcriptional activators, transcriptional repressors, transcription factors, enhancer modulating molecules, recombinases, nucleases, nucleic acid binding-proteins, nucleic acid binding-polynucleotides or oligonucleotides, DNA-binding proteins or DNA-binding nucleic acids, or combinations thereof. Examples of these gene editing agents comprise: Cre recombinases, CRISPR/Cas molecules, TALE transcriptional activators, Cas9 nucleases, nickases, transcriptional regulators or combinations thereof. The anionic molecule optionally comprises one or more detectable labels, radiolabels, tags, negatively charged proteins or peptides, anions, targeting agents or combinations thereof.

In some embodiments, a molecule comprises any one or more sequences set forth as SEQ ID NOS: 1 to 19.

In some embodiments, a molecule comprises any one or more sequences set forth as SEQ ID NOS: 1 to 123.

In other embodiments, the liposome comprises one or more cationic lipids, modified lipids or combinations thereof.

In some embodiments, a liposome, for encapsulating one or more molecules embodied herein, comprises a liposome, a nanoliposome, a niosome, a microsphere, a nanosphere, a nanoparticle, a micelle, or an archaeosome.

In some embodiments, a cationic liposome encapsulates one or more anionic molecules. These molecules can be for example, a single entity (e.g. protein, peptide, nucleic acid, etc), a chimeric entity (e.g. a combination of different molecules or types of molecules), molecular complexes, complexed molecules and the like.

In one embodiment, a cationic liposome encapsulating an anionic molecule comprises at least one protein, peptide, polynucleotide, oligonucleotide or combinations thereof, complexed, fused or linked to a negatively charged molecule. In some embodiments, a negatively charged molecule comprises oligonucleotides, polynucleotides, proteins, peptides, peptide nucleic acids (PNA), synthetic molecules or combinations thereof. In some embodiments, a polynucleotide or oligonucleotide is a guide RNA, a transcriptional modulator, translational modulator, post-translational modulator, and/or modulators that regulate protein expression, function, activity or combinations thereof. In one embodiment, the protein or peptide is a negatively charged fluorescent protein. In another embodiment, the one or more proteins or peptides are cationic, anionic or are neutrally charged. Examples include, without limitation: enzymes, hormones, chemotherapeutic agents, immunotherapeutic agents, gene editing agents, synthetic molecules transcriptional modulators, translational modulators, post-translational modulators, and/or modulators that regulate protein expression, function, activity or combinations thereof.

In another embodiment, gene editing agents comprise: transcriptional activators, transcriptional repressors, transcription factors, enhancer modulating molecules, recombinases, nucleases, nucleic acid binding-proteins, nucleic acid binding-polynucleotides or oligonucleotides, DNA-binding proteins or DNA-binding nucleic acids, or combinations thereof. In one embodiments, gene editing agents comprise: Cre recombinases, CRISPR/Cas molecules, TALE transcriptional activators, Cas9 nucleases, nickases, transcriptional regulators or combinations thereof.

In another embodiment, the anionic molecule optionally comprises one or more detectable labels, radiolabels, tags, anions, targeting agents or combinations thereof.

Modified Proteins or Peptides:

Hybrid proteins comprising a polypeptide or fragment thereof may be linked to other types of polypeptides, for example, a negatively supercharged green fluorescent protein in addition to a reporter polypeptide, or in lieu of a reporter polypeptide. These additional polypeptides may be any amino acid sequence useful for the purification, identification, overall charge of the protein or peptide; and/or therapeutic or prophylactic application of the peptide. In addition, the additional polypeptide can be a signal peptide, or targeting peptide, etc.

In some cases, the other additions, substitutions or deletions may increase the stability (including but not limited to, resistance to proteolytic degradation) of the polypeptide or increase affinity of the polypeptide for its appropriate receptor, ligand and/or binding proteins. In some cases, the other additions, substitutions or deletions may increase the solubility of the polypeptide. In some embodiments sites are selected for substitution with a naturally encoded or non-natural amino acid in addition to another site for incorporation of a non-natural amino acid for the purpose of increasing the polypeptide solubility following expression in recombinant host cells. In some embodiments, the polypeptides comprise another addition, substitution, or deletion that modulates affinity for the associated ligand, binding proteins, and/or receptor, modulates (including but not limited to, increases or decreases) receptor dimerization, stabilizes receptor dimers, modulates circulating half-life, modulates release or bio-availability, facilitates purification, or improves or alters a particular route of administration. Similarly, the non-natural amino acid polypeptide can comprise chemical or enzyme cleavage sequences, protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification, transport through tissues or cell membranes, prodrug release or activation, size reduction, or other traits of the polypeptide.

The methods and compositions described herein include incorporation of one or more non-natural amino acids into a polypeptide. One or more non-natural amino acids may be incorporated at one or more particular positions which do not disrupt activity of the polypeptide. This can be achieved by making "conservative" substitutions, including but not limited to, substituting hydrophobic amino acids with non-natural or natural hydrophobic amino acids, bulky amino acids with non-natural or natural bulky amino acids, hydrophilic amino acids with non-natural or natural hydrophilic amino acids) and/or inserting the non-natural amino acid in a location that is not required for activity.

A variety of biochemical and structural approaches can be employed to select the desired sites for substitution with a non-natural amino acid within the polypeptide. Any position of the polypeptide chain is suitable for selection to incorporate a non-natural amino acid, and selection may be based on rational design or by random selection for any or no particular desired purpose. Selection of desired sites may be based on producing a non-natural amino acid polypeptide (which may be further modified or remain unmodified) having any desired property or activity, including but not limited to agonists, super-agonists, partial agonists, inverse agonists, antagonists, receptor binding modulators, receptor activity modulators, modulators of binding to binder partners, binding partner activity modulators, binding partner conformation modulators, dimer or multimer formation, no change to activity or property compared to the native molecule, or manipulating any physical or chemical property of the polypeptide such as solubility, aggregation, or stability. For example, locations in the polypeptide required for biological activity of a polypeptide can be identified using methods including, but not limited to, point mutation analysis, alanine scanning or homolog scanning methods. Residues other than those identified as critical to biological activity by methods including, but not limited to, alanine or homolog scanning mutagenesis may be good candidates for substitution with a non-natural amino acid depending on the desired activity sought for the polypeptide. Alternatively, the sites identified as critical to biological activity may also be good candidates for substitution with a non-natural amino acid, again depending on the desired activity sought for the polypeptide. Another alternative would be to make serial substitutions in each position on the polypeptide chain with a non-natural amino acid and observe the effect on the activities of the polypeptide. Any means, technique, or method for selecting a position for substitution with a non-natural amino acid into any polypeptide is suitable for use in the methods, techniques and compositions described herein.

Modified Oligonucleotides:

Examples of some oligonucleotides envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. In some embodiments, modified oligonucleotides comprise those with phosphorothioate backbones and those with heteroatom backbones, $CH_2$—NH—O—$CH_2$, CH, —N($CH_3$)—O—$CH_2$ [known as a methylene(methylimino) or MMI backbone], $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester backbone is represented as O—P—O—$CH_1$). The amide backbones disclosed by De Mesmaeker et al. *Acc. Chem. Res.* 1995, 28:366-374) are also embodied herein. In some embodiments, the oligonucleotides having morpholino backbone structures (Summerton and Weller, U.S. Pat. No. 5,034,506), peptide nucleic acid (PNA) backbone wherein the phosphodiester backbone of the oligonucleotide is replaced with a polyamide backbone, the nucleobases being bound directly or indirectly to the aza nitrogen atoms of the polyamide backbone (Nielsen et al. *Science* 1991, 254, 1497). Oligonucleotides may also comprise one or more substituted sugar moieties. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, $N_6$ (6-aminohexyl)adenine and 2,6-diaminopurine. Kornberg, A., DNA Replication, W. H. Freeman & Co., San Francisco, 1980, pp 75-77; Gebeyehu, G., et al. Nucl. Acids Res. 1987, 15:4513). A "universal" base known in the art, e.g., inosine, may be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al., *Proc. Natl. Acad. Sci. USA* 1989, 86, 6553), cholic acid (Manoharan et al. *Bioorg. Med. Chem. Let.* 1994, 4, 1053), a thioether, e.g., hexyl-S-tritylthiol (Manoharan et al. *Ann. N.Y. Acad. Sci.* 1992, 660, 306; Manoharan et al. *Bioorg. Med. Chem. Let.* 1993, 3, 2765), a thiocholesterol (Oberhauser et al., *Nucl. Acids Res.* 1992, 20, 533), an aliphatic chain, e.g., dodecandiol or undecyl residues (Saison-Behmoaras et al. *EMBO J.* 1991, 10, 111; Kabanov et al. *FEBS Lett.* 1990, 259, 327; Svinarchuk et al. *Biochimie* 1993, 75, 49), a phospholipid, e.g., di-hexadecyl-rac-glycerol or triethylammonium 1,2-di-O-hexadecyl-rac-glycero-3-H-phosphonate (Manoharan et al. *Tetrahedron Lett.* 1995, 36, 3651; Shea et al. *Nucl. Acids Res.* 1990, 18, 3777), a polyamine or a polyethylene glycol chain (Manoharan et al. *Nucleosides & Nucleotides* 1995, 14, 969), or adamantane acetic acid (Manoharan et al. *Tetrahedron Lett.* 1995, 36, 3651). Oligonucleotides comprising lipophilic moieties, and methods for preparing such oligonucleotides are known in the art, for example, U.S. Pat. Nos. 5,138,045, 5,218,105 and 5,459,255.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides as hereinbefore defined.

Labeled Molecules:

In another preferred embodiment, the chimeric molecules can be labeled. Uses include therapeutic and imaging for diagnostic and prognostic purposes. The label may be a radioactive atom, an enzyme, or a chromophore moiety. Methods for labeling antibodies have been described, for example, by Hunter and Greenwood, *Nature*, 144:945 (1962) and by David et al. *Biochemistry* 13:1014-1021 (1974). Additional methods for labeling antibodies have been described in U.S. Pat. Nos. 3,940,475 and 3,645,090. Methods for labeling oligonucleotide probes have been described, for example, by Leary et al. *Proc. Natl. Acad. Sci. USA* (1983) 80:4045; Renz and Kurz, *Nucl. Acids Res.* (1984) 12:3435; Richardson and Gumport, *Nucl. Acids Res.* (1983) 11:6167; Smith et al. *Nucl. Acids Res.* (1985) 13:2399; and Meinkoth and Wahl, *Anal. Biochem.* (1984) 138:267.

The label may be radioactive. Some examples of useful radioactive labels include $^{32}P$, $^{125}I$, $^{131}I$, and $^{3}H$. Use of radioactive labels have been described in U.K. 2,034,323, U.S. Pat. No. 4,358,535, and 4,302,204.

Some examples of non-radioactive labels include enzymes, chromophores, atoms and molecules detectable by electron microscopy, and metal ions detectable by their magnetic properties.

Some useful enzymatic labels include enzymes that cause a detectable change in a substrate. Some useful enzymes and their substrates include, for example, horseradish peroxidase (pyrogallol and o-phenylenediamine), β-galactosidase (fluorescein β-D-galactopyranoside), and alkaline phosphatase (5-bromo-4-chloro-3-indolyl phosphate/nitro blue tetrazolium). The use of enzymatic labels has been described in U.K. 2,019,404, EP 63,879, and by Rotman, *Proc. Natl. Acad. Sci. USA*, 47, 1981-1991 (1961).

Useful chromophores include, for example, fluorescent, chemiluminescent, and bioluminescent molecules, as well as dyes. Some specific chromophores useful in the present invention include, for example, fluorescein, rhodamine, Texas red, phycoerythrin, umbelliferone, luminol.

The labels may be conjugated to the chimeric molecule by methods that are well known in the art. The labels may be directly attached through a functional group on the probe. The probe either contains or can be caused to contain such a functional group. Some examples of suitable functional groups include, for example, amino, carboxyl, sulfhydryl, maleimide, isocyanate, isothiocyanate. Alternatively, labels such as enzymes and chromophores may be conjugated to the antibodies or nucleotides by means of coupling agents, such as dialdehydes, carbodiimides, dimaleimides, and the like.

In another preferred embodiment, the chimeric fusion molecules of the invention can be used for imaging. In imaging uses, the complexes are labeled so that they can be detected outside the body. Typical labels are radioisotopes, usually ones with short half-lives. The usual imaging radioisotopes, such as $^{123}I$, $^{124}I$, $^{125}I$, $^{131}I$, $^{99m}TC$, $^{186}Re$, $^{188}Re$, $^{64}Cu$, $^{67}Cu$, $^{212}Bi$, $^{213}Bi$, $^{67}Ga$, $^{90}Y$, $^{111}In$, $^{18}F$, $^{3}H$, $^{14}C$, $^{35}S$ or $^{32}P$ can be used. Nuclear magnetic resonance (NMR) imaging enhancers, such as gadolinium-153, can also be used to label the complex for detection by NMR. Methods and reagents for performing the labeling, either in the polynucleotide or in the protein moiety, are considered known in the art.

Reporter genes useful in the present invention include acetohydroxy acid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Methods to determine modulation of a reporter gene are well known in the art, and include, but are not limited to, fluorometric methods (e.g. fluorescence spectroscopy, Fluorescence Activated Cell Sorting (FACS), fluorescence microscopy), antibiotic resistance determination.

Methods of Treatment

The compositions and molecules embodied herein are useful in those diseases and conditions that would benefit from protein therapeutics. In some embodiments, a method of treatment comprises administering to a patient an effective amount of cationic liposome encapsulating a chimeric molecule embodied herein. In other embodiments, the molecule comprises one or more sequences set forth as SEQ ID NOS: 1 to 19. In other embodiments, a molecule comprises one or more sequences set forth as SEQ ID NOS: 1 to 123.

In other embodiments, the method of treating hearing loss or deafness using the liposomal formulation for complexing protein and nucleic acid embodied herein (e.g. transcription factors with their target binding region as oligonucleotides) for inner ear cell type delivery in vivo, comprises regeneration (e.g. hair cell and auditory neuron regeneration), repair (e.g. re-establishment of connections between hair cells and neurons for hearing recovery) and prevention (e.g. by protein function of isl1 that prevents hair cell death during aging and noise exposure, thus preserving hearing).

Hearing Loss or Deafness and Associated Disorders:

One in 1000 newborns suffers from genetic deafness. Over 80 deafness genes have been identified, and additional 200-300 deafness genes remain to be discovered. Despite the tremendous progress, there is no treatment for any genetic deafness. Thus there are urgent needs to develop treatment that targets different types of genetic deafness.

There are two main categories of genetic deafness: recessive deafness that is generally congenital; and dominant deafness that is mainly progressive. For recessive deafness, delivery and continuous expression of a normal copy of mutant gene could compensate for lost function for hearing recovery. Adeno-associated virus (AAV) based gene therapy has been the choice to be developed as treatment for recessive deafness, due to its long-term expression pattern and good safety record. AAV vectors however can only accommodate inserts less than 4.5 kb, whereas many deafness genes are much larger in size, thus severely limiting usefulness of AAV. For dominant deafness gene delivery will unlikely work.

Non-inherited abnormalities of the inner ear, such as the Mondini malformation, account for roughly 20% of congenital sensorineural deafness. The bulk of the remaining (genetic) deafness is non-syndromic, meaning that it does not have any obvious distinguishing features.

Most non-syndromic hearing losses are caused by connexin gene mutations. In the mammals, at least 20 connexin subtypes have been identified in mouse and human genomics. Connexin genes encode gap junctional channels, which connect two adjacent cells allowing passage of cytoplasmic ions and small molecules up to 1.2 kDa. In the mammalian inner ear, connexin26 (Cx26) and Cx30 are predominant isoforms. Cx26 mutation can induce a high incidence of hearing loss, responsible for 70 to 80 percent of nonsyndromic hearing loss in children.

Non-Syndromic Deafness:

Nonsyndromic means that deafness occurs in isolation, without other associated disorders. About 80% of genetic hearing loss is non-syndromic. Between 1992 and 2001, 38 loci for autosomal dominant non-syndromic deafness have been mapped and 11 genes have been identified. Autosomal dominant loci are called DFNA, autosomal recessive as DFNB, and X-linked as DFN.

Non-syndromic deafness is highly heterogeneous, but mutations in the connexin-26 molecule (gap junction protein, gene GJB2) account for about 49% of patients with non-syndromic deafness and about 37% of sporadic cases. About 1 in 31 individuals of European extraction are likely carriers.

Autosomal Dominant (DFNA):

Autosomal dominant deafness is passed directly through generations. It is often possible to identify an autosomal dominant pattern through simple inspection of the family tree. Examples of autosomal dominant deafness are missense mutation in COL11A2 (DFNA13) and in the TMC1 gene. COL11A2 encodes a chain of type XI collagen whereas TMC1 encodes a hair cell channel protein.

Autosomal Recessive (DFNB):

Autosomal recessive disorders require a gene from both the mother and father.

Syndromic Deafness:

Syndromic deafness, which accounts for the remaining 20% of congenital deafness, comprises an immensely complicated interlinked set of disorders. The descriptions here are only to give the general flavor of the diseases and are not meant to include all features of the disorders. In most cases, an Online Mendelian Inheritance in Man (OMIM) database link to the main type of the genetic disorder is provided. This database is a catalog of human genes and genetic disorders.

Alport Syndrome:

Alport syndrome is caused by mutations in COL4A3, COL4A4 or COL4A5. The classic phenotype is renal failure and progressive sensorineural deafness.

Branchio-Oto-Renal Syndrome:

Branchio-oto-renal syndrome is caused by mutations in EYA1, a gene of 16 exons within a genomic interval of 156 kB. This syndrome is characterized by hearing disturbances and cataract, branchial cleft fistulae, and preauricular pits. Mondini malformations and related dysplasias may occur.

X-Linked Charcot Marie Tooth (CMT):

The dominantly form of X-linked CMT is caused by a mutation in the connexin 32 gene mapped to the Xq13 locus. Usual clinical signs consist of a peripheral neuropathy combined with foot problems and "champagne bottle" calves.

As noted above, the connexin gene is also associated with a large percentage of cases of non-syndromic deafness. There are several other associated neuropathies and deafness syndromes. Autosomal recessive demyelinating neuropathy, autosomal dominant hereditary neuropathies type I and II, and X-linked hereditary axonal neuropathies with mental retardation are all associated with deafness.

Goldenhar's Syndrome:

Oculoauriculovertebral dysplasia (OAVD) or Goldenhar's syndrome was originally described in 1881. It includes a complex of features including hemifacial microtia, otomandibular dysostosis, epibulbar lipodermoids, coloboma, and vertebral anomalies that stem from developmental vascular and genetic field aberrations. It has diverse etiologies and is not attributed to a single genetic locus. The incidence is roughly 1 in 45,000.

Jervell and Lange-Nielsen Syndrome:

Jervell and Lange-Nielsen Syndrome is associated with cardiac arrhythmias. There is, by prolongation of the QT interval, torsade de Pointe arrhythmias (turning of the points, in reference to the apparent alternating positive and negative QRS complexes), sudden syncopal episodes, and severe to profound sensorineural hearing loss.

Mohr-Tranebjaerg Syndrome (DFN-1):

Mohr-Tranebjaerg syndrome (DFN-1) is an X-linked recessive syndromic hearing loss characterized by postlingual sensorineural deafness in childhood, followed by progressive dystonia, spasticity, dysphagia and optic atrophy. The syndrome is caused by a mutation thought to result in mitochondrial dysfunction. It resembles a spinocerebellar degeneration called Fredreich's ataxia which also may exhibit sensorineural hearing loss, ataxia and optic atrophy. The cardiomyopathy characteristic of Freidreich's ataxia is not seen in Mohr-Tranebjaergt syndrome.

Norrie Disease:

Classic features of Norrie Disease include specific ocular symptoms (pseudotumor of the retina, retinal hyperplasia, hypoplasia and necrosis of the inner layer of the retina, cataracts, phthisis bulbi), progressive sensorineural hearing loss, and mental disturbance, although less than one-half of patients are hearing impaired or mentally retarded.

Pendred Syndrome:

Pendred Syndrome is deafness associated with thyroid disease (goiter).

Stickler Syndrome:

Stickler syndrome is caused by mutations in COL11. It is characterized by hearing impairment, midface hypoplasia, progressive myopia in the first year of life, and arthropathy.

Treacher Collins Syndrome:

Treacher Collins syndrome (OMIM entry TCOF1) is characterized by coloboma of the lower eyelid (the upper eyelid is involved in Goldenhar syndrome), micrognathia, microtia, hypoplasia of the zygomatic arches, macrostomia, and inferior displacement of the lateral canthi with respect to the medial canthi.

Waardenburg Syndrome:

The clinical symptoms of Waardenburg Syndrome (WS) type I and II include lateral displacement of the inner canthus of each eye, pigmentary abnormalities of hair, iris, and skin (often white forelock and heterochromia iridis), and sensorineural deafness. The combination of WS type I characteristics with upper limb abnormalities has been called Klein-Waardenburg syndrome or WS type III. The combination of recessively inherited WS type II characteristics with Hirschsprung disease has been called Waardenburg-Shah syndrome or WS type IV.

Usher Syndrome:

Usher syndrome is characterized by hearing impairment and retinitis pigmentosa. Usher syndrome can be classified into three different types on the basis of clinical findings. In type I, there is both hearing impairment and vestibular impairment. In type II, there is hearing impairment without vestibular impairment. In type III, there are variable amounts of vestibular impairment.

Mitochondrial Disorders:

Hearing loss is common in mitochondrial disorders including MELAS (mitochondrial encephalomyopathy, lactic acidosis, and stroke like episodes), Kearns-Sayre syndrome and MERRF (myoclonic epilepsy with ragged red fibers). These disorders are caused by mutations in mitochondrial DNA, and are characterized by muscular weakness, an abnormal muscle biopsy with "ragged red" fibers, and a variety of other findings that define the specific clinical phenotype. In MELAS, hearing loss is caused by cochlear damage. It resembles presbyacusis in that it is generally symmetrical, gradual, and affects the higher frequencies first. Others have also reported hearing loss associated with mitochondrial mutations. Mitochondrial DNA mutations accumulate naturally during life and are presently implicated as an important cause of normal aging. Mitochondrial defects have been reported to cause both unusual sensitivity to aminoglycosides as well as non-syndromic sensorineural deafness.

Mohr-Tranebjaerg syndrome (DFN-1) is also thought to cause deafness via a mitochondrial disturbance.

Non-Inherited Congenital Deafness:

These types of abnormalities account for roughly 20% of congenital deafness, the remainder being genetic in origin.

Mondini Dysplasia:

The normal cochlea has two and one-half turns. A cochlear malformation consists of a membranous abnormality, a bony abnormality, or a combination of these two. If cochlear development is arrested in the embryo, a common cavity may occur instead of the snail like cochlea. This is called the Mondini dysplasia or malformation.

Often accompanying the Mondini dysplasia is abnormal communication between the endolymphatic and perilymphatic spaces of the inner ear and subarachnoid space. It is usually caused by a defect in the cribiform area of the lateral end of the internal auditory canal, presumably because of this abnormal channel, perilymphatic fistulae are more common in this disorder.

A related anomaly and more severe syndrome, the CHARGE association, consists of coloboma, heart disease, choanal atresia, retarded development, genital hypoplasia, ear anomalies including hypoplasia of the external ear and hearing loss. These individuals have a Mondini type deformity and absence of semicircular canals.

Enlarged Vestibular Aqueduct Syndrome:

Enlarged Vestibular Aqueduct Syndrome is defined on the CT scan as a diameter greater than or equal to 1.5 mm measured midway between the operculum and the common crus.

Recently CRISPR (Clustered Regularly Interspaced Short Palindromic Repeats) endonuclease gene editing has been developed with potential to revolutionize genetic therapy. CRISPR uses Cas9 and guide RNA to target any genomic sequence for specific cleavage, resulting disruption or repair of any gene. The process applies to mutant genes regardless the nature of mutations (recessive or dominant), with permanent correction to restore normal gene function.

Conventional approaches with CRISPR involve the use of viral vehicle to deliver Cas9 and guide RNAs (sgRNA, a template homologous to the target genomic region of 20-29 bp) to cells for gene editing. However the viral genome will remain permanently inside cells (for inner ear it means the whole life) with uncertain consequences (e.g. immunogenic response, potential recombination). In addition the efficiency of CRISPR mediated targeted cleavage in vivo has been relatively low (less than 5%).

A major improvement over previous methods is to directly deliver protein and nucleic acid complexes into cells for the CRISPR mediated gene editing. This approach would allow transient delivery of proteins and nucleic acids, which will be degraded after their function, thus limiting possible adverse effect due to long-term presence of both in cells. Delivery of the combination of proteins with nucleic acids has not been achieved in vivo or in vitro.

Nucleic acid deliveries based on cationic lipid formulations have been used widely with high efficiency. The lipid bilayer of liposome protects the encapsulated nucleic acids from degradation and can prevent neutralization by antibodies. Significantly, fusion of liposomes with the endosomal membrane during endosome maturation can enable the efficient endosomal escape of cationic lipid-delivered cargo. As some natural proteins or proteins with modifications can be highly negative (anionic), it is possible to use liposomes based vehicles to deliver proteins into cells directly with high efficiency. It is further possible to combine the delivery of anionic proteins and nucleic acids (which is anionic) together with liposomes.

Accordingly, in some embodiments, a method of gene editing in vitro or in vivo comprises contacting a cell in vitro or administering to a patient in need of treatment a therapeutically effective amount of the composition or molecules embodied herein. In another embodiment, a method of targeting a specific protein, peptide, nucleic acid in vitro or in vivo, comprising: contacting a cell in vitro or administering to a patient in need of treatment a therapeutically effective amount of the composition or molecules embodied herein.

In another embodiment, a method of delivery of a therapeutic agent in vitro or in vivo, comprises contacting a cell in vitro or administering to a patient in need of treatment a therapeutically effective amount of the composition or molecules embodied herein.

In another embodiment, a method of treating deafness associated with a genetic mutation in a patient in need thereof, comprises administering to the patient a therapeutically effective amount of a chimeric molecule comprising at least one protein or peptide fused, complexed or linked to one or more anionic molecules. The chimeric molecule targets one or more genetic loci associated with deafness in a patient and modulates replication, expression, function or activity of the genetic locus. The genotypic variations that can confer abnormal phenotypes, e.g. deafness, comprise: mutations, insertions, deletions, substitutions or combinations thereof wherein the abnormal gene is expressed. In embodiments, the chimeric molecule comprises one or more gene editing agents for repression of the genetic locus associated with deafness in a patient. These gene editing agents comprise: transcriptional activators, transcriptional repressors, recombinases, nucleases, DNA-binding proteins or nucleic acids, or combinations thereof.

In some embodiments, a method of treating deafness associated with a genetic mutation in a patient in need thereof, comprises administering to the patient a therapeutically effective amount of a chimeric molecule comprising at least one protein, peptide, polynucleotide, oligonucleotide or combinations thereof, fused, complexed or linked to one or more anionic molecules.

In embodiments, the anionic molecules comprise: oligonucleotides, polynucleotides, proteins, peptides, peptide nucleic acids (PNA), synthetic molecules or combinations thereof. Examples of oligonucleotides or polynucleotides include: ribonucleic acids (RNA), deoxyribonucleic acids (DNA), synthetic RNA or DNA sequences, modified RNA or DNA sequences, complementary DNA (cDNA), short guide RNA (sgRNA), interference RNA, mRNA, nucleic acid sequences comprising one or more modified nucleobases or backbones, or combinations thereof.

In embodiments, the chimeric molecule is encapsulated in a cationic liposome and is administered to a patient's inner ear.

In another embodiment, a method of treating a patient suffering from deafness due to a genetic mutation comprises: administering to a patient's inner ear, a cationic liposome encapsulating a therapeutically effective amount of an anionic molecule comprising at least one protein, peptide, polynucleotide, oligonucleotide or combinations thereof, fused, complexed or linked to one or more anionic molecules. In these embodiments, the chimeric molecule targets one or more genetic loci associated with deafness in a patient and modulates replication, expression, function or activity of the genetic locus. These genetic loci associated with deafness comprise: mutations, insertions, deletions, substitutions or combinations thereof. The anionic molecule comprises one or more gene editing agents for repression of a genetic locus associated with deafness in a patient. Examples of these gene editing agents comprise: transcriptional activators, transcriptional repressors, transcription factors, enhancer modulating molecules, recombinases, nucleases, nucleic acid binding-proteins, nucleic acid binding-polynucleotides or oligonucleotides, DNA-binding proteins or DNA-binding nucleic acids, or combinations thereof.

Non-exhaustive examples of mutations in genes that cause, for example, nonsyndromic deafness, include, without limitation, mutations in the ACTG1, CDH23, CLDN14, COCH, COL11A2, DFNA5, ESPN, EYA4, GJB2, GJB6, GRXCR1, KCNQ4, MYO3A, MYO15A, MYO6, MYO7A, OTOF, OTOA, PCDH15, POU3F4, RDX, SLC26A4, STRC, TECTA, TMC1, TMIE, TMPRSS3, USH1C, WFS1 and WHRN genes cause nonsyndromic deafness, with weaker evidence currently implicating genes CCDC50, DIAPH1, DSPP, ESRRB, GJB3, GRHL2, GRXCR1, HGF, LHFPLS, LOXHDI, LRTOMT, MARVELD2, MIR96, MYH14, MYH9, MYO1A, MYO3A, OTOA, PJVK, POU4F3, PRPS1, PTPRQ, RDX, SERPINB6, SIX1, SLC17A8, TPRN, TRIOBP, and WHRN.

Accordingly, any one or more genes or genetic loci associated with deafness can be targeted. In other embodiments, the molecules embodied herein are administered to treat patients suffering from diseases or disorders associated with deafness. Examples of these diseases or disorders include: tinnitus, hyperscusis, ADHD.

In some embodiments, the gene editing agents comprise: Cre recombinases, CRISPR/Cas molecules, TALE transcriptional activators, Cas9 nucleases, nickases, transcriptional regulators or combinations thereof.

In other embodiments, the anionic molecule comprises any one or more sequences having a sequence identity of at least about 75% to sequences set forth as SEQ ID NOS: 1 to 123.

In another embodiment, the one or more sequences comprise SEQ ID NOS: 1 to 123.

In another embodiment, the one or more sequences comprise SEQ ID NOS: 1 to 19.

In other embodiments, the chimeric molecules or the encapsulated chimeric or anionic molecules are administered in a pharmaceutical composition.

In another embodiment, a method of treating hearing loss in a patient suffering from deafness or associated disorders comprises administering to a patient's inner ear, a cationic liposome encapsulating a therapeutically effective amount of an anionic molecule comprising a protein or peptide complexed, fused or linked to a negatively charged molecule. The chimeric molecule targets one or more genetic loci associated with deafness or associated disorders thereof, in a patient and modulates replication, expression, function or activity of the genetic locus. The anionic molecule regenerates and/or repairs cells, tissues, neurons, connectivity between cells, neurons and tissues and/or prevents damage to cells, neurons and tissues. The one or more genetic loci associated with deafness and associated disorders thereof, comprise: mutations, insertions, deletions, substitutions or combinations thereof. Examples of gene editing agents comprise: Cre recombinases, CRISPR/Cas molecules, TALE transcriptional activators, Cas9 nucleases, nickases, transcriptional regulators or combinations thereof. In one embodiment, the anionic molecule comprises any one or more sequences having a sequence identity of at least about 75% to sequences set forth as SEQ ID NOS: 1 to 19. In another embodiment, the one or more sequences are set forth as SEQ ID NOS: 1 to 19.

Pharmaceutical Compositions:

The types and amounts of chimeric molecules for use as therapeutic compounds may be believed to have therapeutic activity on the basis of any information available to the artisan. For example, a prototype compound may be believed to have therapeutic activity on the basis of information contained in the Physician's Desk Reference. In addition, by way of non-limiting example, a therapeutic compound may be believed to have therapeutic activity on the basis of experience of a clinician, structure of the compound, structural activity relationship data, $EC_{50}$, assay data, $IC_{50}$ assay data, animal or clinical studies, or any other basis, or combination of such bases.

A therapeutically-active compound is a compound that has therapeutic activity, including for example, the ability of a compound to induce a specified response when administered to a subject or tested in vitro. Therapeutic activity includes treatment of a disease or condition, including both prophylactic and ameliorative treatment. Treatment of a disease or condition can include improvement of a disease or condition by any amount, including prevention, amelioration, and elimination of the disease or condition. Therapeutic activity may be conducted against any disease or condition, including in a preferred embodiment against any disease or disorder that would benefit from dissociation of a tissue or mass of cells, for example. In order to determine therapeutic activity any method by which therapeutic activity of a compound may be evaluated can be used. For example, both in vivo and in vitro methods can be used, including for example, clinical evaluation, $EC_{50}$, and $IC_{50}$ assays, and dose response curves.

In some embodiments, a pharmaceutical composition comprises a cationic lipid encapsulating a chimeric molecule embodied herein. In other embodiments, the molecule comprises one or more sequences set forth as SEQ ID NOS: 1 to 19. In another embodiment, the one or more sequences comprise SEQ ID NOS: 1 to 123.

In another embodiment, a pharmaceutical composition comprises a cationic lipid encapsulating one or more chimeric molecules comprising at least one protein, peptide, polynucleotide, oligonucleotide or combinations thereof, fused, complexed or linked to one or more anionic molecules.

In another embodiment, a pharmaceutical composition comprises a chimeric molecule comprising at least one protein, peptide, polynucleotide, oligonucleotide or combinations thereof, fused, complexed or linked to one or more anionic molecules.

In another embodiment, a composition comprises a cationic lipid encapsulating one or more chimeric molecules comprising one or more proteins or peptides fused, complexed or linked to one or more anionic molecules. In embodiments, the one or more anionic molecules comprise one or more anionic domains or bind to an anionic nucleic acid domain. Preferably, the one or more anionic molecules confer an overall net negative charge to the chimeric molecule. In one embodiment, the anionic molecules comprise: oligonucleotides, polynucleotides, proteins, peptides, peptide nucleic acids (PNA), synthetic molecules or combinations thereof. In other embodiments, the oligonucleotides or polynucleotides comprise: ribonucleic acids (RNA), deoxyribonucleic acids (DNA), synthetic RNA or DNA sequences, modified RNA or DNA sequences, complementary DNA (cDNA), short guide RNA (sgRNA), interference RNA, mRNA, nucleic acid sequences comprising one or more modified nucleobases or backbones, or combinations thereof.

39. In another embodiment, the one or more proteins or peptides are cationic, anionic or are neutrally charged. In embodiments, the proteins or peptides comprise: enzymes, hormones, chemotherapeutic agents, immunotherapeutic agents, gene editing agents, synthetic molecules, transcriptional modulators, translational modulators, post-translational modulators, and/or modulators that regulate protein expression, function, activity or combinations thereof. In embodiments, the gene editing agents comprise: transcriptional activators, transcriptional repressors, transcription factors, enhancer modulating molecules, recombinases, nucleases, nucleic acid binding-proteins, nucleic acid binding-polynucleotides or oligonucleotides, DNA-binding proteins or DNA-binding nucleic acids, or combinations thereof.

In another embodiment, the chimeric molecule comprises one or more detectable labels, anions, radiolabels, tags, targeting agents or combinations thereof.

Formulations, Administration:

The compositions embodied herein, are formulated for administration by any suitable method, for example, as described in Remington: The Science And Practice Of Pharmacy (21st ed., Lippincott Williams & Wilkins). Exemplary routes of administration include, but are not limited to parenteral, oral, subcutaneous, topical, intramuscular, transdermal, transmucosal, sublingual, intranasal, transvascular, subcutaneous, orbital, or combinations thereof.

Kits:

In yet another aspect, the invention provides kits for targeting nucleic acid sequences of cells and molecules associated with modulation of the target molecule. For example, the kits can be used to target any desired nucleic sequence and as such, have many applications.

In one embodiment, a kit comprises: (a) a cationic lipid, and a chimeric molecule or an encapsulated chimeric molecule, or a protein and a separate polyanionic molecule, or any combinations thereof, and (b) instructions to administer to cells or an individual a therapeutically effective amount of the composition. In some embodiments, the kit may comprise pharmaceutically acceptable salts or solutions for administering the composition. Optionally, the kit can further comprise instructions for suitable operational parameters in the form of a label or a separate insert. For example, the kit may have standard instructions informing a physician or laboratory technician to prepare a dose of chimeric molecule.

Optionally, the kit may further comprise a standard or control information so that a patient sample can be compared with the control information standard to determine if the test amount of chimeric molecule is a therapeutic amount consistent with for example, treating deafness in a patient.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1: Efficient Delivery of Genome Editing Proteins In Vitro and In Vivo

It was hypothesized that proteins that are engineered to be highly negatively charged or that are naturally highly anionic may be able to take advantage of the same electrostatics-driven complexation and encapsulation used by cationic liposomal reagents for nucleic acid delivery. While few proteins natively possess the density of negative charges found in the phosphate backbone of nucleic acids, it was speculated that translational fusion to, or non-covalent complexation with, a polyanionic molecule may render the resulting protein or protein complex sufficiently anionic to be efficiently complexed by common cationic lipid reagents.

In this study it was demonstrated that fusion of proteins with an engineered supernegatively charged GFP (Lawrence, M. S., et al. *J. Am. Chem. Soc.* 129, 10110-10112 (2007)) enables efficient complexation and delivery of proteins into cultured mammalian cells by cationic lipids commonly used to transfect nucleic acids. This approach is effective even at low nanomolar protein concentrations and in the presence of serum, resulting in ≥1,000-fold more potent functional protein delivery than methods that use fusion to cationic peptides or proteins. Delivery efficiency depends on the net charge of the fusion protein, and natively anionic peptide tags such as 3×FLAG and VP64 can also enable lipid-mediated protein delivery. It was further shown that Cas9 nuclease protein complexed with polyanionic single guide RNA (sgRNA) can be efficiently delivered in functional form into mammalian cells using cationic lipid formulations. Delivery of Cas9:gRNA complexes is highly efficient (up to 80% modification of cultured human cells from a single treatment) and also induces higher genome modification specificity compared with plasmid transfection, typically resulting in >10-fold higher on-target:off-target DNA modification ratios in human cells. Finally, it was demonstrated that this protein delivery approach can be effective in vivo by delivering functional Cre recombinase and functional Cas9:sgRNA complexes to hair cells in the inner ear of live mice.

The results obtained herein, on the intracellular delivery of polyanionic proteins and protein:nucleic acid complexes by cationic lipids would significantly expand the scope of research and therapeutic applications of proteins including genome-editing agents.

Methods

Oligonucleotides Used in this Study:

All oligonucleotides were purchased from Integrated DNA Technologies.

Primers used for generating PCR products to serve as substrates for T7 transcription of sgRNAs.

T7_gRNA-Rev was used in all cases. DNA template used was EGFP sgRNA plasmid. NTF3 and VEGF sgRNAs for dCas9-VP64 activator experiments were reported previously (Maeder, M. L. et al. *Nat. Methods* 10, 977-979 (2013)).

```
T7_EGFP1-Fwd
                                        (SEQ ID NO: 20)
TAA TAC GAC TCA CTA TA GGGCACGGGCAGCTTGCCGG;

T7-GFP g1-Fwd
                                        (SEQ ID NO: 21)
TAA TAC GAC TCA CTA TA GGCCTCGAACTTCACCTCGGC
GGAAAGGACGAAACACC;

T7-GFP g5-Fwd
                                        (SEQ ID NO: 22)
TAA TAC GAC TCA CTA TA GGCTGAAGGGCATCGACTTCA
GAAAGGACGAAACACC;

T7-GFP g3-Fwd
                                        (SEQ ID NO: 23)
TAA TAC GAC TCA CTA TA GGCAGCTCGATGCGGTTCACC
AGAAAGGACGAAACACC;

T7-GFP g7-Fwd
                                        (SEQ ID NO: 24)
TAA TAC GAC TCA CTA TA GGCAAGGAGGACGGCAACATC
CGAAAGGACGAAACACC;

T7-EMX-Fwd
                                        (SEQ ID NO: 25)
TAA TAC GAC TCA CTA TA GGAGTCCGAGCAGAAGAAGAA
GAAAGGACGAAACACC;

T7-VEG-Fwd
                                        (SEQ ID NO: 26)
TAA TAC GAC TCA CTA TA GGGGTGGGGGGAGTTTGCTCC
GAAAGGACGAAACACC;

T7-CLT2-Fwd
                                        (SEQ ID NO: 27)
TAA TAC GAC TCA CTA TA GGCAGATGTAGTGTTTCCACA
GAAAGGACGAAACACC;

T7_gRNA-Rev
                                        (SEQ ID NO: 28)
AAAAAAAGCACCGACTCGGTG.
```

Primers for generating linear DNA PCR product for transfection.

PCR extension at (72° C., 3 min) on plasmid containing U6 promoter as template with PCR_sgRNA-fwd1, PCR_sgRNA-rev2 and appropriate PCR_sgRNA primers listed below.

```
PCR_gRNA-fwd1
                                        (SEQ ID NO: 29)
CTGTACAAAAAAGCAGGCTTTA;

PCR_gRNA-rev2
                                        (SEQ ID NO: 30)
AAAAAAAGCACCGACTCGGTGCCACTTTTTCAAGTTGATAACG
GACTAGCCTTATTTTAACTTGCTATTTCTAGCTCTAAAAC;

PCR-G-GFP1
                                        (SEQ ID NO: 31)
GAAAGGACGAAACACCGGCCTCGAACTTCACCTCGGCGGTTTT
AGAGCTAGAAATAGCAA;

PCR-G-GFP3
                                        (SEQ ID NO: 32)
GAAAGGACGAAACACCGGCAGCTCGATGCGGTTCACCAGTTTT
AGAGCTAGAAATAGCAA;

PCR-G-GFP5
                                        (SEQ ID NO: 33)
GAAAGGACGAAACACCGGCTGAAGGGCATCGACTTCAGTTTTA
GAGCTAGAAATAGCAA;

PCR-G-GFP7
                                        (SEQ ID NO: 34)
GAAAGGACGAAACACCGGCAAGGAGGACGGCAACATCCGTTTT
AGAGCTAGAAATAGCAA;

PCR-G-CLT2
                                        (SEQ ID NO: 35)
GAAAGGACGAAACACCGGCAGATGTAGTGTTTCCACAGTTTTA
GAGCTAGAAATAGCAA;

PCR-G-EMX
                                        (SEQ ID NO: 36)
GAAAGGACGAAACACCGGAGTCCGAGCAGAAGAAGAAGTTTTA
GAGCTAGAAATAGCAA;

PCR-G-VEG
                                        (SEQ ID NO: 37)
GAAAGGACGAAACACCGGGGTGGGGGGAGTTTGCTCCGTTTTA
GAGCTAGAAATAGCAA.
```

Primers for performing T7 endonuclease I DNA cleavage assay.

```
Survey_GFP-fwd
                                        (SEQ ID NO: 38)
TACGGCAAGCTGACCCTGAA;

Survey_GFP-rev
                                        (SEQ ID NO: 39)
GTCCATGCCGAGAGTGATCC;

Survey_CLTA-fwd
                                        (SEQ ID NO: 40)
GCCAGGGGCTGTTATCTTGG;

Survey_CLTA-rev
                                        (SEQ ID NO: 41)
ATGCACAGAAGCACAGGTTGA;

Survey_EMX-fwd
                                        (SEQ ID NO: 42)
CTGTGTCCTCTTCCTGCCCT;

Survey_EMX-rev
                                        (SEQ ID NO: 43)
CTCTCCGAGGAGAAGGCCAA;

Survey_VEGF-fwd
                                        (SEQ ID NO: 44)
CCACACAGCTTCCCGTTCTC;

Survey_VEGF-rev
                                        (SEQ ID NO: 45)
GAGAGCCGTTCCCTCTTTGC;
```

Primers for high-throughput sequencing of on-target and off-target sites in human genome.

```
HTS_EMX_ON-fwd
                                        (SEQ ID NO: 46)
CACTCTTTCCCTACACGACGCTCTTCCGATCTCCTCCCCATT
GGCCTGCTTC HTS_EMX_Off1-fwd
                                        (SEQ ID NO: 47)
CACTCTTTCCCTACACGACGCTCTTCCGATCTTCGTCCTGCT
CTCACTTAGAC;
```

HTS_EMX_Off2-fwd
(SEQ ID NO: 48)
CACTCTTTCCCTACACGACGCTCTTCCGATCTTTTTGTGGCT
TGGCCCCAGT;

HTS_EMX_Off3-fwd
(SEQ ID NO: 49)
CACTCTTTCCCTACACGACGCTCTTCCGATCTTGCAGTCTCA
TGACTTGGCCT;

HTS_EMX_Off4-fwd
(SEQ ID NO: 50)
CACTCTTTCCCTACACGACGCTCTTCCGATCTTTCTGAGGGC
TGCTACCTGT;

HTS_VEGF_ON-fwd
(SEQ ID NO: 51)
CACTCTTTCCCTACACGACGCTCTTCCGATCTACATGAAGCA
ACTCCAGTCCCA;

HTS_VEGF_Off1-fwd
(SEQ ID NO: 52)
CACTCTTTCCCTACACGACGCTCTTCCGATCTAGCAGACCCA
CTGAGTCAACTG;

HTS_VEGF_Off2-fwd
(SEQ ID NO: 53)
CACTCTTTCCCTACACGACGCTCTTCCGATCTCCCGCCACAG
TCGTGTCAT:

HTS_VEGF_Off3-fwd
(SEQ ID NO: 54)
CACTCTTTCCCTACACGACGCTCTTCCGATCTCGCCCCGGTA
CAAGGTGA;

HTS_VEGF_Off4-fwd
(SEQ ID NO: 55)
CACTCTTTCCCTACACGACGCTCTTCCGATCTGTACCGTACA
TTGTAGGATGTTT;

HTS_CLTA2_ON-fwd
(SEQ ID NO: 56)
CACTCTTTCCCTACACGACGCTCTTCCGATCTCCTCATCTCC
CTCAAGCAGGC;

HTS_CLTA2_Off1-fwd
(SEQ ID NO: 57)
CACTCTTTCCCTACACGACGCTCTTCCGATCTATTCTGCTCT
TGAGGTTATTTGT;

HTS_CLTA2_Off2-fwd
(SEQ ID NO: 58)
CACTCTTTCCCTACACGACGCTCTTCCGATCTCACCTCTGCC
TCAAGAGCAGAAAA;

HTS_CLTA2_Off3-fwd
(SEQ ID NO: 59)
CACTCTTTCCCTACACGACGCTCTTCCGATCTTGTGTGTGTG
TGTGTGTAGGACT;

HTS_EMX_ON-rev
(SEQ ID NO: 60)
GGAGTTCAGACGTGTGCTCTTCCGATCTTCATCTGTGCCCCT
CCCTCC;

HTS_EMX_Off1-rev
(SEQ ID NO: 61)
GGAGTTCAGACGTGTGCTCTTCCGATCTCGAGAAGGAGGTGC
AGGAG;

HTS_EMX_Off2-rev
(SEQ ID NO: 62)
GGAGTTCAGACGTGTGCTCTTCCGATCTCGGGAGCTGTTCAG
AGGCTG;

HTS_EMX_Off3-rev
(SEQ ID NO: 63)
GGAGTTCAGACGTGTGCTCTTCCGATCTCTCACCTGGGCGAG
AAAGGT;

HTS_EMX_Off4-rev
(SEQ ID NO: 64)
GGAGTTCAGACGTGTGCTCTTCCGATCTAAAACTCAAAGAAA
TGCCCAATCA;

HTS_VEFG_ON-rev
(SEQ ID NO: 65)
GGAGTTCAGACGTGTGCTCTTCCGATCTAGACGCTGCTCGCT
CCATTC;

HTS_VEGF_Off1-rev
(SEQ ID NO: 66)
GGAGTTCAGACGTGTGCTCTTCCGATCTACAGGCATGAATCA
CTGCACCT;

HTS_VEGF_Off2-rev
(SEQ ID NO: 67)
GGAGTTCAGACGTGTGCTCTTCCGATCTGCGGCAACTTCAGA
CAACCGA;

HTS_VEGF_Off3-rev
(SEQ ID NO: 68)
GGAGTTCAGACGTGTGCTCTTCCGATCTGACCCAGGGGCACC
AGTT;

HTS_VEGF_Off4-rev
(SEQ ID NO: 69)
GGAGTTCAGACGTGTGCTCTTCCGATCTCTGCCTTCATTGCT
TAAAAGTGGAT;

HTS_CLTA2_ON-rev
(SEQ ID NO: 70)
GGAGTTCAGACGTGTGCTCTTCCGATCTACAGTTGAAGGAAG
GAAACATGC;

HTS_CLTA2_Off1-rev
(SEQ ID NO: 71)
GGAGTTCAGACGTGTGCTCTTCCGATCTGCTGCATTTGCCCA
TTTCCA;

HTS_CLTA2_Off2-rev
(SEQ ID NO: 72)
GGAGTTCAGACGTGTGCTCTTCCGATCTGTTGGGGGAGGAGG
AGCTTAT;

HTS_CLTA2_Off3-rev
(SEQ ID NO: 73)
GGAGTTCAGACGTGTGCTCTTCCGATCTCTAAGAGCTATAAG
GGCAAATGACT;

HTS_EGFP-fwd
(SEQ ID NO: 74)
CACTCTTTCCCTACACGACGCTCTTCCGATCTNNNNACGTAA
ACGGCCACAAGTTC;

HTS_EGFP-rev
(SEQ ID NO: 75)
GGAGTTCAGACGTGTGCTCTTCCGATCTGTCGTCCTTGAAGA
AGATGGTG;

HTS_MusEMX_ON-fwd
(SEQ ID NO: 76)
CACTCTTTCCCTACACGACGCTCTTCCGATCTCCAGGTGAAG
GTGTGGTTCCAG;

HTS_MusEMX_ON-rev
(SEQ ID NO: 77)
GGAGTTCAGACGTGTGCTCTTCCGATCTCCCCTAGTCATTGG
AGGTGAC.

Construction of Cas9, Cre, and TALE fusion and sgRNA expression plasmids.

Sequences of all constructs used are listed below. All protein constructs were generated from previously reported plasmids for protein of interest cloned into a pET29a expression plasmid.

Expression and purification of S. pyogenes Cas9 and other proteins.

E. coli BL21 STAR (DE3) competent cells (Life Technologies) were transformed with pMJ806 (Pattanayak, V. et al. *Nat. Biotechnol.* 31, 839-843 (2013).) encoding the *S. pyogenes* Cas9 fused to an N-terminal 10×His-tag/maltose binding protein. The resulting expression strain was inoculated in Luria-Bertani (LB) broth containing 100 mg/mL of ampicillin at 37° C. overnight. The cells were diluted 1:100 into the same growth medium and grown at 37° C. to $OD_{600}$=~0.6. The culture was incubated at 20° C. for 30 min, and isopropyl β-D-1-thiogalactopyranoside (IPTG) was added at 0.5 mM to induce Cas9 expression. After ~16 h, the cells were collected by centrifugation at 8,000 g and resuspended in lysis buffer (50 mM tris(hydroxymethyl)-aminomethane (Tris)-HCl, pH 8.0, 1 M NaCl, 20% glycerol, 10 mM tris(2-carboxyethyl)phosphine (TCEP)). The cells were lysed by sonication (1 sec pulse-on, 1 sec pulse-off for 15 min total at 6 W output) and the soluble lysate was obtained by centrifugation at 20,000 g for 30 min.

The cell lysate was incubated with His-Pur nickel-nitriloacetic acid (nickel-NTA) resin (Thermo Scientific) at 4° C. for 30 min to capture His-tagged Cas9. The resin was transferred to a 20-mL column and washed with 20 column volumes of lysis buffer. Cas9 was eluted in 50 mM Tris-HCl (pH 8), 0.1 M NaCl, 20% glycerol, 10 mM TCEP, and 300 mM imidazole, and concentrated by Amicon ultra centrifugal filter (Millipore, 100-kDa molecular weight cut-off) to ~50 mg/mL. The 6×His tag and maltose-binding protein were removed by TEV protease treatment at 4° C. for 20 hours and captured by a second Ni-affinity purification step. The eluent, containing Cas9, was injected into a HiTrap SP HP column (GE Healthcare) in purification buffer containing 50 mM Tris-HCl (pH 8), 0.1 M NaCl, 20% glycerol, and 10 mM TCEP. Cas9 was eluted with purification buffer containing a linear NaCl gradient from 0.1 M to 1 M over five column volumes. The eluted fractions containing Cas9 were concentrated down to a concentration of 200 μM as quantified by Bicinchoninic acid assay (BCA) (Pierce Biotechnology), snap-frozen in liquid nitrogen, and stored in aliquots at −80° C. All other proteins were purified by this method but without TEV cleavage step and proteins containing (−30) GFP were purified by anion exchange using a Hi-Trap Q HP anion exchange column (GE Healthcare) using the same purification protocol.

In Vitro Transcription of sgRNAs.

Linear DNA fragments containing the T7 promoter binding site followed by the 20-bp sgRNA target sequence were transcribed in vitro using the T7 High Yield RNA Synthesis Kit (NEB) according to the manufacturer's instructions. In vitro transcribed RNA was precipitated with ethanol and purified by gel electrophoresis on a Criterion 10% polyacrylamide TBE-Urea gel (Bio-Rad). Excised gel fragments were extracted in 420 μL of 300 mM NaCl overnight on a rocking surface at 4° C. Gel-purified sgRNA was precipitated with ethanol and redissolved in water and sgRNA concentration was finally quantified by UV absorbance and snap-frozen at −80° C.

Plasmid Transfection.

Plasmid DNA was transfected using Lipofectamine 2000 (Life Technologies) according the manufacturer's protocol. For TALE activator plasmids, 300 ng of DNA was transfected, and for the activator synergy experiments 60 ng of each of five plasmids was pooled and transfected. For Cas9 nuclease delivery experiments, linear DNA PCR products expressing sgRNAs were used in transfection experiments targeting genomic sites in CLTA, EMX, VEGF, and GFP (sgRNA GFP g1, GFP g3, GFP g5, and GFP g7 for nickase studies). Linear DNA PCR products were generated using plasmid containing the U6 promoter as template and forward primers bearing the U6 promoter upstream sequence and reverse primers containing U6 downstream sequence followed by the sgRNA sequence (20-bp sequence unique to each target plus constant sgRNA backbone architecture sequence). sgRNAs expressed from linear DNA templates contained at least two 5' guanosines to match in vitro transcribed sgRNAs that required these bases for T7 transcription. Primer sequences and PCR conditions are referred to herein. For dCas9 activator experiments, 700 ng of Cas9 or dCas9-VP64 plasmid DNA was co-transfected with 250 ng of the appropriate sgRNA expression plasmid. For activator synergy experiments 50 ng of DNA from each of the six sgRNA was pooled and co-transfected with 700 ng of dCas9-VP64 plasmid.

Delivery of Transcription Factor Proteins Complexed with Cationic Lipids in Cell Culture:

Briefly, cultured cells were plated in 48-well format (250 μL volume) in Dulbecco's Modified Eagle's Media plus GlutaMAX (Life Technologies, Carlsbad, Calif.) with 10% FBS ("full serum media") and antibiotics at a cell density necessary to reach ~70% confluence the next day. Full serum media was replaced with the same media but containing no antibiotics at least one hour before delivery. Delivery of Cre and TALE proteins was performed by combining 1 nM to 1 μM protein (in 275 μL final volume) with 0.5-1.5 μL of commercially available cationic lipids in 25 μL OPTIMEM media (Life Technologies, Carlsbad, Calif.) according to the manufacturer's protocol for normal plasmid transfection, including incubation time. For Cas9 delivery in vitro, transcribed sgRNA was incubated with Cas9 protein for 5 min before complexing with the cationic lipid reagent. 25 μL lipid complexes in OPTIMEM media were added to cells and media was replaced 12-16 hours later fresh media unless otherwise noted. Cells were assayed for recombination 48 hours after delivery, for gene activation either 4 or 16 hours after delivery, and for gene modification 48 hours after delivery.

T7 Endonuclease I Assay to Detect Genomic Modifications.

U2OS-EGFP cells or HEK293T cells were transfected with Cas9 expression and sgRNA expression plasmids or linear DNA PCR products as described above or treated with only Cas9 protein, only in vitro transcribed sgRNA, or only RNAiMAX. Genomic DNA was isolated from cells 2 days after transfection using the DNAdvance Kit (Agencourt) following the manufacturer's instructions. 200 ng of genomic DNA was used as template in PCR reactions to amplify the targeted genomic loci with flanking survey primer pairs specified herein. PCR products were purified with a QIAquick PCR Purification Kit (Qiagen) and quantified with QUANT-IT™ PICOGREEN® dsDNA Kit (Life Technologies). 250 ng of purified PCR DNA was combined with 2 μL of NEBuffer 2 (NEB) in a total volume of 19 μL and denatured then re-annealed with thermocycling at 95° C. for 5 min, 95 to 85° C. at 2° C./s; 85 to 20° C. at 0.2° C./s. The re-annealed DNA was incubated with 1 μl of T7 Endonuclease I (10 U/μl, NEB) at 37° C. for 15 min. 10 μL of 50% glycerol was added to the T7 Endonuclease reaction and 12 μL was analyzed on a 5% TBE 18-well Criterion PAGE gel (Bio-Rad) electrophoresed for 30 min at 200 V, then stained with 1×SYBR Gold (Life Technologies) for 30 min. Cas9-induced cleavage bands and the uncleaved band were visualized on an AlphaImager HP (Alpha Innotech) and quantified using ImageJ software (Schneider, C. A., et al. *Nat. Methods* 9, 671-675 (2012)). The peak intensities of the cleaved bands were divided by the total intensity of all bands (uncleaved+cleaved bands) to determine the fraction cleaved which was used to estimate gene modification levels as previously described (Guilinger, J. P., et al. *Nat. Biotechnol.* 32, 577-582 (2014)). For each sample, transfections and subsequent modification measurements were performed in triplicate on different days.

Stem Cell Culture and Delivery.

Mouse embryonic stem cell (ES) line Tau-GFP (courtesy of Dr. A. Edge, Massachusetts Eye & Ear Infirmary, Boston) containing a permanent GFP gene insertion was cultured in DMEM with 10% FBS (Gibco), 100 mM MEM nonessential amino acids (Gibco), 0.55 mM 2-mercaptoethanol, and leukemia inhibitory factor (1,000 units/ml; Chemicon). After 3 days floating spheres were formed that exhibited GFP fluorescence. Complexes of Cas9:sgRNA and Lipofectamine 2000 were added to the culture containing the floating spheres for 16 hours. After Cas9:sgRNA treatment, the cells were cultured in the above media for 3 days. The floating spheres were treated with trypsin for 5 min then passed through a 70 μm filter to collect single cells. The cells were cultured on laminin-coated slides in DMEM/F12 (1:1) supplemented with 1×N2, 1×B27, penicillin-streptomycin (100 μg/mL) and 10% FBS for two days before labeling. Immunohistochemistry was performed using an anti-GFP antibody (# ab13970, Abcam) to assess GFP expression. To quantify the number of GFP-negative cells, the total number of GFP-positive and GFP-negative cells from three representative visual fields at 20× magnification were counted, and the average efficiency was calculated. Three independent experiments were performed for each condition.

Microinjection of Proteins to Mouse Inner Ear.

P0 floxP-tdTomato mice (The Jackson Laboratory) were used for (−30)GFP-Cre injection and P2 Atoh1-GFP mice (Dr. J Johnson, Southwestern Medical Center, University of Texas) were used for Cas9:sgRNA injection. Animals were used under protocols approved by the Massachusetts Eye & Ear Infirmary ALCUC committee. Mice were anesthetized by lowering their temperature on ice. Cochleostomies were performed by making an incision behind the ear to expose the cochlea. Glass micropipettes held by a micromanipulator were used to deliver the complex into the scala media, which allows access to inner ear hair cells. For delivery of (−30) GFP-Cre, 3 μL of 45 μM protein was mixed with 3 μL of either RNAiMAX or Lipofectamine 2000 and incubated at room temperature for 30 minutes prior to injection. Four mice were injected per treatment group. For delivery of Cas9:sgRNA complexes, 1 μL of 100 μM Cas9 protein was mixed with 2 μL of 100 sgRNA and incubated for 5 minutes at room temperature before mixing with 3 μL of either RNAiMAX or Lipofectamine 2000 and incubating for an additional 30 minutes prior to injection. Three mice were injected per treatment group. The total delivery volume for every injection was 0.3 μL per cochlea and the release was controlled by a micromanipulator at the speed of 32 nL/sec.

Immunohistochemistry and Quantification.

5-10 days after injection, the mice were sacrificed and cochlea were harvested by standard protocols. For immunohistochemistry, antibodies against hair-cell markers (Myo7a and Esp) and supporting cells (Sox2) were used following a previously described protocol (Sage, C. et al. *Science* 307, 1114-1118 (2005)). To quantify the number of tdTomato positive cells after (−30)GFP-Cre or GFP negative cells after Cas9:sgRNA delivery, the total number of outer hair cells were counted in a region spanning 200 μm around the site of injection in the base turn of the cochlea. The efficiency of (−30)GFP-Cre-induced recombination or Cas9:sgRNA-induced genome modification was calculated as the percentage of outer hair cells that expressed tdTomato or that lost GFP expression.

High-Throughput DNA Sequencing of Genome Modifications.

HEK293T cells were either transfected with Cas9 and sgRNA expression plasmids or linear DNA PCR products or treated with 50 nM Cas9 protein, 250 nM purified sgRNA, and cationic lipids as described earlier for Cas9 protein delivery to U2OS-EGFP reporter cells. For plasmid-based transfection experiments, 700 ng of Cas9 expression plasmid plus 250 ng of sgRNA plasmid or 50 ng of a linear DNA PCR product expressing sgRNA for targeting either the EMX1, CLTA2, or VEGF locus were transfected with Lipofectamine 2000 (Life Technologies) and cells were isolated 2 days later. For protein delivery experiments in vivo, ~30 mg of mouse tissue was isolated as previously described from anesthetized mice and genomic DNA was extracted using the Agencourt DNAAdvance Genomic DNA Isolation Kit (Beckman Coulter). For cell culture experiments genomic DNA was isolated as described above. 150 ng of genomic DNA was used as template to amplify by PCR the on-target and off-target genomic sites with flanking HTS primer pairs specified in the herein. Relative amounts of crude PCR products were quantified by gel electrophoresis and samples treated with different sgRNA pairs or Cas9 nuclease types were separately pooled in equimolar concentrations before purification with the QIAquick PCR Purification Kit (Qiagen). ~150 ng of pooled DNA was electrophoresed using a 5% TBE 18-well Criterion PAGE gel (BioRad) for 30 min at 200 V and DNAs ~125 bp to ~300 bp in length were isolated and purified by QIAquick PCR Purification Kit (Qiagen). Purified DNA was amplified by PCR with primers containing sequencing adapters, purified, and sequenced on a MiSeq high-throughput DNA sequencer (Illumina) as previously described (Pattanayak, V. et al. *Nat. Biotechnol.* 31, 839-843 (2013)).

Quantification of Cas9 Protein Uptake.

Alexa Fluor 647 C2 Maleimide (Life Technologies, Carlsbad Calif.) was used to fluorescently label Cas9 protein on surface cysteines. A 10 mM stock solution of Alexa647 was prepared in anhydrous DMSO. In a 0.4 mL reaction, 10 nmol of purified Cas9 protein and 200 nmol of Alexa647 maleimide were combined in buffer conditions used for Cas9 protein storage. The labeling reaction was incubated at 4° C. for 16 hours. At the end of the reaction, excess unconjugated Alexa647 was removed by re-purifying the labeled Cas9 protein by cation exchange chromatography as described above. To measure the amount of protein delivered into treated cells, 20,000 cells were plated in the wells of a 48-well plate 1 day prior to treatment. On the day of treatment, 50 nM of Alexa647-labeled Cas9 (Cas9-Alexa647) and 100 nM of EGFP1 sgRNA were prepared for delivery using 0.8 μL of Lipofectamine 2000 as described above, and applied to the cells. After 4 hours, Cas9-Alexa647:sgRNA Lipofectamine-containing media was removed, and cells were washed three times with 500 μL of PBS containing 20 U/mL heparin.

The cells were trypsinized and prepared for counting and flow cytometry as described above. Cas9-Alexa647 uptake was measured by flow cytometry, while 10,000 cells of the treated population were transferred to a black, flat-bottomed, opaque 96-well plate. Standard curves of Cas9-Alexa647 were prepared by complexing 50 pmol of the Cas9-Alexa647 protein with Lipofectamine 2000 exactly as described for Cas9-Alexa647 delivery, followed by serial 2-fold dilutions in DMEM with 10% FBS containing 10,000 U2OS cells per well in the 96-well plate. The effect of U2OS cells or complexation with Lipofectamine 2000 on Alexa647 fluorescence was determined by preparing three additional Cas9-Alexa647 standard curves: (i) with Lipofectamine 2000 in media lacking U2OS cells, (ii) without Lipofectamine 2000 in media containing U2OS cells, and (iii) without Lipofectamine 2000 in media lacking U2OS cells.

Data Analysis.

Illumina sequencing reads were filtered and parsed with scripts written in Unix Bash. DNA sequences will be deposited in NCBI's Sequencing Reads Archive (SRA) and source code can be found in Supplementary Software. Sample sizes for sequencing experiments were maximized (within practical experimental considerations) to ensure greatest power to detect effects. Statistical analyses for Cas9-modified genomic sites (Table 2) were performed as previously described (Sander, J. D. et al. *Nucleic Acids Res.* 41, e181 (2013)).

Results

Highly Efficient Delivery of Cre Recombinase Fused to Anionic Proteins:

It was speculated that imparting the highly anionic electrostatic properties of nucleic acids to genome-editing proteins may enable their efficient delivery into mammalian cells using cationic lipids (FIG. 1A). For proteins of interest that are not natively highly negatively charged, fusion with a natural or engineered supernegatively charged protein (Thompson, D. B., et al. *Methods Enzymol.* 503, 293-319 (2012)) was envisioned to impart polyanionic character. For nucleic acid-binding proteins, it was speculated that simple complexation with native DNA or RNA substrates might provide sufficient anionic character to support cationic lipid-based delivery (FIG. 1A).

Figures 2A, 2B, 2C, 2D, 2E, 2F:
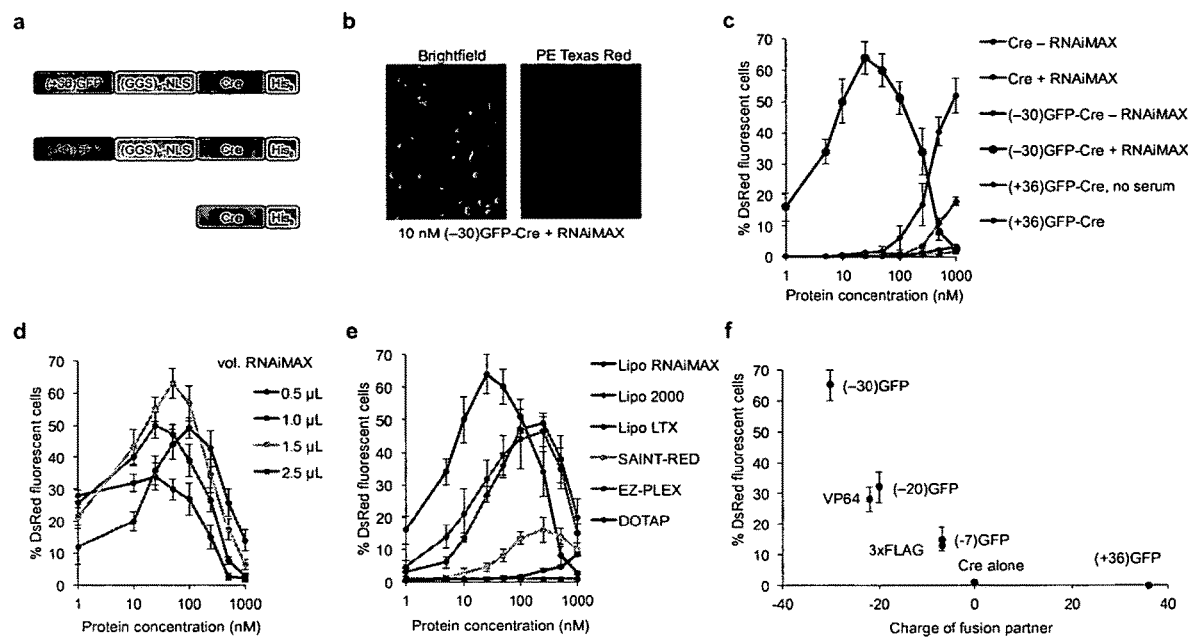
FIGS. 2A-2F show the delivery of Cre recombinase to cultured human cells.

First it was tested if the engineered supernegatively charged GFP variant (Lawrence, M. S., et al. *J. Am. Chem. Soc.* 129, 10110-10112 (2007)), (−30)GFP, could mediate complexation and delivery of fused protein cargo (FIG. 1B). (−30)GFP was translationally fused to Cre recombinase to generate (−30)GFP-Cre; note that (−30) refers to the net theoretical charge of the GFP moiety, not the net charge of the fusion. A variety of commercially available cationic lipids were assayed for their ability to functionally deliver (−30)GFP-Cre into HeLa cells that only express DsRed upon Cre-mediated recombination (FIG. 2A). Lipofectamine RNAiMAX (hereafter referred to as "RNAiMAX", Life Technologies, Carlsbad Calif.) is a commercial reagent designed for delivery of siRNAs. Delivery of 10 nM (−30)GFP-Cre complexed with 1.5 µL RNAiMAX in media containing 10% fetal bovine serum (FBS) led to strong DsRed fluorescence signal among treated cells. Fluorescence-activated cell sorting (FACS) revealed that 48 hours after treatment 52% of cells expressed DsRed consistent with Cre recombination (FIG. 2B).

Figures 7A, 7B, 7C, 7D:
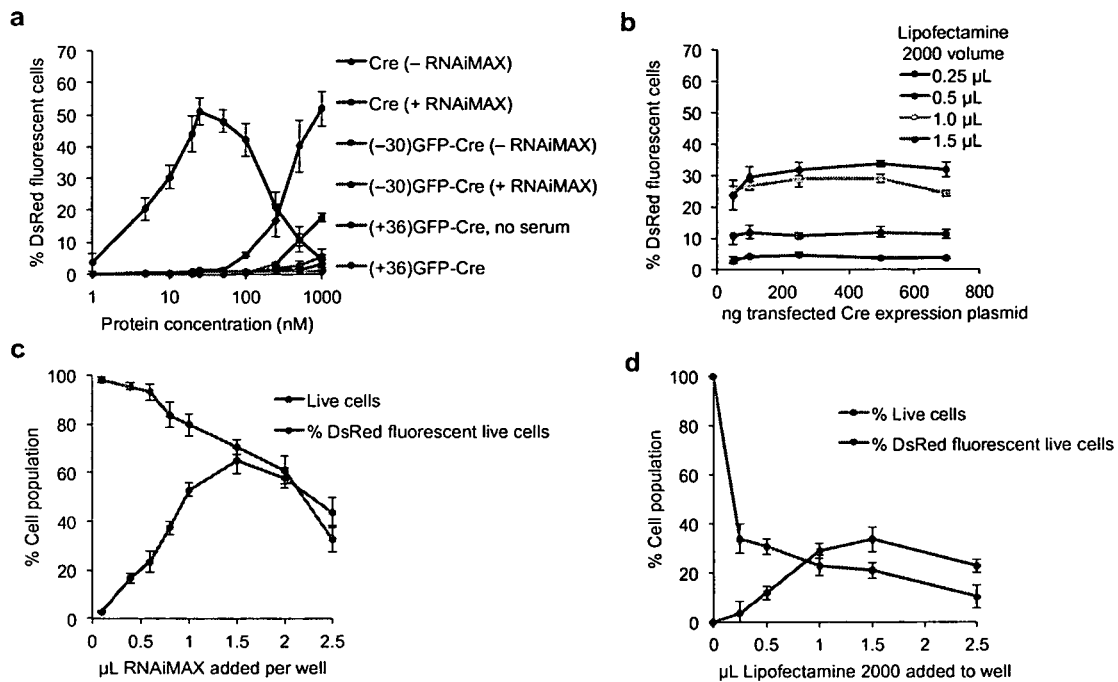
FIGS. 7A-7D show the optimization of cationic lipid-mediated delivery of Cre and comparison to delivery using (+36)GFP-Cre and plasmid transfection.

Optimization resulted in recombination efficiencies of 65% using 25 nM (−30)GFP-Cre complexed with 1.5 µL RNAiMAX in 250 µL of media containing 10% FBS (FIG. 2C). The potency of lipid-mediated (−30)GFP-Cre delivery was remarkable when compared to that of cationic protein-mediated delivery. Only 1 nM (−30)GFP-Cre with cationic lipid was needed to result in 15-20% recombed cells, whereas 1 µM (+36)GFP-Cre was required to achieve this extent of recombination, corresponding to a 1,000-fold difference in delivery potency (FIG. 2C). Nearly identical results were observed in a second Cre reporter cell line (BSR TdTomato) (FIG. 7A). Under the same conditions used to efficiently deliver (−30)GFP-Cre, cationic lipids did not increase the delivery potency of neutral or cationic Cre recombinase fusions (FIG. 1C), indicating that the highly negative charge of (−30)GFP-Cre is required to participate in cationic lipid-mediated delivery. It was also observed that increasing the amount of cationic lipid increased the concentration of protein required for maximal recombination, consistent with a model in which deliverable proteins re complexed with specific stoichiometries of cationic lipids (FIG. 2D). These observations collectively indicate that cationic lipids can mediate the potent delivery of polyanionic proteins into mammalian cells even in the presence of serum.

For comparison, an optimization of plasmid DNA transfection on HeLa reporter cells was performed across a range of plasmid and Lipofectamine 2000 doses, and found that transfection efficiency in this cell line yielded a maximum of 33% DsRed fluorescent cells (FIG. 7B). These findings provide evidence that cationic lipid-based (−30)GFP-Cre protein delivery can result in more functional Cre recombinase activity than well-established high-performance plasmid DNA transfection methods. As nucleic acid transfection by cationic lipids is to known to induce cellular toxicity (Lv, H., et al. *J. Controlled Release* 114, 100-109 (2006)), especially as nucleic acid and lipid amount increases, the toxicity of cationic lipid-mediated (−30)GFP-Cre protein delivery was characterized and the results were compared with those of plasmid transfection methods. Cells undergoing protein delivery or plasmid transfection were analyzed for cell survival by flow cytometry using the TO-PRO-3 live/dead cell stain (Life Technologies, Carlsbad, Calif.). While increasing the amount of RNAiMAX predictably increased toxicity (FIG. 7B), the use of 1.5 µL RNAiMAX per 275 µL of sample volume of DMEM with 10% FBS maximized recombination efficiency from protein delivery (>50% DsRed-positive live cells) while inducing minimal cell toxicity (>80% live cells, FIG. 7C). In contrast, all efficacious plasmid DNA delivery conditions tested exhibited much greater toxicity (FIG. 7D), with fewer than 40% of cells surviving plasmid transfection under any condition that resulted in >5% DsRed-positive live cells. These results indicate that optimized cationic lipid-mediated delivery of anionic Cre recombinase achieves substantially greater delivered Cre activity with much lower toxicity than optimized plasmid DNA delivery.

To determine if the higher potency of cationic lipid-mediated (−30)GFP-Cre delivery relative to cationic protein-mediated delivery arises from more total protein uptake by cells, or from a higher fraction of functional, non-endosomal protein molecules that enter cells, flow cytometry was used to measure GFP fluorescence of cells treated with either (+36)GFP-Cre or liposomal (−30)GFP-Cre under their respective optimal Cre delivery conditions. Comparison of cellular fluorescence and recombination efficiency reveals that lipid-mediated functional delivery of (−30)GFP-Cre is 9,800-fold more potent per amount of endocytosed protein than delivery of (+36)GFP-Cre (FIG. 2A-2D). Taken together, these results provide evidence that the unusually high potency of lipid-mediated delivery of anionic proteins does not arise from unusually high protein uptake in each cell, but rather from post-endocytosis processes that likely include endosomal escape into the cytoplasm and the avoidance of lysosomal protein degradation.

To test whether the ability to deliver polyanionic proteins is dependent on proprietary components in RNAiMAX or if other cationic lipids are capable of mediating similarly potent delivery, several other transfection reagents designed to deliver nucleic acids were tested (FIG. 2E). While RNAiMAX remained the most effective functional delivery agent for (−30)GFP-Cre, other cationic lipid formulations also resulted in potent delivery. Lipofectamine 2000 and Lipofectamine LTX (Life Technologies, Carlsbad Calif.), two plasmid transfection reagents based on cationic lipid formulations (Chesnoy, S. & Huang, L. *Annu. Rev. Biophys. Biomol. Struct.* 29, 27-47 (2000)), and SAINT-Red (Synvolux Therapeutics, Groningen Netherlands), an siRNA delivery formulation containing a synthetic pyridinium-based cationic lipid, all resulted in strong functional (−30) GFP-Cre delivery over a range of concentrations (FIG. 2E). In contrast, strong delivery with the cationic lipid DOTAP (Roche Diagnostics, Indianapolis Ind.) or the peptide-based nucleic acid delivery agent EZ-PLEX (Ascension Bio, Tampa Fla.) was not observed (FIG. 2E). These observations collectively indicate that several, but not all, cationic lipids are able to complex with and deliver negatively charged proteins into human cells.

It was speculated that it should be possible to use cationic lipids to deliver polyanionic proteins other than (−30)GFP. Engineered polyanionic protein domains commonly used in biomedical research include the VP64 activation domain (−22 net theoretical charge) widely used in fusions with engineered zinc finger arrays, TALE repeat arrays, or dCas9 for transcriptional activation, and 3× FLAG (−7 net theoretical charge), an epitope tag used for protein purification and visualization (FIG. 2F). It was observed that both VP64 and 3× FLAG enhance functional delivery of Cre recombinase with cationic lipids, though not as effectively as (−30) GFP, likely due to their lower overall negative charge (FIG. 2F). To further probe the relationship between net anionic charge and protein delivery efficiency, two new anionic GFP-Cre fusions of comparable charge as 3×FLAG-Cre and VP64-Cre were generated using (−7)GFP and (−20)GFP, respectively. The (−7)GPF-Cre and (−20)GFP-Cre fusions showed nearly identical protein delivery efficacy as their like-charged anionic peptide-tagged counterparts (FIG. 2F), providing evidence that anionic proteins and short anionic peptides of comparable net charge induce similarly efficient cationic lipid-mediated protein delivery. These results also demonstrate that the efficacy of delivery by cationic lipids is predominantly a function of the degree net negative charge, and not the distribution or density of charged residues, and establish that unusually negatively charged proteins or peptides other than (−30)GFP can also mediate highly efficient cationic lipid-based delivery into mammalian cells.

Figure 3A:
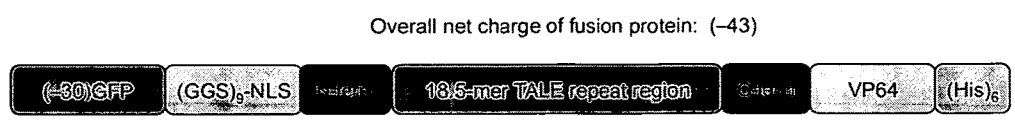
FIGS. 3A, 3B show the delivery of TALE transcriptional activators into cultured human cells.
Figure 3B:
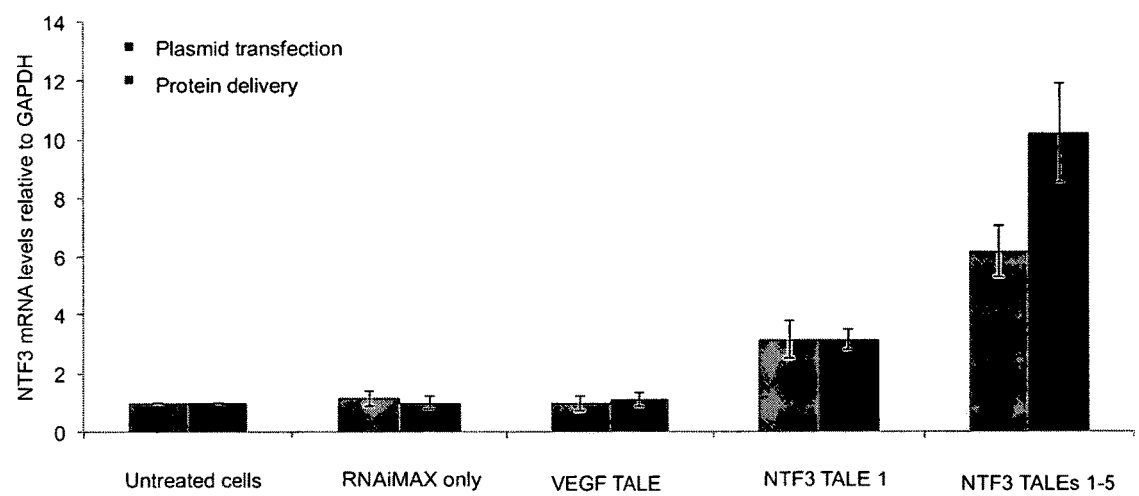

Functional Delivery of TALE Activator Proteins:

Next lipid-mediated delivery of TALE-VP64 transcriptional activators (approximately +4 theoretical net charge, depending on TALE variant used) into cultured human cells was tested. While modestly effective cleavage of endogenous genes by delivered TALEN proteins has been demonstrated in mammalian cells in the absence of serum using cationic peptides such as $Arg_9$ (Liu, J., et al. *PLoS ONE* 9, e85755 (2014)), the delivery of TALE-based transcription factor proteins has not yet been reported, and no effective delivery of TALE proteins in serum has been previously described. The gene for neurotrophin-3 (NTF3), a neural growth factor that has been associated with neurodegenerative diseases was targeted (Tessarollo, L., et al. *Proc. Natl. Acad. Sci. U.S.A* 91, 11844-11848 (1994)). A previously described NTF3-targetting TALE-VP64 (Maeder, M. L. et al. *Nat. Methods* 10, 243-245 (2013)) was fused to (−30) GFP (FIG. 3A) and treated HEK293T cells with 25 nM (−30)GFP-NTF3 TALE1-VP64 and 1.5 μL. RNAiMAX under the conditions optimized for Cre delivery. Gene expression levels of NTF3 4 hours after treatment were 3.5-fold higher in cells treated with 25 nM (−30)GFP-NTF3 TALE-VP64 and RNAiMAX than untreated cells, cells treated with RNAiMAX only, or cells treated with a VEGF-targeting TALE transcriptional activator (FIG. 3*b*B). Comparable levels of NTF3 expression were observed 48 hours after transfection of plasmids encoding the same NTF3-targeting TALE-VP64 (FIG. 3B).

Figures 9A, 9B:
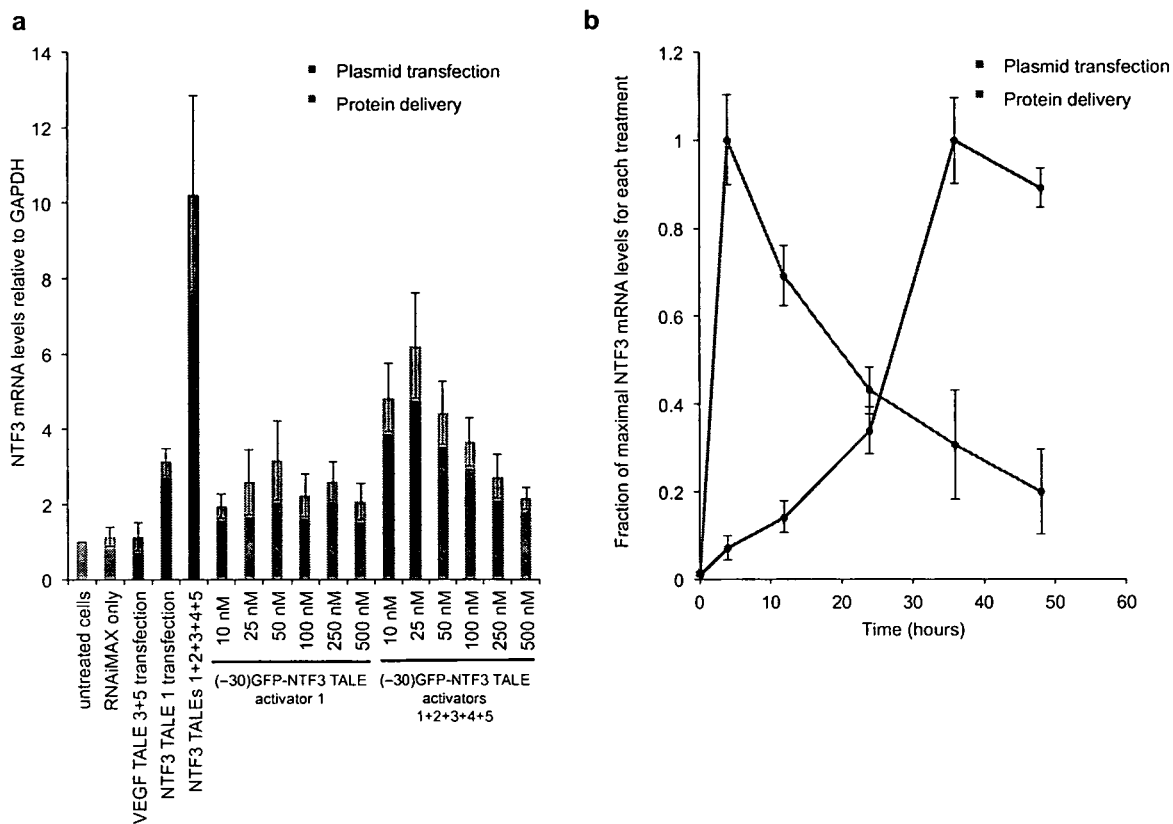
FIGS. 9A, 9B are graphs showing the delivery optimization of TALE activators designed to target the NTF3 gene and time course of observed gene activation.

Since the synergistic expression of multiple TALE activators targeting different sites on the same gene has been shown to augment gene activation (Maeder, M. L. et al. *Nat. Methods* 10, 243-245 (2013)), five distinct NTF3-targeting TALE activators fused to (−30) GFP were simultaneously delivered using RNAiMAX. Protein-lipid complexes were prepared as above by adding the five (−30)GFP-NTF3-TALE-VP64 proteins at 5 nM each, for a total of 25 nM protein. An optimized 6.5-fold increase was observed in NTF3 expression after a 4-hour incubation (FIG. 3B and FIG. 9A), while plasmid co-transfection of all five NTF3 TALE activators, followed by a 48-hour incubation, resulted in a 10-fold increase in NTF3 expression levels (FIG. 3B). To characterize the time course of cationic lipid-delivered TALE activator protein function compared to that of plasmid DNA transfection, NTF3 expression assays were performed 4 to 48 hours following protein or DNA delivery. TALE activator activity following protein delivery peaks ~4 hours post-treatment and falls over the 44 hours (FIG. 9B), whereas plasmid DNA transfection required ~24 hours to show above-background levels of NTF3 activation, which plateaued at ~36-48 hours (FIG. 9B). These findings collectively demonstrate that TALE activator proteins can be delivered using cationic lipids to rapidly and transiently activate gene expression in human cells. The delivery of programmable transcriptional activator proteins may enable the one-time activation of a target gene while avoiding chronic gene expression, a general concern with DNA-based delivery of programmable transcription factors. This capability may prove especially valuable for proteins that effect a one-time permanent change in cell state or cell fate when transiently expressed (Jopling, C., et al. *Nat. Rev. Mol. Cell Biol.* 12, 79-89 (2011)).

Figures 10A, 10B, 10C, 10D:
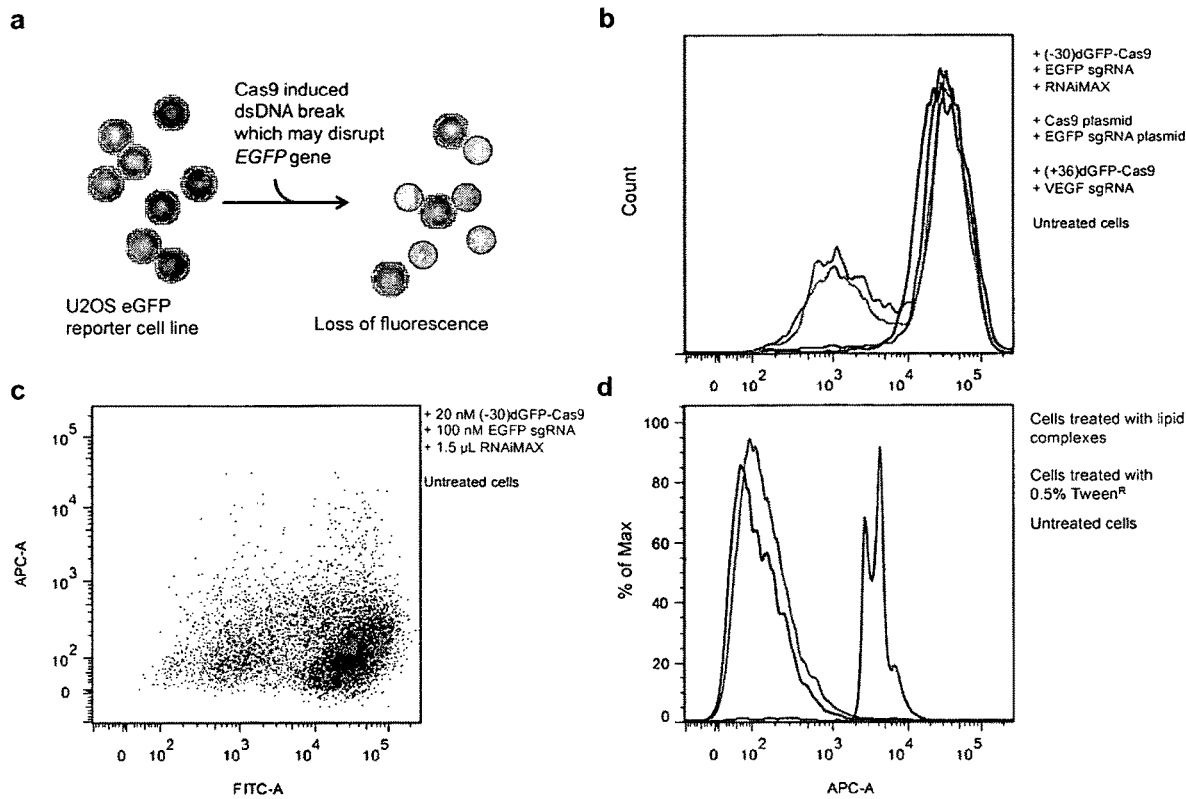
FIGS. 10A-10D show the gene disruption frequency of an EGFP reporter gene by delivery of Cas9:sgRNA and analyzing by flow cytometry.

Highly Efficient Delivery of Cas9:sgRNA Protein:RNA Complexes into Human Cells:

Given the potent lipid-mediated delivery of polyanionic Cre and TALE activator protein variants in full-serum media, it was speculated that CRISPR-Cas9:sgRNA complexes, either as fusions with (−30)GFP or as native polyanionic Cas9:guide RNA complexes, might also be delivered into human cells using this approach. Using a well-established Cas9-induced gene disruption assay (Fu, Y., et al. *Nat. Biotechnol.* 32, 279-284 (2014)), specific sites were targeted within a genomic EGFP reporter gene in human U2OS cells (FIG. 10A). On-target Cas9 cleavage induces non-homologous end joining (NHEJ) in EGFP and the loss of cell fluorescence. To avoid interference from the fluorescence of (−30)GFP, a Y67S mutation was introduced into (−30)GFP to eliminate its fluorescence, and designated this non-fluorescent variant as (−30)dGFP.

Figures 4A, 4B, 4C, 4D, 4E:
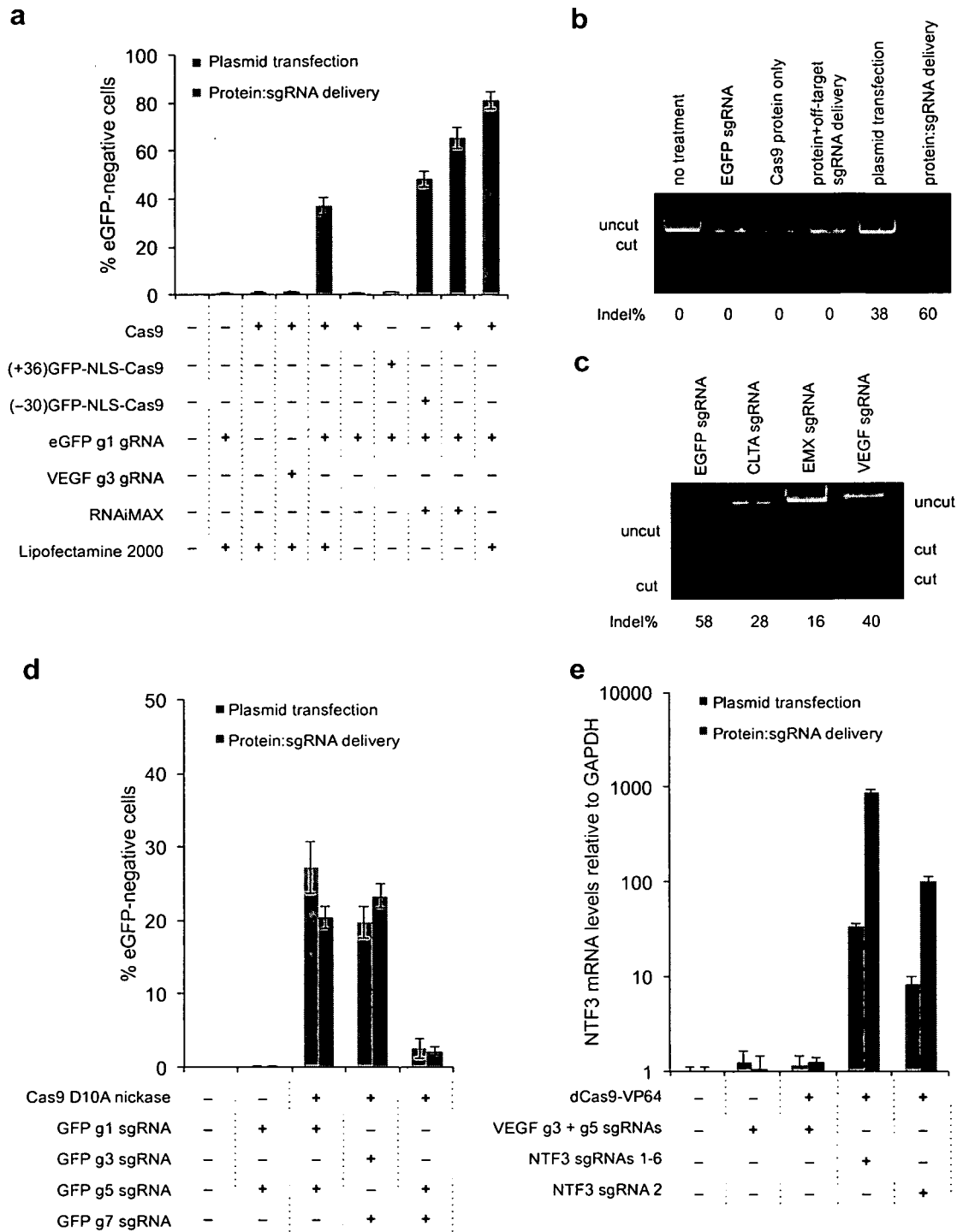
FIGS. 4A-4E show the delivery of Cas9:sgRNA, Cas9 D10A nickase, and dCas9-VP64 transcriptional activators to cultured human cells.

Treatment of U2OS reporter cells with 25 nM (−30) dGFP-NLS-Cas9 and 50 nM EGFP-targeting sgRNA with RNAiMAX in media containing 10% FBS showed loss of EGFP expression in 48% of cells (FIG. 4A). Cotransfection of plasmids expressing Cas9 or sgRNA under optimized plasmid transfection conditions resulted in EGFP loss in 37% of cells (FIG. 4A). No significant EGFP disruption was observed upon transfection of plasmids encoding EGFP sgRNA alone, Cas9 alone, or cotransfection of plasmids encoding Cas9 and an sgRNA designed to target a VEGF locus (FIG. 4A, FIG. 10B). It was confirmed that the robust disruption of EGFP was not a result of cellular toxicity (FIGS. 10C, 10D). It was also observed that treatment of cells with (+36)dGFP-NLS-Cas9 and sgRNA in the presence of 10% FBS serum did not lead to efficient gene disruption (FIG. 4A), providing evidence that cationic-protein based methods of delivery for Cas9 and sgRNA may not be effective, perhaps due to interference of gRNA:Cas9 complex formation or nuclease function by cationic proteins (McNaughton, B. R., et al. *Proc. Natl. Acad. Sci. U.S.A* 106, 6111-6116 (2009)). Consistent with this model, a recent study describing the delivery of Cas9 protein with an oligoarginine peptide tag used orders of magnitude more Cas9 protein and sgRNA than is used in this study, dosed repeatedly, to achieve moderate levels of gene disruption (Ramakrishna, S. et al. *Genome Res.* 24, 1020-1027 (2014)).

Figures 11A, 11B:
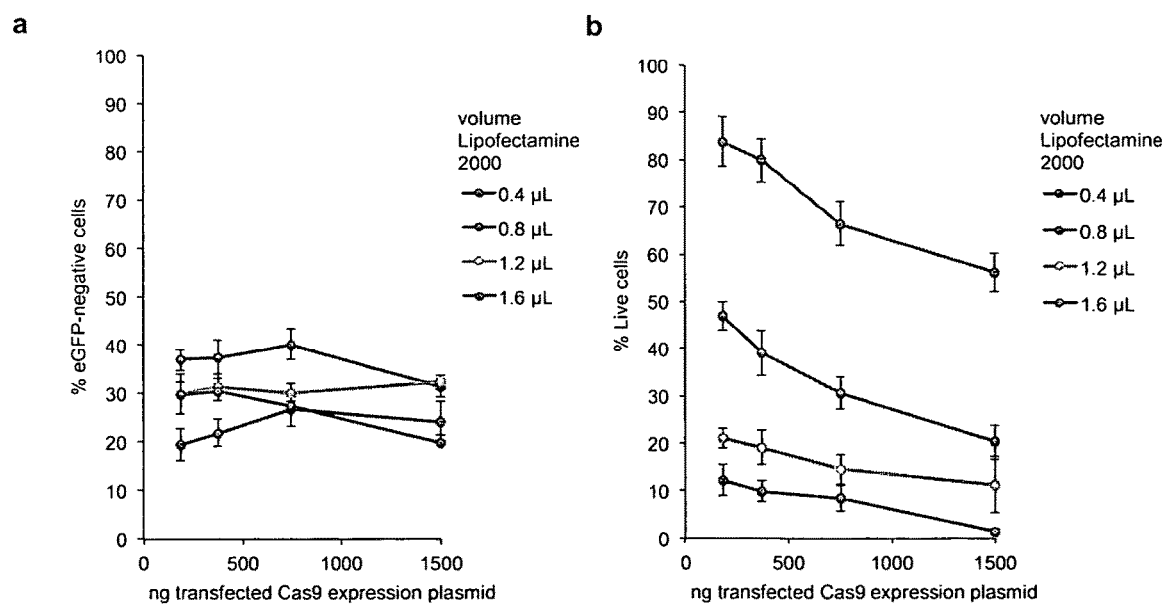
FIGS. 11A, 11B show the optimization of Cas9 plasmid transfection conditions and measurement of cellular toxicity at different doses of Lipofectamine 2000.

Optimization of DNA transfection conditions did not yield higher than 40% EGFP disruption (FIG. 11A) and, similar to the above results with transfection of Cre-encoding plasmids in HeLa dsRed cells, toxicity was substantial in U2OS cells transfected using Lipofectamine 2000 (FIG. 11B), with <50% of cells surviving under conditions that maximize EGFP disruption. Together, these results establish that cationic lipid-mediated delivery of (−30)dGFP-NLS-Cas9:sgRNA complexes can result in efficient sgRNA-dependent target gene disruption in human cells with minimal toxicity, unlike cationic peptide-based protein delivery or plasmid DNA transfection methods.

Polyanionic sgRNA is Necessary and Sufficient for Efficient Lipid-Mediated Cas9 Delivery.

Since the complex of native Cas9 protein (+22 net theoretical charge) and an sgRNA (~103 anionic phosphate groups) should be overall highly anionic, next it was tested if native Cas9:sgRNA complexes without fusion to polyanionic proteins can be delivered into human cells using cationic lipids. Treatment of U2OS EGFP reporter cells with 100 nM Cas9, 100 nM EGFP sgRNA, and 0.8 μL RNAiMAX resulted in 65% disruption of the EGFP reporter gene (FIG. 4A). Treatment of cells with Cas9 protein and sgRNA, but without RNAiMAX, resulted in no loss of GFP fluorescence (FIG. 4A). These observations provide evidence that sgRNA alone, even in the absence of a supernegatively charged fusion protein, can provide the highly anionic character needed to mediate cationic lipid-based delivery of Cas9.

Comparison of gene disruption efficiency arising from the cationic lipid-mediated delivery of (−30)dGFP-NLS-Cas9:sgRNA versus Cas9:sgRNA revealed that at low doses (−30)dGFP-NLS-Cas9 results in more efficient gene disruption than native Cas9 (FIG. 12A), it is outperformed by native Cas9 at higher concentrations, as well as at the respective optimal protein:sgRNA dose of either protein (FIGS. 12B-12C). These results further establish that sgRNA can supply sufficient negative charge to support cationic lipid-based delivery of complexed Cas9 protein.

It was also observed that while overall less protein was required for optimal delivery of (−30)dGFP-NLS-Cas9 than Cas9, a higher sgRNA:protein ratio was required for maximal (−30)dGFP-NLS-Cas9-mediated EGFP gene disruption than for native Cas9-mediated gene disruption (FIG. 12D). It was speculated that more equivalents of sgRNA are needed to complex with (−30)dGFP-NLS-Cas9 since fused (−30)dGFP may electrostatically interfere with Cas9:sgRNA complexation. As the ideal protein dose for (−30)dGFP-NLS-Cas9 mediated EGFP gene disruption is 10-fold lower than that of wild-type Cas9, the results herein also provide evidence that (−30)dGFP-Cas9 forms complexes with cationic liposomes more effectively than native Cas9:sgRNA due to its higher overall negative charge, but this charge magnitude may interfere with Cas9:sgRNA interactions, necessitating more sgRNA per protein and potentially reducing total delivered Cas9 activity. In addition, NLS-Cas9 and Cas9-NLS proteins were generated and tested. It was observed that while the presence of an NLS in (−30)dGFP-NLS-Cas9 could at least partially explain differences in delivery efficacy at very low concentrations, Cas9, NLS-Cas9, and Cas9-NLS all result in higher efficiency of EGFP disruption than (−30)dGFP-NLS-Cas9 at 25 nM or higher concentrations (FIGS. 13A-13C). It was speculated that the lower overall performance of (−30)dGFP-NLS-Cas9 is due to the lower activity of the fusion relative to Cas9 constructs lacking (−30)dGFP. While the (−30)dGFP fusion appears to improve complexation and delivery at lower protein doses, as evidenced by the shape of the dose-response curves of (−30)dGFP-NLS-Cas9, NLS-Cas9, Cas9-NLS, and Cas9 (FIGS. 13A-13C), the reduction in activity due to the presence of the large anionic fusion partner to Cas9 compromises its overall performance.

Figures 14A, 14B, 14C, 14D:
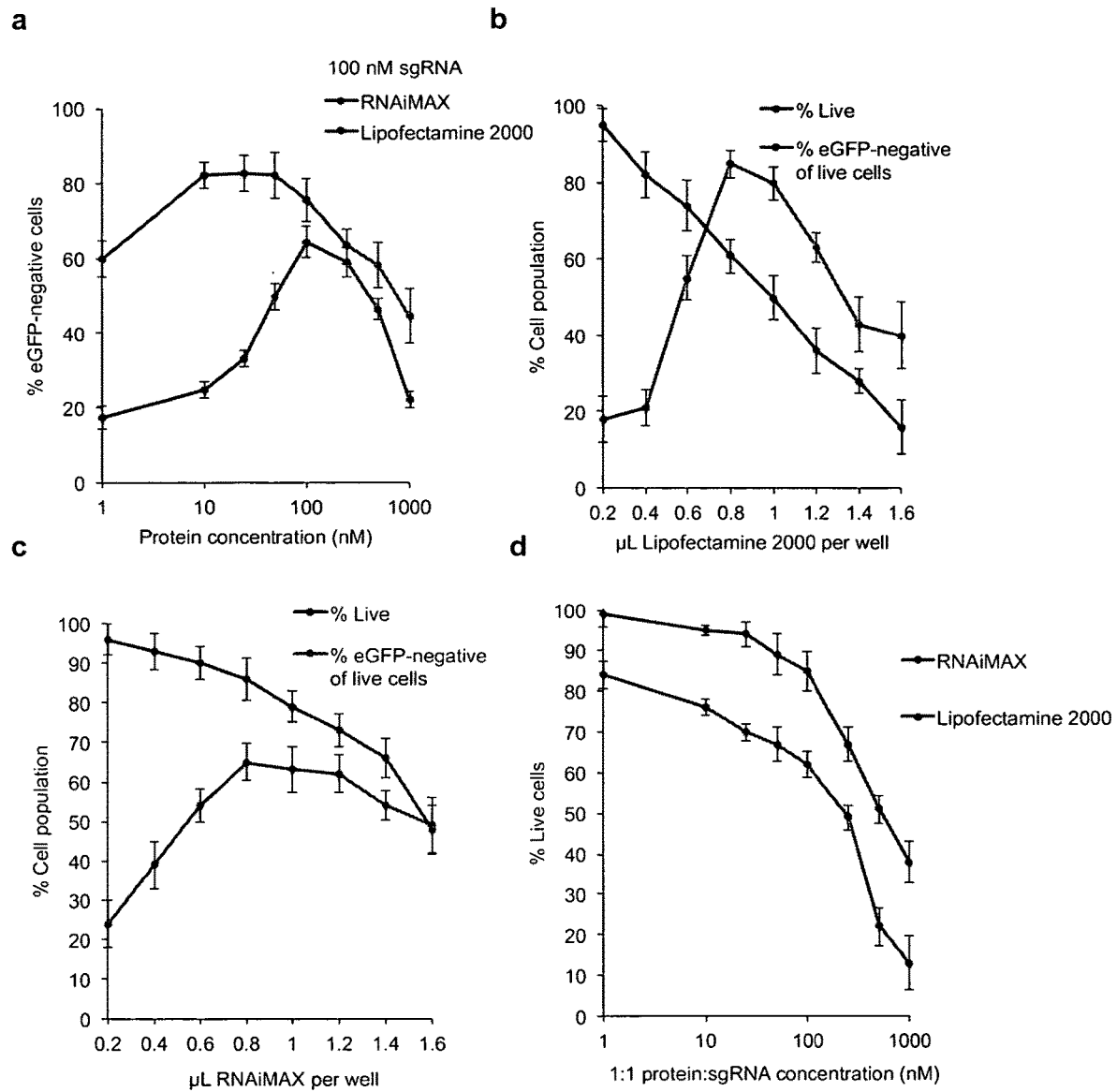
FIGS. 14A-14D are graphs showing the effect of RNAiMAX and Lipofectamine 2000 on Cas9:sgRNA delivery efficiency and cellular toxicity.

Cas9:sgRNA delivery was tested with cationic lipid formulations other than RNAiMAX. EGFP disruption with Lipofectamine 2000 was notably more efficient than with RNAiMAX, resulting in up to 80% Cas9-mediated gene disruption (FIG. 14A), and maintaining high efficiency (60% gene disruption) even at 1 nM protein (FIG. 14A). However, due to the somewhat higher toxicity of Lipofectamine 2000 (FIG. 14B) for protein:sgRNA delivery compared to that of RNAiMAX (FIG. 14C) under cell culture conditions, RNAiMAX was used for subsequent cell culture studies. It was also observed that increasing the dosage of Cas9:sgRNA increased toxicity at constant amounts of either RNAiMAX or Lipofectamine 2000 (FIG. 14D). This relationship may result from increasingly efficient formation of protein:RNA:lipid complexes at higher Cas9 and sgRNA concentrations, resulting in more total transfected material, including toxic cationic lipid components, binding to and being endocytosed by cells.

To verify that EGFP disruption arose from genome modification and not only from Cas9 binding (Qi, L. S. et al. *Cell* 152, 1173-1183 (2013)), the T7 endonuclease I (T7EI) assay (Guschin, D. Y. et al. *Methods Mol. Biol.* Clifton N.J. 649, 247-256 (2010)) was used to detect and quantify the frequency of Cas9-mediated genomic insertion/deletion mutations (indels) at the target EGFP locus (FIG. 4B). The T7EI assay results showed that only those cells treated with both Cas9 and EGFP sgRNA plasmids, or Cas9 protein and purified EGFP sgRNA, contained indels at the target site 48 hours after treatment. Taken together, these findings establish that active Cas9:sgRNA complexes can be potently delivered into human cells with cationic lipids in a manner dependent on the negative charge provided by the sgRNA.

U2OS EGFP reporter cells were treated with a single lipid-mediated delivery treatment of Cas9 complexed with a mixture of four gRNAs targeting EGFP, CLTA, EMX, and VEGF. This treatment resulted in efficient disruption of all four targets, with cleavage efficiencies of 58%, 28%, 16%, and 40%, respectively, as measured by T7E1 cleavage assay. These high gene disruption efficiencies from a single delivery of 50 nM Cas9 and 25 nM of each sgRNA (100 nM total sgRNA) demonstrate that lipid-mediated Cas9:sgRNA delivery can support efficient multiplexed genome editing (FIG. 4C).

Functional Delivery of Cas9 Nickases and dCas9 Activators:

Next it was tested if cationic lipid-based protein delivery could be extended to deliver other Cas9-derived genome engineering tools such as Cas9 nickases (Ran, F. A. et al. *Cell* 154, 1380-1389 (2013)) and Cas9-based transcriptional activators (Maeder, M. L. et al. *Nat. Methods* 10, 977-979

(2013)). Gene disruption efficiency was measured in U2OS EGFP reporter cells resulting from delivery of Cas9 D10A nickase, either by cotransfection of nickase and appropriate paired EGFP-targeting sgRNA plasmids, or as 100 nM purified protein complexed with pairs of EGFP sgRNAs (50 nM each) using RNAiMAX (FIG. 4D). Both plasmid and cationic lipid-mediated protein:RNA delivery of dual Cas9 nickases resulted in EGFP disruption with similar efficiencies (FIG. 4D) only in the presence of sgRNA pairs targeting opposite strands, (sgRNA pairs g1+g5, and g3+g7), but not with sgRNA pairs targeting the same strand (sgRNA pair g5+g7) (FIG. 4D), consistent with previous reports of Cas9 nickase cleavage requirements (Guilinger, J. P., et al. *Nat. Biotechnol.* 32, 577-582 (2014)).

Figures 15A, 15B:
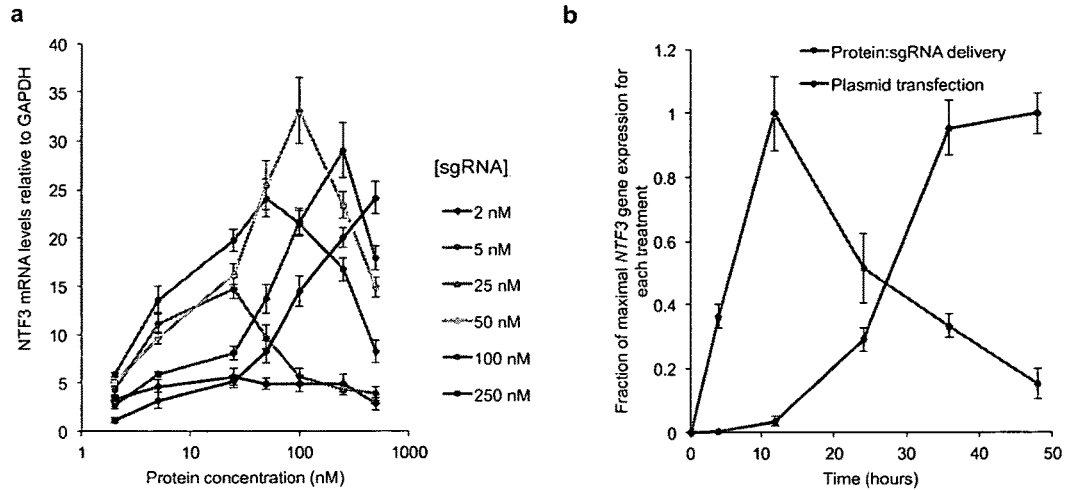
FIGS. 15A, 15B are graphs showing the optimization of dCas9-VP64 delivery targeting the NTF3 gene at varying concentrations of protein and sgRNA.

NTF3 transcriptional activation efficiency was compared in HEK293T cells resulting from either plasmid transfection or direct protein:sgRNA complex delivery of dCas9 fused to a VP64 activation domain (Maeder, M. L. et al. *Nat. Methods* 10, 977-979 (2013)). Delivery of dCas9-VP64 activators either by plasmid transfection or RNAiMAX-mediated protein delivery resulted in strong (≥~10-fold) activation of NTF3 transcription (FIG. 4E and FIG. 15A). Transcriptional activation levels resulting from plasmid transfection were more potent than activation resulting from protein delivery at optimal assay times for each delivery method (FIG. 44), potentially due to the sustained expression both Cas9 activator protein and sgRNA from the plasmids compared to the transient, single dose of purified protein and sgRNA (FIG. 15B). While the above results indicate that such factors do not limit the potency of irreversible genome modification by delivered Cas9 nuclease and nickase proteins (FIGS. 4A and 4D), the low dose and transient nature of the delivered protein may more strongly limit potency of dynamic processes such as transcriptional activation. Nevertheless, these results collectively indicate that both Cas9 nickases and Cas9 transcriptional activators can also be delivered effectively by cationic lipid-mediated protein:sgRNA complex delivery.

Figures 5A, 5B, 5C, 5D:
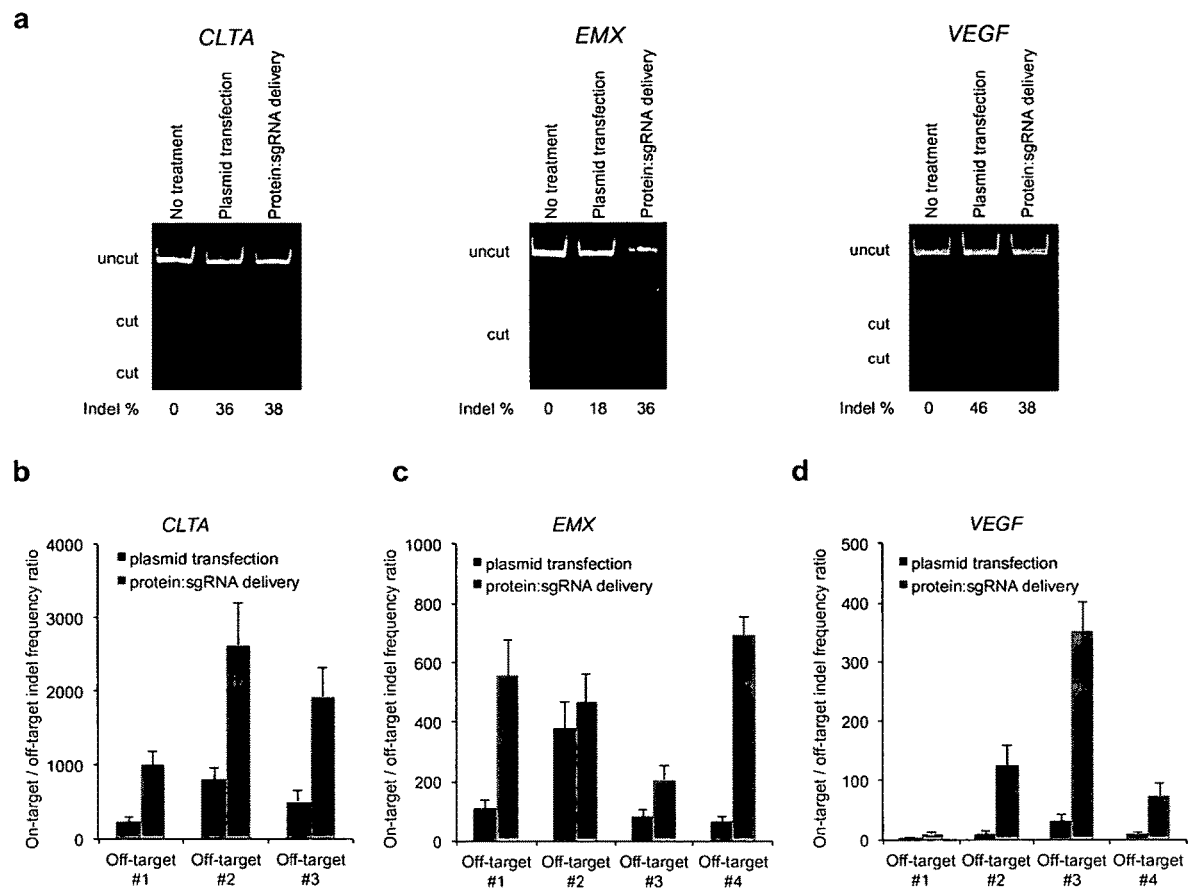
FIGS. 5A-5D show the DNA sequence specificity of Cas9-mediated endogenous gene cleavage in cultured human cells by plasmid transfection or by cationic lipid-mediated protein:sgRNA delivery using 1.6 μL RNAiMAX complexed with 100 nM Cas9 and 100 nM sgRNA for targeting each of the genes of interest.

Cas9:sgRNA Delivery Modifies Genomes with Greater Specificity than DNA Transfection:

DNA-free delivery of functional Cas9:sgRNA complexes circumvents risks associated with viral or other gene delivery methods and has the potential to improve the specificity of genome modification by avoiding the unnecessary expression of genome-editing agent after the target locus is modified. To test if the approach taken can disrupt endogenous genes in human cells, genomic loci were targeted in the EMX1, CLTA2, and VEGF genes due to their potential biomedical relevance and their use in previous studies (Fu, Y., et al. *Nat. Biotechnol.* 32, 279-284 (2014); Guilinger, J. P., et al. *Nat. Biotechnol.* 32, 577-582 (2014); Pattanayak, V. et al. *Nat. Biotechnol.* 31, 839-843 (2013)) of Cas9 off-target cleavage activity. Cationic lipid-mediated delivery of Cas9: sgRNA complexes into HEK293T cells resulted in robust cleavage of all three human genes with efficiencies comparable to or greater than those of plasmid transfection methods as revealed by the T7EI assay using the same Cas9: sgRNA delivery conditions previously optimized for U2OS cells (FIG. 5A).

To compare the endogenous gene modification specificity of plasmid versus protein:RNA delivery methods for Cas9, the on-target locus as well as several known off-target sites (Table 1) were amplified from genomic DNA isolated from HEK293 cells treated either by transfection of Cas9 and sgRNA expression plasmids, or by RNAiMAX-mediated Cas9:sgRNA complex delivery under conditions that resulted in comparable on-target modification efficiencies.

Figures 16A, 16B, 16C:
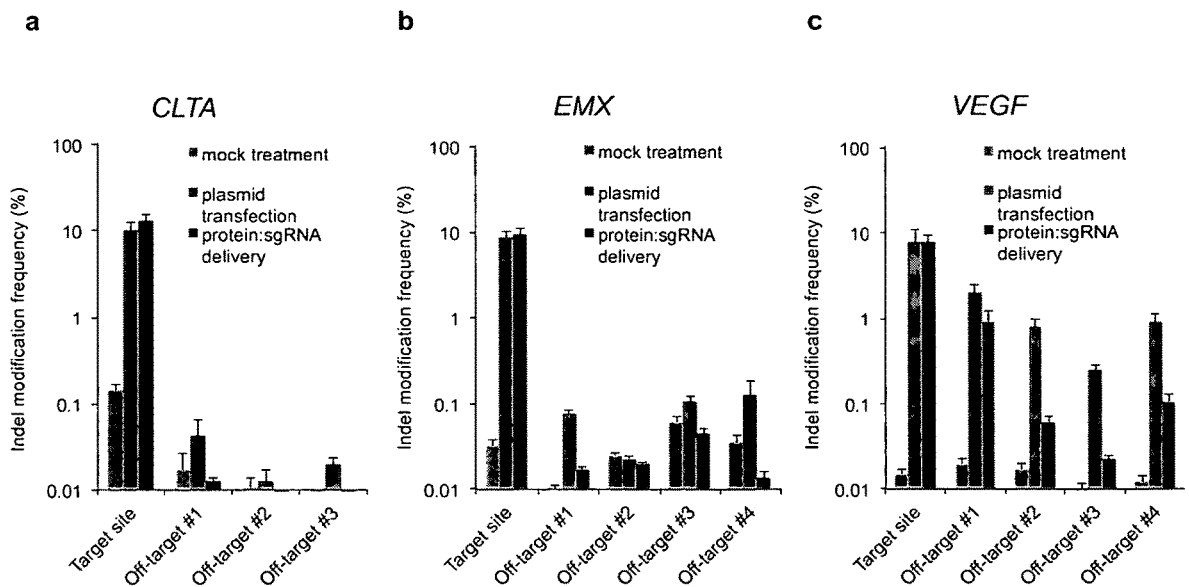
FIGS. 16A-16C are graphs showing the Indel frequencies, measured by high-throughput sequencing, of several human genes treated either by a mock treatment, by transfection of Cas9 plasmid and sgRNA linear DNA PCR product, or by cationic lipid-mediated protein:sgRNA delivery. Mock treatment involved cationic lipid-mediated protein:sgRNA delivery of EGFP-targeting sgRNA instead of one of the three human gene-targeting sgRNAs.
Figures 17A, 17B, 17C, 17D, 17E, 17F:
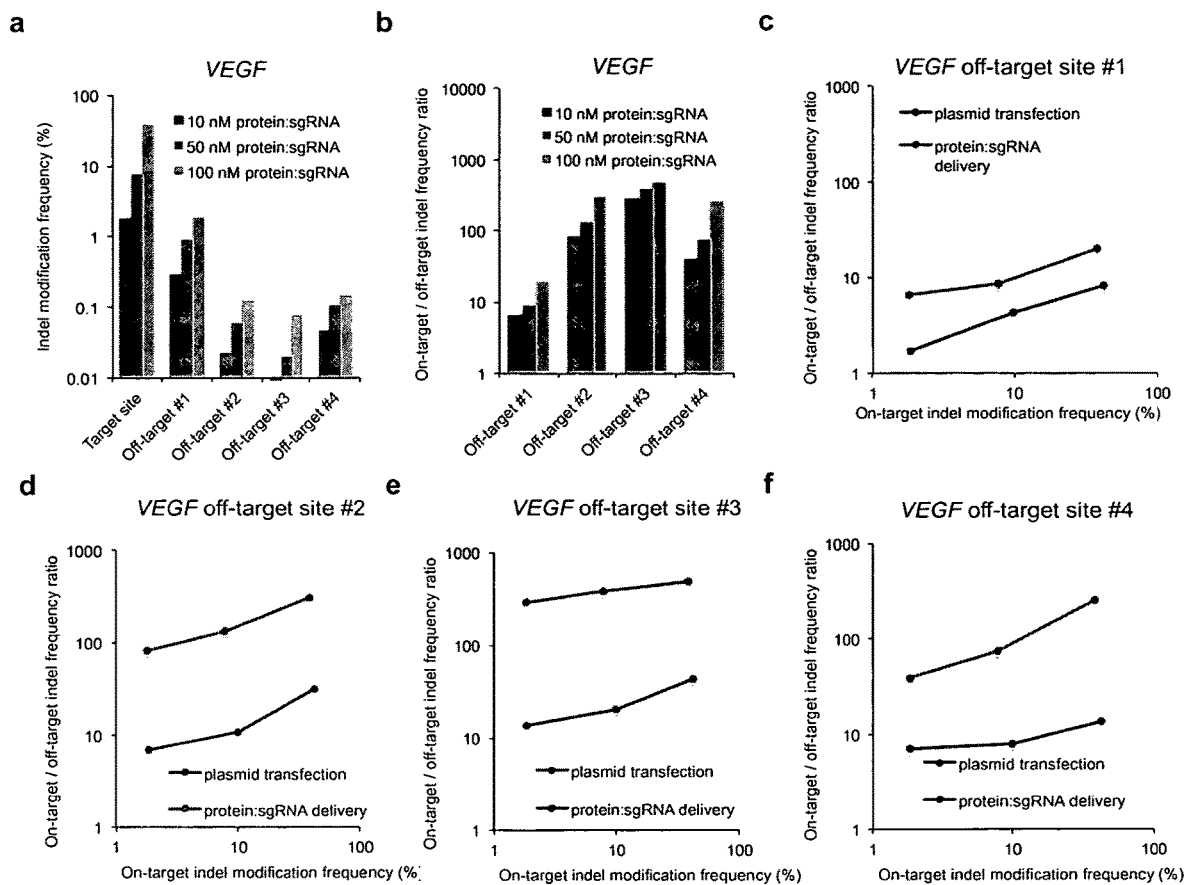
FIGS. 17A-17F are graphs showing the concentration dependence of on-target and off-target indel modification frequencies for Cas9 plasmid transfection or lipid-mediated protein:sgRNA delivery.

The indel frequencies at the three on-target and 11 off-target sites were assayed by high-throughput DNA sequencing (Table 2). For all three target genes, the frequency of on-target DNA modification resulting from either plasmid or protein:sgRNA delivery was ~10% (FIGS. 16A, 16B, 16C), enabling a comparison of off-target modification between the two techniques under treatment conditions that result in very similar on-target genome modification efficiencies. Importantly, the frequency of off-target genome modification for all 11 off-target sites was lower from protein:sgRNA delivery compared with plasmid delivery, and as a result the ratio of on-target to off-target modification ratio for all sites tested was up to 19-fold higher for protein:sgRNA delivery than for plasmid delivery (FIGS. 5B, 5C, 5D).

DNA modification specificity was higher for protein: sgRNA delivery than for plasmid delivery at loci with high levels of off-target modification (such as the four VEGF off-target sites, for which plasmid delivery yielded average on-target:off-target modification ratios between 4- and 20-fold but protein:sgRNA delivery yielded average on-target:off-target modification ratios between 9- and 400-fold) as well as for loci with lower levels of off-target modification (such as the three EMX off-target loci, for which plasmid delivery yielded average on-target:off-target modification ratios as low as 64-fold but protein:RNA delivery yielded average on-target:off-target modification ratios of 500- to 2,000-fold).

Finally, the relationship between the observed increase in specificity for Cas9 protein delivery and on-target modification frequencies was tested using the VEGF target and its four associated off-target sites. The Cas9-mediated on-target modification rates were tuned over a broad range by scaling the amount of Cas9:sgRNA delivered, resulting conditions that yield low (~1%), moderate (~10%), and high (~40%) on-target DNA modification. Conditions were developed to effect a comparable range of on-target modification rates for Cas9 plasmid transfection for comparison. Under the conditions tested, it was observed that on-target and off-target modification efficiencies increased together for both protein and DNA delivery methods (FIGS. 17A, 17B) such that specificity was slightly higher at higher protein or plasmid delivery doses, despite the overall increase in absolute off-target modifications (FIGS. 17B-17F). Importantly, it was observed that across all levels of on-target modification, Cas9:sgRNA delivery always resulted in substantially (typically ~10-fold) higher on:off-target modification ratios than comparable Cas9 plasmid DNA transfections (FIGS. 17C-17F). Taken together, these results show that the delivery of Cas9:sgRNA complexes using cationic lipids can effect target gene modification at high efficiency and with substantially greater specificity than the delivery of DNA expressing Cas9 and sgRNA.

Figure 18:
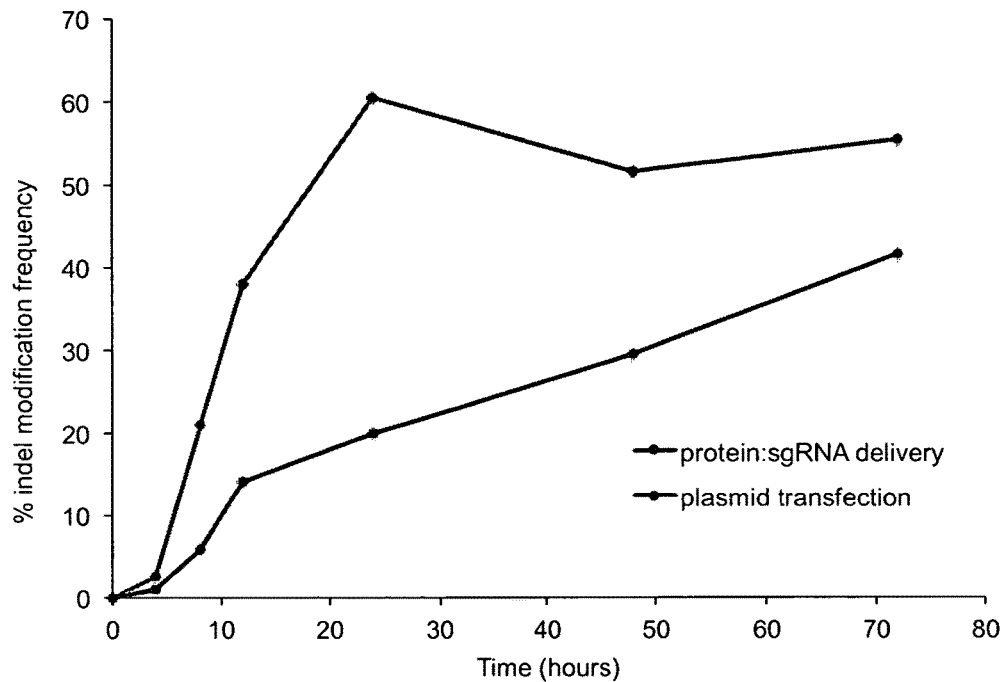
FIG. 18 is a graph showing the time course of Cas9 nuclease activity from protein:sgRNA delivery and plasmid transfection. U2OS EGFP reporter cells were treated with either 50 nM Cas9 protein and 100 nM sgRNA and 0.8 µL Lipofectamine 2000 in 275 µL DMEM-FBS without antibiotics, or transfected with 750 ng Cas9 expression plasmid and 250 ng EGFP sgRNA expression plasmid for 2 hours. Media was removed and samples were either collected after another 2 hours, or at later time points as shown. Samples were analyzed for indels in the EGFP gene using a Surveyor T7E1 cleavage assay. Bands were quantified by ImageJ software. Data presented here represents the average of two independent biological replicates.

The remarkable increases in Cas9 specificity for protein: sgRNA delivery was likely a result of the transient nature of the delivered protein that was directly observed with both TALE-activator and dCas9-activator delivery (FIGS. 3B, 15B). A time course experiment was performed that measured indel modification rate by Surveyor assay from protein:sgRNA or plasmid DNA delivery over the course of 72 hours post-treatment (FIG. 18). Whereas indel formation in U2OS EGFP reporter cells following Cas9 plasmid transfection continued to increase 72 hours after DNA delivery, protein:sgRNA delivery leads to near-maximal indel modification between 12 and 24 hours after treatment (FIG. 18). Together, these results evidence that protein:sgRNA delivery rapidly achieves a transient dose of Cas9:sgRNA activity that mediates efficient genome modification and is degraded before off-target modifications can accumulate to the extent that arises from long-term expression following DNA transfection.

Figures 19A, 19B:
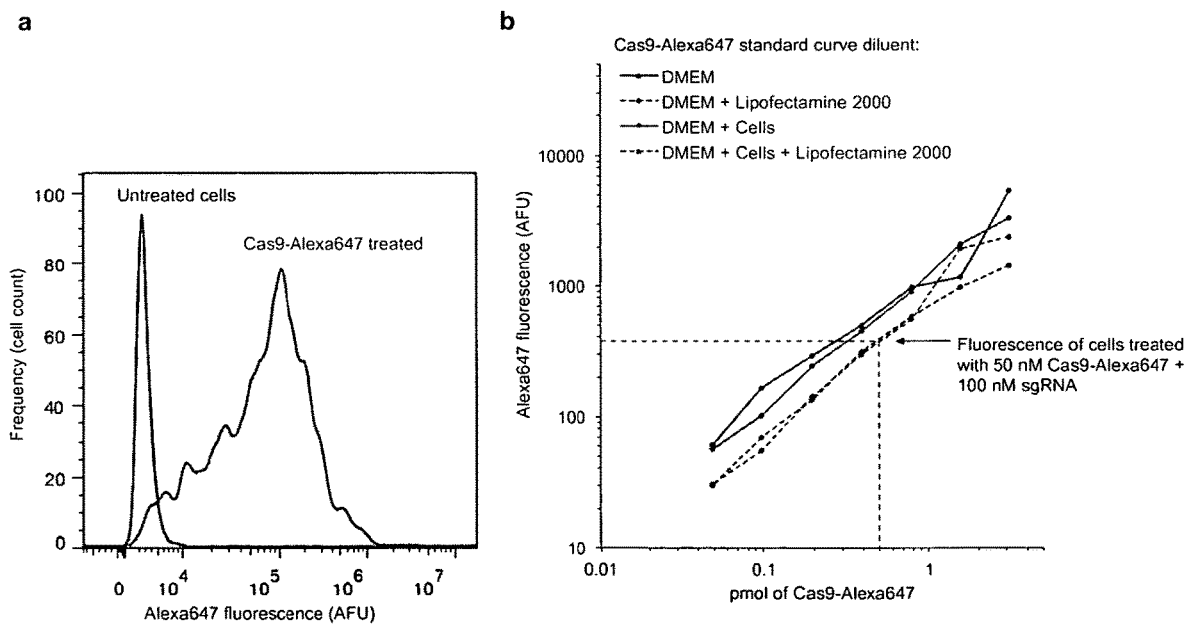
FIGS. 19A, 19B show the quantitation of Cas9 protein uptake into U2OS EGFP reporter cells.

Finally, the amount of protein internalized by cells was quantitated using the cationic lipid-based protein delivery approach. Cas9 protein was labeled with Alexa647 and delivered it to U2OS cells at 50 nM with 100 nM sgRNA. After 4 hours, cells were washed extensively to remove bound protein and trypsinized. Cellular Alexa647 fluorescence was measured and compared to that of a standard curve of known Cas9-Alexa647 amounts in the presence of an identical composition of media, cells, and lipid. Nearly all treated cells were found to have internalized the Cas9-Alexa647 protein (FIG. 19A), and 4% of the total protein used in the treatment was internalized by cells (FIG. 19B). Comparison with the standard curve suggests that $3 \times 10^7$ molecules of Cas9-Alexa647 entered each cell, corresponding to 0.4% of total cellular protein (Lodish, H. et al. *Molecular Cell Biology*. (W. H. Freeman, 2000)). It is noted, however, that the majority of this protein is likely sequestered within endosomes and is not immediately available to effect genome modification (Thompson, D. B., et al. *Chem. Biol.* 19, 831-843 (2012); Gilleron, J. et al. *Nat. Biotechnol.* 31, 638-646 (2013)).

Figures 8A, 8B, 8C, 8D:
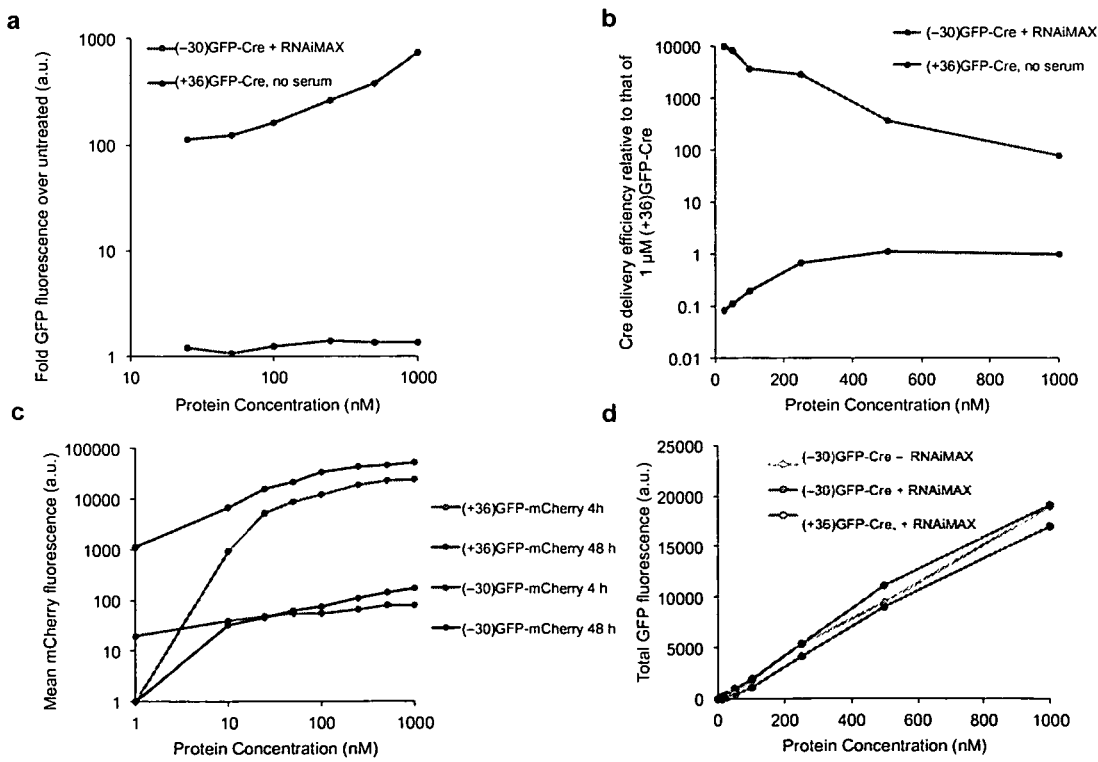
FIGS. 8A-8D are graphs showing the protein uptake by cationic lipid-mediated delivery compared with superpositively charged cationic protein delivery.

Determination of Protein Delivery Efficacy for (−30)GFP-Cre:

To determine if the higher potency of liposome-mediated (−30)GFP-Cre delivery compared with that of cationic protein delivery arises from more total protein uptake by cells or from a higher fraction of functional, non-endosomal protein molecules taken up by the cells, flow cytometry was used to measure GFP fluorescence of cells treated with either (+36)GFP-Cre or liposomal (−30)GFP-Cre under their respective optimal Cre delivery conditions. Cell fluorescence reports total endocytosed (−30)GFP-Cre or (+36) GFP-Cre regardless of endosomal or non-endosomal localization (Putney, S. D. & Burke, P. A. *Nat. Biotechnol.* 16, 153-157 (1998)). Lipid-mediated protein delivery resulted in surprisingly small increases in total protein uptake (FIG. 8A), despite the high efficiency of lipid-mediated functional Cre delivery. While (+36)GFP-Cre treatment increased cellular GFP fluorescence by up to three orders of magnitude in a dose-dependent manner (FIG. 8A), consistent with previous reports (Putney, S. D. & Burke, P. A. *Nat. Biotechnol.* 16, 153-157 (1998); Mullen, L. et al. *Expert Opin. Drug Deliv.* 11, 101-110 (2014)), liposomal (−30)GFP-Cre treatment induced at most 5-fold increases in cellular GFP fluorescence. Comparison of cellular fluorescence and recombination efficiency reveals that lipid-mediated functional delivery of (−30)GFP-Cre is 9,800-fold more potent per amount of endocytosed protein than delivery of (+36) GFP-Cre (FIG. 8B).

To test if complexation of anionic (−30)GFP with cationic lipids interferes with GFP fluorescence and thus masks the true amount of cargo that enters the cell mCherry, which is fluorescent but not highly anionic, was fused to either (−30)GFP or (+36)GFP and delivered both protein fusions to HeLa cells. After washing away protein that may have adhered to cell surface but did not enter the cell with PBS+heparin (20 U/mL), cells were analyzed by FACS for mCherry fluorescence 4 hours and 24 hours after treatment. It was observed that lipid-mediated delivery of (−30)GFP-fused mCherry results in only slight increases in cellular mCherry fluorescence, whereas mCherry fluorescence upon delivery of (+36)GFP-mCherry was generally ≥100-fold higher (FIG. 8C) providing evidence that fusion to (−30) GFP does not cause substantial amounts of protein cargo to enter the cell. Moreover, addition of lipids to (−30)GFP-Cre did not measurably alter the GFP fluorescence signal (FIG. 8D), despite the fact that cationic lipids and anionic (−30) GFP clearly interact. Taken together, these results evidence that the unusually high potency of lipid-mediated delivery of anionic proteins does not arise from unusually high protein uptake in each cell, but rather from post-endocytosis processes that likely include avoidance of protein degradation and endosomal escape into the cytoplasm.

Sensitivity Limit of Off-Target Cleavage Assays:

The sensitivity of the high-throughput sequencing method for detecting genomic off-target cleavage is limited by the amount genomic DNA (gDNA) input into the PCR amplification of each genomic target site. A 1 ng sample of human gDNA represents only ~330 unique genomes, and thus only ~330 unique copies of each genomic site are present. PCR amplification for each genomic target was performed on a total of 150 ng of input gDNA, which provides amplicons derived from at most 50,000, unique gDNA copies, respectively. Therefore, the high-throughput sequencing assay cannot detect rare genome modification events that occur at a frequency of less than 1 in 50,000 (0.002%) (Table 2).

Figures 20A, 20B, 20C, 21A, 21B:
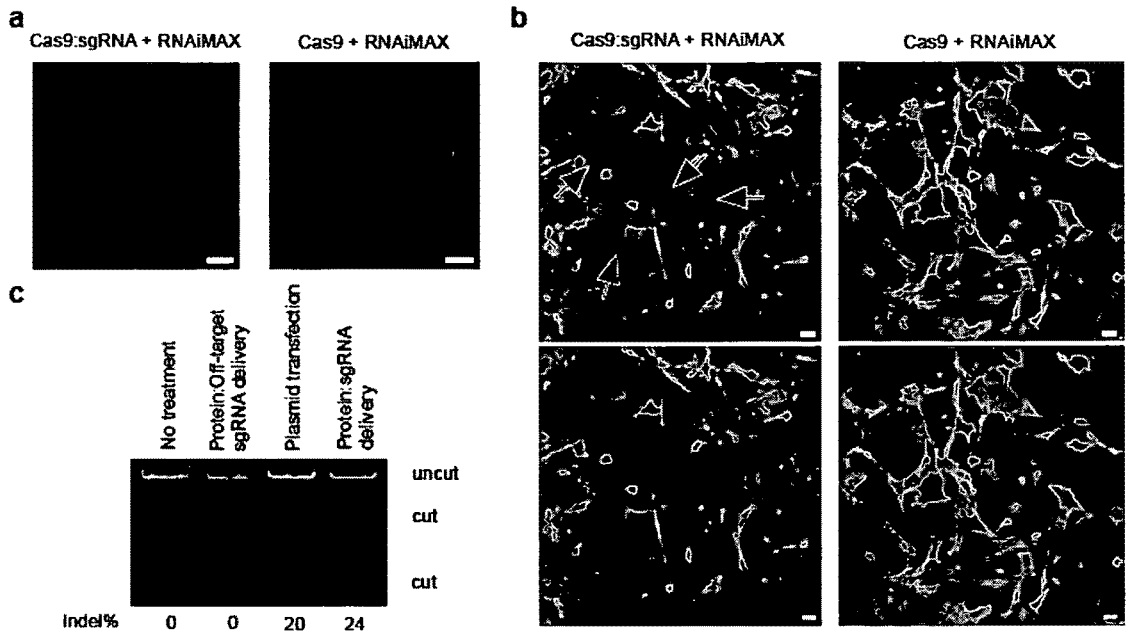
FIGS. 20A-20C show the delivery of Cas9 nuclease to mouse embryonic stem cells. Delivery of Cas9 endonuclease to mouse embryonic stem cells.
FIGS. 21A, 21B show the genome modification induced by cationic lipid-mediated protein delivery of Cas9 nuclease and sgRNA at endogenous loci in vivo. Approximately 10 days after injection of Cas9:sgRNA protein into Atoh1-GFP mice under identical conditions described in FIG. 6D, ~15 mg of mouse hair cell tissue was dissected. 150 ng of isolated genomic DNA was prepared for high-throughput sequencing.

Delivery of Cas9:sgRNA into Mouse Embryonic Stem Cells:

The rapid, potent, and transient cationic lipid-mediated delivery of Cas9:sgRNA to effect genome editing could be especially useful in stem cells, where Cas9 off-target activity over the course of multiple cell divisions could lead to both unwanted mutations, and mosaicism. To test the effectiveness of Cas9:sgRNA delivery in stem cells, mouse embryonic stem cells expressing Tau-EGFP (Li, H. et al. *BMC Neurosci.* 10, 122 (2009)) were treated with Cas9 and an EGFP-targeting sgRNA. Under standard stem-cell culture conditions, EGFP-positive floating spheres were formed. These floating spheres were treated with Cas9:sgRNA complexed with Lipofectamine 2000, or with Cas9 and Lipofectamine 2000 without sgRNA as a control. Three days post-treatment, a reduction in GFP fluorescence was observed in the Cas9:sgRNA-treated spheres compared to the control samples (FIG. 20A). The treated spheres were dissociated, and the cells were allowed to attach to a laminin-coated dish and differentiate into progenitor cells. Immunohistochemistry using an anti-GFP antibody confirmed knockdown of EGFP expression in the cells of Cas9:sgRNA treated samples, with many nuclei lacking any apparent EGFP. In contrast, all cells derived from control spheres were EGFP positive (FIG. 20B). Genomic DNA harvested from Cas9:sgRNA-treated cells was subjected to T7EI assay, resulting in clear evidence of indels at the Tau-EGFP locus (FIG. 20C). From this assay an indel frequency of 24% was calculated from both cationic lipid-mediated Cas9:sgRNA delivery and transfection of Cas9 and sgRNA DNA. No target modification was detected in control samples lacking Cas9:sgRNA or containing Cas9 and an unrelated gRNA. These findings demonstrate that cationic lipid-mediated Cas9:sgRNA delivery can effect efficient gene disruption in mouse embryonic stem cells.

In Vivo Cationic Lipid-Mediated Delivery of Cre Recombinase and Cas9:sgRNA:

The high-efficiency delivery of functional genome-editing proteins in vivo could enable a wide range of applications including non-viral therapeutic genome editing to correct genetic diseases. To evaluate this protein delivery method in a living mammal, delivery to the mouse inner ear was chosen due to its confined space, well-characterized inner ear cell types, and the existence of genetic deafness mouse models that may enable future hearing recovery studies. The in vivo delivery of two types of proteins into the mouse inner year was attempted. First, the delivery of (−30)GFP-Cre protein was tested to assess the targeting of inner ear cell types and the efficiency of functional protein delivery. Second, the delivery of Cas9:sgRNA complexes to the inner ear were evaluated to determine if cationic lipid-mediated protein:sgRNA complex delivery can support CRISPR-based gene editing in vivo.

Figures 6A, 6B, 6C, 6D:
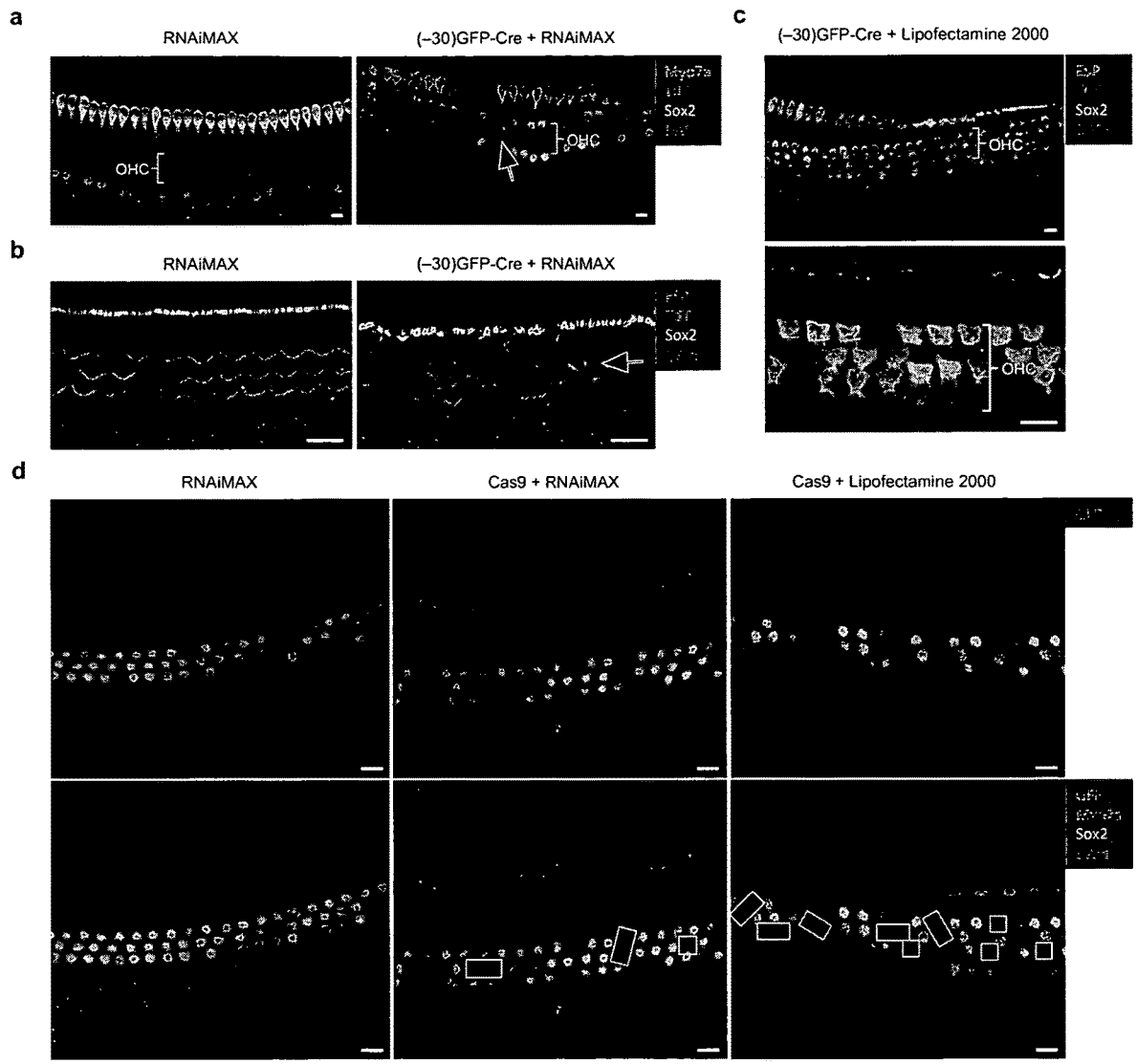
FIGS. 6A-6D show the in vivo delivery of Cre recombinase and Cas9:sgRNA complexes to hair cells in the mouse inner ear.

It was shown that (+36)GFP-Cre could be delivered to mouse retina, although the protein resulted in only modest levels of recombinant conversion suggestive of inefficient in vivo delivery. For the initial inner ear delivery trials, (−30) GFP-Cre was complexed with RNAiMAX and the complex was injected into the cochlea of postnatal day 1 (P1) reporter mice with a genomically integrated floxed-STOP tdTomato reporter. As with the in vitro Cre reporter cell line, functional delivery of Cre to the inner ear cells, followed by endosomal escape, nuclear localization, and Cre-mediated recombination results in expression of tdTomato. After injection, the cochleas were harvested for immunolabeling with inner ear cell markers for co-localization with tdTomato. RNAiMAX injection alone was used as control. Five days following injection of (−30)GFP-Cre and RNAiMAX, cochlear outer hair cells, a type of auditory sensory cells that detect sound, showed strong tdTomato signal that co-localized with the hair cell marker myosin VIIa (Myo7a), demonstrating functional Cre delivery to hair cells (FIGS. 6A, 6B). No tdTomato expression was detected in control cochleas (FIG. 6A). The tdTomato signal was concentrated in the region of the injection site at the basal turn of the cochlea. On average 33±3% of outer hair cells were tdTomato positive at the base of the cochlea (P<0.001; mean±SEM, n=4).

To further determine the effect of cationic lipid-mediated (−30)GFP-Cre protein delivery on targeted cells, hair cell stereocilia was examined, a delicate structure that is essential for hearing, 10 days post-injection. TdTomato positive outer hair cells had typical stereocilia structure as imaged by espin expression, similar to control stereocilia (FIG. 6B). Here again, no tdTomato expression was detected in control cochleas. These observations indicate that cationic lipid-mediated delivery of (−30)GFP-Cre protein effects recombination in cochlear outer hair cells without apparently affecting hair cell architecture.

Because target volume, protein dose, and sgRNA dose in vivo are different than in cell culture experiments, the above experiments were repeated under different delivery conditions. Delivery using Lipofectamine 2000 was tested due to its higher potency in vitro (FIG. 13A) and a dramatically higher recombination efficiency was observed: 91±5% outer hair cells in cochleas treated with (−30)GFP-Cre+Lipofectamine 2000 were tdTomato positive (FIG. 6C). In comparison to control samples, some outer hair cell loss was observed (FIG. 6C) consistent with the previous observation of higher cell toxicity of Lipofectamine 2000, although overall cochlear architecture was preserved.

To test the effectiveness of Cas9:sgRNA delivery in vivo, Cas9 and sgRNA targeting EGFP were combined with RNAiMAX and the resulting complexes were injected into postnatal day 2 (P2) transgenic Atoh1-GFP mouse cochlea in which all hair cells express GFP under the control of a hair cell-specific enhancer for transcription factor Atoh1 (Lumpkin, E. A. et al. *Gene Expr. Patterns GEP* 3, 389-395 (2003)). Using this model, Cas9:sgRNA-mediated disruption of EGFP results in loss of EGFP fluorescence in outer hair cells. Ten days after injection of Cas9:sgRNA with cationic lipid, the absence of GFP in 13% of outer hair cells near the injection site was observed. In contrast, control cochlea injected with Cas9 protein and RNAiMAX without any sgRNA showed no loss of EGFP signal (FIG. 6D). The outer hair cells of cochlea injected with Cas9:sgRNA RNAiMAX complexes appeared to be otherwise unaffected, with stereotypical expression of Myo7a and healthy nuclei, consistent with minimal hair cell toxicity (FIG. 6D). High-throughput DNA sequencing of genomic DNA isolated from cochlea tissue samples revealed indels consistent with GFP target gene disruption in the treated samples, but not in the control samples that lacked sgRNA (FIG. 21A). In addition, inner ear in vivo delivery of Cas9:sgRNA using an sgRNA that targets the EMX gene was repeated and similarly observed indels in the EMX gene in treated animals, but not control animals (FIG. 21B).

As (−30)GFP-Cre complexed with Lipofectamine 2000 resulted in more efficient modification of the target hair cell population than (−30)GFP-Cre complexed with RNAiMAX (FIGS. 6A, 6C), its use was tested on Cas9:sgRNA delivery to Atoh1-GFP cochlea as above. Loss of GFP expression was observed in 20±3% of outer hair cells near the injection site after 10 days, whereas all outer hair cells maintained strong GFP expression in control cochlea injected with Cas9 and Lipofectamine 2000 but no sgRNA (FIG. 6D). In contrast to modest hair cell loss observed following Lipofectamine 2000 delivery of (−30)GFP-Cre (FIG. 6C), outer hair cells targeted by Cas9:sgRNA exhibited no obvious toxicity or structural alteration (FIG. 6D).

As with (−30)GFP-Cre, virus-free, cationic lipid-mediated delivery of Cas9:sgRNA into the mouse inner ear successfully modified a specific genomic locus in the outer hair cell population, leading to loss of target gene expression. Nearly half of all types of genetic deafness arise from hair cell loss or dysfunction, these results evidence a strategy based on the delivery of Cas9:sgRNA complexes to genetically modify these cells to effect hearing recovery. Taken together, these findings evidence that cationic lipid-mediated delivery of genome-editing proteins can serve as a powerful tool and a potential in vivo strategy for the treatment of genetic disease.

Discussion

Efficient intracellular protein delivery in vitro and especially in vivo has been a persistent challenge in biomedical research and protein therapeutics. While delivery using cationic peptides and proteins has been widely studied for over two decades; sensitivity to serum proteins, neutralization by antibodies, degradation by extracellular and intracellular proteases, and poor endosomal escape post-internalization have limited the scope of protein delivery applications using that approach.

In the work herein, a general strategy for protein delivery that makes use of anionic protein complexation with cationic liposomes is reported. This method is used to deliver diverse protein classes, including the Cre tyrosine recombinase, TALE transcriptional activators, and Cas9 nucleases, nickases, and transcriptional activators (FIG. 1A) to cultured cell lines, stem cell colonies, and therapeutically relevant in vivo sites within the mouse inner ear. This approach is highly efficient, producing modification rates similar to or exceeding those of established nucleic acid transfection methods in cell culture, and enabling Cre recombinase- and Cas9-mediated genome modification rates of up to 90% and 20%, respectively, within the inner ear hair cell population of live mice (FIGS. 6C and 6D). Lipid-mediated protein delivery of TALE-activators, Cas9-activators, and Cas9 nuclease were observed to reach peak activity levels in ~4 h, ~12 h, and ~24 h, respectively, well before corresponding activity levels following DNA transfection are achieved (FIGS. 9B, 15B, and 18). These results also evidence that it may be possible to use cationic lipids to efficiently deliver other nucleic acid-binding proteins, including transcription factors that induce therapeutically relevant changes in cell fate, by complexing them with nucleic acids.

Cationic lipid-based anionic protein delivery outperforms a potent cationic protein delivery fusion partner, (+36)GFP, by up to 9,800-fold per amount of endocytosed protein, inducing more efficient modification of treated cells with orders of magnitude lower doses of protein (FIG. 2C and FIG. 8A-8D). For Cas9 nuclease delivery, this approach also typically results in >10-fold more specific genome modification than traditional plasmid transfection (FIGS. 5B-5C), likely due to the transient window of Cas9 activity to which each genome is exposed (FIG. 18) compared to DNA delivery methods (Sojung Kim, D. K. *Genome Res.* (2014)).

The approach herein implemented using purified deliverable protein and the use of popular commercial nucleic acid transfection reagents (FIG. 1B). Rendering a given protein amenable to this approach requires simple translational fusion to a highly anionic partner, such as (−30)GFP (FIG. 1A), and is even effective with common translational fusion tags including the VP64 activation domain, and the 3×FLAG affinity tag (FIG. 2F). In certain cases, as with the Cas9 protein, pre-complexation with a cognate nucleic acid (sgRNA in this case) is sufficient (FIG. 4A), as the partially exposed bound nucleic acid likely provides sufficient anionic charge to mediate complexation with cationic lipids.

This study establishes that protein delivery is a viable approach to in vivo genome editing. Since the commercial lipid reagents used in the current study were optimized for the delivery of DNA and RNA, it is likely that future development of specific components of the liposomal formulation will further improve the performance of the platform, especially for in vivo use.

TABLE 1

On-target and known off-target substrates of Cas9:sgRNAs that target sites in EMX, VEGF, and CLTA. List of genomic on-target and off-targets sites for EMX, VEGF, and CLTA are shown with mutations from the on-target sequence shown in lower case. PAMs are shown in bold.

| | | |
|---|---|---|
| EMX_On | GAGTCCGAGCAGAAGAAGAAGGG | (SEQ ID NO: 78) |
| EMX_Off1 | GAGgCCGAGCAGAAGAAagACGG | (SEQ ID NO: 79) |
| EMX_Off2 | GAGTCCtAGCAGgAGAAGAAGaG | (SEQ ID NO: 80) |
| EMX_Off3 | GAGTCtaAGCAGAAGAAGAAGaG | (SEQ ID NO: 81) |
| EMX_Off4 | GAGTtaGAGCAGAAGAAGAAAGG | (SEQ ID NO: 82) |
| VEGF_On | GGGTGGGGGGAGTTTGCTCCTGG | (SEQ ID NO: 83) |
| VEGF_Off1 | GGaTGGaGGGAGTTTGCTCCTGG | (SEQ ID NO: 84) |
| VEGF_Off2 | GGGaGGGtGGAGTTTGCTCCTGG | (SEQ ID NO: 85) |
| VEGF_Off3 | cGGgGGaGGGAGTTTGCTCCTGG | (SEQ ID NO: 86) |
| VEGF_Off4 | GGGgaGGGGaAGTTTGCTCCTGG | (SEQ ID NO: 87) |
| CLTA_On | GCAGATGTAGTGTTTCCACAGGG | (SEQ ID NO: 88) |
| CLTA_Off1 | aCAtATGTAGTaTTTCCACAGGG | (SEQ ID NO: 89) |
| CLTA_Off2 | cCAGATGTAGTaTTcCCACAGGG | (SEQ ID NO: 90) |
| CLTA_Off3 | ctAGATGaAGTGcTTCCACATGG | (SEQ ID NO: 91) |

TABLE 2

Indel frequencies, P values, and on-target:off-target cleavage specificity ratios for EMX, CLTA, and VEGF on-target sites and 11 known off-target sites.

| | Mock treatment | Plasmid transfection | Protein:sgRNA delivery |
|---|---|---|---|
| CLTA Sites | | | |
| CLTA_On | | | |
| Indels | 14 | 1228 | 1498 |
| Total | 10000 | 10000 | 10000 |
| Modified (%) | 0.140 | 12.280 | 14.980 |
| P-value | | <1.0E−300 | <1.0E−300 |
| On:off specificity | 1 | 1 | 1 |
| CLTA_Off1 | | | |
| Indels | 7 | 29 | 14 |
| Total | 41518 | 205204 | 125370 |
| Modified (%) | 0.017 | 0.014 | 0.011 |
| P-value | | 6.6E−01 | 4.5E−01 |
| On:off specificity | | 869 | 1341 |
| CLTA_Off2 | | | |
| Indels | 5 | 11 | 8 |
| Total | 25338 | 83944 | 54409 |
| Modified (%) | 0.020 | 0.013 | 0.015 |
| P-value | | 5.5E−01 | 5.7E−01 |
| On:off specificity | | 937 | 1019 |
| CLTA_Off3 | | | |
| Indels | 6 | 22 | 8 |
| Total | 41643 | 189886 | 76863 |
| Modified (%) | 0.014 | 0.012 | 0.010 |
| P-value | | 6.2E−01 | 5.8E−01 |
| On:off specificity | | 1060 | 1439 |
| EMX Sites | | | |
| EMX_On | | | |
| Indels | 3 | 930 | 1140 |
| Total | 10000 | 10000 | 10000 |
| Modified (%) | | 0.030 | 9.300 |
| P-value | | 1.6E−264 | <1.0E−300 |
| On:off specificity | 1 | 1 | 1 |
| EMX_Off1 | | | |
| Indels | 0 | 6 | 6 |
| Total | 24623 | 90935 | 100778 |
| Modified (%) | | <0.002 | 0.007 |
| P-value | | 3.5E−01 | 6.1E−01 |
| On:off specificity | | 1409 | 1915 |
| EMX_Off2 | | | |
| Indels | 16 | 53 | 38 |
| Total | 36061 | 204068 | 130084 |
| Modified (%) | | 0.044 | 0.026 |
| P-value | | 6.4E−02 | 1.8E−01 |
| On:off specificity | | 358 | 390 |
| EMX_Off3 | | | |
| Indels | 20 | 147 | 44 |
| Total | 32575 | 157848 | 110878 |
| Modified (%) | | 0.061 | 0.093 |
| P-value | | 8.1E−02 | 1.3E−01 |
| On:off specificity | | 100 | 287 |
| EMX_Off4 | | | |
| Indels | 16 | 141 | 23 |
| Total | 45548 | 86586 | 73451 |
| Modified (%) | | 0.035 | 0.163 |
| P-value | | 2.8E−12 | 7.4E−01 |
| On:off specificity | | 57 | 364 |
| VEGF Sites | | | |
| VEGF_On | | | |
| Indels | 1 | 989 | 785 |
| Total | | 10000 | 10000 |
| Modified (%) | 0.010 | 9.890 | 7.850 |
| P-value | | 1.5E−285 | 5.7E−228 |
| On:off specificity | 1 | 1 | 1 |

TABLE 2-continued

Indel frequencies, P values, and on-target:off-target cleavage specificity ratios for EMX, CLTA, and VEGF on-target sites and 11 known off-target sites.

|  | Mock treatment | Plasmid transfection | Protein:sgRNA delivery |
|---|---|---|---|
| VEGF_Off1 | | | |
| Indels | 4 | 4240 | 602 |
| Total | | 38625 | 184554 |
| Modified (%) | 0.010 | 2.297 | 0.394 |
| P-value | | <1.0E−300 | 3.7E−52 |
| On:off specificity | | 4 | 20 |
| VEGF_Off2 | | | |
| Indels | 5 | 727 | 18 |
| Total | | 30301 | 79164 |
| Modified (%) | 0.017 | 0.918 | <0.002 |
| P-value | | 4.7E−93 | 1.3E−04 |
| On:off specificity | | 11 | 3925 |
| VEGF_Off3 | | | |
| Indels | 2 | 536 | 21 |
| Total | | 26379 | 110902 |
| Modified (%) | 0.008 | 0.483 | 0.022 |
| P-value | | 2.0E−46 | 2.0E−01 |
| On:off specificity | | 20 | 352 |
| VEGF_Off4 | | | |
| Indels | 0 | 1531 | 45 |
| Total | | 26012 | 122403 |

Total: total number of sequence counts; only the first 10,000 sequences were analyzed for the on-target site sequences.
Modified: number of indels divided by total number of sequences as percentages.
Upper limits of potential modification were calculated for sites with no observed indels by assuming there is less than one indel then dividing by the total sequence count to arrive at an upper limit modification percentage, or taking the theoretical limit of detection (1/49,500), whichever value was larger.
P-values: for mock treatment, Cas9 plasmid transfection, and liposomal Cas9 protein: sgRNA delivery, P-values were calculated using a two-sided Fisher's exact test between each CLTA-targeted treatment sample (either DNA transfection or protein:sgRNA delivery) versus the control sample (mock treatment) treated with Cas9 protein and an sgRNA targeting EGFP.
On:off specificity is the ratio of on-target to off-target genomic modification frequency for each site.
(b) Experimental and analytic methods as in (a) applied to EMX target sites.
(c) Experimental and analytic methods as in (a) applied to VEGF target sites.
Indel numbers in the mock treatment control were subtracted from both plasmid transfection and protein:sgRNA delivery indel numbers for determining total #indels and for calculating on-target:off-target ratios in FIG. 5 in the main text and also for FIG. 15.

Amino Acid Sequences of Proteins Used in this Study (+36)GFP-Cre-6xHis (SEQ ID NO: 1):
MGASKGERLFRGKVPILVELKGDVNGHKFSVRGKGKGDATRGKLTL
KFICTTGKLPVPWPTLVTTLTYGVQCFSRYPKHMKRHDFFKSAMPK
GYVQERTISFKKDGKYKTRAEVKFEGRTLVNRIKLKGRDFKEKGNI
LGHKLRYNFNSHKVYITADKRKNGIKAKFKIRHNVKDGSVQLADHY
QQNTPIGRGPVLLPRNHYLSTRSKLSKDPKEKRDHMVLLEFVTAAG
IKHGRDERYKTGGSGGSGGSGGSGGSGGSGGSGGTASNLLTVH
QNLPALPVDATSDEVRKNLMDMFRDRQAFSEHTWKMLLSVCRSWAA
WCKLNNRKWFPAEPEDVRDYLLYLQARGLAVKTIQQHLGQLNMLHR
RSGLPRPSDSNAVSLVMRRIRKENVDAGERAKQALAFERTDFDQVR
SLMENSDRCQDIRNLAFLGIAYNTLLRIAEIARIRVKDISRTDGGR
MLIHIGRTKTLVSTAGVEKALSLGVTKLVERWISVSGVADDPNNYL
FCRVRKNGVAAPSATSQLSTRALEGIFEATHRLIYGAKDDSGQRYL
AWSGHSARVGAARDMARAGVSIPEIMQAGGWTNVNIVMNYIRNLDS
ETGAMVRLLEDGDGGSHHHHHH (−7)GFP-Cre-6xHis (SEQ ID NO: 2):
MGASKGEELFTGVVPILVELDGDVNGHKFSVRGEGEGDATNGKLTL
KFICTTGKLPVPWPTLVTTLTYGVQCFSRYPDHMKQHDFFKSAMPE
GYVQERTISFKDDGTYKTRAEVKFEGDTLVNRIELKGIDFKEDGNI
LGHKLEYNFNSHNVYITADKQKNGIKANFKIRHNVEDGSVQLADHY
QQNTPIGDGPVLLPDNHYLSTQSALSKDPNEKRDHMVLLEFVTAAG
ITHGMDELYKTGGSGGSGGSGGSGGSGGSGGSGGSGGTASNLLTVH
QNLPALPVDATSDEVRKNLMDMFRDRQAFSEHTWKMLLSVCRSWAA
WCKLNNRKWFPAEPEDVRDYLLYLQARGLAVKTIQQHLGQLNMLHR
RSGLPRPSDSNAVSLVMRRIRKENVDAGERAKQALAFERTDFDQVR
SLMENSDRCQDIRNLAFLGIAYNTLLRIAEIARIRVKDISRTDGGR
MLIHIGRTKTLVSTAGVEKALSLGVTKLVERWISVSGVADDPNNYL
FCRVRKNGVAAPSATSQLSTRALEGIFEATHRLIYGAKDDSGQRYL
AWSGHSARVGAARDMARAGVSIPEIMQAGGWTNVNIVMNYIRNLDS
ETGAMVRLLEDGDGGSHHHHHH (−20)GFP-Cre-6xHis (SEQ ID NO: 3):
MGASKGEELFTGVVPILVELDGDVNGHKFSVRGEGEGDATNGKLTL
KFICTTGKLPVPWPTLVTTLTYGVQCFSRYPDHMDQHDFFKSAMPE
GYVQERTISFKDDGTYKTRAEVKFEGDTLVNRIELKGIDFKEDGNI
LGHKLEYNFNSHDVYITADKQENGIKAEFEIRHNVEDGSVQLADHY
QQNTPIGDGPVLLPDDHYLSTESALSKDPNEDRDHMVLLEFVTAAG
IDHGMDELYKTGGSGGSGGSGGSGGSGGSGGSGGSGGTASNLLTVH
QNLPALPVDATSDEVRKNLMDMFRDRQAFSEHTWKMLLSVCRSWAA
WCKLNNRKWFPAEPEDVRDYLLYLQARGLAVKTIQQHLGQLNMLHR
RSGLPRPSDSNAVSLVMRRIRKENVDAGERAKQALAFERTDFDQVR
SLMENSDRCQDIRNLAFLGIAYNTLLRIAEIARIRVKDISRTDGGR
MLIHIGRTKTLVSTAGVEKALSLGVTKLVERWISVSGVADDPNNYL
FCRVRKNGVAAPSATSQLSTRALEGIFEATHRLIYGAKDDSGQRYL
AWSGHSARVGAARDMARAGVSIPEIMQAGGWTNVNIVMNYIRNLDS
ETGAMVRLLEDGDGGSHHHHHH (−30)GFP-Cre-6xHis (SEQ ID NO: 4):
MGASKGEELFDGVVPILVELDGDVNGHEFSVRGEGEGDATEGELTL
KFICTTGELPVPWPTLVTTLTYGVQCFSDYPDHMDQHDFFKSAMPE
GYVQERTISFKDDGTYKTRAEVKFEGDTLVNRIELKGIDFKEDGNI
LGHKLEYNFNSHDVYITADKQENGIKAEFEIRHNVEDGSVQLADHY
QQNTPIGDGPVLLPDDHYLSTESALSKDPNEDRDHMVLLEFVTAAG
IDHGMDELYKTGGSGGSGGSGGSGGSGGSGGSGGSGGTASNLLTVH
QNLPALPVDATSDEVRKNLMDMFRDRQAFSEHTWKMLLSVCRSWAA
WCKLNNRKWFPAEPEDVRDYLLYLQARGLAVKTIQQHLGQLNMLHR -continued RSGLPRPSDSNAVSLVMRRIRKENVDAGERAKQALAFERTDFDQVR
SLMENSDRCQDIRNLAFLGIAYNTLLRIAEIARIRVKDISRTDGGR
MLIHIGRTKTLVSTAGVEKALSLGVTKLVERWISVSGVADDPNNYL
FCRVRKNGVAAPSATSQLSTRALEGIFEATHRLIYGAKDDSGQRYL
AWSGHSARVGAARDMARAGVSIPEIMQAGGWTNVNIVMNYIRNLDS
ETGAMVRLLEDGDGGSHHHHHH Cre-6xHis (SEQ ID NO: 5):
MASNLLTVHQNLPALPVDATSDEVRKNLMDMFRDRQAFSEHTWKML
LSVCRSWAAWCKLNNRKWFPAEPEDVRDYLLYLQARGLAVKTIQQH
LGQLNMLHRRSGLPRPSDSNAVSLVMRRIRKENVDAGERAKQALAF
ERTDFDQVRSLMENSDRCQDIRNLAFLGIAYNTLLRIAEIARIRVK
DISRTDGGRMLIHIGRTKTLVSTAGVEKALSLGVTKLVERWISVSG
VADDPNNYLFCRVRKNGVAAPSATSQLSTRALEGIFEATHRLIYGA
KDDSGQRYLAWSGHSARVGAARDMARAGVSIPEIMQAGGWTNVNIV
MNYIRNLDSETGAMVRLLEDGDGGSHHHHHH Cas9 (SEQ ID NO: 6):
MDKKYSIGLAIGTNSVGWAVITDEYKVPSKKFKVLGNTDRHSIKKN
LIGALLFDSGETAEATRLKRTARRRYTRRKNRKYLQEIFSNEMAKV
DDSFFHRLEESFLVEEDKKHERHPIFGNIVDEVAYHEKYPTIYHLR
KKLVDSTDKADLRLIYLALAHMIKFRGHFLIEGDLNPDNSDVDKLF
IQLVQTYNQLFEENPINASGVDAKAILSARLSKSRRLENLIAQLPG
EKKNGLFGNLIALSLGLTPNFKSNFDLAEDAKLQLSKDTYDDDLDN
LLAQIGDQYADLFLAAKNLSDAILLSDILRVNTEITKAPLSASMIK
RYDEHHQDLTLLKALVRQQLPEKYKEIFFDQSKNGYAGYIDGGASQ
EEFYKFIKPILEKMDGTEELLVKLNREDLLRKQRTFDNGSIPHQIH
LGELHAILRRQEDFYPFLKDNREKIEKILTFRIPYYVGPLARGNSR
FAWMTRKSEETITPWNFEEVVDKGASAQSFIERMTNFDKNLPNEKV
LPKHSLLYEYFTVYNELTKVKYVTEGMRKPAFLSGEQKKAIVDLLF
KTNRKVTVKQLKEDYFKKIECFDSVEISGVEDRFNASLGTYHDLLK
IIKDKDFLDNEENEDILEDIVLTLTLFEDREMIEERLKTYAHLFDD
KVMKQLKRRRYTGWGRLSRKLINGIRDKQSGKTILDFLKSDGFANR
NFMQLIHDDSLTFKEDIQKAQVSGQGDSLHEHIANLAGSPAIKKGI
LQTVKVVDELVKVMGRHKPENIVIEMARENQTTQKGQKNSRERMKR
IEEGIKELGSQILKEHPVENTQLQNEKLYLYYLQNGRDMYVDQELD
INRLSDYDVDHIVPQSFLKDDSIDNKVLTRSDKNRGKSDNVPSEEV
VKKMKNYWRQLLNAKLITQRKFDNLTKAERGGLSELDKAGFIKRQL
VETRQITKHVAQILDSRMNTKYDENDKLIREVKVITLKSKLVSDFR
KDFQFYKVREINNYHHAHDAYLNAVVGTALIKKYPKLESEFVYGDY
KVYDVRKMIAKSEQEIGKATAKYFFYSNIMNFFKTEITLANGEIRK
RPLIETNGETGEIVWDKGRDFATVRKVLSMPQVNIVKKTEVQTGGF
SKESILPKRNSDKLIARKKDWDPKKYGGFDSPTVAYSVLVVAKVEK
GKSKKLKSVKELLGITIMERSSFEKNPIDFLEAKGYKEVKKDLIIK
LPKYSLFELENGRKRMLASAGELQKGNELALPSKYVNFLYLASHYE
KLKGSPEDNEQKQLFVEQHKHYLDEIIEQISEFSKRVILADANLDK
VLSAYNKHRDKPIREQAENIIHLFTLTNLGAPAAFKYFDTTIDRKR
YTSTKEVLDATLIHQSITGLYETRIDLSQLGGD Cas9-6xHis (SEQ ID NO: 7):
MDKKYSIGLAIGTNSVGWAVITDEYKVPSKKFKVLGNTDRHSIKKN
LIGALLFDSGETAEATRLKRTARRRYTRRKNRKYLQEIFSNEMAKV
DDSFFHRLEESFLVEEDKKHERHPIFGNIVDEVAYHEKYPTIYHLR
KKLVDSTDKADLRLIYLALAHMIKFRGHFLIEGDLNPDNSDVDKLF
IQLVQTYNQLFEENPINASGVDAKAILSARLSKSRRLENLIAQLPG
EKKNGLFGNLIALSLGLTPNFKSNFDLAEDAKLQLSKDTYDDDLDN
LLAQIGDQYADLFLAAKNLSDAILLSDILRVNTEITKAPLSASMIK
RYDEHHQDLTLLKALVRQQLPEKYKEIFFDQSKNGYAGYIDGGASQ
EEFYKFIKPILEKMDGTEELLVKLNREDLLRKQRTFDNGSIPHQIH
LGELHAILRRQEDFYPFLKDNREKIEKILTFRIPYYVGPLARGNSR
FAWMTRKSEETITPWNFEEVVDKGASAQSFIERMTNFDKNLPNEKV
LPKHSLLYEYFTVYNELTKVKYVTEGMRKPAFLSGEQKKAIVDLLF
KTNRKVTVKQLKEDYFKKIECFDSVEISGVEDRFNASLGTYHDLLK
IIKDKDFLDNEENEDILEDIVLTLTLFEDREMIEERLKTYAHLFDD
KVMKQLKRRRYTGWGRLSRKLINGIRDKQSGKTILDFLKSDGFANR
NFMQLIHDDSLTFKEDIQKAQVSGQGDSLHEHIANLAGSPAIKKGI
LQTVKVVDELVKVMGRHKPENIVIEMARENQTTQKGQKNSRERMKR
IEEGIKELGSQILKEHPVENTQLQNEKLYLYYLQNGRDMYVDQELD
INRLSDYDVDHIVPQSFLKDDSIDNKVLTRSDKNRGKSDNVPSEEV
VKKMKNYWRQLLNAKLITQRKFDNLTKAERGGLSELDKAGFIKRQL
VETRQITKHVAQILDSRMNTKYDENDKLIREVKVITLKSKLVSDFR
KDFQFYKVREINNYHHAHDAYLNAVVGTALIKKYPKLESEFVYGDY
KVYDVRKMIAKSEQEIGKATAKYFFYSNIMNFFKTEITLANGEIRK
RPLIETNGETGEIVWDKGRDFATVRKVLSMPQVNIVKKTEVQTGGF
SKESILPKRNSDKLIARKKDWDPKKYGGFDSPTVAYSVLVVAKVEK
GKSKKLKSVKELLGITIMERSSFEKNPIDFLEAKGYKEVKKDLIIK
LPKYSLFELENGRKRMLASAGELQKGNELALPSKYVNFLYLASHYE
KLKGSPEDNEQKQLFVEQHKHYLDEIIEQISEFSKRVILADANLDK
VLSAYNKHRDKPIREQAENIIHLFTLTNLGAPAAFKYFDTTIDRKR
YTSTKEVLDATLIHQSITGLYETRIDLSQLGGDHHHHHH NLS-Cas9-6xHis (SEQ ID NO: 8):
MPKKKRKVMDKKYSIGLAIGTNSVGWAVITDEYKVPSKKFKVLGNT
DRHSIKKNLIGALLFDSGETAEATRLKRTARRRYTRRKNRKYLQEI
FSNEMAKVDDSFFHRLEESFLVEEDKKHERHPIFGNIVDEVAYHEK
YPTIYHLRKKLVDSTDKADLRLIYLALAHMIKFRGHFLIEGDLNPD
NSDVDKLFIQLVQTYNQLFEENPINASGVDAKAILSARLSKSRRLE -continued
NLIAQLPGEKKNGLFGNLIALSLGLTPNFKSNFDLAEDAKLQLSKD
TYDDDLDNLLAQIGDQYADLFLAAKNLSDAILLSDILRVNTEITKA
PLSASMIKRYDEHHQDLTLLKALVRQQLPEKYKEIFFDQSKNGYAG
YIDGGASQEEFYKFIKPILEKMDGTEELLVKLNREDLLRKQRTFDN
GSIPHQIHLGELHAILRRQEDFYPFLKDNREKIEKILTFRIPYYVG
PLARGNSRFAWMTRKSEETITPWNFEEVVDKGASAQSFIERMTNFD
KNLPNEKVLPKHSLLYEYFTVYNELTKVKYVTEGMRKPAFLSGEQK
KAIVDLLFKTNRKVTVKQLKEDYFKKIECFDSVEISGVEDRFNASL
GTYHDLLKIIKDKDFLDNEENEDILEDIVLTLTLFEDREMIEERLK
TYAHLFDDKVMKQLKRRYTGWGRLSRKLINGIRDKQSGKTILDFL
KSDGFANRNFMQLIHDDSLTFKEDIQKAQVSGQGDSLHEHIANLAG
SPAIKKGILQTVKVVDELVKVMGRHKPENIVIEMARENQTTQKGQK
NSRERMKRIEEGIKELGSQILKEHPVENTQLQNEKLYLYYLQNGRD
MYVDQELDINRLSDYDVDHIVPQSFLKDDSIDNKVLTRSDKNRGKS
DNVPSEEVVKKMKNYWRQLLNAKLITQRKFDNLTKAERGGLSELDK
AGFIKRQLVETRQITKHVAQILDSRMNTKYDENDKLIREVKVITLK
SKLVSDFRKDFQFYKVREINNYHHAHDAYLNAVVGTALIKKYPKLE
SEFVYGDYKVYDVRKMIAKSEQEIGKATAKYFFYSNIMNFFKTEIT
LANGEIRKRPLIETNGETGEIVWDKGRDFATVRKVLSMPQVNIVKK
TEVQTGGFSKESILPKRNSDKLIARKKDWDPKKYGGFDSPTVAYSV
LVVAKVEKGKSKKLKSVKELLGITIMERSSFEKNPIDFLEAKGYKE
VKKDLIIKLPKYSLFELENGRKRMLASAGELQKGNELALPSKYVNF
LYLASHYEKLKGSPEDNEQKQLFVEQHKHYLDEIIEQISEFSKRVI
LADANLDKVLSAYNKHRDKPIREQAENIIHLFTLTNLGAPAAFKYF
DTTIDRKRYTSTKEVLDATLIHQSITGLYETRIDLSQLGGDHHHHH
H Cas9-NLS-6xHis (SEQ ID NO: 9):
MDKKYSIGLAIGTNSVGWAVITDEYKVPSKKFKVLGNTDRHSIKKN
LIGALLFDSGETAEATRLKRTARRRYTRRKNRKYLQEIFSNEMAKV
DDSFFHRLEESFLVEEDKKHERHPIFGNIVDEVAYHEKYPTIYHLR
KKLVDSTDKADLRLIYLALAHMIKFRGHFLIEGDLNPDNSDVDKLF
IQLVQTYNQLFEENPINASGVDAKAILSARLSKSRRLENLIAQLPG
EKKNGLFGNLIALSLGLTPNFKSNFDLAEDAKLQLSKDTYDDDLDN
LLAQIGDQYADLFLAAKNLSDAILLSDILRVNTEITKAPLSASMIK
RYDEHHQDLTLLKALVRQQLPEKYKEIFFDQSKNGYAGYIDGGASQ
EEFYKFIKPILEKMDGTEELLVKLNREDLLRKQRTFDNGSIPHQIH
LGELHAILRRQEDFYPFLKDNREKIEKILTFRIPYYVGPLARGNSR
FAWMTRKSEETITPWNFEEVVDKGASAQSFIERMTNFDKNLPNEKV
LPKHSLLYEYFTVYNELTKVKYVTEGMRKPAFLSGEQKKAIVDLLF
KTNRKVTVKQLKEDYFKKIECFDSVEISGVEDRFNASLGTYHDLLK
IIKDKDFLDNEENEDILEDIVLTLTLFEDREMIEERLKTYAHLFDD KVMKQLKRRYTGWGRLSRKLINGIRDKQSGKTILDFLKSDGFANR
NFMQLIHDDSLTFKEDIQKAQVSGQGDSLHEHIANLAGSPAIKKGI
LQTVKVVDELVKVMGRHKPENIVIEMARENQTTQKGQKNSRERMKR
IEEGIKELGSQILKEHPVENTQLQNEKLYLYYLQNGRDMYVDQELD
INRLSDYDVDHIVPQSFLKDDSIDNKVLTRSDKNRGKSDNVPSEEV
VKKMKNYWRQLLNAKLITQRKFDNLTKAERGGLSELDKAGFIKRQL
VETRQITKHVAQILDSRMNTKYDENDKLIREVKVITLKSKLVSDFR
KDFQFYKVREINNYHHAHDAYLNAVVGTALIKKYPKLESEFVYGDY
KVYDVRKMIAKSEQEIGKATAKYFFYSNIMNFFKTEITLANGEIRK
RPLIETNGETGEIVWDKGRDFATVRKVLSMPQVNIVKKTEVQTGGF
SKESILPKRNSDKLIARKKDWDPKKYGGFDSPTVAYSVLVVAKVEK
GKSKKLKSVKELLGITIMERSSFEKNPIDFLEAKGYKEVKKDLIIK
LPKYSLFELENGRKRMLASAGELQKGNELALPSKYVNFLYLASHYE
KLKGSPEDNEQKQLFVEQHKHYLDEIIEQISEFSKRVILADANLDK
VLSAYNKHRDKPIREQAENIIHLFTLTNLGAPAAFKYFDTTIDRKR
YTSTKEVLDATLIHQSITGLYETRIDLSQLGGDPKKKRKVMDKHHH
HHH (+36)dGFP-NLS-Cas9-6xHis (Y67S)
(SEQ ID NO: 10):
MGASKGERLFRGKVPILVELKGDVNGHKFSVRGKGKGDATRGKLTL
KFKTTGKLPVPWPTLVTTLSGVQCFSRYPKHMKRHDFFKSAMPKG
YVQERTISFKKDGKYKTRAEVKFEGRTLVNRIKLKGRDFKEKGNIL
GHKLRYNFNSHKVYITADKRKNGIKAKFKIRHNVKDGSVQLADHYQ
QNTPIGRGPVLLPRNHYLSTRSKLSKDPKEKRDHMVLLEFVTAAGI
KHGRDERYKTGGSGGSGGSGGSGGSGGSGGSGGTALALPKKKR
KVMDKKYSIGLDIGTNSVGWAVITDEYKVPSKKFKVLGNTDRHSIK
KNLIGALLFDSGETAEATRLKRTARRRYTRRKNRKYLQEIFSNEMA
KVDDSFFHRLEESFLVEEDKKHERHPIFGNIVDEVAYHEKYPTIYH
LRKKLVDSTDKADLRLIYLALAHMIKFRGHFLIEGDLNPDNSDVDK
LFIQLVQTYNQLFEENPINASGVDAKAILSARLSKSRRLENLIAQL
PGEKKNGLFGNLIALSLGLTPNFKSNFDLAEDAKLQLSKDTYDDDL
DNLLAQIGDQYADLFLAAKNLSDAILLSDILRVNTEITKAPLSASM
IKRYDEHHQDLTLLKALVRQQLPEKYKEIFFDQSKNGYAGYIDGGA
SQEEFYKFIKPILEKMDGTEELLVKLNREDLLRKQRTFDNGSIPHQ
IHLGELHAILRRQEDFYPFLKDNREKIEKILTFRIPYYVGPLARGN
SRFAWMTRKSEETITPWNFEEVVDKGASAQSFIERMTNFDKNLPNE
KVLPKHSLLYEYFTVYNELTKVKYVTEGMRKPAFLSGEQKKAIVDL
LFKTNRKVTVKQLKEDYFKKIECFDSVEISGVEDRFNASLGTYHDL
LKIIKDKDFLDNEENEDILEDIVLTLTLFEDREMIEERLKTYAHLF
DDKVMKQLKRRYTGWGRLSRKLINGIRDKQSGKTILDFLKSDGFA
NRNFMQLIHDDSLTFKEDIQKAQVSGQGDSLHEHIANLAGSPAIKK
GILQTVKVVDELVKVMGRHKPENIVIEMARENQTTQKGQKNSRERM -continued KRIEEGIKELGSQILKEHPVENTQLQNEKLYLYYLQNGRDMYVDQE
LDINRLSDYDVDHIVPQSFLKDDSIDNKVLTRSDKNRGKSDNVPSE
EVVKKMKNYWRQLLNAKLITQRKFDNLTKAERGGLSELDKAGFIKR
QLVETRQITKHVAQILDSRMNTKYDENDKLIREVKVITLKSKLVSD
FRKDFQFYKVREINNYHHAHDAYLNAVVGTALIKKYPKLESEFVYG
DYKVYDVRKMIAKSEQEIGKATAKYFFYSNIMNFFKTEITLANGEI
RKRPLIETNGETGEIVWDKGRDFATVRKVLSMPQVNIVKKTEVQTG
GFSKESILPKRNSDKLIARKKDWDPKKYGGFDSPTVAYSVLVVAKV
EKGKSKKLKSVKELLGITIMERSSFEKNPIDFLEAKGYKEVKKDLI
IKLPKYSLFELENGRKRMLASAGELQKGNELALPSKYVNFLYLASH
YEKLKGSPEDNEQKQLFVEQHKHYLDEIIEQISEFSKRVILADANL
DKVLSAYNKHRDKPIREQAENIIHLFTLTNLGAPAAFKYFDTTIDR
KRYTSTKEVLDATLIHQSITGLYETRIDLSQLGGDHHHHHH (-30)dGFP-NLS-Cas9-6xHis (Y67S)
(SEQ ID NO: 11):
MGASKGEELFDGVVPILVELDGDVNGHEFSVRGEGEGDATEGELTL
KFKTTGELPVPWPTLVTTLSGVQCFSDYPDHMDQHDFFKSAMPEG
YVQERTISFKDDGTYKTRAEVKFEGDTLVNRIELKGIDFKEDGNIL
GHKLEYNFNSHDVYITADKQENGIKAEFEIRHNVEDGSVQLADHYQ
QNTPIGDGPVLLPDDHYLSTESALSKDPNEDRDHMVLLEFVTAAGI
DHGMDELYKTGGSGGSGGSGGSGGSGGSGGSGGTALALPKKKR
KVMDKKYSIGLDIGTNSVGWAVITDEYKVPSKKFKVLGNTDRHSIK
KNLIGALLFDSGETAEATRLKRTARRRYTRRKNRKYLQEIFSNEMA
KVDDSFFHRLEESFLVEEDKKHERHPIFGNIVDEVAYHEKYPTIYH
LRKKLVDSTDKADLRLIYLALAHMIKFRGHFLIEGDLNPDNSDVDK
LFIQLVQTYNQLFEENPINASGVDAKAILSARLSKSRRLENLIAQL
PGEKKNGLFGNLIALSLGLTPNFKSNFDLAEDAKLQLSKDTYDDDL
DNLLAQIGDQYADLFLAAKNLSDAILLSDILRVNTEITKAPLSASM
IKRYDEHHQDLTLLKALVRQQLPEKYKEIFFDQSKNGYAGYIDGGA
SQEEFYKFIKPILEKMDGTEELLVKLNREDLLRKQRTFDNGSIPHQ
IHLGELHAILRRQEDFYPFLKDNREKIEKILTFRIPYYVGPLARGN
SRFAWMTRKSEETITPWNFEEVVDKGASAQSFIERMTNFDKNLPNE
KVLPKHSLLYEYFTVYNELTKVKYVTEGMRKPAFLSGEQKKAIVDL
LFKTNRKVTVKQLKEDYFKKIECFDSVEISGVEDRFNASLGTYHDL
LKIIKDKDFLDNEENEDILEDIVLTLTLFEDREMIEERLKTYAHLF
DDKVMKQLKRRRYTGWGRLSRKLINGIRDKQSGKTILDFLKSDGFA
NRNFMQLIHDDSLTFKEDIQKAQVSGQGDSLHEHIANLAGSPAIKK
GILQTVKVVDELVKVMGRHKPENIVIEMARENQTTQKGQKNSRERM
KRIEEGIKELGSQILKEHPVENTQLQNEKLYLYYLQNGRDMYVDQE
LDINRLSDYDVDHIVPQSFLKDDSIDNKVLTRSDKNRGKSDNVPSE
EVVKKMKNYWRQLLNAKLITQRKFDNLTKAERGGLSELDKAGFIKR
QLVETRQITKHVAQILDSRMNTKYDENDKLIREVKVITLKSKLVSD
FRKDFQFYKVREINNYHHAHDAYLNAVVGTALIKKYPKLESEFVYG
DYKVYDVRKMIAKSEQEIGKATAKYFFYSNIMNFFKTEITLANGEI
RKRPLIETNGETGEIVWDKGRDFATVRKVLSMPQVNIVKKTEVQTG
GFSKESILPKRNSDKLIARKKDWDPKKYGGFDSPTVAYSVLVVAKV
EKGKSKKLKSVKELLGITIMERSSFEKNPIDFLEAKGYKEVKKDLI
IKLPKYSLFELENGRKRMLASAGELQKGNELALPSKYVNFLYLASH
YEKLKGSPEDNEQKQLFVEQHKHYLDEIIEQISEFSKRVILADANL
DKVLSAYNKHRDKPIREQAENIIHLFTLTNLGAPAAFKYFDTTIDR
KRYTSTKEVLDATLIHQSITGLYETRIDLSQLGGDHHHHHH dCas9-VP64-6xHis (D10A and H840A)
(SEQ ID NO: 12):
MDKKYSIGLAIGTNSVGWAVITDEYKVPSKKFKVLGNTDRHSIKKN
LIGALLFDSGETAEATRLKRTARRRYTRRKNRKYLQEIFSNEMAKV
DDSFFHRLEESFLVEEDKKHERHPIFGNIVDEVAYHEKYPTIYHLR
KKLVDSTDKADLRLIYLALAHMIKFRGHFLIEGDLNPDNSDVDKLF
IQLVQTYNQLFEENPINASGVDAKAILSARLSKSRRLENLIAQLPG
EKKNGLFGNLIALSLGLTPNFKSNFDLAEDAKLQLSKDTYDDDLDN
LLAQIGDQYADLFLAAKNLSDAILLSDILRVNTEITKAPLSASMIK
RYDEHHQDLTLLKALVRQQLPEKYKEIFFDQSKNGYAGYIDGGASQ
EEFYKFIKPILEKMDGTEELLVKLNREDLLRKQRTFDNGSIPHQIH
LGELHAILRRQEDFYPFLKDNREKIEKILTFRIPYYVGPLARGNSR
FAWMTRKSEETITPWNFEEVVDKGASAQSFIERMTNFDKNLPNEKV
LPKHSLLYEYFTVYNELTKVKYVTEGMRKPAFLSGEQKKAIVDLLF
KTNRKVTVKQLKEDYFKKIECFDSVEISGVEDRFNASLGTYHDLLK
IIKDKDFLDNEENEDILEDIVLTLTLFEDREMIEERLKTYAHLFDD
KVMKQLKRRRYTGWGRLSRKLINGIRDKQSGKTILDFLKSDGFANR
NFMQLIHDDSLTFKEDIQKAQVSGQGDSLHEHIANLAGSPAIKKGI
LQTVKVVDELVKVMGRHKPENIVIEMARENQTTQKGQKNSRERMKR
IEEGIKELGSQILKEHPVENTQLQNEKLYLYYLQNGRDMYVDQELD
INRLSDYDVDAIVPQSFLKDDSIDNKVLTRSDKNRGKSDNVPSEEV
VKKMKNYWRQLLNAKLITQRKFDNLTKAERGGLSELDKAGFIKRQL
VETRQITKHVAQILDSRMNTKYDENDKLIREVKVITLKSKLVSDFR
KDFQFYKVREINNYHHAHDAYLNAVVGTALIKKYPKLESEFVYGDY
KVYDVRKMIAKSEQEIGKATAKYFFYSNIMNFFKTEITLANGEIRK
RPLIETNGETGEIVWDKGRDFATVRKVLSMPQVNIVKKTEVQTGGF
SKESILPKRNSDKLIARKKDWDPKKYGGFDSPTVAYSVLVVAKVEK
GKSKKLKSVKELLGITIMERSSFEKNPIDFLEAKGYKEVKKDLIIK
LPKYSLFELENGRKRMLASAGELQKGNELALPSKYVNFLYLASHYE
KLKGSPEDNEQKQLFVEQHKHYLDEIIEQISEFSKRVILADANLDK
VLSAYNKHRDKPIREQAENIIHLFTLTNLGAPAAFKYFDTTIDRKR
YTSTKEVLDATLIHQSITGLYETRIDLSQLGGDGSPKKKRKVSSDY

```
KDHDGDYKDHDIDYKDDDDKAAGGGGSGRADALDDFDLDMLGSDAL

DDFDLDMLGSDALDDFDLDMLGSDALDDFDLDMLHHHHHH

Cas9 nickase (D10A) (SEQ ID NO: 13):
MDKKYSIGLAIGTNSVGWAVITDEYKVPSKKFKVLGNTDRHSIKKN

LIGALLFDSGETAEATRLKRTARRRYTRRKNRKYLQEIFSNEMAKV

DDSFFHRLEESFLVEEDKKHERHPIFGNIVDEVAYHEKYPTIYHLR

KKLVDSTDKADLRLIYLALAHMIKFRGHFLIEGDLNPDNSDVDKLF

IQLVQTYNQLFEENPINASGVDAKAILSARLSKSRRLENLIAQLPG

EKKNGLFGNLIALSLGLTPNFKSNFDLAEDAKLQLSKDTYDDDLDN

LLAQIGDQYADLFLAAKNLSDAILLSDILRVNTEITKAPLSASMIK

RYDEHHQDLTLLKALVRQQLPEKYKEIFFDQSKNGYAGYIDGGASQ

EEFYKFIKPILEKMDGTEELLVKLNREDLLRKQRTFDNGSIPHQIH

LGELHAILRRQEDFYPFLKDNREKIEKILTFRIPYYVGPLARGNSR

FAWMTRKSEETITPWNFEEVVDKGASAQSFIERMTNFDKNLPNEKV

LPKHSLLYEYFTVYNELTKVKYVTEGMRKPAFLSGEQKKAIVDLLF

KTNRKVTVKQLKEDYFKKIECFDSVEISGVEDRFNASLGTYHDLLK

IIKDKDFLDNEENEDILEDIVLTLTLFEDREMIEERLKTYAHLFDD

KVMKQLKRRRYTGWGRLSRKLINGIRDKQSGKTILDFLKSDGFANR

NFMQLIHDDSLTFKEDIQKAQVSGQGDSLHEHIANLAGSPAIKKGI

LQTVKVVDELVKVMGRHKPENIVIEMARENQTTQKGQKNSRERMKR

IEEGIKELGSQILKEHPVENTQLQNEKLYLYYLQNGRDMYVDQELD

INRLSDYDVDHIVPQSFLKDDSIDNKVLTRSDKNRGKSDNVPSEEV

VKKMKNYWRQLLNAKLITQRKFDNLTKAERGGLSELDKAGFIKRQL

VETRQITKHVAQILDSRMNTKYDENDKLIREVKVITLKSKLVSDFR

KDFQFYKVREINNYHHAHDAYLNAVVGTALIKKYPKLESEFVYGDY

KVYDVRKMIAKSEQEIGKATAKYFFYSNIMNFFKTEITLANGEIRK

RPLIETNGETGEIVWDKGRDFATVRKVLSMPQVNIVKKTEVQTGGF

SKESILPKRNSDKLIARKKDWDPKKYGGFDSPTVAYSVLVVAKVEK

GKSKKLKSVKELLGITIMERSSFEKNPIDFLEAKGYKEVKKDLIIK

LPKYSLFELENGRKRMLASAGELQKGNELALPSKYVNFLYLASHYE

KLKGSPEDNEQKQLFVEQHKHYLDEIIEQISEFSKRVILADANLDK

VLSAYNKHRDKPIREQAENIIHLFTLTNLGAPAAFKYFDTTIDRKR

YTSTKEVLDATLIHQSITGLYETRIDLSQLGGDHHHHHH (-30)GFP-Cre-6xHis (SEQ ID NO: 14):
ATGGGTGCTAGCAAAGGTGAAGAGCTGTTTGACGGTGTAGTACCGA

TCTTAGTGGAATTAGACGGCGACGTGAACGGTCACGAATTTAGCGT

GCGCGGCGAGGGCGAAGGTGACGCTACCGAGGGTGAATTGACCCTG

AAGTTTATTTGCACAACAGGCGAATTACCCGTTCCGTGGCCCACCT

TAGTGACCACCCTGACCTATGGCGTTCAGTGCTTCAGTGATTACCC

AGATCATATGGATCAACACGATTTTTTCAAATCAGCCATGCCTGAA

GGATATGTTCAAGAGCGTACAATCAGCTTCAAGGACGATGGCACCT

ATAAAACGCGTGCGGAAGTGAAATTTGAAGGCGACACATTAGTAAA

CCGTATCGAACTGAAAGGTATCGACTTCAAAGAAGACGGCAACATT

TTAGGCCATAAGCTGGAATATAACTTTAATTCTCATGACGTGTATA

TTACGCCGATAAACAGGAAAACGGTATCAAGGCAGAATTTGAAAT

TCGCCATAACGTGGAGGACGGCAGCGTTCAATTAGCGGATCATTAT

CAACAAAACACGCCGATTGGTGATGGGCCTGTACTGTTACCTGACG

ATCACTACCTGAGCACGGAGTCAGCCCTGAGCAAAGATCCGAACGA

AGACCGCGATCACATGGTTCTGTTAGAATTCGTGACCGCTGCAGGC

ATTGATCATGGAATGGACGAGCTGTACAAGACCGGTGGTAGCGGTG

GTTCTGGTGGTTCTGGTGGTAGCGGCGGTAGCGGTGGTAGCGGTGG

TAGCGGTGGCAGCGGCGGTACCGCGAGCAATTTACTGACCGTACAC

CAAAATTTGCCTGCATTGCCGGTCGATGCAACGAGTGATGAGGTTC

GCAAGAACCTGATGGACATGTTCAGGGATCGCCAGGCGTTTTCTGA

GCATACCTGGAAAATGCTTCTGTCCGTTTGCCGGTCGTGGGCGGCA

TGGTGCAAGTTGAATAACCGGAAATGGTTTCCCGCAGAACCTGAAG

ATGTTCGCGATTATCTTTATATCTTCAGGCGCGCGGTCTGGCAGTA

AAAACTATCCAGCAACATTTGGGCCAGCTAAACATGCTTCATCGTC

GGTCCGGGCTGCCACGACCAAGTGACAGCAATGCTGTTTCACTGGT

TATGCGGCGTATCCGAAAAGAAAACGTTGATGCCGGTGAACGTGCA

AAACAGGCTCTAGCGTTCGAACGCACTGATTTCGACCAGGTTCGTT

CACTCATGGAAAATAGCGATCGCTGCCAGGATATACGTAATCTGGC

ATTTCTGGGGATTGCTTATAACACCCTGTTACGTATAGCCGAAATT

GCCAGGATCAGGGTTAAAGATATCTCACGTACTGACGGTGGGAGAA

TGTTAATCCATATTGGCAGAACGAAAACGCTGGTTAGCACCGCAGG

TGTAGAGAAGGCACTTAGCCTGGGGGTAACTAAACTGGTCGAGCGA

TGGATTTCCGTCTCTGGTGTAGCTGATGATCCGAATAACTACCTGT

TTTGCCGGGTCAGAAAAAATGGTGTTGCCGCGCCATCTGCCACCAG

CCAGCTATCAACTCGCGCCCTGGAAGGGATTTTTGAAGCAACTCAT

CGATTGATTTACGGCGCTAAGGATGACTCTGGTCAGAGATACCTGG

CCTGGTCTGGACACAGTGCCCGTGTCGGAGCCGCGCGAGATATGGC

CCGCGCTGGAGTTTCAATACCGGAGATCATGCAAGCTGGTGGCTGG

ACCAATGTAAATATTGTCATGAACTATATCCGTAACCTGGATAGTG

AAACAGGGGCAATGGTGCGCCTGCTGGAAGATGGCGACGGCGGATC

CCATCACCACCACCATCAC

Cre-6xHis (SEQ ID NO: 15):
ATGGGCGAGCAATTTACTGACCGTACACCAAAATTTGCCTGCATTGC

CGGTCGATGCAACGAGTGATGAGGTTCGCAAGAACCTGATGGACAT

GTTCAGGGATCGCCAGGCGTTTTCTGAGCATACCTGGAAAATGCTT

CTGTCCGTTTGCCGGTCGTGGGCGGCATGGTGCAAGTTGAATAACC

GGAAATGGTTTCCCGCAGAACCTGAAGATGTTCGCGATTATCTTCT

ATATCTTCAGGCGCGCGGTCTGGCAGTAAAAACTATCCAGCAACAT
```

```
TTGGGCCAGCTAAACATGCTTCATCGTCGGTCCGGGCTGCCACGAC
CAAGTGACAGCAATGCTGTTTCACTGTTTTATGCGGCGTATCCGAA
AAGAAAACGTTGATGCCGGTGAACGTGCAAAACAGGCTCTAGCGTT
CGAACGCACTGATTTCGACCAGGTTCGTTCACTCATGGAAAATAGC
GATCGCTGCCAGGATATACGTAATCTGGCATTTCTGGGGATTGCTT
ATAACACCCTGTTACGTATAGCCGAAATTGCCAGGATCAGGGTTAA
AGATATCTCACGTACTGACGGTGGGAGAATGTTAATCCATATTGGC
AGAACGAAAACGCTGGTTAGCACCGCAGGTGTAGAGAAGGCACTTA
GCCTGGGGGTAACTAAACTGGTCGAGCGATGGATTTCCGTCTCTGG
TGTAGCTGATGATCCGAATAACTACCTGTTTTGCCGGGTCAGAAAA
AATGGTGTTGCCGCGCCATCTGCCACCAGCCAGCTATCAACTCGCG
CCCTGGAAGGGATTTTTGAAGCAACTCATCGATTGATTTACGGCGC
TAAGGATGACTCTGGTCAGAGATACCTGGCCTGGTCTGGACACAGT
GCCCGTGTCGGAGCCGCGCGAGATATGGCCCGCGCTGGAGTTTCAA
TACCGGAGATCATGCAAGCTGGTGGCTGGACCAATGTAAATATTGT
CATGAACTATATCCGTAACCTGGATAGTGAAACAGGGGCAATGGTG
CGCCTGCTGGAAGATGGCGACGGCGGATCCCATCACCACCACCATC
AC
(-30)dGFP-NLS-Cas9-6xHis (SEQ ID NO: 16):
ATGGGTGCTAGCAAAGGTGAAGAGCTGTTTGACGGTGTAGTACCGA
TCTTAGTGGAATTAGACGGCGACGTGAACGGTCACGAATTTAGCGT
GCGCGGCGAGGGCGAAGGTGACGCTACCGAGGGTGAATTGACCCTG
AAGTTTATTTGCACAACAGGCGAATTACCCGTTCCGTGGCCCACCT
TAGTGACCACCCTGACCTATGGCGTTCAGTGCTTCAGTGATTACCC
AGATCATATGGATCAACACGATTTTTTCAAATCAGCCATGCCTGAA
GGATATGTTCAAGAGCGTACAATCAGCTTCAAGGACGATGGCACCT
ATAAAACGCGTGCGGAAGTGAAATTTGAAGGCGACACATTAGTAAA
CCGTATCGAACTGAAAGGTATCGACTTCAAAGAAGACGGCAACATT
TTAGGCCATAAGCTGGAATATAACTTTAATTCTCATGACGTGTATA
TTACGGCCGATAAACAGGAAAACGGTATCAAGGCAGAATTTGAAAT
TCGCCATAACGTGGAGGACGGCAGCGTTCAATTAGCGGATCATTAT
CAACAAAACACGCCGATTGGTGATGGGCCTGTACTGTTACCTGACG
ATCACTACCTGAGCACGGAGTCAGCCCTGAGCAAAGATCCGAACGA
AGACCGCGATCACATGGTTCTGTTAGAATTCGTGACCGCTGCAGGC
ATTGATCATGGAATGGACGAGCTGTACAAGACCGGTGGTAGCGGTG
GTTCTGGTGGTTCGGTGGTAGCGGCGGTAGCGGTGGTAGCGGTGG
TAGCGGTGGCAGCGGCGGTACCGCGCTCGCGCTGCCCAAGAAGAAG
AGGAAGGTGATGGATAAGAAATACTCAATAGGCTTAGATATCGGCA
CAAATAGCGTCGGATGGGCGGTGATCACTGATGAATATAAGGTTCC
GTCTAAAAAGTTCAAGGTTCTGGGAAATACAGACCGCCACAGTATC
AAAAAAAATCTTATAGGGGCTCTTTTATTTTGACAGTGGAGAGACA
GCGGAAGCGACTCGTCTCAAACGGACAGCTCGTAGAAGGTATACAC
GTCGGAAGAATCGTATTTGTTATCTACAGGAGATTTTTTCAAATGA
GATGGCGAAAGTAGATGATAGTTTCTTTCATCGACTTGAAGAGTCT
TTTTTGGTGGAAGAAGACAAGAAGCATGAACGTCATCCTATTTTTG
GAAATATAGTAGATGAAGTTGCTTATCATGAGAAATATCCAACTAT
CTATCATCTGCGAAAAAAATTGGTAGATTCTACTGATAAAGCGGAT
TTGCGCTTAATCTATTTGGCCTTAGCGCATATGATTAAGTTTCGTG
GTCATTTTTTGATTGAGGGAGATTTAAATCCTGATAATAGTGATGT
GGACAAACTATTTATCCAGTTGGTACAAACCTACAATCAATTATTT
GAAGAAAACCCTATTAACGCAAGTGGAGTAGATGCTAAAGCGATTC
TTTCTGCACGATTGAGTAAATCAAGACGATTAGAAAATCTCATTGC
TCAGCTCCCCGGTGAGAAGAAAAATGGCTTATTTGGGAATCTCATT
GCTTTGTCATTGGGTTTGACCCCTAATTTTAAATCAAATTTTGATT
TGGCAGAAGATGCTAAATTACAGCTTTCAAAAGATACTTACGATGA
TGATTTAGATAATTTATTGGCGCAAATTGGAGATCAATATGCTGAT
TTGTTTTTGGCAGCTAAGAATTTATCAGATGCTATTTTACTTTCAG
ATATCCTAAGAGTAAATACTGAAATAACTAAGGCTCCCCTATCAGC
TTCAATGATTAAACGCTACGATGAACATCATCAAGACTTGACTCTT
TTAAAAGCTTTAGTTCGACAACAACTTCCAGAAAAGTATAAAGAAA
TCTTTTTTGATCAATCAAAAAACGGATATGCAGGTTATATTGATGG
GGGAGCTAGCCAAGAAGAATTTTATAAATTTATCAAACCAATTTTA
GAAAAAATGGATGGTACTGAGGAATTATTGGTGAAACTAAATCGTG
AAGATTTGCTGCGCAAGCAACGGACCTTTGACAACGGCTCTATTCC
CCATCAAATTCACTTGGGTGAGCTGCATGCTATTTTGAGAAGACAA
GAAGACTTTTATCCATTTTTAAAAGACAATCGTGAGAAGATTGAAA
AAATCTTGACTTTTCGAATTCCTTATTATGTTGGTCCATTGGCGCG
TGGCAATAGTCGTTTTGCATGGATGACTCGGAAGTCTGAAGAAACA
ATTACCCCATGGAATTTTGAAGAAGTTGTCGATAAAGGTGCTTCAG
CTCAATCATTTATTGAACGCATGACAAACTTTGATAAAAATCTTCC
AAATGAAAAGTACTACCAAAACATAGTTTGCTTTATGAGTATTTT
ACGGTTTATAACGAATTGACAAAGGTCAAATATGTTACTGAAGGAA
TGCGAAAACCAGCATTTCTTTCAGGTGAACAGAAGAAAGCCATTGT
TGATTTACTCTTCAAAACAAATCGAAAGTAACCGTTAAGCAATTA
AAAGAAGATTATTTCAAAAAAATAGAATGTTTTGATAGTGTTGAAA
TTTCAGGAGTTGAAGATAGATTTAATGCTTCATTAGGTACCTACCA
TGATTTGCTAAAAATTATTAAAGATAAAGATTTTTTGGATAATGAA
GAAAATGAAGATATCTTAGAGGATATTGTTTTAACATTGACCTTAT
TTGAAGATAGGGAGATGATTGAGGAAAGACTTAAAACATATGCTCA
CCTCTTTGATGATAAGGTGATGAAACAGCTTAAACGTCGCCGTTAT
ACTGGTTGGGGACGTTTGTCTCGAAAATTGATTAATGGTATTAGGG
ATAAGCAATCTGGCAAAACAATATTAGATTTTTTGAAATCAGATGG
```

-continued

TTTTGCCAATCGCAATTTTATGCAGCTGATCCATGATGATAGTTTG

ACATTTAAAGAAGACATTCAAAAAGCACAAGTGTCTGGACAAGGCG

ATAGTTTACATGAACATATTGCAAATTTAGCTGGTAGCCCTGCTAT

TAAAAAAGGTATTTTACAGACTGTAAAAGTTGTTGATGAATTGGTC

AAAGTAATGGGCGGCATAAGCCAGAAAATATCGTTATTGAAATGG

CACGTGAAAATCAGACAACTCAAAAGGGCCAGAAAAATTCGCGAGA

GCGTATGAAACGAATCGAAGAAGGTATCAAAGAATTAGGAAGTCAG

ATTCTTAAAGAGCATCCTGTTGAAAATACTCAATTGCAAAATGAAA

AGCTCTATCTCTATTATCTCCAAAATGGAAGAGACATGTATGTGGA

CCAAGAATTAGATATTAATCGTTTAAGTGATTATGATGTCGATCAC

ATTGTTCCACAAAGTTTCCTTAAAGACGATTCAATAGACAATAAGG

TCTTAACGCGTTCTGATAAAAATCGTGGTAAATCGGATAACGTTCC

AAGTGAAGAAGTAGTCAAAAAGATGAAAAACTATTGGAGACAACTT

TAAACGCCAAGTTAATCACTCAACGTAAGTTTGATAATTTAACGAA

AGCTGAACGTGGAGGTTTGAGTGAACTTGATAAAGCTGGTTTTATC

AAACGCCAATTGGTTGAAACTCGCCAAATCACTAAGCATGTGGCAC

AAATTTTGGATAGTCGCATGAATACTAAATACGATGAAAATGATAA

ACTTATTCGAGAGGTTAAAGTGATTACCTTAAAATCTAAATTAGTT

TCTGACTTCCGAAAAGATTTCCAATTCTATAAAGTACGTGAGATTA

ACAATTACCATCATGCCCATGATGCGTATCTAAATGCCGTCGTTGG

AACTGCTTTGATTAAGAAATATCCAAAACTTGAATCGGAGTTTGTC

TATGGTGATTATAAAGTTTATGATGTTCGTAAAATGATTGCTAAGT

CTGAGCAAGAAATAGGCAAAGCAACCGCAAAATATTTCTTTTACTC

TAATATCATGAACTTCTTCAAAACAGAAATTACACTTGCAAATGGA

GAGATTCGCAAACGCCCTCTAATCGAAACTAATGGGGAAACTGGAG

AAATTGTCTGGGATAAAGGGCGAGATTTTGCCACAGTGCGCAAAGT

ATTGTCCATGCCCCAAGTCAATATTGTCAAGAAAACAGAAGTACAG

ACAGGCGGATTCTCCAAGGAGTCAATTTTACCAAAAAGAAATTCGG

ACAAGCTTATTGCTCGTAAAAAAGACTGGGATCCAAAAAAATATGG

TGGTTTTGATAGTCCAACGGTAGCTTATTCAGTCCTAGTGGTTGCT

AAGGTGGAAAAGGGAAATCGAAGAAGTTAAAATCCGTTAAAGAGT

TACTAGGGATCACAATTATGGAAAGAAGTTCCTTTGAAAAAAATCC

GATTGACTTTTTAGAAGCTAAAGGATATAAGGAAGTTAAAAAAGAC

TTAATCATTAAACTACCTAAATATAGTCTTTTTGAGTTAGAAAACG

GTCGTAAACGGATGCTGGCTAGTGCCGGAGAATTACAAAAAGGAAA

TGAGCTGGCTCTGCCAAGCAAATATGTGAATTTTTATATTTAGCT

AGTCATTATGAAAGTTGAAGGGTAGTCCAGAAGATAACGAACAAA

AACAATTGTTTGTGGAGCAGCATAAGCATTATTTAGATGAGATTAT

TGAGCAAATCAGTGAATTTTCTAAGCGTGTTATTTTAGCAGATGCC

AATTTAGATAAAGTTCTTAGTGCATATAACAAACATAGAGACAAAC

-continued

CAATACGTGAACAAGCAGAAAATATTATTCATTTATTTACGTTGAC

GAATCTTGGAGCTCCCGCTGCTTTTAAATATTTTGATACAACAATT

GATCGTAAACGATATACGTCTACAAAAGAAGTTTTAGATGCCACTC

TTATCCATCAATCCATCACTGGTCTTTATGAAACACGCATTGATTT

GAGTCAGCTAGGAGGTGACCATCACCACCACCATCAC (+36)dGFP-NLS-Cas9 (SEQ ID NO: 17):
ATGGGTGCTAGCAAAGGTGAACGTCTGTTTCGTGGTAAAGTACCGA

TCTTAGTGGAATTAAAGGGCGACGTGAACGGTCATAAATTTAGCGT

GCGCGGCAAAGGCAAAGGTGACGCTACCCGTGGTAAATTGACCCTG

AAGTTTATTTGCACAACAGGCAAATTACCCGTTCCGTGGCCCACCT

TAGTGACCACCCTGACCTATGGCGTTCAGTGCTTCAGTCGTTACCC

TAAACATATGAAACGTCACGATTTTTTCAAATCAGCCATGCCTAAA

GGATATGTTCAAGAGCGTACAATCAGCTTCAAGAAGGATGGCAAAT

ATAAAACGCGTGCGGAAGTGAAATTTGAAGGCCGCACATTAGTAAA

TCGTATCAAACTGAAAGGTCGTGACTTCAAAGAAAAAGGCAACATT

TTAGGCCATAAACTGCGTTATAACTTTAATTCTCATAAGGTGTATA

TTACGCCGATAAACGCAAGAATGGTATCAAGGCAAAATTCAAAAT

CGCCATAACGTGAAAGACGGCAGCGTTCAATTAGCGGATCATTAT

CAACAAAACACGCCGATTGGTCGCGGGCCTGTACTGTTACCTCGCA

ACCACTACCTGAGCACCCGTTCTAAACTGAGCAAAGATCCGAAAGA

AAAACGCGATCACATGGTTCTGTTAGAATTCGTGACCGCTGCAGGC

ATTAAGCACGGACGCGACGAACGCTACAAGACCGGTGGTAGCGGTG

GTTCTGGTGGTTCTGGTGGTAGCGGCGGTAGCGGTGGTAGCGGTGG

TAGCGGTGGCAGCGGCGGTACCGCGCTCGCGCTGCCCAAGAAGAAG

AGGAAGGTGATGGATAAGAAATACTCAATAGGCTTAGATATCGGCA

CAAATAGCGTCGGATGGGCGGTGATCACTGATGAATATAAGGTTCC

GTCTAAAAAGTTCAAGGTTCTGGGAAATACAGACCGCCACAGTATC

AAAAAAAATCTTATAGGGGCTCTTTTATTTGACAGTGGAGAGACAG

CGGAAGCGACTCGTCTCAAACGGACAGCTCGTAGAAGGTATACACG

TCGGAAGAATCGTATTTGTTATCTACAGGAGATTTTTCAAATGAG

ATGGCGAAAGTAGATGATAGTTTCTTTCATCGACTTGAAGAGTCTT

TTTTGGTGGAAGAAGACAAGAAGCATGAACGTCATCCTATTTTTGG

AAATATAGTAGATGAAGTTGCTTATCATGAGAAATATCCAACTATC

TATCATCTGCGAAAAAATTGGTAGATTCTACTGATAAAGCGGATT

TGCGCTTAATCTATTTGGCCTTAGCGCATATGATTAAGTTTCGTGG

TCATTTTTTGATTGAGGGAGATTTAAATCCTGATAATAGTGATGTG

GACAAACTATTTATCCAGTTGGTACAAACCTACAATCAATTATTTG

AAGAAAACCCTATTAACGCAAGTGGAGTAGATGCTAAAGCGATTCT

TTCTGCACGATTGAGTAAATCAAGACGATTAGAAAATCTCATTGCT

CAGCTCCCCGGTGAGAAGAAAATGGCTTATTTGGGAATCTCATTG

CTTTGTCATTGGGTTTGACCCCTAATTTTAAATCAAATTTTGATTT

-continued

```
GGCAGAAGATGCTAAATTACAGCTTTCAAAAGATACTTACGATGAT
GATTTAGATAATTTATTGGCGCAAATTGGAGATCAATATGCTGATT
TGTTTTTGGCAGCTAAGAATTTATCAGATGCTATTTTACTTTCAGA
TATCCTAAGAGTAAATACTGAAATAACTAAGGCTCCCCTATCAGCT
TCAATGATTAAACGCTACGATGAACATCATCAAGACTTGACTCTTT
TAAAAAGCTTTAGTTCGACAACAACTTCCAGAAAAGTATAAAGAAAT
CTTTTTTGATCAATCAAAAAACGGATATGCAGGTTATATTGATGGG
GGAGCTAGCCAAGAAGAATTTTATAAATTTATCAAACCAATTTTAG
AAAAAATGGATGGTACTGAGGAATTATTGGTGAAACTAAATCGTGA
AGATTTGCTGCGCAAGCAACGGACCTTTGACAACGGCTCTATTCCC
CATCAAATTCACTTGGGTGAGCTGCATGCTATTTTGAGAAGACAAG
AAGACTTTTATCCATTTTTAAAAGACAATCGTGAGAAGATTGAAAA
AATCTTGACTTTTCGAATTCCTTATTATGTTGGTCCATTGGCGCGT
GGCAATAGTCGTTTTGCATGGATGACTCGGAAGTCTGAAGAAACAA
TTACCCCATGGAATTTTGAAGAAGTTGTCGATAAAGGTGCTTCAGC
TCAATCATTTATTGAACGCATGACAAACTTTGATAAAAATCTTCCA
AATGAAAAGTACTACCAAACATAGTTTGCTTTATGAGTATTTTA
CGGTTTATAACGAATTGACAAAGGTCAAATATGTTACTGAAGGAAT
GCGAAAACCAGCATTTCTTTCAGGTGAACAGAAGAAAGCCATTGTT
GATTTACTCTTCAAAACAAATCGAAAAGTAACCGTTAAGCAATTAA
AAGAAGATTATTTCAAAAAAATAGAATGTTTTGATAGTGTTGAAAT
TTCAGGAGTTGAAGATAGATTTAATGCTTCATTAGGTACCTACCAT
GATTTGCTAAAAATTATTAAAGATAAAGATTTTTTGGATAATGAAG
AAAATGAAGATATCTTAGAGGATATTGTTTTAACATTGACCTTATT
TGAAGATAGGGAGATGATTGAGGAAAGACTTAAAACATATGCTCAC
CTCTTTGATGATAAGGTGATGAAACAGCTTAAACGTCGCCGTTATA
CTGGTTGGGGACGTTTGTCTCGAAAATTGATTAATGGTATTAGGGA
TAAGCAATCTGGCAAAACAATATTAGATTTTTTGAAATCAGATGGT
TTTGCCAATCGCAATTTTATGCAGCTGATCCATGATGATAGTTTGA
CATTTAAAGAAGACATTCAAAAAGCACAAGTGTCTGGACAAGGCGA
TAGTTTACATGAACATATTGCAAATTTAGCTGGTAGCCCTGCTATT
AAAAAAGGTATTTTACAGACTGTAAAAGTTGTTGATGAATTGGTCA
AAGTAATGGGGCGGCATAAGCCAGAAAATATCGTTATTGAAATGGC
ACGTGAAAATCAGACAACTCAAAAGGGCCAGAAAAATTCGCGAGAG
CGTATGAAACGAATCGAAGAAGGTATCAAAGAATTAGGAAGTCAGA
TTCTTAAAGAGCATCCTGTTGAAAATACTCAATTGCAAAATGAAAA
GCTCTATCTCTATTATCTCCAAAATGGAAGAGACATGTATGTGGAC
CAAGAATTAGATATTAATCGTTTAAGTGATTATGATGTCGATCACA
TTGTTCCACAAAGTTTCCTTAAAGACGATTCAATAGACAATAAGGT
CTTAACGCGTTCTGATAAAAATCGTGGTAAATCGGATAACGTTCCA
AGTGAAGAAGTAGTCAAAAAGATGAAAAACTATTGGAGACAACTTC
TAAACGCCAAGTTAATCACTCAACGTAAGTTTGATAATTTAACGAA
AGCTGAACGTGGAGGTTTGAGTGAACTTGATAAAGCTGGTTTTATC
AAACGCCAATTGGTTGAAACTCGCCAAATCACTAAGCATGTGGCAC
AAATTTTGGATAGTCGCATGAATACTAAATACGATGAAAATGATAA
ACTTATTCGAGAGGTTAAAGTGATTACCTTAAAATCTAAATTAGTT
TCTGACTTCCGAAAAGATTTCCAATTCTATAAAGTACGTGAGATTA
ACAATTACCATCATGCCCATGATGCGTATCTAAATGCCGTCGTTGG
AACTGCTTTGATTAAGAAATATCCAAAACTTGAATCGGAGTTTGTC
TATGGTGATTATAAAGTTTATGATGTTCGTAAAATGATTGCTAAGT
CTGAGCAAGAAATAGGCAAAGCAACCGCAAAATATTTCTTTTACTC
TAATATCATGAACTTCTTCAAAACAGAAATTACACTTGCAAATGGA
GAGATTCGCAAACGCCCTCTAATCGAAACTAATGGGGAAACTGGAG
AAATTGTCTGGGATAAAGGGCGAGATTTTGCCACAGTGCGCAAAGT
ATTGTCCATGCCCCAAGTCAATATTGTCAAGAAAACAGAAGTACAG
ACAGGCGGATTCTCCAAGGAGTCAATTTTACCAAAAAGAAATTCGG
ACAAGCTTATTGCTCGTAAAAAGACTGGGATCCAAAAAAATATGG
TGGTTTTGATAGTCCAACGGTAGCTTATTCAGTCCTAGTGGTTGCT
AAGGTGGAAAAAGGGAAATCGAAGAAGTTAAAATCCGTTAAAGAGT
TACTAGGGATCACAATTATGGAAAGAAGTTCCTTTGAAAAAAATCC
GATTGACTTTTTAGAAGCTAAAGGATATAAGGAAGTTAAAAAAGAC
TTAATCATTAAACTACCTAAATATAGTCTTTTTGAGTTAGAAAACG
GTCGTAAACGGATGCTGGCTAGTGCCGGAGAATTACAAAAAGGAAA
TGAGCTGGCTCTGCCAAGCAAATATGTGAATTTTTTATATTTAGCT
AGTCATTATGAAAAGTTGAAGGGTAGTCCAGAAGATAACGAACAAA
AACAATTGTTTGTGGAGCAGCATAAGCATTATTTAGATGAGATTAT
TGAGCAAATCAGTGAATTTTCTAAGCGTGTTATTTTAGCAGATGCC
AATTTAGATAAAGTTCTTAGTGCATATAACAAACATAGAGACAAAC
CAATACGTGAACAAGCAGAAAATATTATTCATTTATTTACGTTGAC
GAATCTTGGAGCTCCCGCTGCTTTTAAATATTTTGATACAACAATT
GATCGTAAACGATATACGTCTACAAAAGAAGTTTTAGATGCCACTC
TTATCCATCAATCCATCACTGGTCTTTATGAAACACGCATTGATTT
GAGTCAGCTAGGAGGTGACCATCACCACCACCATCAC
Cas9-NLS-6xHis (SEQ ID NO: 18):
ATGGATAAGAAATACTCAATAGGCTTAGATATCGGCACAAATAGCG
TCGGATGGGCGGTGATCACTGATGAATATAAGGTTCCGTCTAAAAA
GTTCAAGGYTCTGGGAAATACAGACCGCCACAGTATCAAAAAAAAT
CTTATAGGGGCTCTTTTATTTGACAGTGGAGAGACAGCGGAAGCGA
CTCGTCTCAAACGGACAGCTCGTAGAAGGTATACACGTCGGAAGAA
TCGTATTTGTTATCTACAGGAGATTTTTTCAAATGAGATGGCGAAA
GTAGATGATAGTTTCTTTCATCGACTTGAAGAGTCTTTTTTGGTGG
AAGAAGACAAGAAGCATGAACGTCATCCTATTTTTGGAAATATAGT
```

```
AGATGAAGTTGCTTATCATGAGAAATATCCAACTATCTATCATCTG
CGAAAAAAATTGGTAGATTCTACTGATAAAGCGGATTTGCGCTTAA
TCTATTTGGCCTTAGCGCATATGATTAAGTTTCGTGGTCATTTTT
GATTGAGGGAGATTTAAATCCTGATAATAGTGATGTGGACAAACTA
TTTATCCAGTTGGTACAAACCTACAATCAATTATTTGAAGAAAACC
CTATTAACGCAAGTGGAGTAGATGCTAAAGCGATTCTTTCTGCACG
ATTGAGTAAATCAAGACGATTAGAAAATCTCATTGCTCAGCTCCCC
GGTGAGAAGAAAATGGCTTATTTGGGAATCTCATTGCTTTGTCAT
TGGGTTTGACCCCTAATTTTAAATCAAATTTTGATTTGGCAGAAGA
TGCTAAATTACAGCTTTCAAAAGATACTTACGATGATGATTTAGAT
AATTTATTGGCGCAAATTGGAGATCAATATGCTGATTTGTTTTGG
CAGCTAAGAATTTATCAGATGCTATTTTACTTTCAGATATCCTAAG
AGTAAATACTGAAATAACTAAGGCTCCCCTATCAGCTTCAATGATT
AAACGCTACGATGAACATCATCAAGACTTGACTCTTTTAAAAGCTT
TAGTTCGACAACAACTTCCAGAAAAGTATAAAGAAATCTTTTTTGA
TCAATCAAAAAACGGATATGCAGGTTATATTGATGGGGGAGCTAGC
CAAGAAGAATTTTATAAATTTATCAAACCAATTTTAGAAAAAATGG
ATGGTACTGAGGAATTATTGGTGAAACTAAATCGTGAAGATTTGCT
GCGCAAGCAACGGACCTTTGACAACGGCTCTATTCCCCATCAAATT
CACTTGGGTGAGCTGCATGCTATTTTGAGAAGACAAGAAGACTTTT
ATCCATTTTTAAAAGACAATCGTGAGAAGATTGAAAAAATCTTGAC
TTTTCGAATTCCTTATTATGTTGGTCCATTGGCGCGTGGCAATAGT
CGTTTTGCATGGATGACTCGGAAGTCTGAAGAAACAATTACCCCAT
GGAATTTTGAAGAAGTTGTCGATAAAGGTGCTTCAGCTCAATCATT
TATTGAACGCATGACAAACTTTGATAAAAATCTTCCAAATGAAAAA
GTACTACCAAAACATAGTTTGCTTTATGAGTATTTTACGGTTTATA
ACGAATTGACAAAGGTCAAATATGTTACTGAAGGAATGCGAAAACC
AGCATTTCTTTCAGGTGAACAGAAGAAAGCCATTGTTGATTTACTC
TTCAAAACAAATCGAAAGTAACCGTTAAGCAATTAAAAGAAGATT
ATTTCAAAAAAATAGAATGTTTTGATAGTGTTGAAATTTCAGGAGT
TGAAGATAGATTTAATGCTTCATTAGGTACCTACCATGATTTGCTA
AAAATTATTAAAGATAAAGATTTTTTGGATAATGAAGAAAATGAAG
ATATCTTAGAGGATATTGTTTTAACATTGACCTTATTTGAAGATAG
GGAGATGATTGAGGAAAGACTTAAAACATATGCTCACCTCTTTGAT
GATAAGGTGATGAAACAGCTTAAACGTCGCCGTTATACTGGTTGGG
GACGTTTGTCTCGAAAATTGATTAATGGTATTAGGGATAAGCAATC
TGGCAAAACAATATTAGATTTTTTGAAATCAGATGGTTTTGCCAAT
CGCAATTTTATGCAGCTGATCCATGATGATAGTTTGACATTTAAAG
AAGACATTCAAAAAGCACAAGTGTCTGGACAAGGCGATAGTTTACA
TGAACATATTGCAAATTTAGCTGGTAGCCCTGCTATTAAAAAAGGT
ATTTTACAGACTGTAAAAGTTGTTGATGAATTGGTCAAAGTAATGG
GGCGGCATAAGCCAGAAAATATCGTTATTGAAATGGCACGTGAAAA
TCAGACAACTCAAAAGGGCCAGAAAAATTCGCGAGAGCGTATGAAA
CGAATCGAAGAAGGTATCAAAGAATTAGGAAGTCAGATTCTTAAAG
AGCATCCTGTTGAAAATACTCAATTGCAAAATGAAAAGCTCTATCT
CTATTATCTCCAAAATGGAAGAGACATGTATGTGGACCAAGAATTA
GATATTAATCGTTTAAGTGATTATGATGTCGATCACATTGTTCCAC
AAAGTTTCCTTAAAGACGATTCAATAGACAATAAGGTCTTAACGCG
TTCTGATAAAAATCGTGGTAAATCGGATAACGTTCCAAGTGAAGAA
GTAGTCAAAAAGATGAAAAACTATTGGAGACAACTTCTAAACGCCA
AGTTAATCACTCAACGTAAGTTTGATAATTTAACGAAAGCTGAACG
TGGAGGTTTGAGTGAACTTGATAAAGCTGGTTTTATCAAACGCCAA
TTGGTTGAAACTCGCCAAATCACTAAGCATGTGGCACAAATTTTGG
ATAGTCGCATGAATACTAAATACGATGAAAATGATAAACTTATTCG
AGAGGTTAAAGTGATTACCTTAAAATCTAAATTAGTTTCTGACTTC
CGAAAAGATTTCCAATTCTATAAAGTACGTGAGATTAACAATTACC
ATCATGCCCATGATGCGTATCTAAATGCCGTCGTTGGAACTGCTTT
GATTAAGAAATATCCAAAACTTGAATCGGAGTTTGTCTATGGTGAT
TATAAAGTTTATGATGTTCGTAAAATGATTGCTAAGTCTGAGCAAG
AAATAGGCAAAGCAACCGCAAAATATTTCTTTTACTCTAATATCAT
GAACTTCTTCAAAACAGAAATTACACTTGCAAATGGAGAGATTCGC
AAACGCCCTCTAATCGAAACTAATGGGGAAACTGGAGAAATTGTCT
GGGATAAAGGGCGAGATTTTGCCACAGTGCGCAAAGTATTGTCCAT
GCCCCAAGTCAATATTGTCAAGAAAACAGAAGTACAGACAGGCGGA
TTCTCCAAGGAGTCAATTTTACCAAAAAGAAATTCGGACAAGCTTA
TTGCTCGTAAAAAGACTGGGATCCAAAAAAATATGGTGGTTTTGA
TAGTCCAACGGTAGCTTATTCAGTCCTAGTGGTTGCTAAGGTGGAA
AAAGGGAAATCGAAGAAGTTAAAATCCGTTAAAGAGTTACTAGGGA
TCACAATTATGGAAAGAAGTTCCTTTGAAAAAAATCCGATTGACTT
TTTAGAAGCTAAAGGATATAAGGAAGTTAAAAAAGACTTAATCATT
AAACTACCTAAATATAGTCTTTTTGAGTTAGAAAACGGTCGTAAAC
GGATGCTGGCTAGTGCCGGAGAATTACAAAAAGGAAATGAGCTGGC
TCTGCCAAGCAAATATGTGAATTTTTTATATTTAGCTAGTCATTAT
GAAAAGTTGAAGGGTAGTCCAGAAGATAACGAACAAAAACAATTGT
TTGTGGAGCAGCATAAGCATTATTTAGATGAGATTATTGAGCAAAT
CAGTGAATTTTCTAAGCGTGTTATTTTAGCAGATGCCAATTTAGAT
AAAGTTCTTAGTGCATATAACAAACATAGAGACAAACCAATACGTG
AACAAGCAGAAAATATTATTCATTTATTTACGTTGACGAATCTTGG
AGCTCCCGCTGCTTTTAAATATTTTGATACAACAATTGATCGTAAA
CGATATACGTCTACAAAAGAAGTTTTAGATGCCACTCTTATCCATC
AATCCATCACTGGTCTTTATGAAACACGCATTGATTTGAGTCAGCT
```

AGGAGGTGACCCCAAGAAGAAGAGGAAGGTGATGGATAAGCATCAC

CACCACCATCAC dCas9-VP64-6xHis (SEQ ID NO: 19):
ATGGATAAGAAATACTCAATAGGCTTAGCTATCGGCACAAATAGCG

TCGGATGGGCGGTGATCACTGATGAATATAAGGTTCCGTCTAAAAA

GTTCAAGGTTCTGGGAAATACAGACCGCCACAGTATCAAAAAAAAT

CTTATAGGGGCTCTTTTATTTGACAGTGGAGAGACAGCGGAAGCGA

CTCGTCTCAAACGGACAGCTCGTAGAAGGTATACACGTCGGAAGAA

TCGTATTTGTTATCTACAGGAGATTTTTTCAAATGAGATGGCGAAA

GTAGATGATAGTTTCTTTCATCGACTTGAAGAGTCTTTTTTGGTGG

AAGAAGACAAGAAGCATGAACGTCATCCTATTTTTGGAAATATAGT

AGATGAAGTTGCTTATCATGAGAAATATCCAACTATCTATCATCTG

CGAAAAAAATTGGTAGATTCTACTGATAAAGCGGATTTGCGCTTAA

TCTATTTGGCCTTAGCGCATATGATTAAGTTTCGTGGTCATTTTTT

GATTGAGGGAGATTTAAATCCTGATAATAGTGATGTGGACAAACTA

TTTATCCAGTTGGTACAAACCTACAATCAATTATTTGAAGAAAACC

CTATTAACGCAAGTGGAGTAGATGCTAAAGCGATTCTTTCTGCACG

ATTGAGTAAATCAAGACGATTAGAAAATCTCATTGCTCAGCTCCCC

GGTGAGAAGAAAAATGGCTTATTTGGGAATCTCATTGCTTTGTCAT

TGGGTTTGACCCCTAATTTTAAATCAAATTTTGATTTGGCAGAAGA

TGCTAAATTACAGCTTTCAAAAGATACTTACGATGATGATTTAGAT

AATTTATTGGCGCAAATTGGAGATCAATATGCTGATTTGTTTTTGG

CAGCTAAGAATTTATCAGATGCTATTTTACTTTCAGATATCCTAAG

AGTAAATACTGAAATAACTAAGGCTCCCCTATCAGCTTCAATGATT

AAACGCTACGATGAACATCATCAAGACTTGACTCTTTTAAAAGCTT

TAGTTCGACAACAACTTCCAGAAAAGTATAAAGAAATCTTTTTTGA

TCAATCAAAAAACGGATATGCAGGTTATATTGATGGGGGAGCTAGC

CAAGAAGAATTTTATAAATTTATCAAACCAATTTTAGAAAAAATGG

ATGGTACTGAGGAATTATTGGTGAAACTAAATCGTGAAGATTTGCT

GCGCAAGCAACGGACCTTTGACAACGGCTCTATTCCCCATCAAATT

CACTTGGGTGAGCTGCATGCTATTTTGAGAAGACAAGAAGACTTTT

ATCCATTTTTAAAAGACAATCGTGAGAAGATTGAAAAAATCTTGAC

TTTTCGAATTCCTTATTATGTTGGTCCATTGGCGCGTGGCAATAGT

CGTTTTGCATGGATGACTCGGAAGTCTGAAGAAACAATTACCCCAT

GGAATTTTGAAGAAGTTGTCGATAAAGGTGCTTCAGCTCAATCATT

TATTGAACGCATGACAAACTTTGATAAAAATCTTCCAAATGAAAAA

GTACTACCAAAACATAGTTTGCTTTATGAGTATTTTACGGTTTATA

ACGAATTGACAAAGGTCAAATATGTTACTGAAGGAATGCGAAAACC

AGCATTTCTTTCAGGTGAACAGAAGAAAGCCATTGTTGATTTACTC

TTCAAAACAAATCGAAAAGTAACCGTTAAGCAATTAAAAGAAGATT

ATTTCAAAAAAATAGAATGTTTTGATAGTGTTGAAATTTCAGGAGT

TGAAGATAGATTTAATGCTTCATTAGGTACCTACCATGATTTGCTA

AAAATTATTAAAGATAAAGATTTTTTGGATAATGAAGAAAATGAAG

ATATCTTAGAGGATATTGTTTTAACATTGACCTTATTTGAAGATAG

GGAGATGATTGAGGAAAGACTTAAAACATATGCTCACCTCTTTGAT

GATAAGGTGATGAAACAGCTTAAACGTCGCCGTTATACTGGTTGGG

GACGTTTGTCTCGAAAATTGATTAATGGTATTAGGGATAAGCAATC

TGGCAAAACAATATTAGATTTTTTGAAATCAGATGGTTTTGCCAAT

CGCAATTTTATGCAGCTGATCCATGATGATAGTTTGACATTTAAAG

AAGACATTCAAAAAGCACAAGTGTCTGGACAAGGCGATAGTTTACA

TGAACATATTGCAAATTTAGCTGGTAGCCCTGCTATTAAAAAAGGT

ATTTTACAGACTGTAAAAGTTGTTGATGAATTGGTCAAAGTAATGG

GGCGGCATAAGCCAGAAAATATCGTTATTGAAATGGCACGTGAAAA

TCAGACAACTCAAAAGGGCCAGAAAAATTCGCGAGAGCGTATGAAA

CGAATCGAAGAAGGTATCAAAGAATTAGGAAGTCAGATTCTTAAAG

AGCATCCTGTTGAAAATACTCAATTGCAAATGAAAAGCTCTATCT

CTATTATCTCCAAAATGGAAGAGACATGTATGTGGACCAAGAATTA

GATATTAATCGTTTAAGTGATTATGATGTCGATGCCATTGTTCCAC

AAAGTTTCCTTAAAGACGATTCAATAGACAATAAGGTCTTAACGCG

TTCTGATAAAAATCGTGGTAAATCGGATAACGTTCCAAGTGAAGAA

GTAGTCAAAAAGATGAAAAACTATTGGAGACAACTTCTAAACGCCA

AGTTAATCACTCAACGTAAGTTTGATAATTTAACGAAAGCTGAACG

TGGAGGTTTGAGTGAACTTGATAAAGCTGGTTTTATCAAACGCCAA

TTGGTTGAAACTCGCCAAATCACTAAGCATGTGGCACAAATTTTGG

ATAGTCGCATGAATACTAAATACGATGAAAATGATAAACTTATTCG

AGAGGTTAAAGTGATTACCTTAAAATCTAAATTAGTTTCTGACTTC

CGAAAAGATTTCCAATTCTATAAAGTACGTGAGATTAACAATTACC

ATCATGCCCATGATGCGTATCTAAATGCCGTCGTTGGAACTGCTTT

GATTAAGAAATATCCAAAACTTGAATCGGAGTTTGTCTATGGTGAT

TATAAAGTTTATGATGTTCGTAAAATGATTGCTAAGTCTGAGCAAG

AAATAGGCAAAGCAACCGCAAAATATTTCTTTTACTCTAATATCAT

GAACTTCTTCAAAACAGAATTACACTTGCAAATGGAGAGATTCGC

AAACGCCCTCTAATCGAAACTAATGGGGAAACTGGAGAAATTGTCT

GGGATAAAGGGCGAGATTTTGCCACAGTGCGCAAAGTATTGTCCAT

GCCCCAAGTCAATATTGTCAAGAAAACAGAAGTACAGACAGGCGGA

TTCTCCAAGGAGTCAATTTTACCAAAAAGAAATTCGGACAAGCTTA

TTGCTCGTAAAAAAGACTGGGATCCAAAAAAATATGGTGGTTTTGA

TAGTCCAACGGTAGCTTATTCAGTCCTAGTGGTTGCTAAGGTGGAA

AAAGGGAAATCGAAGAAGTTAAAATCCGTTAAAGAGTTACTAGGGA

TCACAATTATGGAAAGAAGTTCCTTTGAAAAAAATCCGATTGACTT

TTTAGAAGCTAAAGGATATAAGGAAGTTAAAAAAGACTTAATCATT

```
-continued
AAACTACCTAAATATAGTCTTTTTGAGTTAGAAAACGGTCGTAAAC

GGATGCTGGCTAGTGCCGGAGAATTACAAAAAGGAAATGAGCTGGC

TCTGCCAAGCAAATATGTGAATTTTTTATATTTAGCTAGTCATTAT

GAAAAGTTGAAGGGTAGTCCAGAAGATAACGAACAAAAACAATTGT

TTGTGGAGCAGCATAAGCATTATTTAGATGAGATTATTGAGCAAAT

CAGTGAATTTTCTAAGCGTGTTATTTTAGCAGATGCCAATTTAGAT

AAAGTTCTTAGTGCATATAACAAACATAGAGACAAACCAATACGTG

AACAAGCAGAAAATATTATTCATTTATTTACGTTGACGAATCTTGG

AGCTCCCGCTGCTTTTAAATATTTTGATACAACAATTGATCGTAAA

CGATATACGTCTACAAAAGAAGTTTTAGATGCCACTCTTATCCATC

AATCCATCACTGGTCTTTATGAAACACGCATTGATTTGAGTCAGCT

AGGAGGTGACGGTTCTCCCAAGAAGAAGAGGAAAGTCTCGAGCGAC

TACAAAGACCATGACGGTGATTATAAAGATCATGACATCGATTACA

AGGATGACGATGACAAGGCTGCAGGAGGCGGTGGAAGCGGGCGCGC

CGACGCGCTGGACGATTTCGATCTCGACATGCTGGGTTCTGATGCC

CTCGATGACTTTGACCTGGATATGTTGGGAAGCGACGCATTGGATG

ACTTTGATCTGGACATGCTCGGCTCCGATGCTCTGGACGATTTCGA

TCTCGATATGTTACATCACCACCACCATCAC
```

List of upstream and downstream flanking sequences for each genomic target site.

| Target Site | Downstream genomic sequence | Upstream genomic sequence |
|---|---|---|
| EMX_On | GGCCTGCTTCGTGGCAATGC (SEQ ID NO: 92) | ACCTGGGCCAGGGAGGGAGG (SEQ ID NO: 93) |
| EMX_Off1 | CTCACTTAGACTTTCTCTCC (SEQ ID NO: 94) | CTCGGAGTCTAGCTCCTGCA (SEQ ID NO: 95) |
| EMX_Off2 | TGGCCCCAGTCTCTCTTCTA (SEQ ID NO: 96) | CAGCCTCTGAACAGCTCCCG (SEQ ID NO: 97) |
| EMX_Off3 | TGACTTGGCCTTTGTAGGAA (SEQ ID NO: 98) | GAGGCTACTGAAACATAAGT (SEQ ID NO: 99) |
| EMX_Off4 | TGCTACCTGTACATCTGCAC (SEQ ID NO: 100) | CATCAATGATTGGGCATTTC (SEQ ID NO: 101) |
| VEG_On | ACTCCAGTCCCAAATATGTA (SEQ ID NO: 102) | ACTAGGGGCGCTCGGCCAC (SEQ ID NO: 103) |
| VEG_Off1 | CTGAGTCAACTGTAAGCATT (SEQ ID NO: 104) | GGCCAGGTGCAGTGATTCAT (SEQ ID NO: 105) |
| VEG_Off2 | TCGTGTCATCTTGTTTGTGC (SEQ ID NO: 106) | GGCAGAGCCCAGCGGACACT (SEQ ID NO: 107) |
| VEG_Off3 | CAAGGTGAGCCTGGGTCTGT (SEQ ID NO: 108) | ATCACTGCCCAAGAAGTGCA (SEQ ID NO: 109) |
| VEG_Off4 | TTGTAGGATGTTTAGCAGCA (SEQ ID NO: 110) | ACTTGCTCTCTTTAGAGAAC (SEQ ID NO: 111) |
| CLT2_On | CTCAAGCAGGCCCCGCTGGT (SEQ ID NO: 112) | TTTTGGACCAAACCTTTTTG (SEQ ID NO: 113) |
| CLT2_Off1 | TGAGGTTATTTGTCCATTGT (SEQ ID NO: 114) | TAAGGGGAGTATTTACACCA (SEQ ID NO: 115) |
| CLT2_Off2 | TCAAGAGCAGAAAATGTGAC (SEQ ID NO: 116) | CTTGCAGGGACCTTCTGATT (SEQ ID NO: 117) |
| CLT2_Off3 | TGTGTGTAGGACTAAACTCT (SEQ ID NO: 118) | GATAGCAGTATGACCTTGGG (SEQ ID NO: 119) |
| EGFP | AGCGTGTCCGGCGAGGGCGA (SEQ ID NO: 120) | AGCGTGTCCGGCGAGGGCGA (SEQ ID NO: 121) |
| MusEMX | CAGAATCGGAGGACAAAATACAAAC (SEQ ID NO: 122) | ACGAAGCAGGCCAACGGGGAGACA (SEQ ID NO: 123) |

Example 2: Rescue of Hearing Loss by Cas9/gRNA Delivery In Vivo and CRISPR Mediated Gene Editing in a Genetic Deaf Mouse Model To use liposomal formulation that complexes Cas9 with gRNA for CRISPR mediated gene editing as a potential treatment for genetic deafness, a rescue effect on Pmca2 deafness mouse mutant was studied. Pmca2 is a plasma membrane $Ca^{2+}$ pump that is highly expressed in the inner ear hair cells, with the function that actively pumps out $Ca^{2+}$ that enters hair cells during signal mechanoelectrical transduction during hearing and vestibular function. PMCA2 mutation has been shown to increase hearing loss severity human (M Schultz et al., *N Engl J Med* 352, no. 15 (Apr. 14, 2005): 1557-64, doi:10.1056/NEJMoa043899). In the mouse mutant (Oblivion) with a point mutation (S877F), severe to profound (i.e. complete) hearing loss is observed in heterozygous and homozygous mice (Spiden et al., *PLoS Genetics* 4, e1000238-e1000238.2008). This mouse mutant thus serves as an excellent model to determine if the Cas9/gRNA approach can be used to disrupt the Pmca2 mutation in heterozygous mice for hearing recovery, with implication to reduce hearing loss in human.

Figure 22:
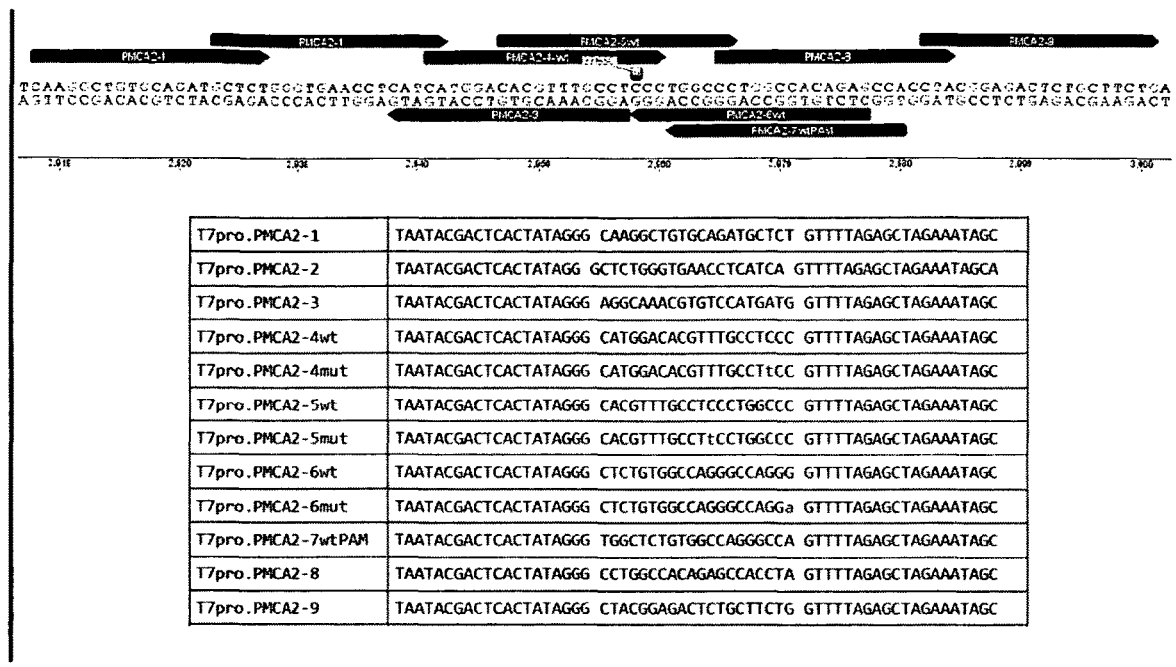
FIG. 22 shows the Cas9/gRNA protein delivery in the Pmca2 mouse mutant restores hearing. Left panel: ABR study shows three and four weeks after Cas9/gRNA-Pmca2-2.4 injection, the injected inner ears show significant restoration of hearing across different frequencies. In the uninjected inner ears, profound deafness defined as ABR over 100 dB in all frequencies and over 95 dB at 45.24 kHz. Comparing four weeks to three weeks, the hearing restoration is stable. Right panel: DPAOE study shows similar restoration in the Cas9/gRNA-Pmca2-2.4 injected inner ears vs. severely elevated thresholds in the uninjected inner ears. *$P<0.05$; *$P<0.001$; **$P<0.0001$. 2-way ANOVA test, means (±SEMs). n=4 for each group.

To study the hearing rescue effect, 12 guide RNAs were designed, 4 of which targeted the mutation (FIG. 22). Following lipofectamine 2000 formulation that complexes Cas9 with each gRNA, the complex was injected into postnatal day 3 (P3) mouse cochleas. Both mouse mutants and wildtype control mice were injected. For each mouse right ear was injected and the left ear was uninjected. Three weeks or four weeks after injection, acoustic Auditory brainstem response (ABR) and distortion product otoacoustic emissions (DPOAE) tests were performed.

For ABR and DPOAE tests, injected mice of either sex were anesthetized with xylazine (10 mg/kg, i.p.) and ketamine (100 mg/kg, i.p.). ABR and DPOAE were performed as previously described (Huang et al., 2013). ABR measures the auditory pathway from hair cells to brain; whereas DPOAE measures primarily outer hair cell function. By their combination it could be inferred if the hearing defects are of hair cells or central pathway deficiency.

At three weeks after injection, in the heterozygous Pmca2 mice, uninjected inner ears had profound hearing loss as shown by ABR and DPOAE. In the Cas9/gRNA-Pmca-2.4 (with the guide RNA 2.4) injected ears, significant hearing recovery in frequencies of 16, 22.64, 32 and 45.24 kHz by ABR was observed. By DPOAE, significant recovery in frequencies from 16 to 45.24 kHz was detected in the Cas9/gRNA-Pmca-2.4 injected inner ear, corresponding to ABR recovery. Recovery of DPOAE is an indication of restoration of hair cell function. To study long-term effect of hearing recovery, a hearing study was performed four weeks after injection and observed similar hearing recovery. The hearing study will be continued at 6, 12 and 26 weeks after injection. In addition to the uninjected control ears, Pmca2 heterozygous mice injected with Cas9 complexed with other Pmca2 guide RNAs were also studied. No hearing recover was detected either by ABR or DPOAE was detected (data not shown). Thus guide RNA Pmca2-2.4 complexed with Cas9 induced sequence specific gene editing of Pmca2 mutation, leading to significant improvement of hearing.

To study potential toxicity associated with Cas9/gRNA delivery, Cas9/gRNA-Pmca-2.4 was injected into P3 wild-type (WT) mice and performed hearing study 3 weeks after injection. Slight elevation was observed in ABR and DPOAE at the highest frequency (45.24 kHz), but not in any other frequencies. Thus Cas9/gRNA-Pmca-2.4 complex does not cause additional damage to healthy hair cells or inner ear function. All together the study demonstrates that Cas9/gRNA that targets Pmca2 mutation in hair cells restores hearing in otherwise complete deaf mouse mutants. The similar strategy thus can be applied to human deaf patients with Pmca2 mutations to improve or restore hearing.

Figure 23:
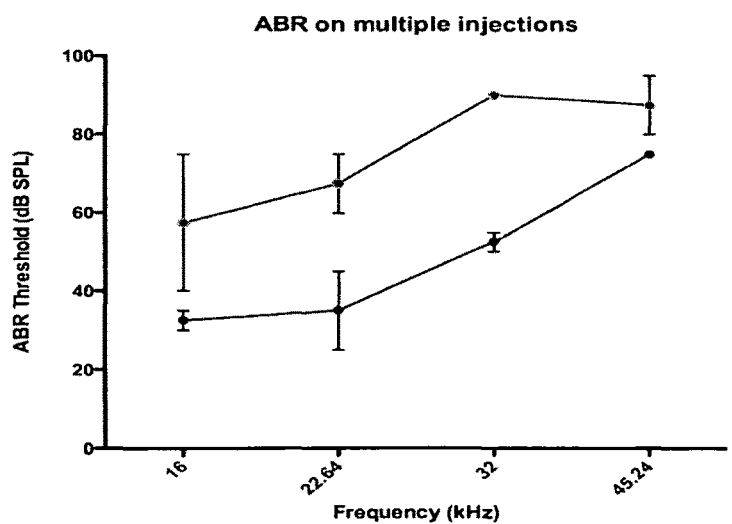
FIG. 23 is a graph showing that four weeks after multiple injections, ABR in the Cas9/gRNA-Pmca2-2.4 injected inner ears show dramatic hearing restoration at 16, 22.64, 32 and 45.24 kHz comparing to the uninjected control ears. Hearing restoration at 16, 22.64 and 32 kHz are improved by 40 dB.

The hearing recovery in the Cas9/gRNA-Pmca-2.4 injected ear was not uniform across all frequencies (e.g. no recovery in 8 kHz). Further the recovery was uneven as better recovery was seen at the highest frequency of 45.24 kHz. This is likely due to the surgical procedure used only allowed for access to primarily the base of the cochlea, which is responsible for high-frequency hearing. The lack of recovery at the low frequency is likely due to the insufficient diffusion of Cas9/gRNA complex to the apical region of the cochlea. To test this hypothesis, additional experiments by multiple injections were performed in the Pmca2 mice over 6 days. By four weeks much greater hearing recovery was observed (40 dB) covering a majority of frequencies from 16 to 45.24 kHz (FIG. 23). The mouse inner ear is extremely small in size, about 1/50th of the size of human inner ear. While the mouse inner ear presents a surgical challenge in protein delivery, it is anticipated that in human inner ear the delivery would be considerably easier. Thus multiple injections result in greatly improved hearing restoration across most frequencies.

One of the most important applications of the technology is the ability to deliver the Cas9/gRNA complex in mature mammalian inner ear. The first set of experiments were conducted and showed that when injected into P9 mouse cochlea, a similar hearing rescue effect was observed (data not shown).

The work demonstrates the utility of direct Cas9/gRNA delivery into mammalian inner ear hair cells in vivo in disruption of mutations that leads to functional recovery of hearing. As 20% of genetic deafness is due to dominant mutations, this method can be tailored to target those mutations to restore hearing.

The most common form of deafness is recessive, for which repair of mutations will be needed for hearing restoration. One of the most common forms of deafness in human is age-related hearing loss (ARHL) or presbycusis, affecting over hundreds of millions of people worldwide. While the major mechanisms underlying ARHL is unknown, it is likely that genes will be identified with mutations or polymorphisms that make hair cells vulnerable to aging. Under this condition, the Cas9/gRNA could be applied to disrupt or repair the mutations/polymorphisms, to restore or slow down the progression of hearing loss. While the method currently targets hair cells, modifications will be made so that the method can be used to target inner ear cell types such as supporting cells, strial vascular and neurons, in which similar gene editing can be achieved for functional recovery of hearing. Finally, many recessive genetic deafness is congenital, by the time of birth, simple gene editing may not be sufficient to restore cell function or hearing due to degeneration of the cell types. However it is possible to combine regeneration of the cell types with gene editing, to produce new cells while correcting mutations. These combinations can be applied to restore hearing in patients suffering from hearing loss due to different causes.

What is claimed is:

1. A method of treating deafness in a patient in need thereof, wherein the patient has a mutation in a genetic locus comprising Pmca2, said method comprising: administering to an ear of the patient a therapeutically effective amount of a chimeric molecule comprising at least one gene editing agent and a short guide RNA (sgRNA), fused, complexed or linked to one or more anionic molecules, wherein the sgRNA is specific for Pmca2, wherein the at least one gene editing agent comprises Cre recombinases, CRISPR/Cas molecules, TALE transcriptional activators, Cas9 nucleases, nickases, thereby treating deafness.

2. The method of claim 1, wherein the chimeric molecule is anionic and is encapsulated in a cationic lipid formulation.

3. The method of claim 1, wherein the chimeric molecule targets one or more genetic loci associated with deafness in a patient and modulates expression of the Pmca2 genetic locus.

4. The method of claim 3, wherein the chimeric molecule comprises a Cas9 nuclease.

5. The method of claim 4, wherein the gene editing agents comprise nucleic acids.

6. The method of claim 1, wherein the anionic molecules comprise: oligonucleotides.

7. The method of claim 6, wherein the proteins or peptides comprise: genome or gene editing agents.

8. The method of claim 2, wherein the cationic liposome encapsulated chimeric molecule is administered to a patient's inner ear.

9. The method of claim 1, wherein the anionic molecule comprises any one or more sequences having a sequence identity of at least about 75% to sequences comprising SEQ ID NOS: 1 to 19.

10. The method of claim 9, wherein the one or more sequences comprise at least one or more of SEQ ID NOS: 1 to 19.

* * * * *

UNITED STATES PATENT AND TRADEMARK OFFICE
CERTIFICATE OF CORRECTION

| | |
|---|---|
| PATENT NO. | : 10,583,201 B2 |
| APPLICATION NO. | : 15/518183 |
| DATED | : March 10, 2020 |
| INVENTOR(S) | : Zheng-Yi Chen et al. |

It is certified that error appears in the above-identified patent and that said Letters Patent is hereby corrected as shown below:

On the Title Page

Column 1, item (72) Inventors, after "David Liu, Cambridge, MA (US)" insert:
-- David B. Thompson, Cambridge, MA (US)
John Zuris, Cambridge, MA (US) --

Signed and Sealed this
Twenty-second Day of November, 2022

Katherine Kelly Vidal
*Director of the United States Patent and Trademark Office*